United States Patent [19]

Hunkapiller

[11] Patent Number: 4,837,726
[45] Date of Patent: Jun. 6, 1989

[54] QUANTITATION OF CHROMATOGRAPHIC INFORMATION

[75] Inventor: Michael W. Hunkapiller, San Carlos, Calif.

[73] Assignee: Applied Biosystems, Inc., Foster City, Calif.

[21] Appl. No.: 65,012

[22] Filed: Jun. 19, 1987

[51] Int. Cl.$^4$ .................. G06F 15/46; G01N 30/02
[52] U.S. Cl. .................. 364/498; 73/23.1; 364/497; 364/571.05; 364/571.02
[58] Field of Search .......... 364/497, 498, 571, 572, 364/733, 833; 73/23.1

[56] References Cited

U.S. PATENT DOCUMENTS

| | | | |
|---|---|---|---|
| 4,054,384 | 10/1977 | Hawes | 73/23.1 |
| 4,170,893 | 10/1979 | Kleiss | 364/571 |
| 4,314,343 | 2/1982 | Tomlinson | 364/733 |
| 4,353,242 | 10/1982 | Harris et al. | 73/23.1 |
| 4,357,668 | 11/1982 | Schwartz et al. | 73/23.1 |
| 4,374,424 | 2/1983 | Coustre et al. | 364/497 |
| 4,468,742 | 8/1984 | Jenden et al. | 364/497 |
| 4,546,643 | 10/1985 | Bonneyrat et al. | 364/498 |
| 4,631,687 | 12/1986 | Kowalski et al. | 364/497 |
| 4,674,323 | 6/1987 | Rulf et al. | 364/497 |

OTHER PUBLICATIONS

Applied Biosystems Model 900A Instrument Control and Data Analysis Maodule Booklet, 1986.
Applied Biosystems Model 120A PTH Analyzer Booklet, 1985.
Michael W. Hunkapiller, PTH Amino Acid Analysis, Applied Biosystems User Bulletin, Protein Sequencer, Issue No. 14, Nov. 18, 1985.
Werner Macleidt and Helmut Hofner, "Quantitative Amino Acid Sequencing by High Pressure Liquid Chromatography Operating On-Line to a Solid Phase Sequencer", 1981, High Performance Chromatography in Protein and Peptide Chemistry.
Rodney M. Hewick, Michael W. Hunkapiller, Leroy E. Hood, and William J. Dreyer, "A Gas-Liquid Solid Phase Peptide and Protein Sequenator" the Journal of Biological Chemistry, vol. 256, No. 15, Aug. 10, 1981, pp. 7990-7997.
Werner Machleidt and Helmut Hofner, "Methods in Peptide and Protein Sequence Analysis", Oct. 1-4, 1979, pp. 35-47.
Werner Machleidt and Helmut Hofner, "Methods in Protein Sequence Analysis" edited by Marshall Elzinga, 1982, pp. 173-180.
Keith Ashman and Brigitte Wittmann-Liebold, "A New Isocratic HPLC Separation for Pth-Amino Acids, based on 2-Propanol", Oct. 1985, Federation of European Biochemical Societies, pp. 129-132.
Henry Rodgreguez, "Automated On-Line Identification of Phenylthiohydantoin-Amino Acids from a Vapor Phase Protein Sequencer", Journal of Chromatography, 350 (1985) 217-225.

(List continued on next page.)

Primary Examiner—Parshotam S. Lall
Assistant Examiner—Kevin J. Teska
Attorney, Agent, or Firm—Joseph H. Smith

[57] ABSTRACT

A process and apparatus for quantitating chromatographic information uses a discrete, linear, translation invariant filter function $a_N{}^\alpha$, where N is a measure of the filter function width and $\alpha$ is a parameter whose value determines signal to noise characteristics of the filter function. First a chromatographic analysis of a sample is performed to obtain a first chromatogram. Then the first chromatogram is filtered with the filter function, with N set to approximate the width of peaks obtained in the first chromatogram, and $\alpha$ is set to filter out high frequency noise from the first chromatogram to obtain a second chromatogram having a first filtered baseline. The second chromatogram is then filtered with $\alpha$ set to resolution enhance peaks in the second chromatogram to obtain a third chromatogram having a baseline which is substantially the same as the first filtered baseline. The second chromatogram is then subtracted from the third chromatogram to obtain a fourth chromatogram which is baseline corrected.

7 Claims, 32 Drawing Sheets

OTHER PUBLICATIONS

Stephen Kent et al., "Approaches to Sub-Picomole Protein Sequencing" from: Modern Methods in Protein Chemistry, James J. L'Italien (ed), Plenum Press, New York (1985), in press.

O. Smithies et al., "Quantitative Procedures for Use with the Edman-Begg Sequenator, Partial Sequences of Two Unusual Immunoglobulin Light Chains, Rzf and Sac" Biochemistry, vol. 10, No. 26, 1971, pp. 4912-4921.

R. P. Goehner, "Background Subtract Subroutine for Spectral Data" Analytical Chemistry, vol. 50, No. 8, Jul. 1978, pp. 1223-1225.

G. J. de Groot, "Fast Fourier Transformation Filter Program as Part of a System for Processing Chromatographic Data with an Apple II Microcomputer" Trends in Analytical Chemistry, vol. 4, No. 6, 1985, pp. 134-137.

De Groot et al., "A System for High Performance Liquid Chromatography of 99 mTc-Compounds with On--Line Radiometric Detection and Data Processing" Int. J. Appl. Radiat. Isot., vol. 36, No. 5, pp. 349-355, 1985.

P. Edman and G. Begg, "A Protein Sequenator" European J. Biochem. 1 (1967), pp. 80-91.

Pehr Edman, "On the Mechanism of the Phenyl Isothiocyantae Degradation of Peptides" Acta Chemica Scandinavica 10 (1956), pp. 761-768.

Brigitte Witmann-Liebold, "Amino Acid Sequence Studies on Ten Ribosomal Proteins of Escherichia coli with an Improved Sequenator Equipped with an Automatic Conversion Device" Hoppe-Seyler's Z. Physiol. Chem. Bd. 354, S. 1415-1431, Oct./Nov. 1973.

Bromba and Zeigler, "Variable Filter for Digital Smoothing and Resolution Enhancement of Noisy Spectra" Anal. Chem. 1984, 56, pp. 2052-2058.

Analytical Chemistry, vol. 58, No. 3, Mar. 86, Washington, G. Biermann, H. Ziegler, "Properties of a Variable Digital Filter for Smoothing and Resolution Enhancement", pp. 536-539.

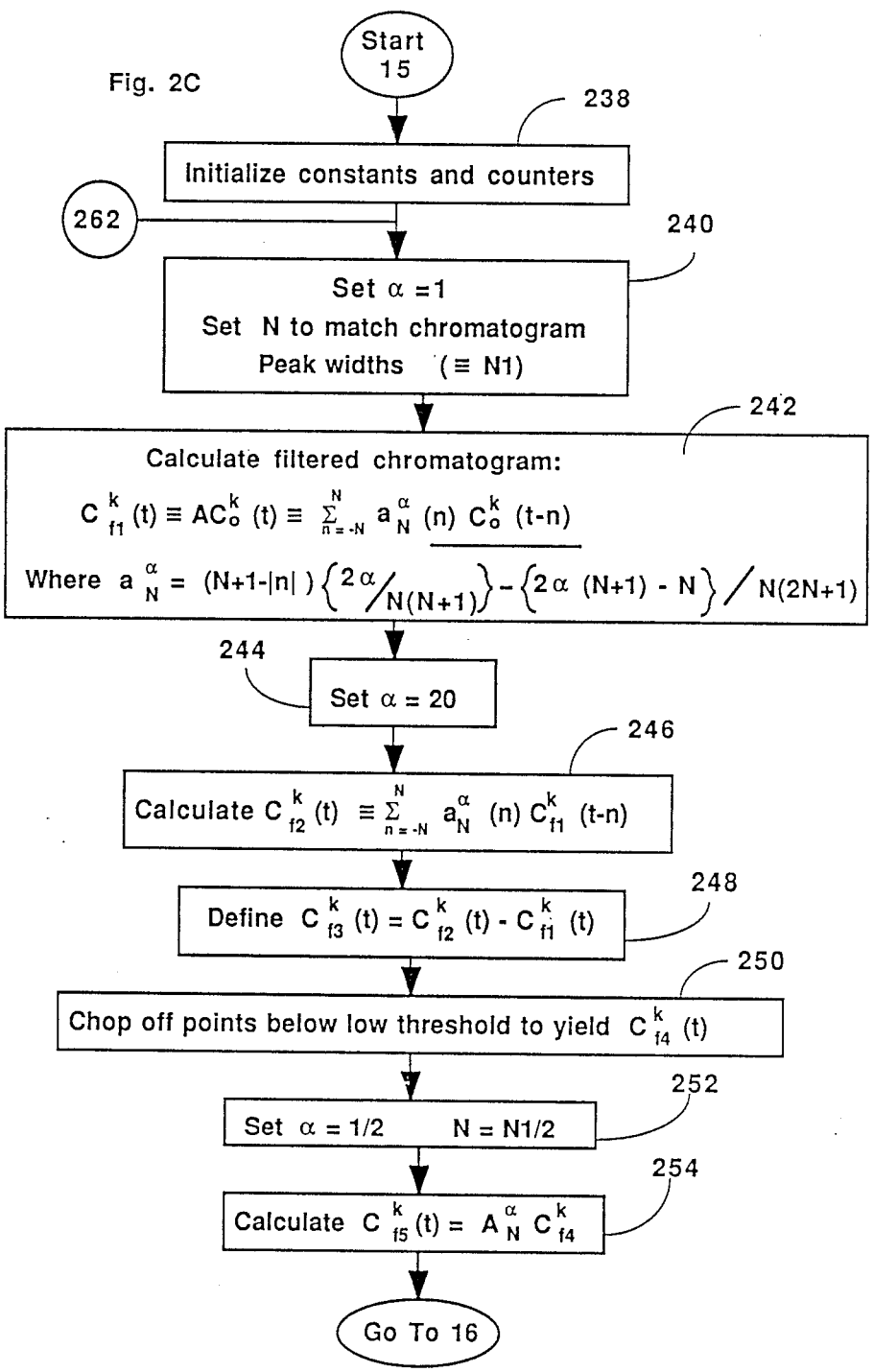

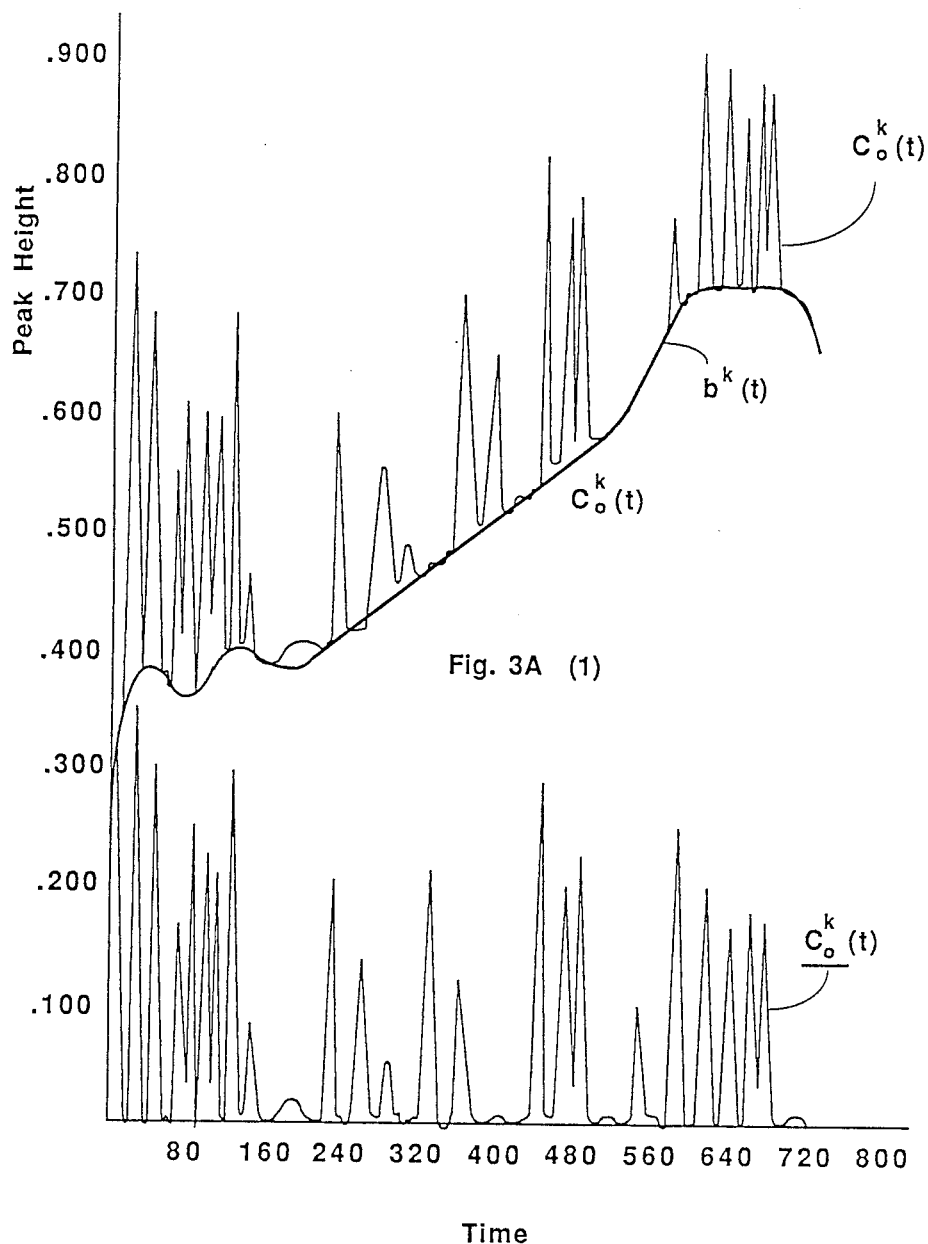
Fig. 3A (2)

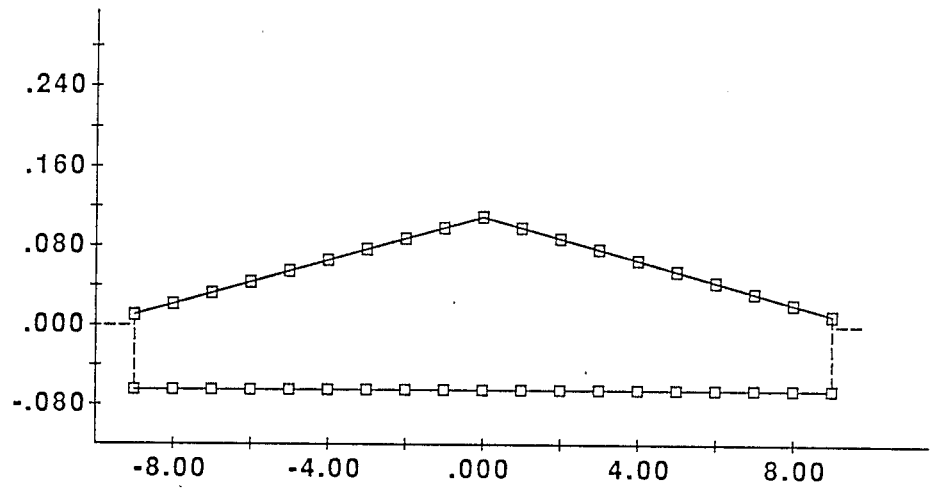
Fig. 3B (1)
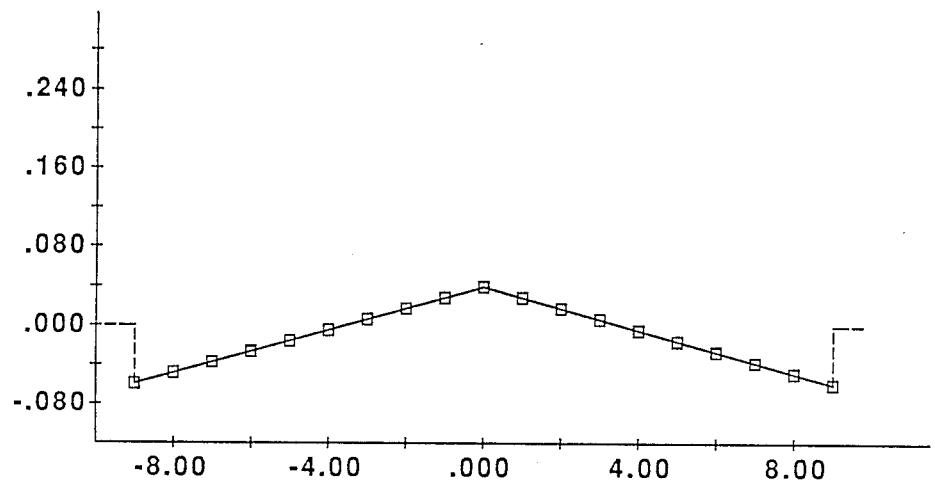
Fig. 3B (2)

Fig. 5A (Lag correction)

511 Sort $\underline{PTH}_j(k)$ and set $Y_k = \max \underline{PTH}_j(k)$ for all cycles $k = 1$ to $N$

513 Set $Y_{k,k+1} = \underline{PTH}_j(k+1)$ for all $k = 1$ to $N$, where $j$ corresponds to amino acid number for which $\underline{PTH}_j(k)$ is a maximum in cycle $k$ (5AB)

515 Initialize cycle counter: $n = 1$

517 Calculate lag coefficients $Y_{k,k+1} / Y_k = k\,b(k)$ for $k = n$ to $N$

519 Fit $q\,b(q)$ with polynomial $B(q)$ of degree $Z$ for $q = 1$ to $N$

521 Calculate $\sigma_B$, the standard deviation of $B(q)$ from the actual measurements $Y_{q,q+1} / Y_q$ over the domain $N$ Go to 5BA

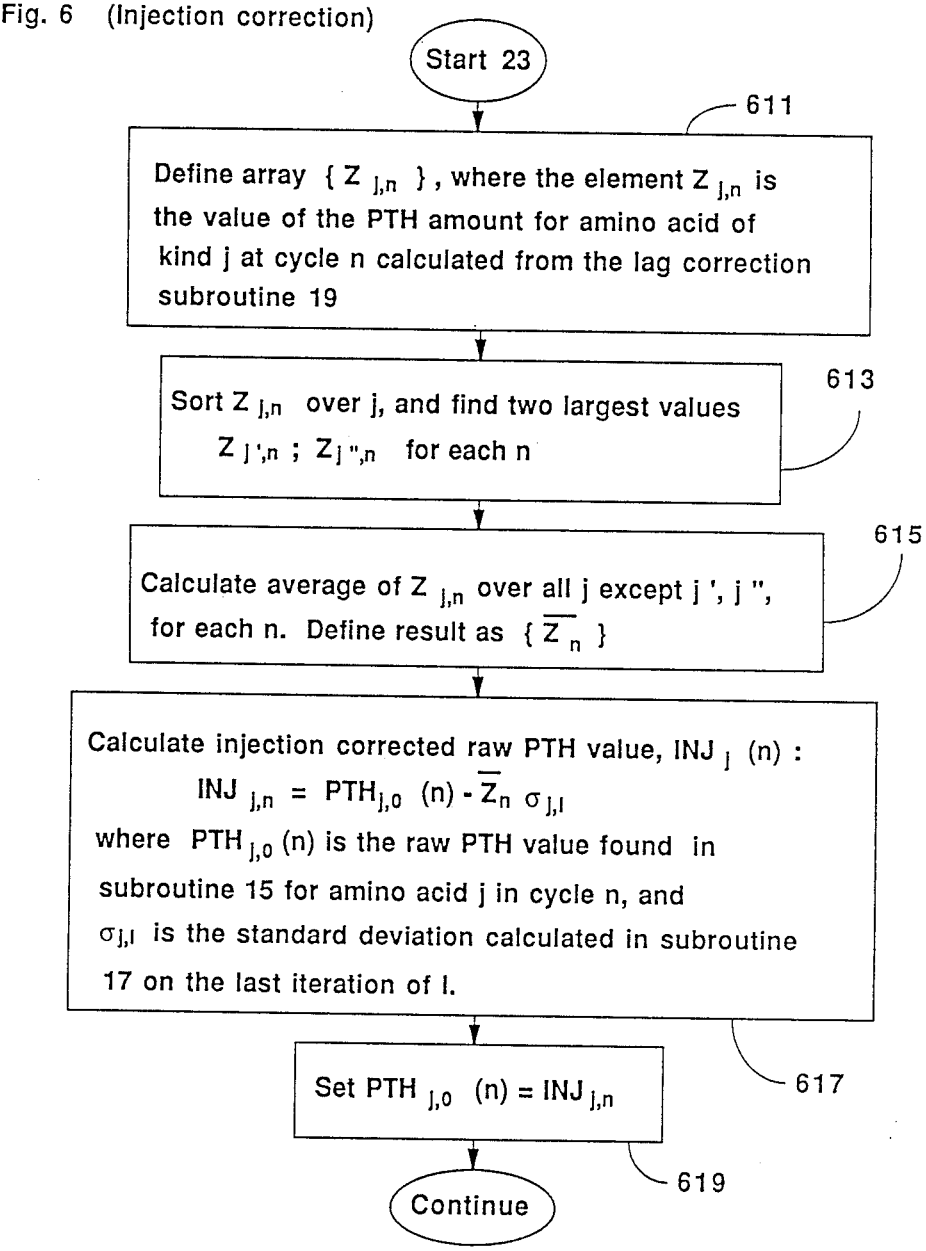
Fig. 6 (Injection correction)

QUANTITATION OF CHROMATOGRAPHIC INFORMATION

BACKGROUND OF THE INVENTION

This invention relates to a method and apparatus of general utility for analyzing chromatographic information, and particularly to the use of such for analyzing chromatographic information pertaining to the automatic determination of peptide sequences.

The chemical process employed by protein/peptide sequencers is derived from a technique originated by Pehr Edman in the 1950s for the sequential degradation of peptide chains (Edman, *Acta Chem. Scand.* 4, 283, 1950; Edman and Begg, *Eur. J. Biochem.* 1, 80, 1967). The first step in this degradation is selective coupling of a peptide's amino-terminal amino acid with the Edman reagent, phenylisothiocyanate (PITC), a reaction catalyzed by an organic base delivered with the coupling reagent. The second step is cleavage of this derivatized amino acid from the remainder of the peptide, a reaction effected by treating the peptide with a strong organic acid. Each repeated coupling/cleavage cycle occurs at the newly-formed amino-terminal amino acid left by the previous cycle. Thus, repetitive cycles provide sequential separation of the amino acids which form the primary structure of the peptide.

The sequencing process is not completed by the Edman degradation alone. Once the amino acids are removed from the sample, they must be analyzed to determine their identity. Since the cleaved amino acid derivative, the anilinothiazolinone (ATZ), is not generally suitable for analysis, it is converted to the more stable phenylthiohydantoin (PTH) form before analysis is attempted. In modern sequencers (Wittmann-Liebold et al. *Anal. Biochem* 75, 621, 1976; Hewick et al. *J. Biol. Chem.* 256, 7990, 1981), this conversion is accomplished automatically in a reaction vessel separate from that in which the Edman degradation occurs. The ATZ produced at each degradation cycle is extracted from the peptide with an organic solvent, transferred to the reaction vessel and treated with an aqueous solution of a strong organic acid to effect conversion to the PTH. The PTHs produced from each degradation cycle may be transferred to fraction collector vials until several are manually collected and prepared for analysis. Alternatively, the PTHs may be transferred directly and automatically from the sequencer conversion vessel to an on-line analysis system (Machleidt, W. and Hoffner, H., in *Methods in Peptide and Protein Sequence Analysis*, pp 35–47, Birr, ed., Elsevier (1980); Wittman-Liebold and Ashman, in *Modern Methods in Protein Chemistry*, pp 303–327, Tschesche, ed., de Gruyter (1985); Rodriguez, *J. Chromatography* 350, pp 217–225, (1985)).

Although a variety of analytical procedures have been used to identify the amino acids released during the Edman degradation, only high performance liquid chromatography (HPLC) is currently in widespread use. In fact, HPLC on reverse phase, silica-based packings has revolutionized peptide sequencing. It provides rapid, sensitive and quantitative analysis of PTH amino acides and is presently the only technique used for PTH analysis that can reliably resolve all of the PTH amino acids in a single chromatograph run. Moreover, because it provides quantitative data at the picomole level, HPLC is the only analytical method suitable for microsequencing by automated Edman sequencers at the present time.

Ideally, each chromatogram would provide a simple qualitative answer, i.e., the presence of one and only one PTH. As a practical matter, this is never the case; each chromatogram contains some amount of all PTHs, and a quantitative evaluation of the relative amounts must be made in order to make the sequence assignment. Several factors give rise to this problem. First, protein or peptide samples are unlikely to be pure. They always contain some level of other peptides or free amino acids that give rise to PTH signals during sequencing. Second, repeated exposure of the sample to the cleavage acid during the Edman chemistry causes splitting of the peptide chain at sites other than the amino terminus. The newly exposed amino terminii resulting from these internal splits then produce PTHs after subsequent coupling/cleavage cycles. As a result, each type of amino acid generally exhibits a background PTH level that slowly changes during the sequence run, typically rising through the early cycles and falling slowly during later ones. The absolute levels of the background are dependent on the amino acid composition of the peptide, the Edman chemistry conditions, and the molecular weight of the peptide. Third, removal of an amino terminal amino acid at any given cycle of the Edman chemistry is incomplete. Therefore, some of the amino acid that should have been released at that cycle will remain for the next coupling/cleavage cycle and be released then. This carryover, or lag, is cumulative; multiple failures on any single peptide molecule will result in a steadily increasing proportion of a population of molecules being out of phase with the expected release order. Fourth, the recovery of the expected PTH is slowly decreased during the run by side reactions that block the amino terminal group, physical loss of peptide from the reaction chamber, internal chain cleavage, and lag. This decrease in signal, measured as the repetitive cycle yield, occurs simultaneously with the increase in noise (due to the factors described above), making correct amino acid assignment ever more difficult as a sequencing run proceeds further into the peptide. Fifth, the relative recoveries of the PTH amino acids from the Edman chemistry vary. Some are recovered almost quantitatively, while others are largely destroyed before analysis.

Despite these problems, rigorous interpretation of the chromatographic data from a sequencer run in terms of an amino acid sequence has not received as much attention as the chemistry and instrumentation employed. Many, perhaps most, sequences are assigned by visual inspection of chromatograms to distinguish the specific increase in the PTH level of one amino acid at each cycle from the general background level of all the PTHs. This method is remarkably simple and effective, but it does have limitations. It relies on the scientist's pattern recognition abilities, skills that are largely subjective and limited to direct comparison of only two or three chromatograms at any one time.

Because of these limitations, an increasing number of scientists are using HPLC peak integration systems to translate the analog signals displayed on chart recorder traces into a simpler set of digital numbers. This allows the recovery of each PTH at each cycle to be plotted on a graph that more clearly shows the specific sequence signals superimposed on the background noise levels. Smithies et al., see Biochemistry, 10, 4912, (1971), were the first to define the mathematics of the sequencing chemistry in terms of initial yield, repetitive yield, lag, and amino acid background and to attempt quantitative sequence analysis based on peak integration. Machleidt, W. and Hofner, F., (1981), in *High Performance Chromatography in Protein & Peptide Chemistry*, pp 245-258, Walter de Gruyter, Berlin, have also contributed to this process, but all of the previous methods have relied on the subjective grading of the integrated peak values by the skilled scientist performing the sequence analysis. The scientist's subjective interpretation of the relative importance of an elevated level of one amino acid versus another at any given cycle has still been required for the final sequence assignment.

In addition to all of the above difficulties having to do with background PTH levels, cumulative lag, side reactions, etc., other important problems are associated with the chromatographic data itself. While most chromatography software available commercially works well with ideal data (i.e. with large, well-resolved peaks), they perform much less well with real world data. With respect to analyses of amino acid derivatives, such non-ideal data is the rule rather than the exception. Generally, amino acid analyses involve separations of a complex mixture of closely-related compounds, frequently at such minute levels that conventional software fails to provide satisfactory results unless the user provides extensive manual input to correct the deficiencies in the software.

In concept, HPLC data systems collect chromatographic data by periodically sampling the output of the HPLC detector and then process this digitized data. Quantitation is then performed using peak integration, which requires locating the start and end points of a peak, measuring the total signal between these points, and subtracting any background signal. The center position of the peak (i.e., its retention time) is also required to identify it as a known component based on retention times obtained with standards. Then, the measured area of a sample peak can be converted to a molar amount based on the measured area of the corresponding standard. This conceptually simply process is, however, complicated by several factors, e.g. such as chromatographic noise, peak overlap, and retention time drift.

The chromatographic noise arises from the detector electronics, incomplete mixing of solvents during gradient chromatography, passage of gas bubbles or particulates through the detector, refractive index changes due to solvent or temperature gradients, and the elution of solvent or column contaminants. At the present time, conventional HPLC systems deal rather imperfectly with both low and high frequency chromatographic noise. Most high frequency filtering relies on hardware implementations and is performed by analog filters built into the detector circuitry, and some HPLC systems attempt to remove low frequency noise (often called baseline drift) by using point-by-point subtraction of a blank chromatogram from the sample data. This latter technique is particularly troublesome since it introduces additional high frequency noise and because baselines can vary substantially from run to run. New and less cumbersome techniques are clearly needed for the reduction of chromatographic noise.

Peak overlap, i.e., incompletely resolved peaks are particularly troublesome to HPLC software. Small peaks that partially overlap larger ones may be missed by the slope threshold routines and hence incorrect chromatogram quantitation can result. When fused peaks are detected, several methods for splitting the total area can be used, which are distinguished by the method by which the baseline under the peak components is set. These include (i) a linear extrapolation between the beginning and end points of the multiplet with a linear drop from the valley batween the peaks to the baseline, (ii) a similar extrapolation to set the baseline of a major component with a tangent skim to set the baseline of a minor component, and (iii) linear extrapolations between the beginning and end points of each separate component. The method which gives the most accurate peak measurements depends on both the degree of resolution between the peaks and the relative peak heights. It is, therefore, highly sample dependent and frequently requires user adjustment from one sample to another in a set of chromatograms in which these parameters are not constant.

Retention time drift is also a particular problem since once peaks have been located and quantitated, they must be identified by matching their retention times to those of known standards. This is simple if the variation in retention times from run-to-run is always less than the time separation between closely eluting peaks within a run. Typically, software routines are set to search an elution time "window" centered on the standard elution time to find the best match of an unknown peak with the standard. With complex separations that produce closely spaced peaks, this does not always work since elution time drift may move one peak outside its window and place another in it. This problem can be minimized, however, by using easily identified reference peaks to measure the drift and empirically correct the search windows for other peaks. The reference peaks must be well-separated from any neighboring peaks and present in all chromatograms so their search windows can be large enough to allow for the maximum observable drift.

What is needed is a method that resolves most of these problems with chromatogram quantitation and which can be used by a computer to evaluate the set of HPLC data derived from a peptide sequencing run to automatically arrive at an unequivocal call of the sequences, without having to rely on the subjective interpretations of especially skilled individuals.

SUMMARY OF THE INVENTION

In accordance with preferred embodiments of the invention, an apparatus and a process are disclosed for unequivocally determining the sequence of a peptide. According to the method, the peptide to be sequenced is degraded cyclicly, arriving at a set of amino acid residues for each cycle. The amount of each amino acid residue is quantitatively measured in each set, then a background level is fit to each cycle to obtain a background fit. A measure of dispersion is then calculated for the background fit, and the measured amounts of amino acid residues in each cycle are normalized relative to the background fit. The largest normalized background-corrected residue amount in each cycle then provides a sequence assignment that can be used for further correction steps if desired. These further steps include correcting at least some of the normalized background-corrected residue amounts for lag into subsequent cycles, thereby obtaining lag-corrected background-corrected residue amounts for each cycle. These lag-corrected background-corrected residue amounts can then be used to correct the original measurements of the amino acid residues in each cycle for differences in injection quantity between cycles, thereby obtaining an injection-corrected residue amount for each cycle. The previous steps of background correction and lag correction are then performed on the injection-corrected residue amounts, and the largest such amount is determined for each cycle to arrive at a definitive sequence assignment for the peptide.

In the preferred mode, the initial step of measuring the amount of amino acid residue in each cycle usually involves several sub-steps. In particular, as the peptide is degraded cyclicly using an Edman degradation scheme, a chromatographic analysis is performed for each cycle, the raw data providing a determination of the amount of amino acid of each kind found at each cycle. In one embodiment, the results of that determination are then subjected to low pass filtering and high pass filtering to remove measurement noise resulting in a baseline-corrected chromatogram. This baseline-corrected chromatogram is then used in the background-correction process.

In another embodiment, the baseline-corrected chromatogram is obtained using a linear, translation-invariant, discrete filter function $aN^\alpha$, where N is a measure of the filter width and $\alpha$ determines the resolution enhancement characteristics of the filter function. In that embodiment, the chromatogram is first smoothed with the filter function to suppress high frequency noise thereby providing a second (filtered) chromatogram with a first filtered baseline. Then the second chromatogram is filtered with the parameter $\alpha$ set for peak resolution enhancement to obtain a third chromatogram having substantially the same filtered baseline. The second chromatogram is then subtracted from the third chromatogram, yielding a fourth chromatogram which has the baseline removed. The fourth (baseline-corrected) chromatogram can then be operated on to yield quantitative values of the PTH's to be used in the background-correction process.

The apparatus for carrying out the method of the invention includes a degradation element for degrading the peptide cyclicly to obtain the set of amino acid residues for each cycle, a quantitation element for measuring the amount of each amino acid residue in each set, and a computer element for controlling the degradation element and the quantitation element. The computer element is also for fitting a background level to each cycle, for calculating a measure of dispersion for the background fit relative to the measured amounts of residues in each set, for normalizing the measured amount of each residue relative to the dispersion to obtain normalized background-corrected residue amounts for each cycle, and for identifying the largest normalized background-corrected residue amount in each cycle.

BRIEF DESCRIPTION OF THE DRAWINGS

FIGS. 2C and 2D show the steps of the method for quantitating HPLC peaks according to a second embodiment of the invention.

FIG. 3A(1) shows a raw chromatogram of a standard PTH mix.

FIG. 3A(2) shows a baseline-corrected chromatogram performed according to a method of the invention for the standard mix having the raw chromatogram of FIG. 3A(1).

FIG. 3B(1) shows two components of a house filter according to the method of the invention.

FIG. 3B(2) shows the house filter formed by adding the two components of FIG. 3B(1).

FIGS. 3C—3I show the results of applying a filtering method according to the invention to the standard PTH mix of FIG. 3A(1).

FIGS. 3C', 3D', and 3I' show the results illustrated in FIGS. 3C, 3D, and 3I, but on an expanded scale.

FIGS. 5A–5D are a flow chart of the method used to correct for lag of each amino acid residue into subsequent cycles.

FIG. 6 is a flow chart illustrating the method used to correct for differences in injection amounts for different cycles.

FIG. 7A shows the injection-corrected raw data. FIG. 7B shows the results of the method after performing background correction on the injection-corrected raw data of FIGS. 7A. FIG. 7C shows the results of performing a lag correction after performing the background correction illustrated in FIG. 7B.

FIG. 8A shows the raw data (injection-corrected). FIG. 8B shows the results of the method after performing background correction on the injection-corrected raw data of FIG. 8A. FIG. 8C shows the results of performing a lag correction after performing the background correction illustrated in FIG. 8B.

DETAILED DESCRIPTION OF THE PREFERRED EMBODIMENTS

Figure 1A:
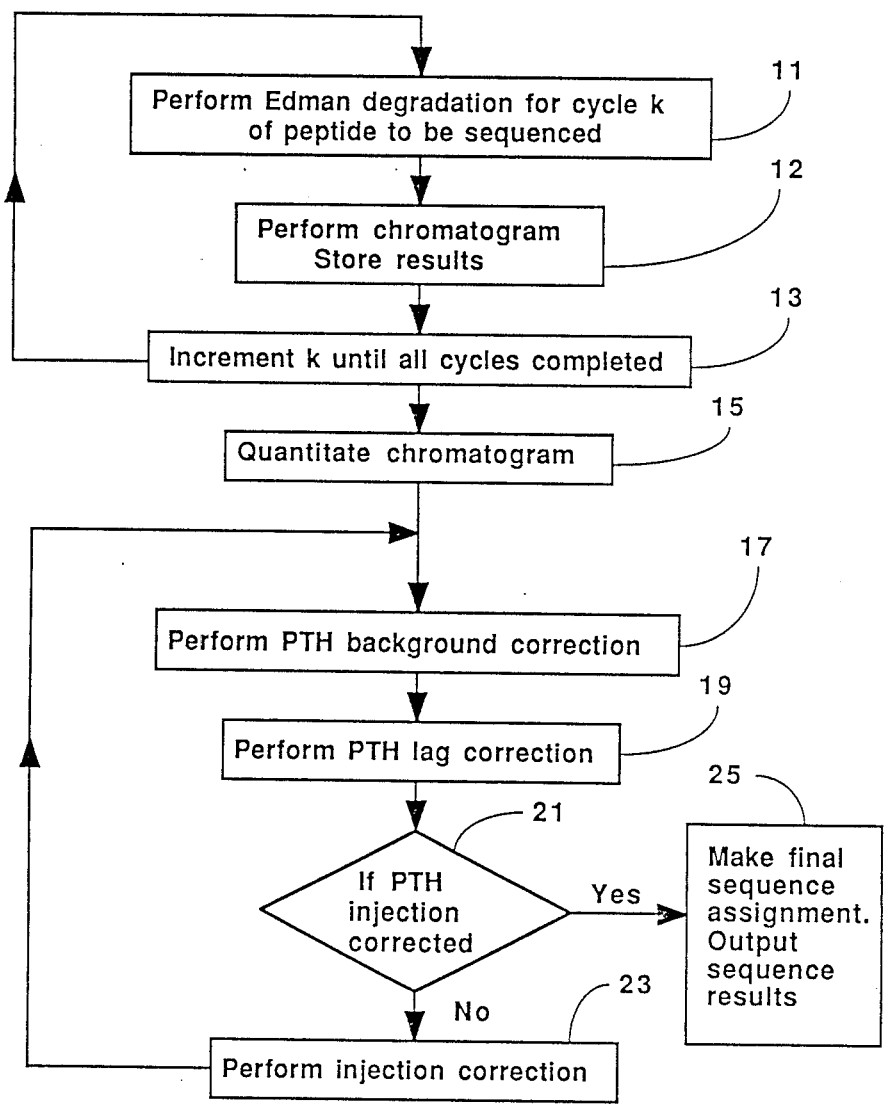
FIG. 1A is a flow chart of a method in accordance with the preferred embodiment of the invention.

In accordance with preferred embodiments of the invention, illustrated in FIG. 1A is a flow chart showing a general method for determining the sequence of a peptide chain. In this method, the various steps comprise both direct physical measurements and computational elements based on those measurements. Since the method can be implemented entirely automatically, with the various physical measurements being performed by instruments under computer control, the language of computer programming lends itself to a description of the invention. Hence, to be relatively consistent with that language, hereinafter each step of the method will be referred to either as a "program element" or as a "subroutine", rather than as a "step" as the case may be. The term "subroutine" will be used to describe computer subprograms of the method which are substantially complete in themselves in performing a particular computational task. The term "program element" will be used loosely to describe one or more individual steps of a particular computer program or an identifiable set of steps which make up a complete task, be it a physical measurement or a computation, but which is not in itself necessarily a single subroutine.

Figure 1B:
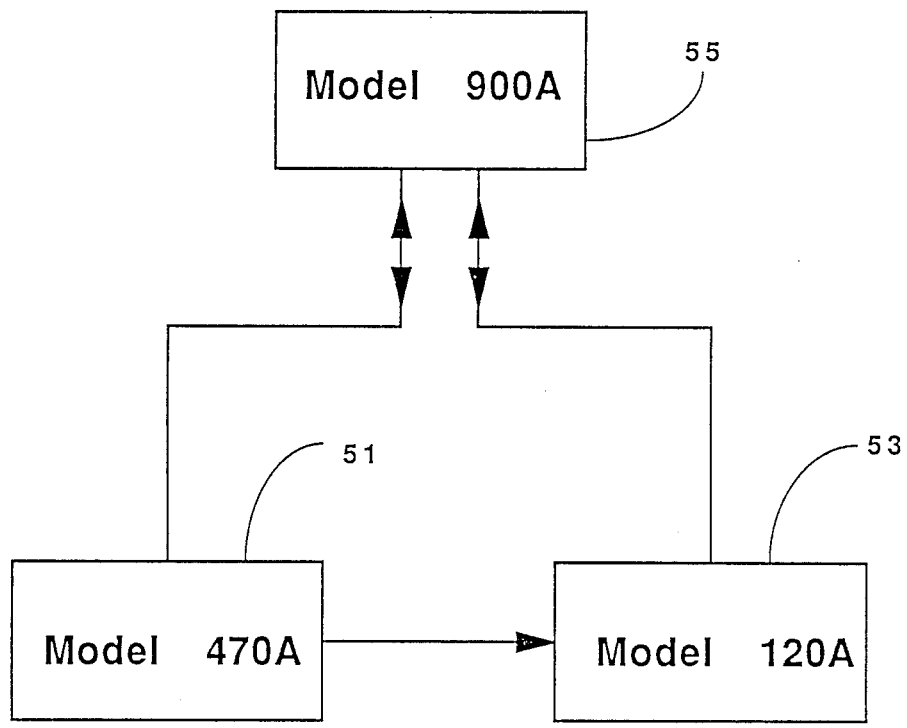
FIG. 1B is a diagram of the apparatus of the invention.

The physical apparatus used to implement the method is illustrated in FIG. 1B and includes a sequencing system 51 for performing sequential Edman degradations, a PTH analyzer 53 which provides on-line PTH analysis using HPLC for the samples provided by the sequencing system, and a computer module 55, which acts both as a system controller and as the analysis device for the entire system for performing the various steps used to arrive at a quantitative call for the peptide sequence. As a system controller the computer module is responsible for timing and incrementing degradation events in the sequencing system, for transferring materials to the PTH analyzer, and for controlling the PTH identification process. As an analysis device, the computer module stores the data provided by the PTH analyzer, and performs the various steps described below to eliminate noise and systematic errors from the raw PTH values measured by the PTH analyzer in order to identify the largest relative PTH value in each cycle and thereby determine the peptide sequence. In the preferred mode, the computer module 55 is an Applied Biosystems Model 900A which includes a 16/8-bit microprocessor such as the Intel 8088, a separate math co-processor, 640 kilobytes of RAM, a 10-megabyte hard disk drive, a 360-kilobyte floppy disk drive, a touchscreen CRT, and a graphics printer. Also in the preferred mode, the sequencing system 51 is an Applied Biosystems Model 470A Sequencer and the PTH analyzer 53 is an applied Biosystems Model 120A.

To begin the method, the peptide sequence to be analyzed is first subjected to an automated Edman degradation cycle at program element 11, and HPLC is performed by the PTH Analyzer at program element 12 to identify the amino acid released. For that Edman cycle, the chromatogram is collected in digitized form by the computer module, and the values of the chromatogram are stored. At program element 13, the cycle number of the degradation just performed is incremented and the process is repeated, until the degradation and chromatograms are performed for all amino acids in the peptide chain, each amino acid corresponding to one degradation cycle. At subroutine 15, each chromatogram is identified and quantitated to determine the amount of each PTH for each cycle of the degradation.

Once the identification and quantitation is complete, a first pass at PTH background noise removal is performed in subroutine 17, and a preliminary sequence assignment is made. This is followed by a lag correction in subroutine 19. The lag correction is made to account for the fact that during the Edman degradation, the removal of the amino acid residue is only partial, so that a fraction of the amino acid appears at subsequent cycles.

Once the lag correction is performed, the remaining PTH values for each cycle can be used to correct for any variation in the amount of sample injected into the PTH analyzer at each cycle, if desired. This injection correction is performed in subroutine 23. Upon completion of the injection correction, the background and lag corrections are repeated and the amino acid assignments are made in program element 25 based on the largest corrected PTH signal at each cycle. The second pass through the background correction and the PTH lag correction can be accomplished in any number of ways. The approach shown in FIG. 1A is to set up a program counter to test at program element 21 to determine if the PTH injection correction has been made, and, if it has been made, to go ahead with sequence selection at program element 25. If it has not been made, the background and lag corrections are repeated. Any of several equivalent program counters can be used to keep track or whether the PTH injection correction has been made. For example, for program element 21, one could use a counter for the background correction subroutine 17, for the lag correction subroutine 19, or for the injection correction subroutine 23 itself. Another less practical, but equivalent approach which is not illustrated is to avoid using a program counter and a program loop at all, and to simply repeat the background correction subroutine 17 and the PTH lag correction subroutine 19 after the injection correction subroutine 23, before making the sequence selection.

Each of the various subroutines and program elements will now be discussed in more detail by referring to the various figures enumerated above in the Brief Description of the Drawings. In addition, further specific details for program elements 17-25 can be found in Appendix I which provides a specific example of a preferred source code for carrying out those program elements.

Figure 2A:
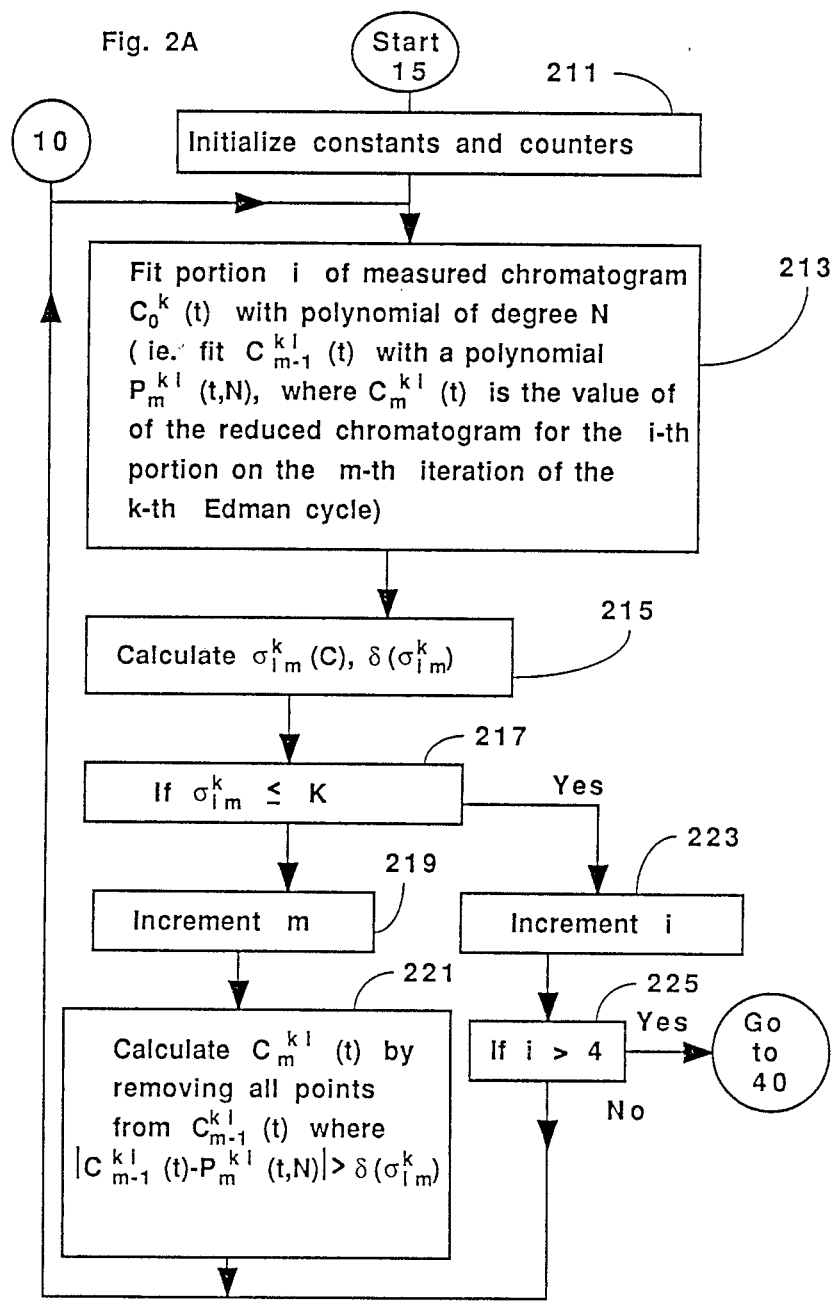
FIGS. 2A and 2B show the steps of the method for quantitating HPLC peaks.
Figure 2B:
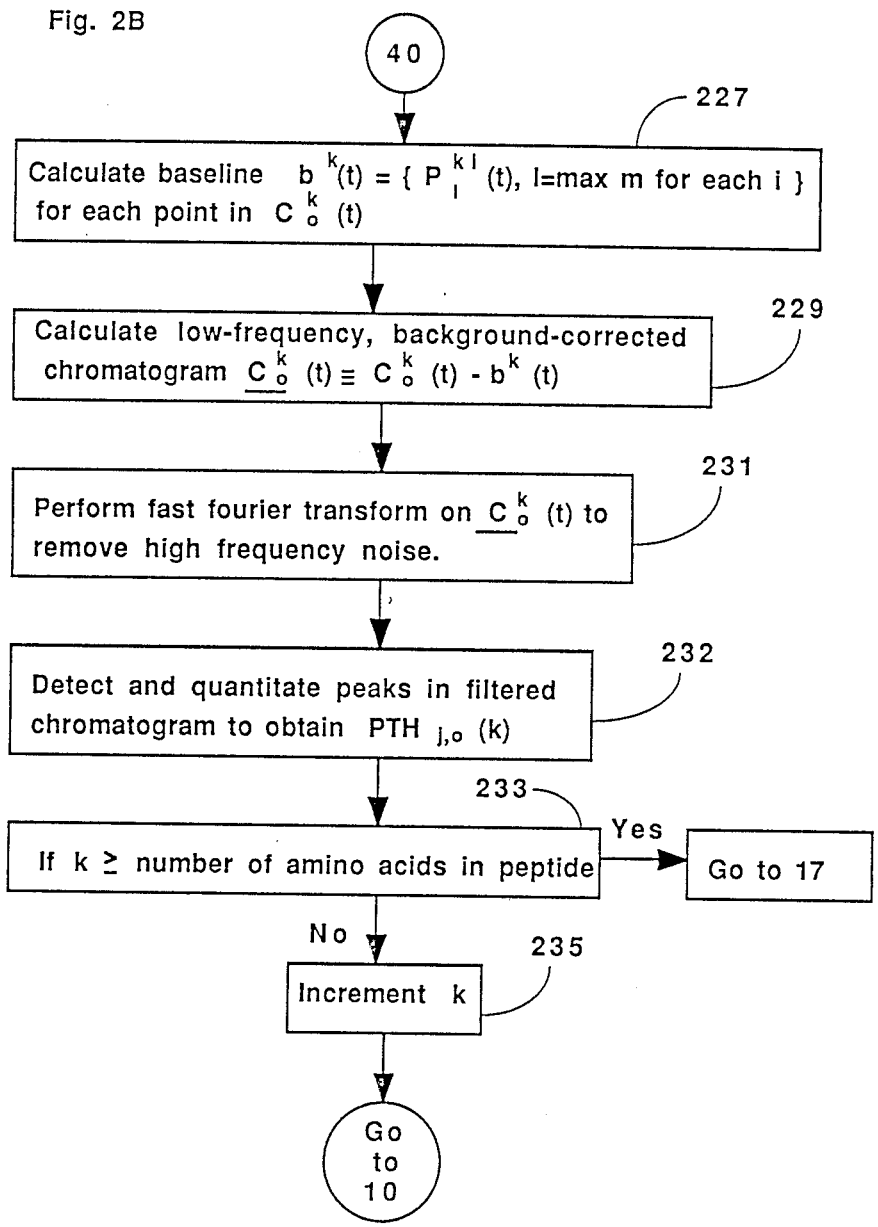
Figure 2D:
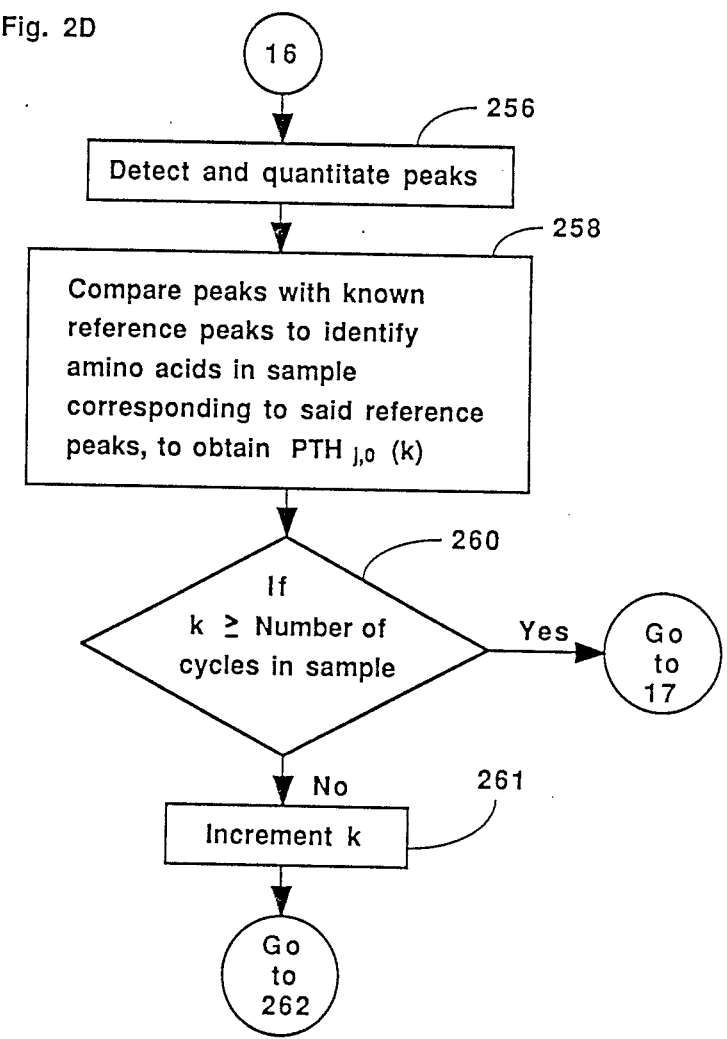

Quantitation of PTH Yields:

Shown in FIGS. 2A and 2B, and in FIGS. 2C and 2D are flow charts providing details of a first embodiment and a second embodiment, respectively, of subroutine 15 for identifying and quantitating the HPLC peaks. Although standard HPLC integration routines can be used successfully for identifying and quantitating HPLC peaks when the amount of peptide being sequenced is relatively large (i.e. when the HPLC signal-to-noise levels are high), modern Edman sequencers can work with sample levels that severely test these routines. HPLC peaks can be obscured by both high frequency noise (typically from the UV absorbance detectors used to monitor PTH elution from the analytical columns) and low frequency noise (typically from both temperature-induced detector drift and absorbance/refractive index changes that occur during gradient HPLC elution). Hence, peak analysis should be preceded by chromatogram filtering to minimize the effects of both types of noise.

According to the first embodiment, after each chromatogram is collected in digitized form by the computer module 55, low frequency noise is filtered from it by an adaptation of the method described by Goehner, *Anal. Chem* 50. 1223 (1978). The entire chromatogram is first piecewise fitted to a polynomial curve of degree N. Then all points that are more than selected amounts (in standard deviation units) above or below the calculated curve are rejected, and a new fit is made using the remaining points. This procedure continues until the standard deviation between actual and calculated points reaches a set minimum level (i.e. the fitted curve has converged on the baseline of the chromatogram). The polynomial coefficients of the calculated curve are then used to calculate a baseline point for each point in the original chromatogram; the difference between the two sets of values represents the baseline-corrected chromatogram.

In practice, the number of original chromatogram points and the number of baseline slope changes (which defines the degree N of the polynomial used for the fit) generally exceeds the practical computing power of microcomputers. Thus, the routine is performed sequentially on overlapping segments of the chromatogram, with each round of the fit routine used to establish the background for a portion of the total chromatogram. Typically, the first 3/9 of the chromatogram points are fit first and used to set the first 5/18 of the baseline points. Then, 3/9 of the points starting at the 2/9 position from the front end of the chromatogram are fit and used to set the next 4/18 of the baseline points. Next, 3/9 of the points starting at the 4/9 position from the chromatogram front are fit and used to set the next 4/18 of the baseline points. Finally, the last 3/9 of the points are fit and used to set the last 5/18 of the baseline points. Since, where possible, only the middle section of each calculated curve is used, discontinuities in the baseline-corrected chromatogram where the individual fitted curves meet are minimal.

This baseline calculation process of the first embodiment is illustrated in detail in FIGS. 2A and 2B, which begins at program element 211, where all program counters and constants are initialized. In particular, at least three counters are used, say "i", "k", and "m". A counter i is used to index the particular portion of the chromatogram being fit, a counter k is required to identify the particular Edman cycle being fit, and a counter m is used to keep track of the iteration number of the fit. Similarly, it is necessary to pick the degree N of the polynomial to be used to fit the chromatograms, and to decide on the closeness of fit desired for the background calculation. As a practical matter, N is generally chosen to be about 6, and the closeness of fit is generally chosen to be when the standard deviation of the fitted curve to the background points is less than or equal to a constant K (typically twice the high frequency noise level of the detector output). Once the constants and counters are initialized, the method continues at program element 213 fitting the i-th portion of a measured chromatogram C(t) corresponding the the k-th Edman cycle. On the first pass, i=k=1 and a polynomial $P_1^{ki}(t,N)$ (i.e. $P_1^{11}(t,N)$ on the first iteration) of degree N is used to fit $C_o^k(t)$ typically using a least squares approach. At program element 215, the standard deviation $\sigma_{i1}^k(C)$ is calculated for the fit, and a function $\delta(\sigma_{i1}^k)$ is defined which corresponds to the maximum point-by-point deviation allowed. Here $\delta(\sigma_{i1}^k)$ is chosen to be $0.1\sigma_{i1}^k$. The magnitude of the standard deviation $\sigma_{i1}^k$ is tested at program element 217 to see if it is less than or equal to the chosen constant K. If it is less than K, the counter i is incremented at program element 223. The counter i is then tested to see if it is greater than 4 at program element 225. If it is not greater than 4, the next portion of the chromatogram of the k-th cycle is fit in program element 213, etc.

If at program element 217, the magnitude of the standard deviation is larger than K, the program increments m, the iteration counter, at program element 219. Then at program element 221, a new function $C_m^{ki}(t)$ (in this first pass $C_1^{11}(t)$) is calculated, hereinafter called the reduced chromatogram, by removing all points from the chromatogram for which $|C_{m-1}^{ki}(t) - P_m^{ki}(t,N)| > \delta(\sigma_{im}^k)$. This reduced chromatogram has the same values as the originally measured chromatogram, but its domain is reduced. Then beginning again at program element 213, this reduced chromatogram is fit with a new polynomial, and so forth through the program elements 213 through 225 until the reduced chromatograms for all portions of the chromatogram of the k-th cycle are fit according to the fit criterion established.

Once the polynomial fits are completed for each portion i of the chromatogram of the k-th cycle, the baseline of the k-th cycle is calculated at program element 227, the values of the fitting polynomials $P_l^{ki}(t)$ being used to calculate the baseline points $b^k(t)$ for each point in the measured chromatogram $C_o^k(t)$, where l=max.m (the last criterion) for the i-th portion. A background-corrected chromatogram $\underline{C}_o^k(t)$ is then calculated at program element 229 by subtracting the calculated baseline points $b^k(t)$ from the measured chromatogram $C_o^k(t)$, which corresponds to having removed the low-frequency background components from the chromatogram. Those skilled in the art will understand that the above approach for filtering out low frequency noise in this embodiment is but one of many equivalent approaches. For example, any complete set of functions could be used for the fitting function rather than a polynomial.

Once these low frequency components have been stripped from the chromatogram, high frequency noise is removed at program element 231 using a standard fast Fourier transform filter as is known in the art. Then peaks in the filtered chromatogram are detected and quantitated at program element 232. Several approaches can be used. For example, time windows set on the basis of the observed elution times of each PTH in a standard mixture can be used to search the filtered chromatogram $\underline{C}(t)$ to determine the amount of each PTH represented in the chromatogram. The amounts can be determined by standard first derivative peak finding and peak integration procedures known in the art, or by fitting the points in each window to a Gaussian curve and calculating the area under the curve (see Kent et al, in *Biotechniques*, 5, pp 314–321 (1978) or, more simply, the maximum point value in each window can be taken as the peak height for the corresponding PTH. The latter approach is faster but requires good separation of the PTHs by the HPLC system.

Performing the peak location and quantitation yields a transformed chromatogram PTH(k) for each cycle k, which corresponds to the amount of PTH of amino acid of kind j in the cycle k. The program then tests for the cycle number at program element 233, and if all the cycles required to degrade the peptide in the sample are not completed, the cycle number k is incremented at program element 235 and the background-correction process begins again at program element 213 for a new cycle.

FIGS. 3A(1) and 3A(2) show the results of using the technique illustrated in FIGS. 2A and 2B for this first embodiment to remove low frequency noise. In FIG. 3A(1), a raw chromatogram $C_o^k(t)$ is shown with its many peaks as a function of time for a 5-pmol PTH standard. The fitted baseline $b^k(t)$ is shown as a relatively smooth dark solid line at the bottom of the curve $C_o^k(t)$. FIG. 3B(2) shows $\underline{C}_o^k(t)$, the baseline-corrected chromatogram of the sample as determined according to the method of the invention at program element 229.

As an alternative preferred embodiment, another approach can be used to quantitate the chromatogram which utilizes the techniques of digital filtering. Although, digital filtering is generally well known for smoothing and resolution emhancement of noisy spectra, and has been applied specifically to the physical measurments obtained by ENDOR (electron nuclear double resonance), it has not apparently been applied to chromatogram quantitation. (See "Variable Filter for Digital Smoothing and Resolution Enhancement of Noisy Spectra," by Bromba et al, *Anal. Chem.* (1984), 56, 2052–2058, and "Properties of a Variable Digital Filter for Smoothing and Resolution Enhancement", by Biermann et al, *Anal. Chem.* (1986), 58, 536–539, for a general discussion of digital filtering in noise reduction). The particular approach disclosed in these references pertains to the use of digital filtering which is a discrete, linear, translation-invariant convolution operation defined by:

$$Af(k) = \sum_{n=-N}^{N} a(n)f(k - n),$$

where A denotes the filter operator, a(n) is the filter function (kernel), f is the unfiltered spectrum, and Af the filtered spectrum. In particular, the filter function is a vertically shifted triangular filter where $$a(n) = \frac{(2\alpha + 1)}{2N + 1} - \frac{2\alpha|n|}{N(N + 1)} \text{ with } n \leq N.$$

For calculation purposes this filter function is typically separated into two parts $$a(n) = a1(n) + a2(n)$$

where $a1(n) = (N + 1 - 1|n|) \frac{2\alpha}{N(N + 1)}$, a triangular filter, and $$a2(n) = \frac{-2\alpha(N + 1) - N}{N(2N + 1)},$$

which is a rectangular filter. Hereinafter this combination will be called a "house" filter, because filter functions a1(n) and a2(n) when superposed on a graph have the appearance of a house. (See FIG. 3B(1) for an example of a triangular filter superposed on a rectangular filter, using $\alpha = 1$, $N = 9$. FIG. 3B(2) shows the resulting house filter.)

In this filter function, N is the filter width and $\alpha$ determines the degree of resolution enhancement. The basis for resolution enhancement with this filter is a reduction in line width, since the frequency response exceeds 1 for $\alpha > 1$ at low frequencies. At higher frequencies the frequency response decreases rapidly and ensures that the high frequency noise in the signal is suppressed. The properties of the filter vary, of course, depending on $\alpha$ and N. Generally, $\alpha = \frac{1}{2}$ is considered to be particularly well suited for signal to noise enhancement of unknown spectrometric functions and approximates a matched filter and also produces the best high frequency attenuation. Generally, $\alpha = 1$ is the largest value which enables frequency responses not in excess of 1, so that $\alpha = 1$ marks the boundary between smoothing filters and resolution enhancement filters. For $\alpha > 1$ the frequency response of the filter increases beyond the frequency $f = 0$, and then falls off rapidly providing general resolution enhancement. For $\alpha \gg 1$ resolution enhancement increases monotonically with $\alpha$, but so does noise amplification.

Although these digital filtering techniques could be applied directly to the chromatogram quantitation problem, the result would still contain residual low frequency noise, due to systematic errors inherent in the chromatographic technique at the time of measurement. To avoid that problem, an alternative approach is used which constitutes a second embodiment of the invention. This second approach is illustrated in the flow chart of FIGS. 2C and 2D.

As for the previous embodiment, the calculation begins by initializing constants and counters this time at program element 238. In particular the counter k corresponding to the Edman cycle number is set to 1, so that the calculation can proceed cycle by cycle. At program element 240, the filter parameter is generally set equal to a number in the interval between $\frac{1}{2}$ and 1, and in the preferred mode is set equal to 1. The filter width is set to match the chromatogram peak width N1, so that in the preferred mode, the filter function approximates a Savitzky-Golay filter, corresponding to smoothing without resolution enhancement. At program element 242, the measured chromatogram for cycle k, $C_o^k(t)$, is filtered by convolving it with the house filter kernel. This generates a smoothed chromatogram $C_{f1}^k(t)$, i.e. high frequency noise has been filtered out. Next, $\alpha$ is set equal to a number greater than 1 for resolution enhancement at program element 244, which in the preferred mode in this case has been set equal to 20. At program element 246, the smoothed chromatogram $C_{f1}^k(t)$ is convolved with the new house kernel to yield an enhanced smoothed chromatogram $C_{f2}^k(t)$. This chromatogram typically has substantially the same baseline as the smoothed chromatogram $C_{f1}(t)$ but with enhanced peaks and negative sidelobes, since the house kernel is area preserving. As a result, by subtracting the smoothed chromatogram $C_{f1}^k(t)$ from the enhanced smoothed chromatogram $C_{f2}^k(t)$ at program element 248, one obtains a chromatogram $C_{f3}^k(t)$ which preserves only the peak and sidelobe data. Furthermore, the low frequency baseline noise has been completely removed, thereby eliminating an important source of error in quantitating the chromatograms. Since the peaks are the only information of interest, the sidelobes are chopped off at program element 250, to yield a new chromatogram $C_{f4}^k(t)$. Typically this is done by removing those points below a given threshold (typically zero). At program element 252, the conditions for a new house kernel are established by setting $\alpha$ equal to $\frac{1}{2}$ and the width N equal to $N\frac{1}{2}$, to set up a matched filter for chromatogram C(t). A new chromatogram $C_{f5}^k(t)$ is then calculated using this new kernel at program element 254, which essentially just smoothes the chopped chromatogram $C_{f4}^k(t)$. At program element 256, the peaks of chromatogram $C_{f5}^k(t)$ are detected and quantitated, and at program element 258, these peaks are compared with known reference peaks for different amino acids, in order to correlate each of the peaks in the particular Edman cycle with particular amino acids, thereby obtaining the quantitated values $PTH_{j,o}(k)$. At program element 260, the cycle number K is tested to see if it is greater than or equal to the number of amino acids in the peptide. If it is, the program continues to subroutine 17. If not, the cycle number is incremented at program element 261, and the chromatogram quantitation begins again at program element 240 for the new cycle. The reference peaks used for comparison above are obtained by running chromatograms on pure samples of each amino acid and running the filtering routine for each of them to obtain the filtered reference chromatograms for comparison with the sample chromatograms.

Figure 3C:
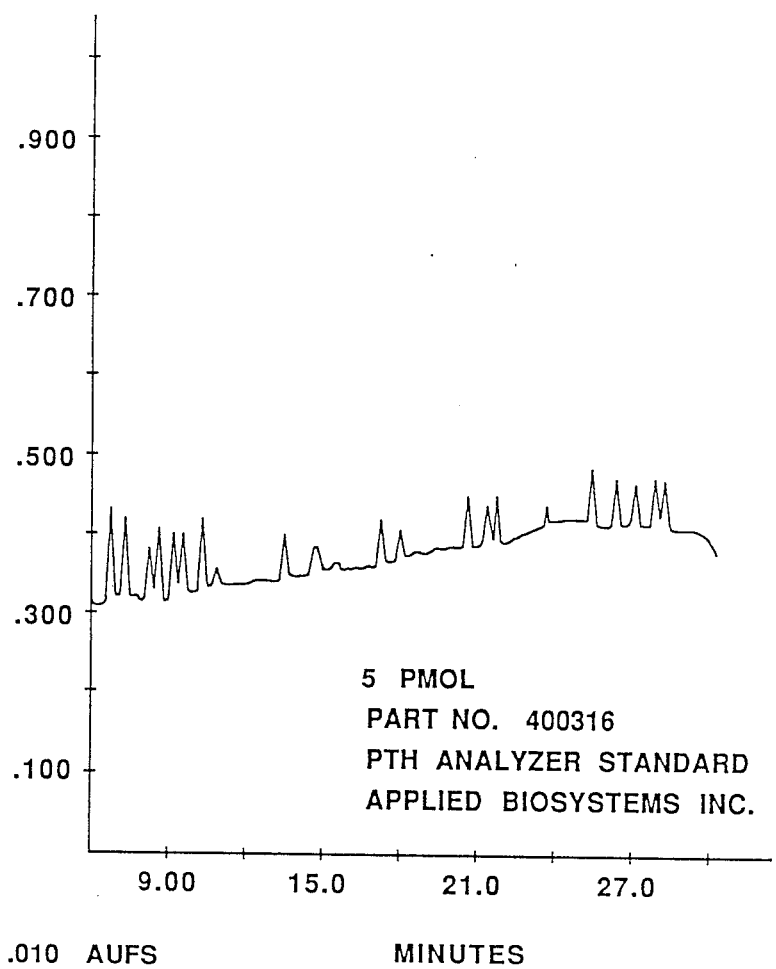
Figure 3C:
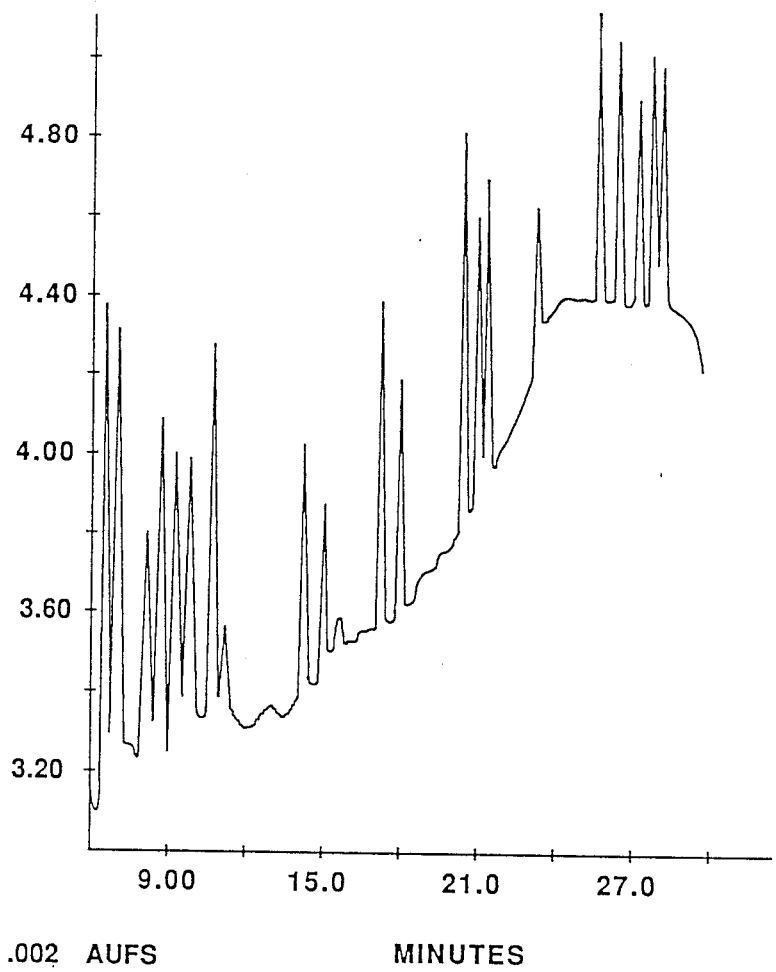
Figure 3D:
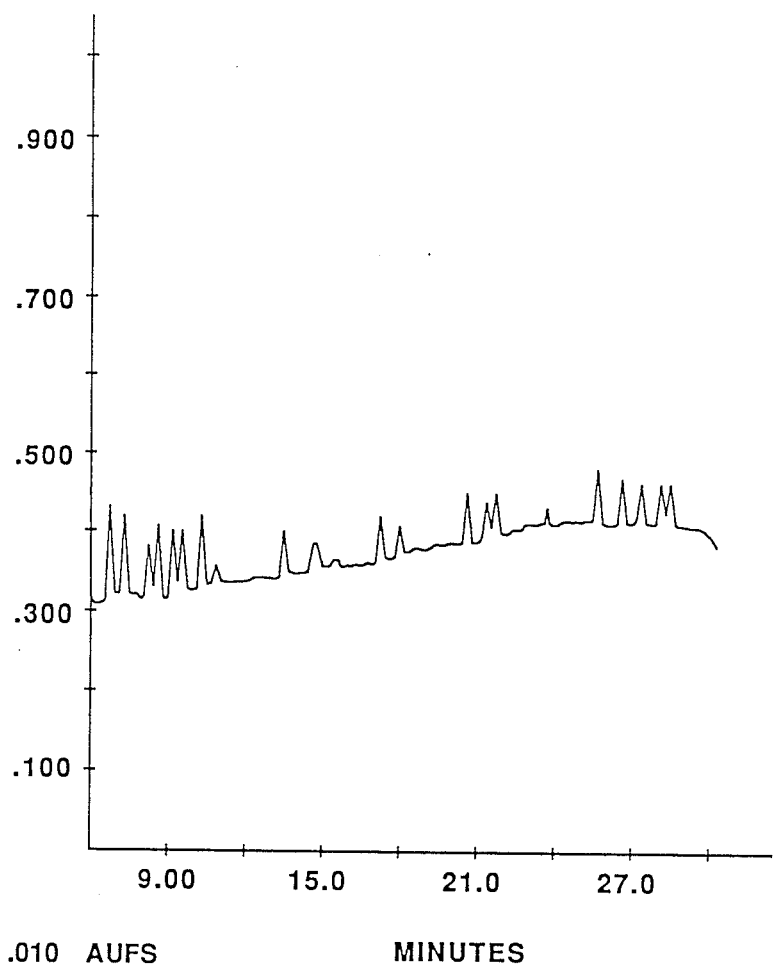
Figure 3D:
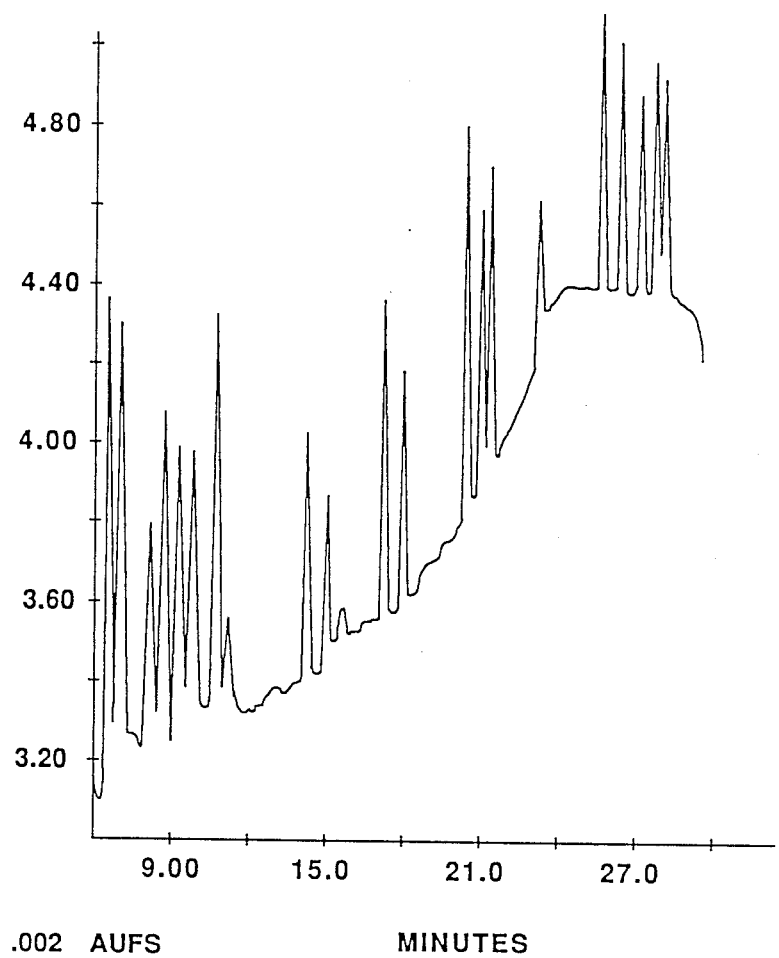
Figure 3E:
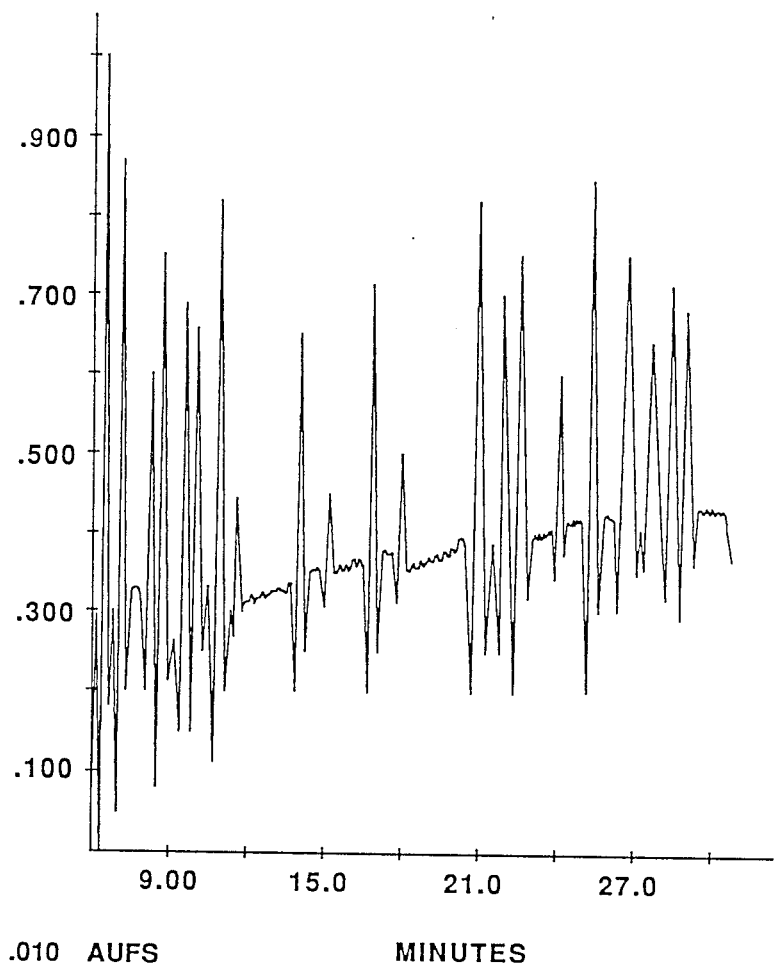
Figure 3F:
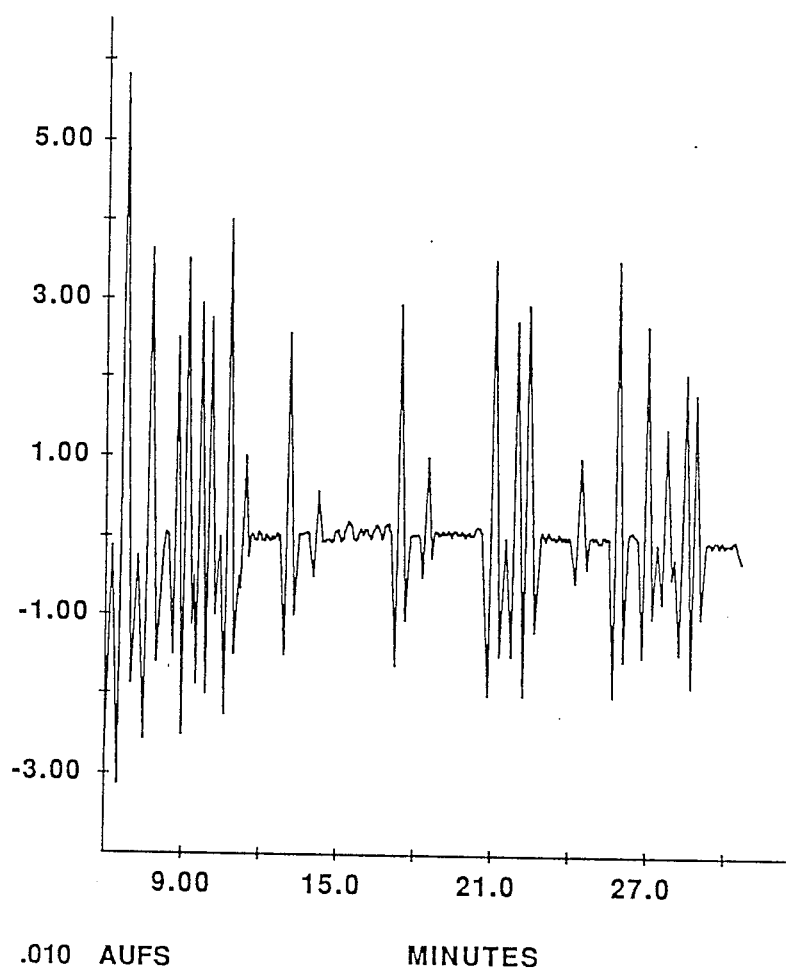
Figure 3G:
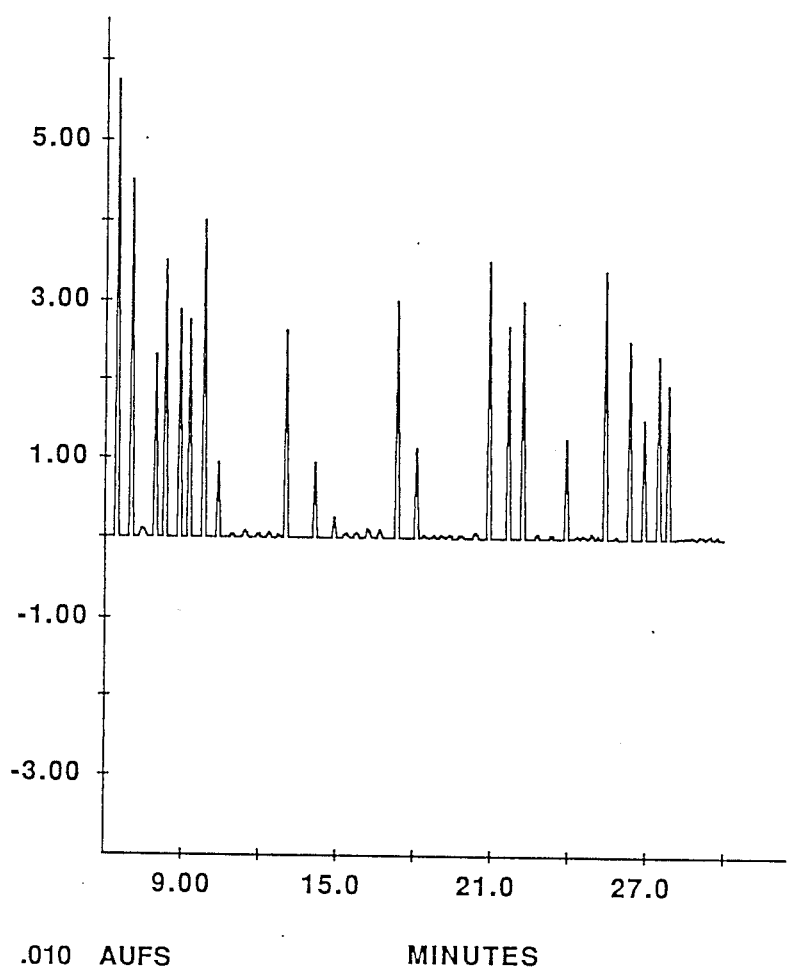
Figure 3H:
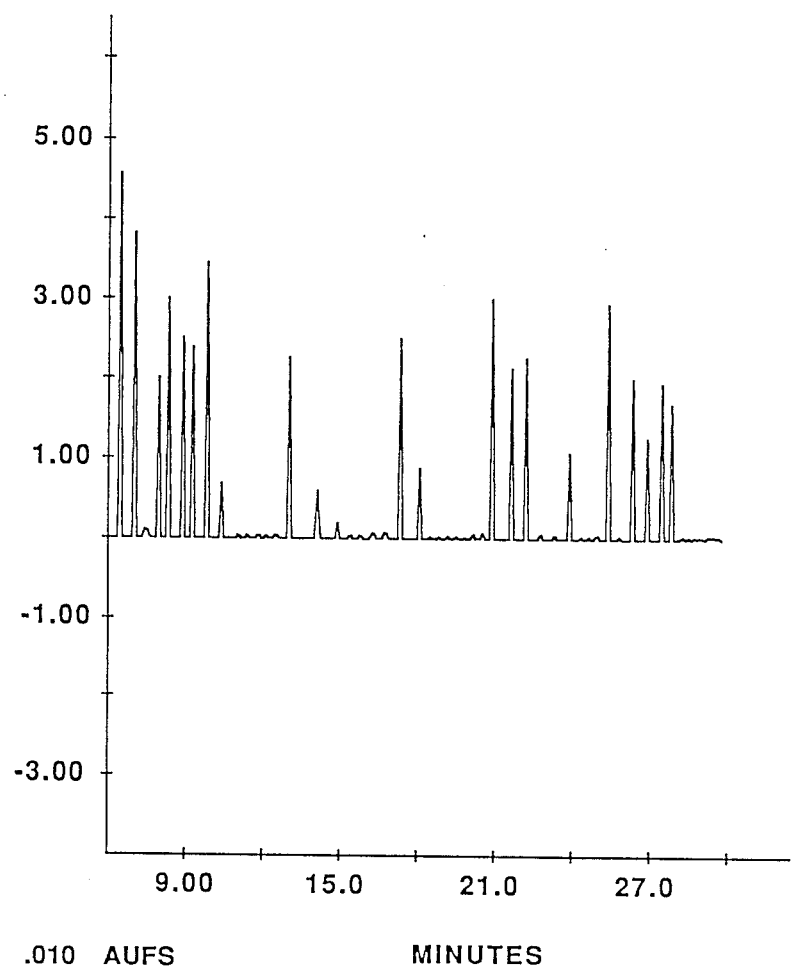
Figure 31:
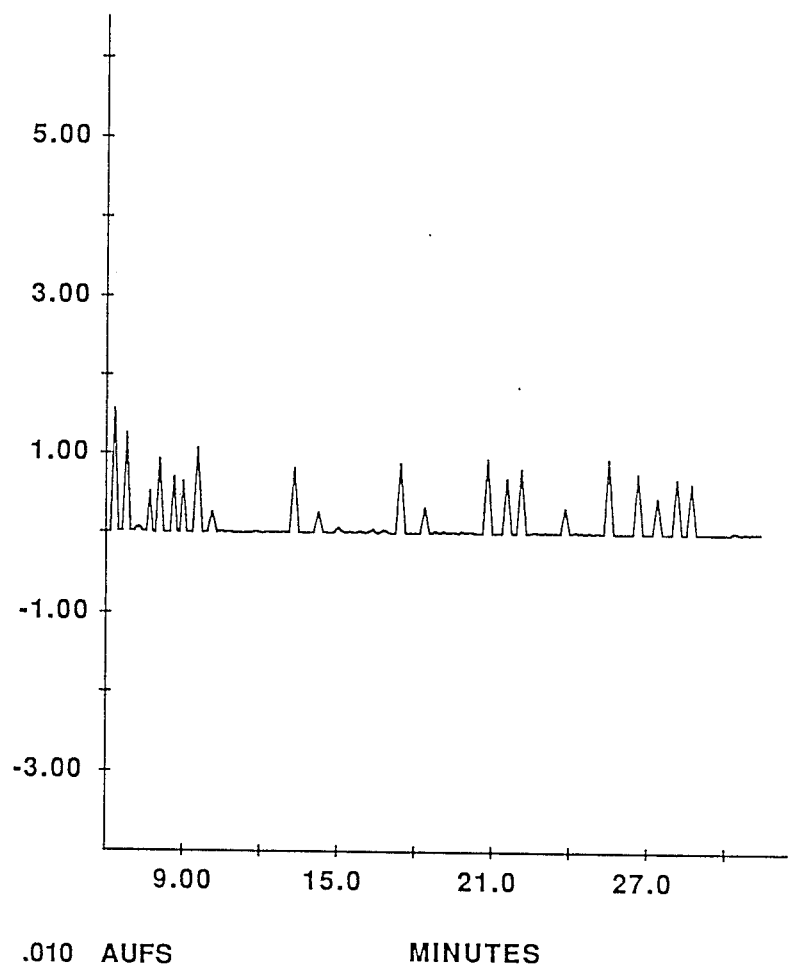
Figure 31:
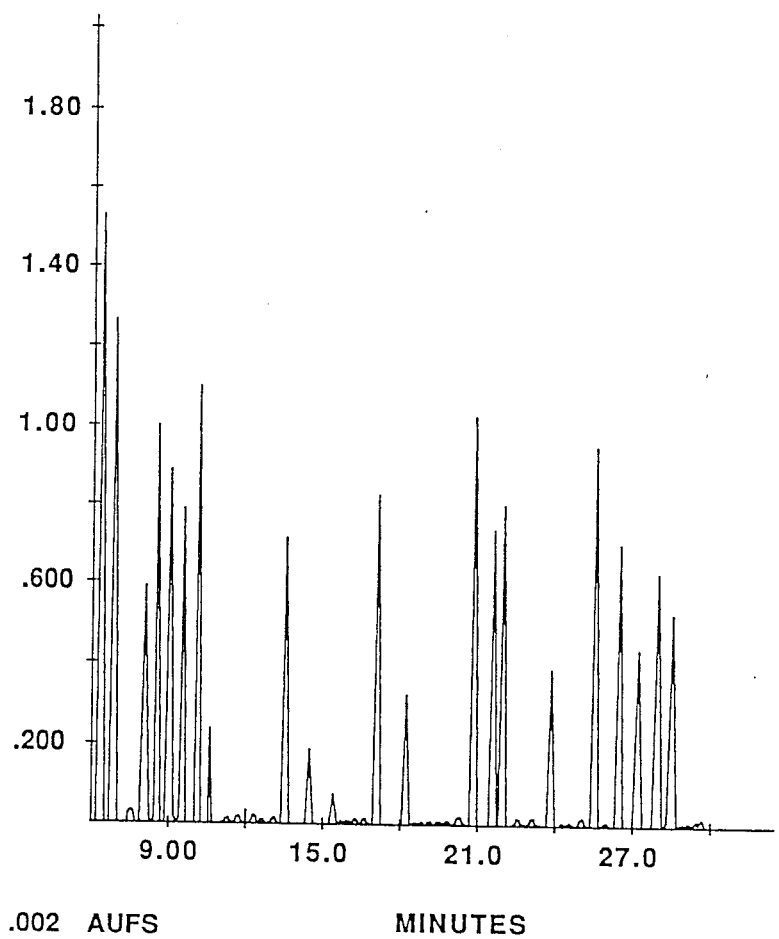

FIGS. 3C—3H show the results of applying the above smoothing and baseline subtraction method to the standard PTH mix having the raw chromatogram of FIG. 3A(1). FIG. 3C shows the raw chromatogram of FIG. 3A(1) on a reduced scale. FIG. 3D shows the results of filtering the chromatogram of FIG. 3C using a house filter with N=3, $\alpha=1$, to remove high frequency noise. FIG. 3E shows the results of applying the house filter again (i.e. applying it to the filtered chromatogram of FIG. 3D), this time with N=3, $\alpha=20$. FIG. 3F shows the results of subtracting the chromatogram of FIG. 3D from the chromatogram of FIG. 3E. FIG. 3G shows the chromatogram of FIG. 3F after chopping at zero. FIG. 3H shows the chromatogram of FIG. 3G after smoothing with the house filter with N=2, and $\alpha=\frac{1}{2}$. FIG. 3I shows the results of scaling the chromatogram of FIG. 3H (dividing by an arbitrary scale factor of 3) to obtain a peak height more comparable to the peak height of FIG. 3C in order to compare the two curves. To illustrate the sensitivity of the method, these results are shown using an expanded scale in FIGS. 3C', 3D', and 3I', which correspond to FIGS. 3C, 3D, and 3I, respectively.

Figure 3J:
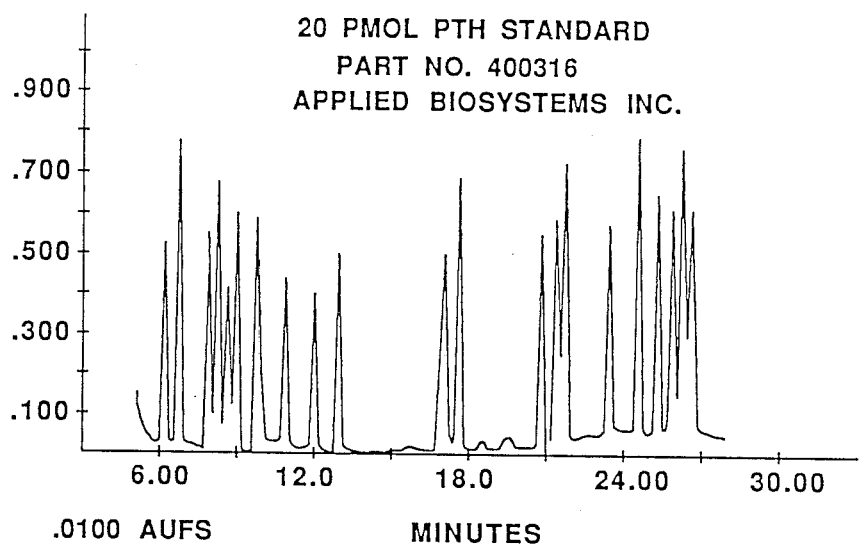
FIGS. 3J–3M show the results of applying the filtering method according to the invention to a second standard PTH mix.
Figure 3K:
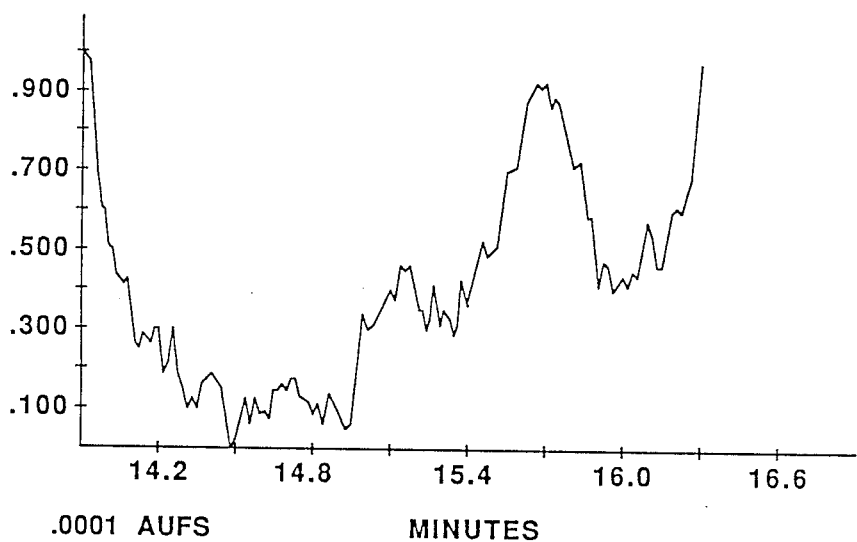
Figure 3L:
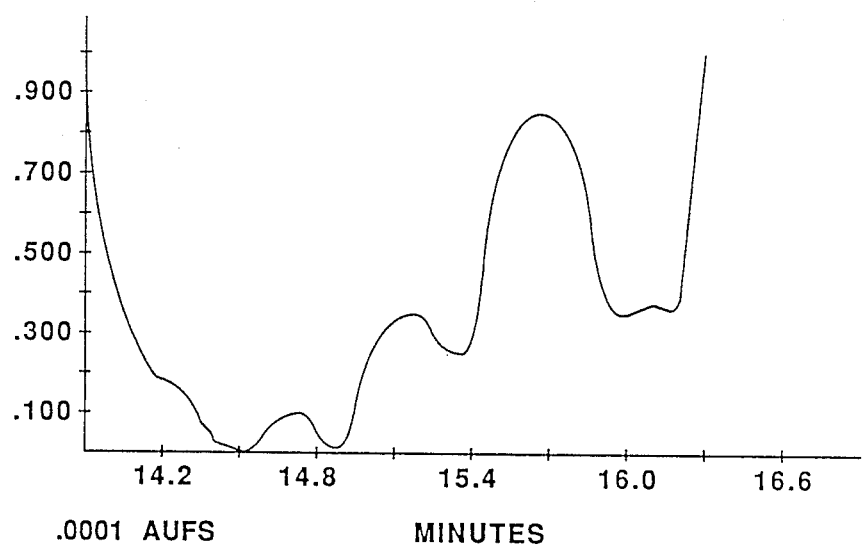
Figure 3M:
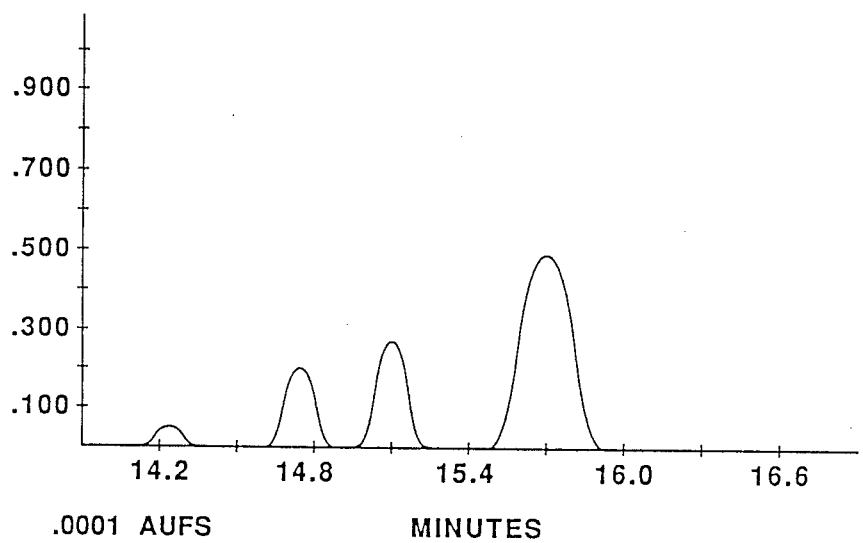

To illustrate further the sensitivity of the method using the house filter, the results of applying the method to a 20 pmole PTH standard are shown in FIGS. 3J–3M. FIG. 3J shows the raw chromatogram for the sample. FIG. 3K shows the raw chromatogram on an expanded time scale in the time interval between 14.0 and 16.6 minutes, which clearly reveals a substantial high frequency noise content in the measured chromatogram. FIG. 3L shows the results of using the house filter to remove the high frequency noise, with N6, $\alpha=1$. FIG. 3M shows the results of applying the entire digital filtering method to the raw chromatogram of FIG. 3J, and illustates that the final filtered chromatogram is quite smooth and exhibits peaks that are quite well resolved. The subsequent filtering parameters used were N=6, =20, for the resolution enhancement, and N=3, =$\frac{1}{2}$ for the final smoothing.

PTH Background Correction:

Processing all of the chromatograms from the sequencing run with the routines described above in FIGS. 2A and 2B or 2C and 2D produces a data array containing raw values for all of the PTHs at all of the cycles. A plot of any individual PTH versus cycle typically shows a rising and/or falling background level of the PTH with one or more cycles where the PTH value is substantially higher than this background level. This background level can be stripped from the remaining PTH yields by a variation of the recursive least squares fit to a polynomial routine used above for low frequency filtering of the chromatograms. In this variation, the iterations of the fit algorithm are continued until the ratio of the standard deviation between actual and fitted data points for successive iterations is above a set value, say S. Once the iterations are concluded, the calculated background PTH values are subtracted from the raw values to yield background-corrected PTH values.

Next, an estimate of the dispersion of this background corrected data is made by performing three iterations of the least squares polynomial fit routine with degree of polynomial=1. The standard deviation of the last iteration then provides an estimate of the variation in the background level, an estimate that allows assignment of a probability that elevated levels at particular cycles are indeed high by a statistically relevant amount. Once the iterations are concluded, the calculated background-corrected PTH values are divided by the standard deviation of the background fit to obtain normalized background-corrected PTH values. This process is then repeated for each PTH so that the remaining PTH values are also expressed in units of standard deviation above (or below) the values calculated from the fitted background curves. At this point, a preliminary sequence assignment is made for each cycle by picking the PTH whose background-corrected normalized value is statistically highest in that cycle.

Figure 4A:
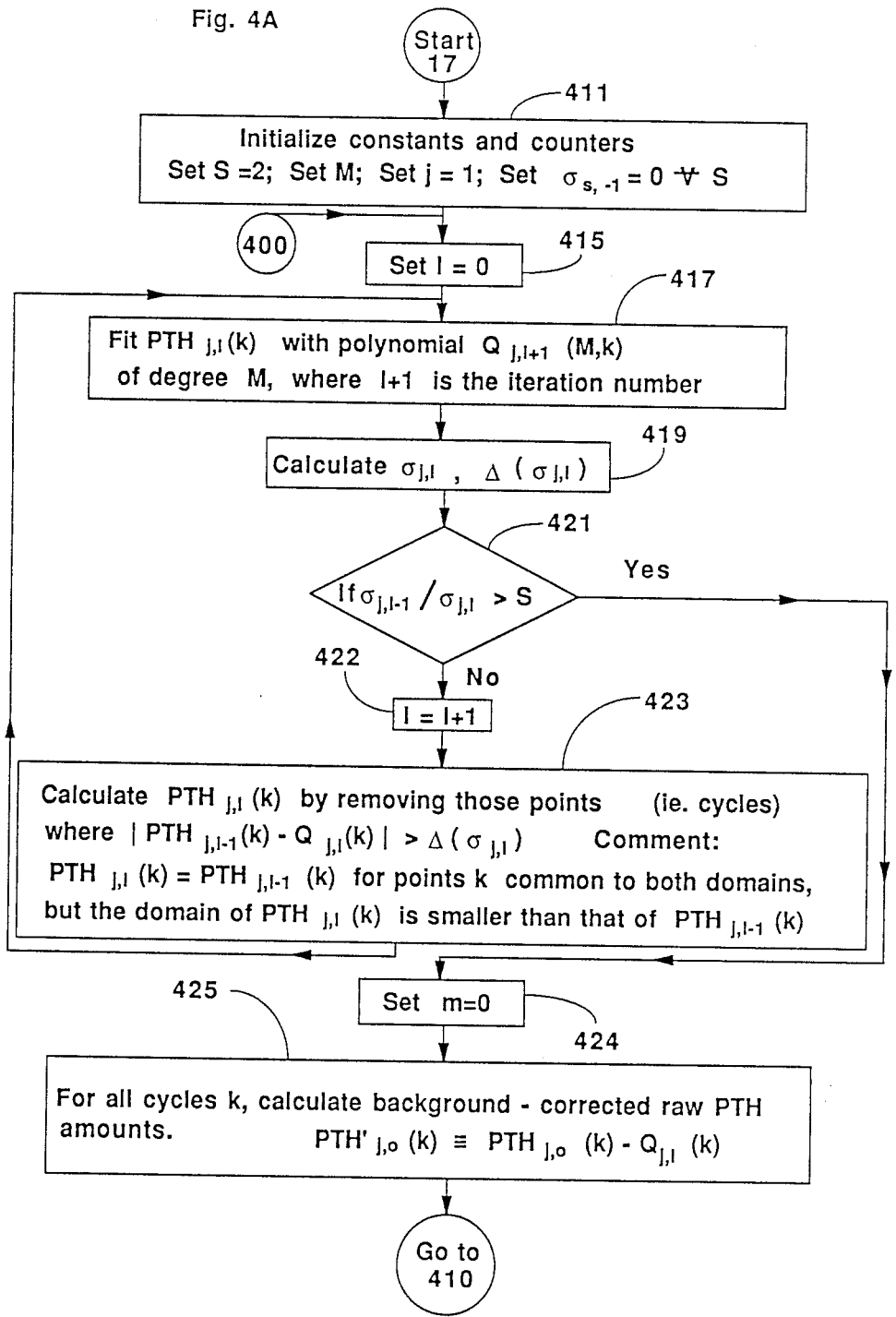
FIGS. 4A and 4B are a flow chart showing the method used for correction of background levels in the amount of each amino acid residue measured for each cycle.
Figure 4B:
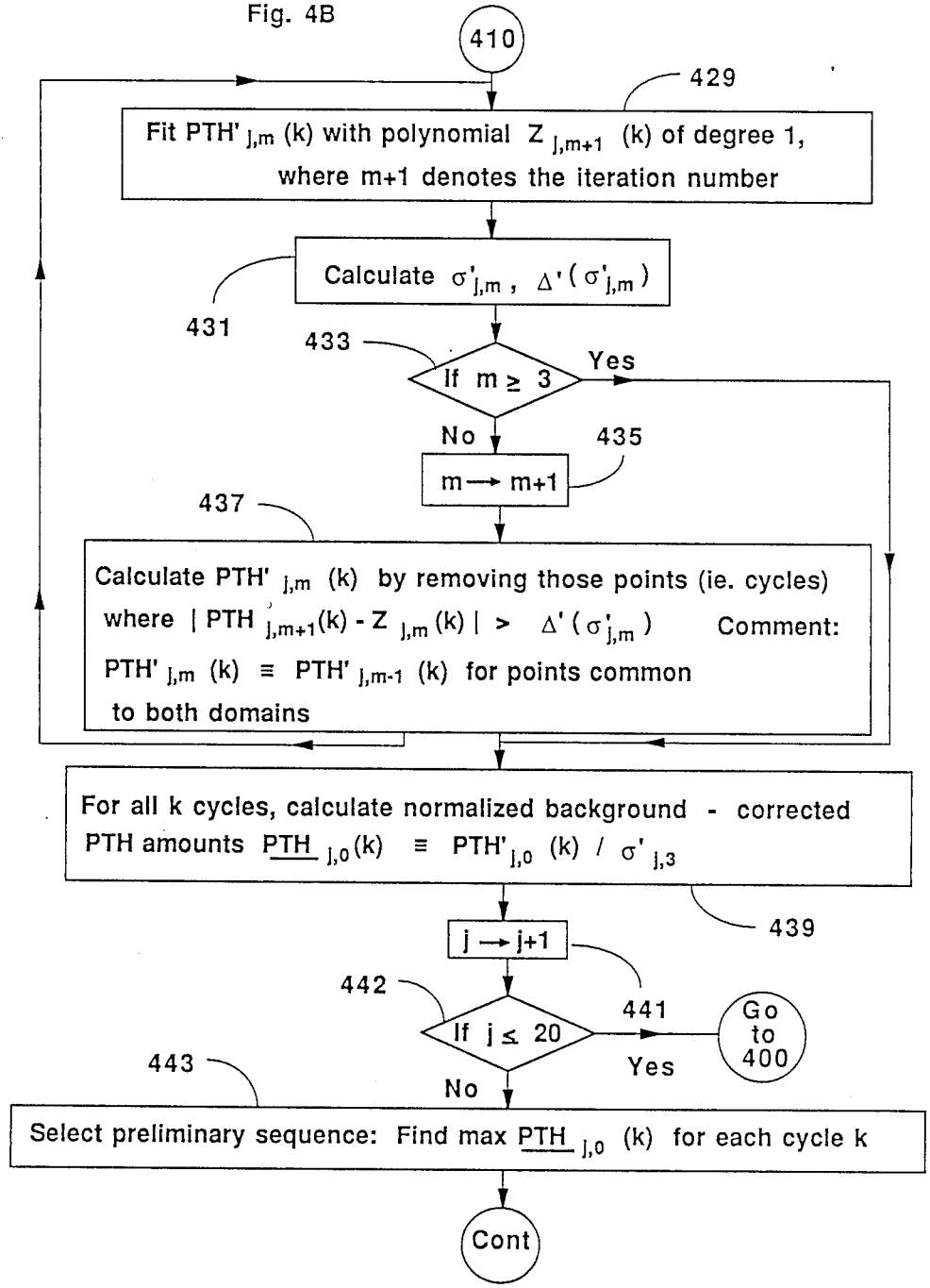

This process is illustrated in more detail in the flow chart of FIGS. 4A and 4B. Here, the process begins at program element 411, where required constants and program counters are initialized. A program counter, "j", is initialized to the value 1. The counter j is used to index the PTH values to denote an amino acid of kind j. An integer M is set equal to the number of cycles divided by 12 (rounded to the nearest integer), which corresponds to the degree of the polynomial that is used to fit the PTH values. Also, an array $\sigma_{s,-1}$ is set equal to zero for all s=1 to 20. In addition, the value of S is set equal to 2, S being the cutoff value of the ratio of the standard deviation between actual and fitted data for successive iterations, in order to determine when the iterations can be terminated in the least squares fit routine. At program element 415, another counter "1" is initialized to zero, the counter 1 corresponding to the iteration number in the least squares fit routine. At program element 417, $PTH_{j,l}(k)$ is fit with a polynomial $Q_{j,l+1}(M,k)$ of degree M. Initially this means $PTH_{1,0}(k)$ (the totality of values for amino acid number 1 as a function of cycle) is fit with a polynomial $Q_{1,1}(M,k)$. At program element 419, the standard deviation of the fit for the j-th amino acid on the l-th iteration is calculated and is called $\sigma_{j,l}$ (i.e. $\sigma_{1,o}$ initially), and a measure of the fit function $\Delta(\sigma_{j,l})$ is calculated. Here $\Delta(\sigma_{j,l})$ is defined to be the standard deviation $\sigma_{j,l}$ for points higher than the raw data and twice the standard deviation for points below the raw data. The ratio of $\sigma_{j,l-1}$ to $\sigma_{j,l}$ is then calculated at program element 421, and, if the ratio is greater than S, the program proceeds to calculate the background corrected normalized PTH amounts at program element 425. If the ratio is less than S, the counter 1 is incremented at program element 422, and at program element 423, a new $PTH_{j,l}(k)$ is calculated by removing those points (i.e. cycles) where $|PTH_{j,l-1}(k)-Q_{j,l}(k)|>\Delta(\sigma_{j,l})$. Here $PTH_{j,l}(k)=PTH_{j,o}(k)$ for all points k common to the domains of both functions. Once the points are removed, the fitting routine begins again at program element 417, and the iteration process is continued until the ratio $\sigma_{j,l-1}/\sigma_{j,l}$ is greater than S. An iteration counter m is then initialized at 424, and, as indicated earlier, at program element 425, the background-corrected raw PTH amounts, $PTH'_{j,o}(k)$, are calculated for each cycle. This is done by subtracting the last fitted value $Q_{j,l}(k)$ for the PTH of amino acid j at cycle k, from the measured PTH amount $PTH_{j,o}(k)$. At program element 429, the background-corrected raw PTH amount $PTH'_{j,o}(k)$ is fitted with a first degree polynomial $Z_{j,m+1}(k)$ ($Z_{j,1}(k)$ for the first iteration). The standard deviation of the fit $\sigma'_{j,m}$, and a measure of the fit function $\Delta'(\sigma'_{j,m})$ is then calculated at program element 431. Here $\Delta'(\sigma'_{j,m})$ is typically chosen to be equal to the standard deviation for points falling above the fitted line and to be equal to 1.67 times the standard deviation for points falling below the fitted lilne. The program then tests the value of the iteration counter m at program element 433 in order to stop the iterations at three for this particular sequence of fits. The iteration counter is then incremented at program element 435, and at program element 437 a new $PTH'_{j,m}(k)$ is calculated by removing those points from the background-corrected raw values where the difference between $PTH'_{j,o}(k)$ and the fitted value is greater than the measure of the fit function. This iteration process is then continued twice more, i.e. for a total of three times, and after the third time a normalized background-corrected PTH amount $PTH_{j,o}(k)$ is calculated at program element 439 by dividing the background-corrected raw value by the standard deviation calculated on the last iteration. Once the background-corrected normalized PTH amounts are calculated for amino acid j, the counter j is incremented at program element 441 and j is tested to see if it is less than or equal to 20 at program element 422. If j is less than or equal to 20, the program loops back through the background fit and correction process, starting again with program element 415. If j is greater than 20, the method then proceeds to program element 443 where a preliminary sequence assignment is made by finding the maximum normalized PTH amount for each cycle.

Those skilled in the art will understand that there are many ways of performing the background correction. For example, different fitting functions may be used, and a measure of dispersion different from the standard deviation may be used for fitting. The important aspect of this background-correction process is to arrive at a normalized sequence of PTH amounts, so that results from cycle to cycle can be quantitatively compared.

Lag Correction:

After the normalized background-corrected PTH amounts have been calculated and a preliminary sequence assignment has been made, the lag correction is performed. At each cycle, k, of the Edman degradation, the removal of the amino acid residue is only partial, i.e. a fraction of the amino acid appears at subsequent cycles $k+1, k+2, \ldots, k+i$. At any given cycle, the coupling and/or cleavage failure typically adds 1 to 2% to the out-of-phase signal, or lag. Since these failures are cumulative, the observed lag becomes progressively larger as the sequence proceeds, and in long runs more signal may appear in cycle $n+1$ than in cycle n. Hence, the lag correction is particularly important for accurate sequence assignments for later cycles.

If one defines "$Y_o$" as the theoretical initial signal, "b" as the fraction of reaction failure, and "$Y_{1,j}$" as the yield of amino acid 1 appearing in cycle j, and assumes that no signal is irreversibly lost due to side reactions that prevent the Edman degradation or physical extraction of peptide, then:

$Y_{1,1} = 1Y_0(1-b)$ $Y_{1,2} = 1Y_0(1-b)b$ $Y_{1,3} = 1Y_0(1-b)b^2$ $Y_{1,4} = 1Y_0(1-b)b^3$

Similarly, for amino acids 2 and 3:

$Y_{2,2} = 1Y_0(1-b)^2$ $Y_{2,3} = 2Y_0(1-b)^2 b$ $Y_{2,4} = 3Y_0(1-b)^2 b^2$ $Y_{2,5} = 4Y_0(1-b)^2 b^3$ $Y_{3,3} = 1Y_0(1-b)^3$ $Y_{3,4} = 3Y_0(1-b)^3 b$ $Y_{3,5} = 6Y_0(1-b)^3 b^2$ $Y_{3,6} = 10Y_0(1-b)^3 b^3$ if the lag yields are expressed as a ratio to the observed primary cycle yield, these expressions reduce to:

$Y_{1,2}/Y_{1,1} = 1b$ $Y_{1,3}/Y_{1,1} = 1b^2$ $Y_{1,4}/Y_{1,1} = 1b^3$ $Y_{2,3}/Y_{2,2} = 2b$ $Y_{2,4}/Y_{2,2} = 3b^2$ $Y_{2,5}/Y_{2,2} = 4b^3$ $Y_{3,4}/Y_{3,3} = 3b$ $Y_{3,5}/Y_{3,3} = 6b^2$ $Y_{3,6}/Y_{3,3} = 10b^3$

In general terms, if $Y_k$ is the primary cycle yield (i.e. $Y_{k,k}$) and $Y_{k+i}$ is the lag yield (i.e. $Y_{k,k+i}$), then:

$Y_{k+1}/Y_k = ([k+0]/1)b$ $Y_{k+2}/Y_k = ([k+1]/2)([k+0]/1)b^2$ $Y_{k+3}/Y_k = ([k+2]/3)([k+1]/2)([k+0]/1)b^3$ $Y_{k+i}/Y_k = ([k+i-1]/i) \ldots$
$([k+2]/3)([k+1]/2)([k+0]/1)b^i$ This expression is not strictly correct because of the assumptions that irreversible signal losses are nonexistent and that the failure fraction b is the same at each cycle. However, the former assumption introduces a relatively small error as long as the irreversible losses are less than 10% per cycle and therefore does not interfere significantly with subsequent calculations. The effect of the latter assumption, which is clearly incorrect, is more difficult to evaluate. Empirically, it does not seem to interfere when b is measured at each cycle as a cumulative average lag.

Figure 5B:
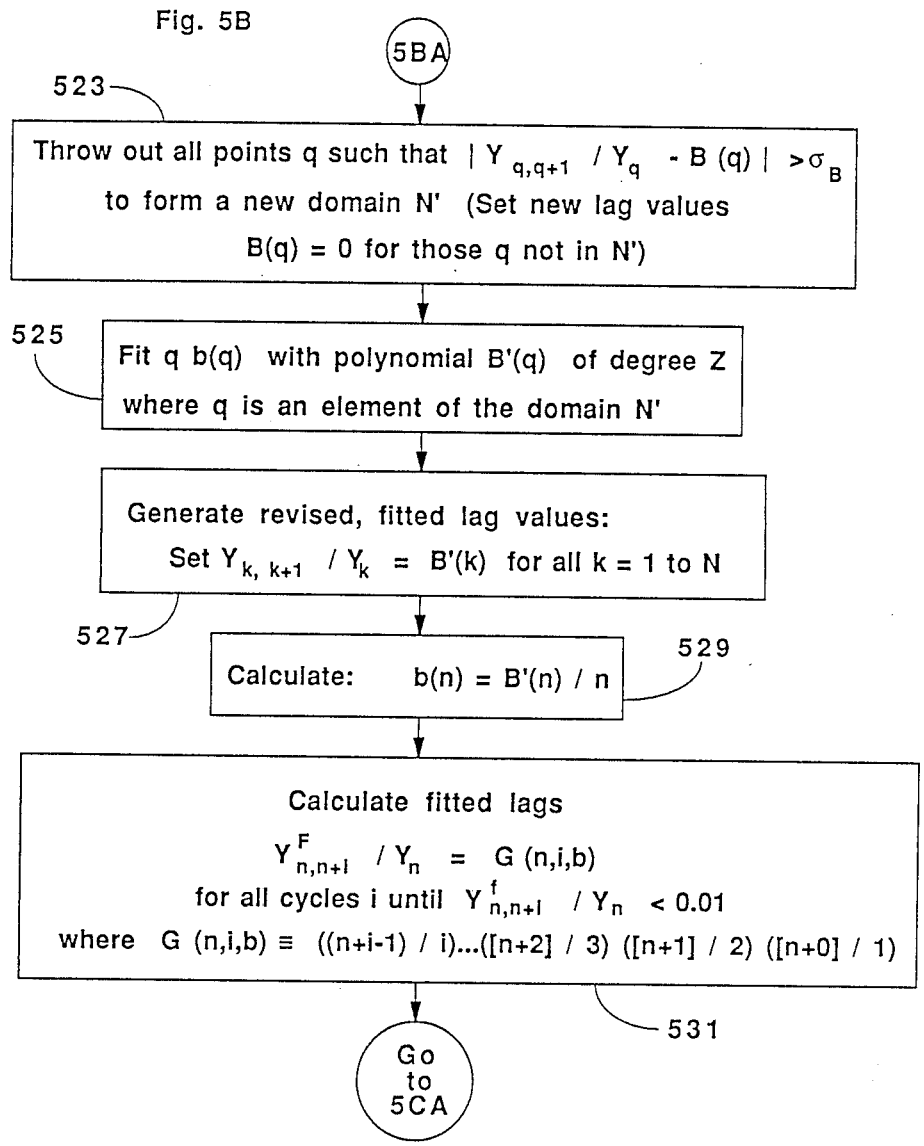
Figure 5C:
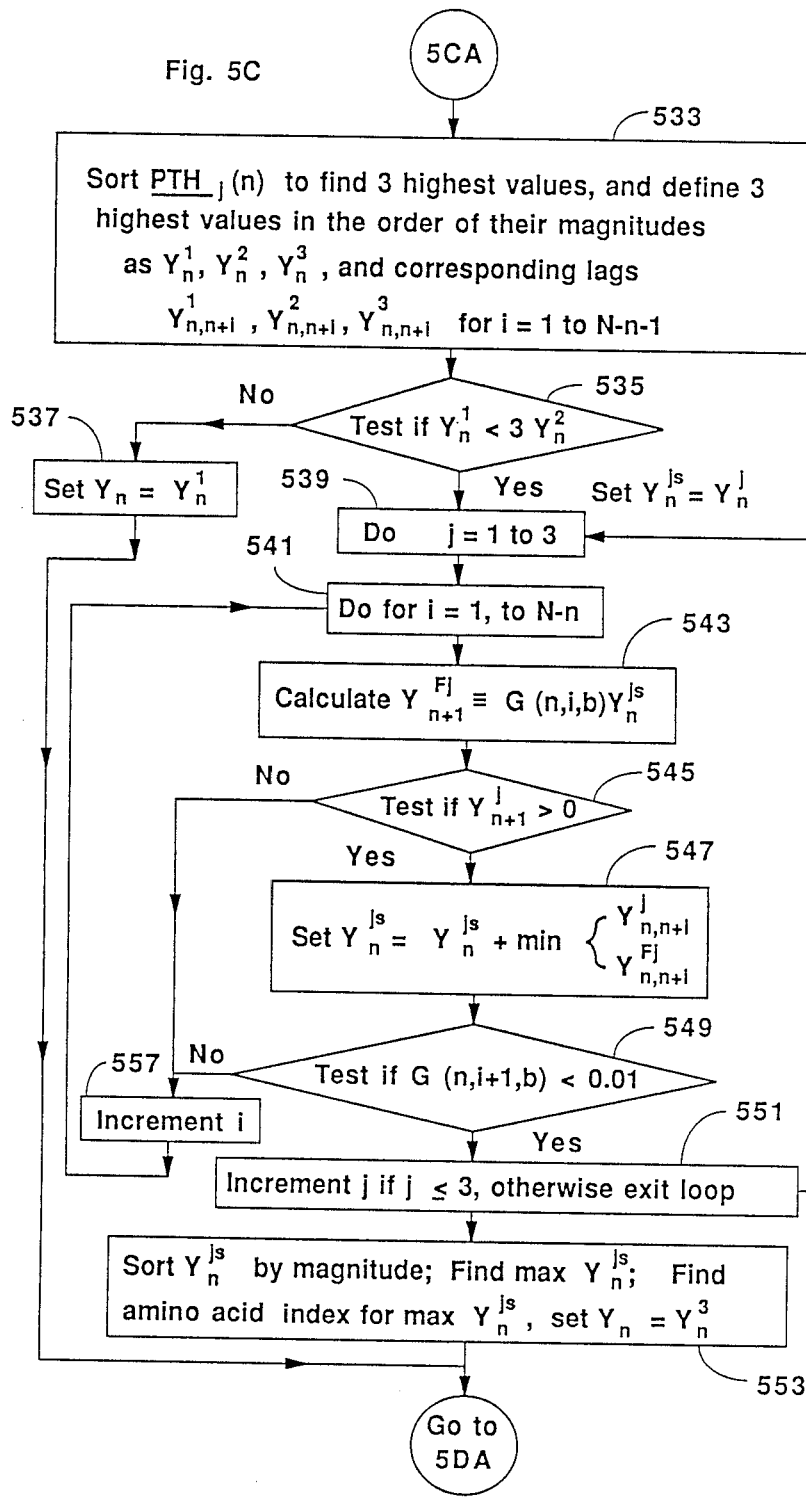
Figure 5D:
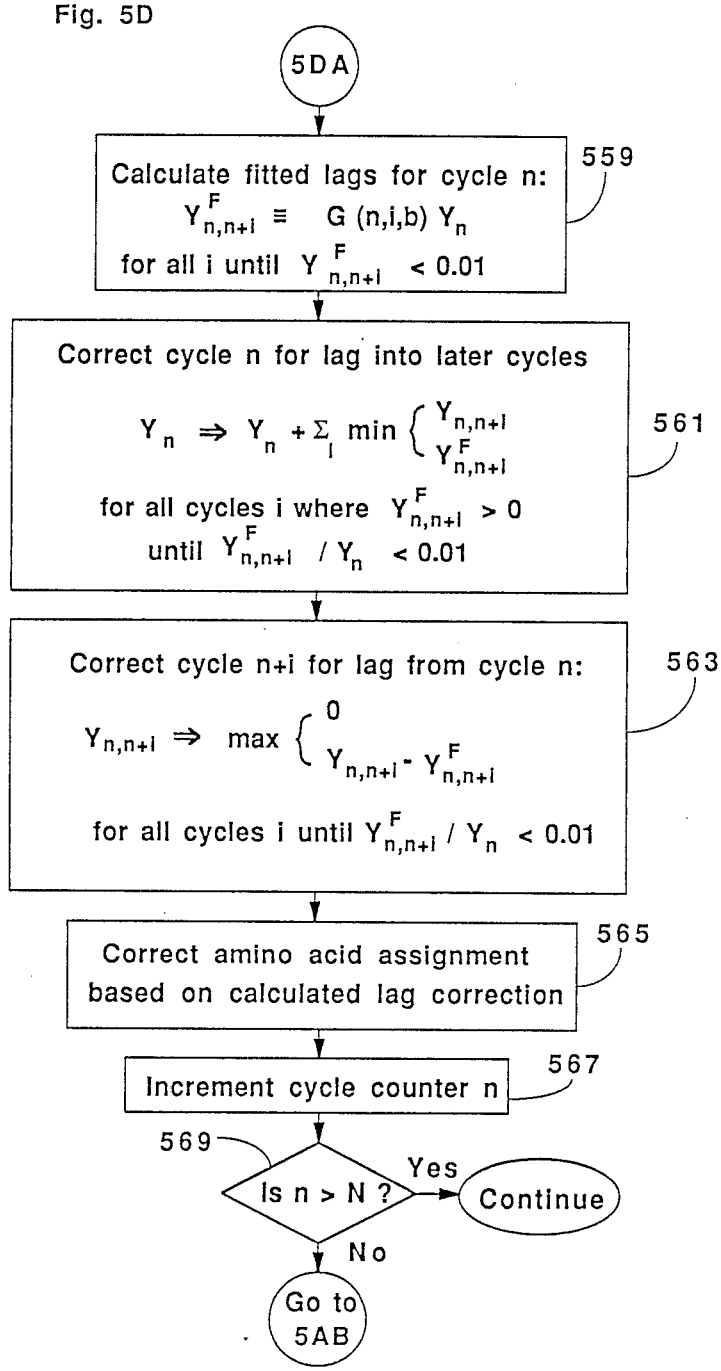

The preferred method of the lag correction is illustrated in FIGS. 5A, 5B, and 5C. At program element 511, the preliminary sequence assignment determined from subroutine 17 is used to define the primary cycle yield array $Y_k$ (i.e. $Y_k = MAX(PTH_j(k))$. This preliminary sequence assignment is then used to calculate a working value for cumulative lag, kb, at each cycle. This calculation is set out in program elements 513, 515, and 517. First, at program element 513, $Y_{k,k+1}$ is set equal to $PTH_j(k+1)$ for all Edman cycles in the sample, where j is chosen to correspond to the amino acid selected in the preliminary sequence assignment for cycle k. A cycle counter "n" is then initialized at program element 515 so that each cycle is corrected one at a time, and the working values for the lag coefficients are calculated for each remaining cycle (i.e. where $k \geq n$) at program element 517 using the formula $Y_{k,k+1}/Y_k = kb(k)$. In program element 519, these working values of kb(k) are then fitted to a polynomial curve B(k) of degree $Z = N/15$ (rounded to the nearest integer), using the method of least squares. Then the measured values of the lag coefficients that differ from the fitted values by more than one standard deviation are discarded, and the remaining data points are refitted. To accomplish this, the standard deviation, $\sigma_B$, of the fitting function B(k) from the actual measurements $Y_{k,k+1}/Y_k$ over the domain N of all Edman cycles is calculated at program element 521. At program element 523, all points k for which the actual value $Y_{k,k+1}/Y_k$ differs from B(k), the fitted value, by more than one standard deviation $\sigma_B$, are removed from the domain N, forming a new domain N'. A least squares polynomial fit of kb(k) is then performed at program element 525 using the new domain. At program element 527, the revised fitted lag values B'(k) are generated for all cycles k=1 to N. Then the failure fraction b(n), is calculated for cycle n at program element 529, using the fitted values of B'(k), and at program element 531 b(n) is used to generate the fitted lag amounts G(n,i,b) into the next few cycles using the equation $G(n,i,b) = ([n+i-1]/i) \ldots ([n+2]/3)([n+0]/1)b^i(n)$ or all cycles i until G(n,i,b)<0.01, i.e. until the cycle n+i yield is less than 1% of the cycle n yield. At program element 533, the normalized PTH values are sorted for cycle n to find the three largest values, $Y_n^1$, $Y_n^2$, and $Y_n^3$ and their corresponding lags $Y_{n,n+i}$, $Y_{n,n+i^2}$, $Y_{n,n+i^3}$. At program element 535, the largest value is tested to see if it is less than three times as large as the next highest value, and if it is not (i.e. it is greater than or equal to 3 times the next highest value), the program leaves the amino acid assignment as it was by setting $Y_n$ equal to $Y_n^1$ at program element 537. If, however, $Y_n^1$ is less than 3 times $Y_n^2$ each of the three largest values $Y_n^1$, $Y_n^2$, $Y_n^3$ are lag corrected in program elements 535 through 557 using the fitted lag based on the original sequence assignment to determine if the lag correction would make any changes in sequence assignment. In particular, each of the fitted lags $Y_{n+iFj}$ is calculated as $G(n,i,b)Y_n^j$ at program element 543, and if the actual $Y_{n,n+i^j}$ is greater than zero, the yeild $Y_n$ is corrected for the lag in cycle n+i. this correction is made by adding $Y_{n+i}^{Fj}$ to $Y_n^j$ if $Y_{n,n+i^j} > Y_{n+i}^{Fj}$ or by adding $Y_{n,n+i^j}$ to $Y_n^j$ if $Y_{n+i}^{Fj} > Y_{n,n+i^j}$ at program element 547. This correction process is continued for the next few cycles i past the cycle number n, the criterion for cutoff being that the fitted lag be less than 1% of the actual value as is tested at program element 549. This process continues for each cycle i and each value $Y_n^j$ until each $Y_n^j$ is corrected by replacing $Y_n^j$ with $$Y_n^j + \Sigma \text{ MIN} \begin{cases} Y_{n,n+i}^j \\ Y_{n+i}^{Fj} \end{cases}$$

At program element 553, each of these lag corrections is tested to find the maximum lag corrected value and the sequence value $Y_n$ is set equal to that maximum, and the amino acid index is determined in order to select the proper sequence call for that cycle n. Once the sequence call for cycle n is completed, either after program element 537 or after element 553, the fitted lags for that sequence call are calculated at program element 559, for the next few cycles past the cycle n, again using the same termination criterion as before, i.e. until the fitted lag is less than 1% of the actual lag. Cycle n is then corrected for lag from the later cycles n+i that have positive lag values using the same cutoff criteria as before at program element 561 by increasing the cycle n yield by the lesser of the calculated lag amount or the actual cycle yield. Next cycles n+i are corrected for lag from cycle n by replacing the lag value at cycle n+i by the greater of zero or the difference between the observed yield $Y_{n,n+i}$ and the calculated lag amount $Y_{n+i}^F$ at program element 563 for all cycles i where the fitted lag coefficient is less than 1%.

At this point, cycle n is fixed and cycle n+1 is free from lag from cycle n that would interfere with the sequence assignment of cycle n+1. At program element 565, the amino acid assignments are corrected based on the calculated lag corrections and at program element 567 the cycle counter n is incremented to calculate the lag for the next cycle. The cycle counter is tested at program element 569 to see if all cycles have been corrected. If they have not, the method returns to program element 517 to determine the empirical lag calculations. The polynomial fit routines 519–525 are repeated based on the new sequence assignments and lag coefficients, and the process is continued until the lag for cycle n+1 is corrected and the lag from cycle n+1 is removed from the next few cycles. This procedure continues until all cycles, one at a time, are corrected for lag. As the lag corrections are made during each pass through the procedure, one more cycle is made free of lag interference with its amino acid assignment, until eventually all cycles can be assigned independent of lag effects. The process then proceeds to the injection correction subroutine 23, or the results of the sequence assignment are output directly depending on whether the injection correction has been made. Those skilled in the art will understand that there are other approximations that can be made in arriving at the effects of the lag correction. For example, instead of using the highest three values of the normalized PTH's, one could use just the highest value, or one could use the two highest values to see if the sequence assignment changes, and if it does, go back and check for other sequence choices. Similarly, one could choose more than the three highest values if after lag correction, the sequence call still appears to be equivocal.

Injection Correction:

Once the background and lag corrections have been made, the remaining PTH values at each cycle can, if desired, be used to correct for any variation in the amount of sample injected onto the PTH analyzer at each cycle. For each cycle, all but the two highest PTH values are averaged. Since the corrected PTH values are in standard deviation units, this average would be near zero if the injection for any given cycle were precise. Any nonzero average for a cycle is used to correct the raw PTH yield data for that cycle by subtracting from each raw PTH value the product of the corrected cycle average and that PTH's standard deviation unit (calculated in the PTH background correction routine). This procedure, in effect, uses the set of nonassigned amino acid values at each cycle as an internal sampling standard. Thus, injection corrections can be made in the absence of any added internal HPLC standard.

Shown in FIG. 6 is a flow chart illustrating the injection correction. First, at program element 611, an array $\{Z_{j,n}\}$ is defined, where the element $Z_{j,n}$ represents the value of the PTH amount of amino acid of kind j at Edman cycle n, as calculated from the lag correction subroutine 19. At program element 613; the array is sorted by amino acid to determine the two largest values, say $Z_{j',n}$ and $Z_{j'',n}$ for each cycle. The array is then averaged at program element 615, for those amino acids other than the two highest, yielding a column array defined as $\{\bar{Z}_n\}$. An injection corrected PTH value is then calculated at program element 617 by the equation $INJ_{j,n} = PTH_{j,o}(n) - \bar{Z}_n \sigma_{j,l}$, where $PTH_{j,o}(n)$ is the raw PTH value found in subroutine 17 on the last iteration 1 for amino acid j. Finally at program element 619, the array $PTH_{j,o}(n)$ is set equal $INJ_{j,n}$, to set up the name required for the PTH array to be used in subroutine 17.

Once all the injection corrections to the raw PTH data set are made, the PTH background and lag corrections must be recalculated using this adjusted data. Once this is done, the subsequent amino acid assignments should be as error free as is possible given the starting chromatograms.

Utility of the Invention

Appendix II is a sequence of Tables that illustrate at several steps of the method, results of the series of corrections described above. Table 1 shows the raw data resulting from quantitation of 60 cycles of an Edman sequencing of an 18 Kilodalton chain (i.e. through program element 15). Table 2 shows the same raw data with the first column, aspartate, background-corrected according to program element 17. Table 3 shows the results of the next loop through the background correction subroutine 17 in order to correct for background in the second column, asparagine. As described earlier, this background correction process is repeated until the PTH amounts for each amino acid are background-corrected. Then a preliminary sequence assignment can be made. Table 4 shows the results of the background correction.

The circled elements in Table 4 are the maximum PTH values in each cycle and correspond to a first preliminary sequence assignment.

Using the preliminary sequence assignment, the lag correction subroutine 19 is then performed which is followed by the injection correction subroutine 23. Once the injection correction is completed, the injection-corrected sequence of PTH's is then background-corrected at program element 17. The results of the lag correction on the background corrected data for cycles 1-37 are shown in Table 5. For comparison, Table 6 shows the results of the lag correction on the background-corrected data for cycles 1-38. Table 7 shows the results of the lag correction for all 60 cycles. The results of the injection correction for cycle 1 is shown in Table 8. Table 9 shows the results of injection correction for cycles 1 and 2. This injection correction process is then continued for each cycle until all cycles are lag corrected. The results are shown in Table 10. Table 11 shows the results of background correction on the injection corrected data of FIG. 10. FIG. 12 shows the results of lag correction for all cycles of the background corrected data of FIG. 11. Again, the maximum values in each cycle correspond to the sequence assignment, which is seen to be different from the preliminary sequence assignment shown in Table 4, now that the injection correction has been performed.

Figure 7A:
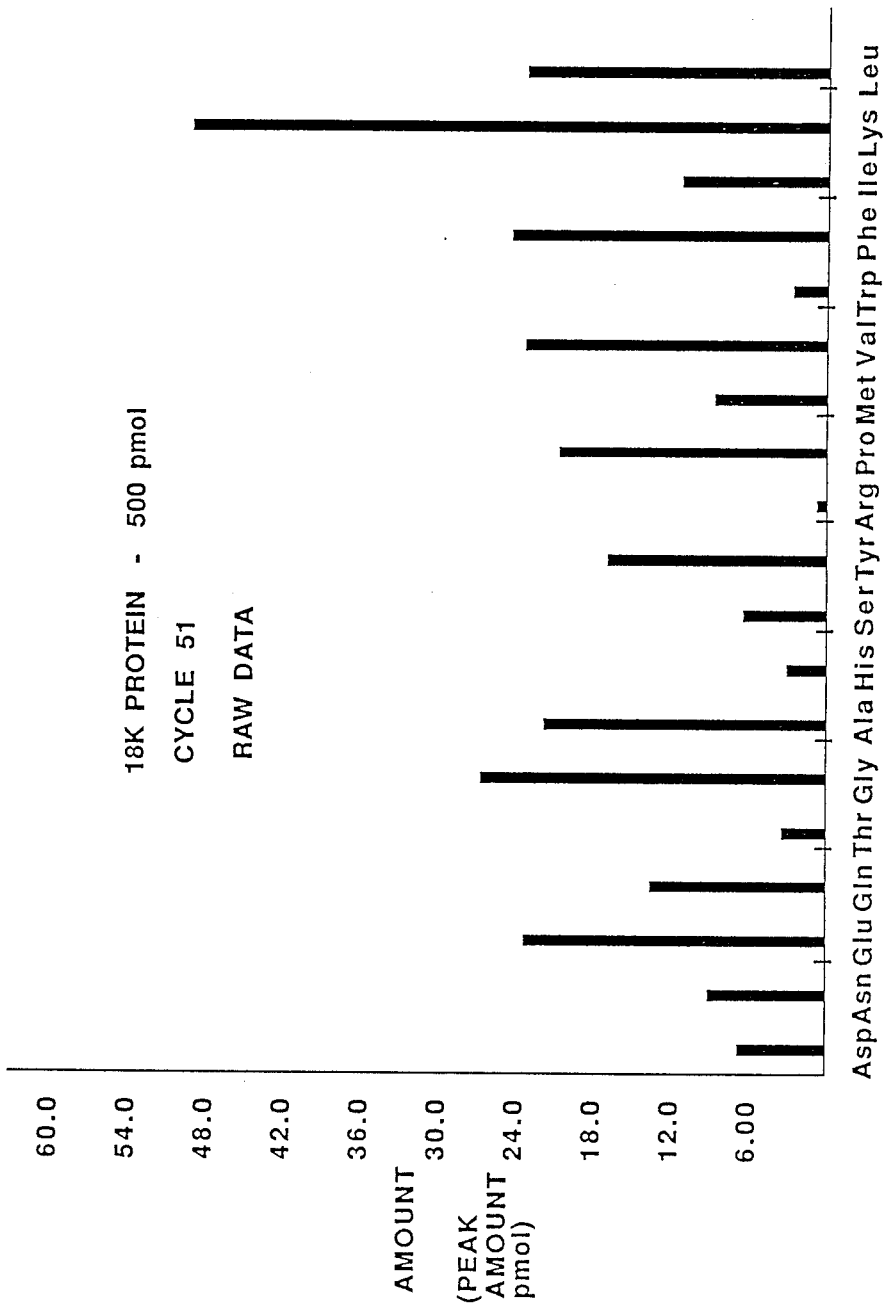
FIGS. 7A–7C show the results of the method of the invention at different stages of the correction process for the 51st cycle in the degradation of a protein.
Figure 7B:
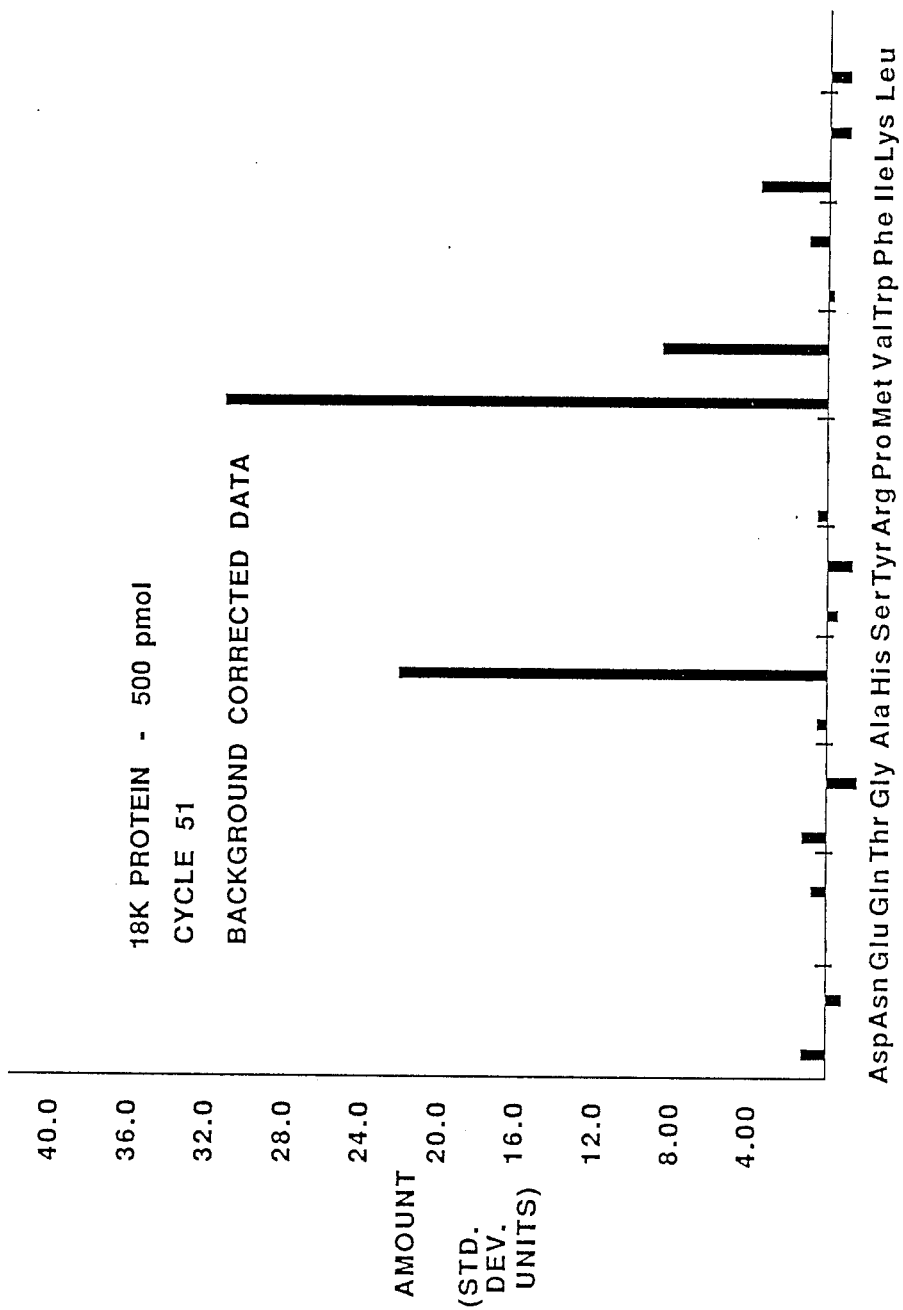
Figure 7C:
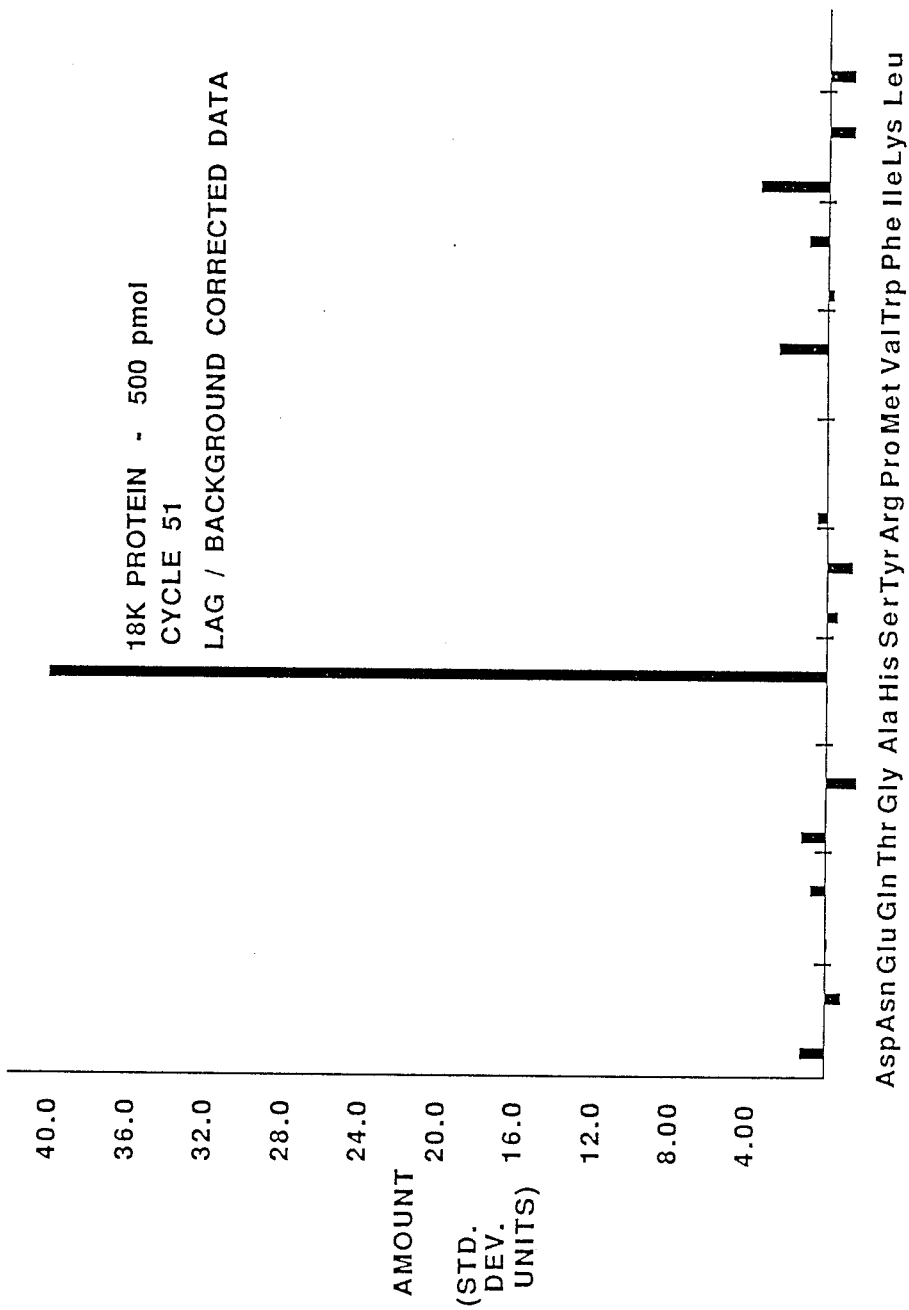
Figure 8A:
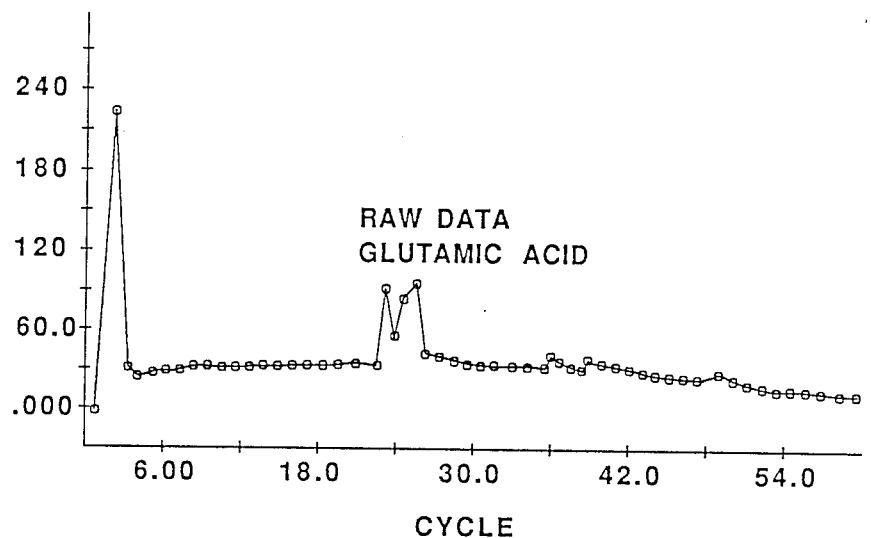
FIGS. 8A–8C show the results of the method of the invention at different stages of the correction process for glutamic acid at different cycles in the degradation of a protein.
Figure 8B:
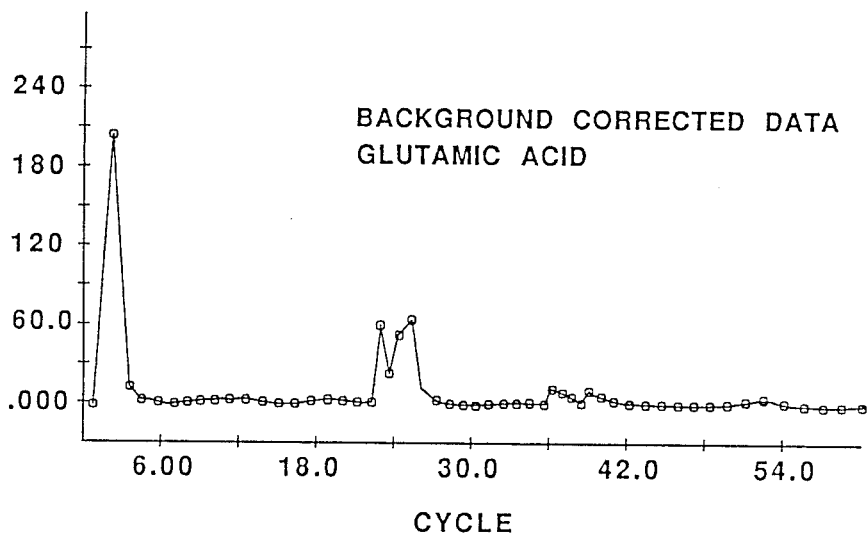
Figure 8C:
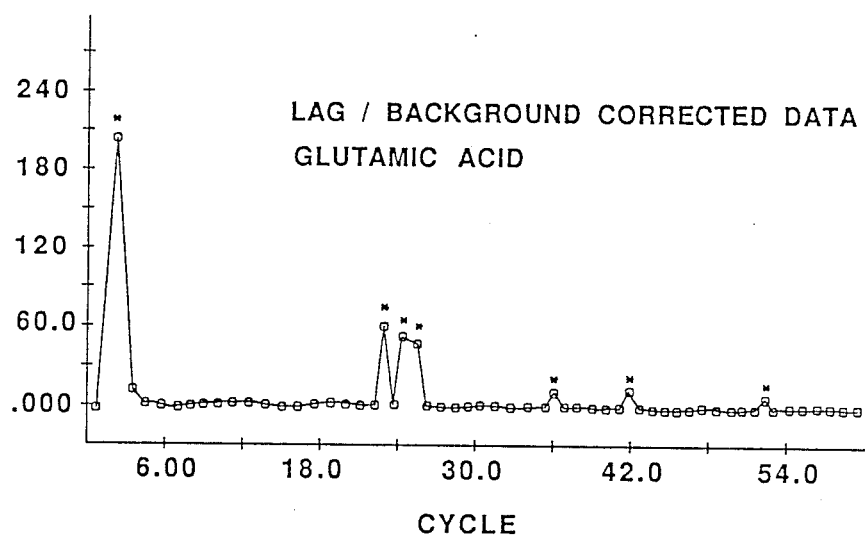

This difference in sequence assignment can be seen more clearly in FIGS. 7A, 7B, and 7C which show results of the above sequence of steps for cycle 51 of the 18 Kilodalton protein. In FIG. 7A, a preliminary assignment would appear to be lysine for that cycle. Once the injection correction has been made, and the background has been corrected, as illustrated in FIG. 7B, the selection for cycle 51 is not so clear, but appears to be histidine. This selection is then confirmed on performing the lag correction as seen in FIG. 7C. The effects of the correction process can also be viewed in terms a particular amino acid, as illustrated in FIGS. 8A, 8B, and 8C, which show the results of the correction process for glutamic acid by cycle. FIG. 8A shows the raw data (injection corrected) for glutamic acid by cycle. FIG. 8B shows the results after background correction of the data of FIG. 8A, and FIG. 8C shows the results after both background and lag correction.

Those skilled in the art will appreciate that there are many equivalent ways of implementing the above method and different combinations of apparatus can be used to accomplish the method. For example, many of the computational program elements could be implemented separately from the computer module as long as the apparatus used for those computations were under appropriate control of the computer module. In addition it should be appreciated that the particular program counters and constants chosen in the preferred embodiment may vary, for example depending on the number of cycles being degraded, on the desired accuracy of the calculations, and the desired time to complete the sequence call of the peptide. For these and other reasons, it is intended that the scope of the invention be interpreted with reference to the appended claims and equivalents thereto and not be limited to the specific example chosen to describe it.

APPENDIX I

```
INTEGER SCALAR #CYCLES \ number of cycles in raw data file
   SCALAR #AAS \ number of amino acids (AAs) in raw data file
   SCALAR CYCLE# \ current cycle number
   SCALAR AA# \ current AA number
   SCALAR AA.FIT.TIMES \ maximum number of fit iterations
   SCALAR AA.POLY.TIMES \ background fit polynomial degree
   SCALAR LAG.POLY.TIMES \ lag correction polynomial degree
   SCALAR LAGCYCLES \ lag calculation loop counter
   SCALAR TYPE# \ data array type
   SCALAR COLOR1 \ graphics color 1
   SCALAR COLOR2 \ graphics color 2
   SCALAR COLOR3 \ graphics color 3
   SCALAR COLOR4 \ graphics color 4
   SCALAR COLOR5 \ graphics color 5
```

```
SCALAR COLOR6 \ graphics color 6
SCALAR POINTS1 \ array subset counter
SCALAR POINTS2 \ array subset counter
SCALAR INDEX1 \ array subset counter
SCALAR INDEX2 \ array subset counter
SCALAR INDEX3 \ array subset counter
SCALAR INDEX4 \ array subset counter
SCALAR N \ house filter parameter
SCALAR N1 \ house filter parameter
SCALAR M \ array size counter
SCALAR PN \ number of HPLC data points
SCALAR PS \ HPLC plot offset
SCALAR PR \ number of HPLC plot points
SCALAR PEAK.WINDOW \ search window for AA peaks
SCALAR REFPEAK1 \ HPLC reference peak 1 position
SCALAR REFPEAK2 \ HPLC reference peak 2 position
SCALAR REFPOINT \ HPLC reference midpoint
SCALAR REFSHIFT1 \ REFPEAK1 HPLC shift
SCALAR REFSHIFT2 \ REFPEAK2 HPLC shift
SCALAR CYCLE.OFFSET \ HPLC data file name offset
SCALAR DATA.OFFSET \ HPLC data start point offset
SCALAR EGAFLAG \ display type
SCALAR HPFLAG \ graphics output site
SCALAR PAPERFLAG \ HP plotter paper size
SCALAR PRINTFLAG \ text output site
SCALAR FDPLOTFLAG \ HPLC plot data type
SCALAR S'FLAG \ include S' peak in calculations?
SCALAR STDFLAG \ PTH standard HPLC?
SCALAR SCALEFLAG \ plot Y scale method
SCALAR FULLFLAG \ print full peak listing?
SCALAR FITFLAG \ number of fix segments INTEGER DIM[ 2000 ] ARRAY AA.POS.DATA \ raw data peak position array
   DIM[ 100 ] ARRAY SEQUENCE# \ AA numbers assigned by CALL.SEQUENCE
   DIM[ 100 ] ARRAY PP \ HPLC peak positions
   DIM[ 100 ] ARRAY R1P \ Reference peak 1 shifts
   DIM[ 100 ] ARRAY R2P \ Reference peak 2 shifts
   DIM[ 25 ] ARRAY CYCLE.POS \ HPLC AA peak positions
   DIM[ 25 ] ARRAY SP \ HPLC standard AA peak positions REAL SCALAR AA.MAX.DISCARD \ high limit for acceptable data point in fits
   SCALAR AA.MIN.DISCARD \ low limit for acceptable data point in fits
   SCALAR AA.VAL \ value (amount) of AA
   SCALAR AA.STD.DEV \ standard deviation value of fit
   SCALAR STD.DEV \ standard deviation of fit
   SCALAR BETA \ single cycle lag value (Yn+1/Yn/n)
   SCALAR BETA.POINT \ single cycle lag value (Yn+i/Yn+i-1)
   SCALAR INJECT.DEV \ raw cycle data correction set by INJECT.CORRECT
   SCALAR CYCLE.SCALE \ value used to set Y axis scale in plots
   SCALAR REP.YIELD \ calculated repetitive yield value
   SCALAR ALPHA \ house filter parameter
   SCALAR ALPHA1 \ house filter parameter
   SCALAR ALPHA2 \ house filter parameter
   SCALAR LOW.THRESH \ HPLC Y value minimum
   SCALAR STD.PMOL \ number of pmol in HPLC standard REAL DIM[ 2000 ] ARRAY AA.RAW.DATA \ raw data array
   DIM[ 2000 ] ARRAY AA.BACK.DATA \ background corrected data array
   DIM[ 2000 ] ARRAY AA.LAG.DATA \ lag/background corrected data array
```

```
DIM[ 100 ] ARRAY AA.FIT.INDEX \ AA.BACK.FIT dynamic X values
DIM[ 100 ] ARRAY AA.FIT.DATA \ AA.BACK.FIT dynamic Y values
DIM[ 100 ] ARRAY AA.WORK.DATA \ AA.BACK.FIT raw AA values
DIM[ 100 ] ARRAY AA.POLY.DATA \ AA.BACK.FIT fitted AA values
DIM[ 100 ] ARRAY AA.RESIDS \ AA.BACK.FIT (raw - fitted) AA values
DIM[ 100 ] ARRAY BETA.VAL \ raw lag values vs cycle
DIM[ 100 ] ARRAY BETA.WORK \ acceptable raw lag values vs. cycle
DIM[ 100 ] ARRAY BETA.FIT \ fitted lag values vs. cycle
DIM[ 100 ] ARRAY SEQUENCE.VAL \ values of AAs assigned by CALL.SEQUENCE
DIM[ 25 ] ARRAY AA.STD.DEV1 \ standard deviation values vs AA
DIM[ 25 ] ARRAY AA.STD.DEV2 \ standard deviation values vs AA
DIM[ 10 ] ARRAY STD.DEV.WORK \ AA.BACK.FIT iterative deviations
DIM[ 10 ] ARRAY BETA.DATA \ fitted lag values (Yn+i/Yn)
DIM[ 1920 ] ARRAY RD \ raw HPLC data
DIM[ 1920 ] ARRAY FD \ filtered HPLC data
DIM[ 1920 ] ARRAY SD \ scaled HPLC data
DIM[ 100 ] ARRAY PV \ HPLC peak values
DIM[ 25 ] ARRAY SV \ HPLC standard AA peak values DP.REAL SCALAR RDPLOT.MAX \ raw data Y value plot maximum
   SCALAR FDPLOT.MAX \ filtered data Y value plot maximum DP.REAL DIM[ 25 ] ARRAY CYCLE.VAL \ HPLC AA peak values 60 STRING AA.RY.NAME \ AA label for repetitive yield report
40 STRING PROTEIN.NAME \ protein name label
40 STRING TYPE.NAME \ data type label
20 STRING EXEC.NAME \ string execution name
16 STRING CYCLE.NAME \ cycle name label
14 STRING FILENAME \ disk data filename
14 STRING AANAME \ AA name label
12 STRING LINE2.LABEL \ plot label
12 STRING LINE3.LABEL \ plot label
12 STRING LINE4.LABEL \ plot label
 2 STRING DRIVE.LETTER \ disk drive indicator
\ full name AA plot labels
14 STRING AA1   14 STRING AA2   14 STRING AA3   14 STRING AA4   14 STRING AA5
14 STRING AA6   14 STRING AA7   14 STRING AA8   14 STRING AA9   14 STRING AA10
14 STRING AA11  14 STRING AA12  14 STRING AA13  14 STRING AA14  14 STRING AA15
14 STRING AA16  14 STRING AA17  14 STRING AA18  14 STRING AA19  14 STRING AA20
14 STRING AA21  14 STRING AA22  14 STRING AA23  14 STRING AA24  14 STRING AA25

\ 3 letter code AA plot labels
3 STRING 1AA   3 STRING 2AA   3 STRING 3AA   3 STRING 4AA   3 STRING 5AA
3 STRING 6AA   3 STRING 7AA   3 STRING 8AA   3 STRING 9AA   3 STRING 10AA
3 STRING 11AA  3 STRING 12AA  3 STRING 13AA  3 STRING 14AA  3 STRING 15AA
3 STRING 16AA  3 STRING 17AA  3 STRING 18AA  3 STRING 19AA  3 STRING 20AA
3 STRING 21AA  3 STRING 22AA  3 STRING 23AA  3 STRING 24AA  3 STRING 25AA \ default parameters
19 #AAS :=
6 AA.FIT.TIMES :=
6 AA.POLY.TIMES :=
5 LAG.POLY.TIMES :=
6 N1 :=
1740 PN :=
1 PS :=
0 CYCLE.OFFSET :=
80 DATA.OFFSET :=
```

```
1 EGAFLAG :=
0 HPFLAG :=
0 PAPERFLAG :=
0 PRINTFLAG :=
1 FDPLOTFLAG :=
1 S'FLAG :=
0 STDFLAG :=
0 SCALEFLAG :=
1 FULLFLAG :=
1 FITFLAG :=
.01 RDPLOT.MAX :=
.01 FDPLOT.MAX :=
1. AA.MAX.DISCARD :=
.6 AA.MIN.DISCARD :=
1. ALPHA1 :=
20. ALPHA2 :=
0. LOW.THRESH :=
1. STD.PMOL :=
0 R1P :=
0 R2P :=
0 CYCLE.POS :=
0. AA.RAW.DATA :=
0. AA.BACK.DATA :=
0. AA.STD.DEV1 :=
0. AA.STD.DEV2 :=
1. SV :=
0. CYCLE.VAL :=
16 GRAPHICS.DISPLAY.MODE
-1 2 FIX.FORMAT
\ default full name AA labels
" ASPARTIC ACID" AA1 ":= " ASPARAGINE" AA2 ":= " SERINE" AA3 ":=
" GLUTAMINE" AA4 ":= " THREONINE" AA5 ":= " GLYCINE" AA6 ":=
" GLUTAMIC ACID" AA7 ":= " ALANINE" AA8 ":= " HISTIDINE" AA9 ":=
" TYROSINE" AA10 ":= " ARGININE" AA11 ":= " PROLINE" AA12 ":=
" METHIONINE" AA13 ":= " VALINE" AA14 ":= " TRYPTOPHAN" AA15 ":=
" PHENYLALANINE" AA16 ":= " ISOLEUCINE" AA17 ":= " LYSINE" AA18 ":=
" LEUCINE" AA19 ":= " SERINE'" AA20 ":= "    " AA21 ":= "    " AA22 ":=
"    " AA23 ":= "    " AA24 ":= "    " AA25 ":=

\ default 3 letter code AA labels
" Asp" 1AA  ":= " Asn" 2AA  ":= " Ser" 3AA  ":= " Gln" 4AA  ":= " Thr" 5AA  ":=
" Gly" 6AA  ":= " Glu" 7AA  ":= " Ala" 8AA  ":= " His" 9AA  ":= " Tyr" 10AA ":=
" Arg" 11AA ":= " Pro" 12AA ":= " Met" 13AA ":= " Val" 14AA ":= " Trp" 15AA ":=
" Phe" 16AA ":= " Ile" 17AA ":= " Lys" 18AA ":= " Leu" 19AA ":= " S'" 20AA ":=
"    " 21AA ":= "    " 22AA ":= "    " 23AA ":= "    " 24AA ":= "    " 25AA ":=

\ Set graphics display colors.
: DISPLAY.COLORS

EGAFLAG
  CASE
    0 OF 1 COLOR1 :=
      1 COLOR2 :=
      1 COLOR3 :=
      1 COLOR4 :=
      1 COLOR5 :=
      1 COLOR6 := ENDOF
    1 OF 7 COLOR1 :=
      4 COLOR2 :=
```

```
        1 COLOR3 :=
       14 COLOR4 :=
       13 COLOR5 :=
        2 COLOR6 := ENDOF
   ENDCASE
   COLOR1 COLOR

;

\ Set HP plotter colors.
: PLOT.COLORS

1 COLOR1 :=
   2 COLOR2 :=
   3 COLOR3 :=
   4 COLOR4 :=
   5 COLOR5 :=
   6 COLOR6 :=

;

\ Change color display type.
: SET.EGAFLAG
   ." COLOR DISPLAY (0) OR ENHANCED COLOR DISPLAY (1) > " #INPUT DUP
   EGAFLAG :=
   CASE
      0 OF 6 GRAPHICS.DISPLAY.MODE ENDOF
      1 OF 16 GRAPHICS.DISPLAY.MODE ENDOF
   ENDCASE

;

\ Set graphics output parameters.
: GET.HPFLAG

HPFLAG
   CASE
      0 OF GRAPHICS.DISPLAY
         AXIS.DEFAULTS
         DISPLAY.COLORS
         COLOR1 COLOR
         .15 .0 VUPORT.ORIG .8 1. VUPORT.SIZE ENDOF
      1 OF HP7475
         PLOT.COLORS
         COLOR1 COLOR
         PLOTTER.DEFAULTS
         0. 0. VUPORT.ORIG 1. 1. VUPORT.SIZE
         PAPERFLAG 0 =
         IF
            7.65 10.3 PLOTTER.SIZE
            DEVICE.INIT
         THEN ENDOF
   ENDCASE

;

\ Set graphics output site.
: SET.HPFLAG
```

```
      CR ." OUTPUT TO DISPLAY (0) OR HP PLOTTER (1) > " #INPUT
      HPFLAG :=
      GET.HPFLAG

;

\ Set text output site.
: SET.PRINTFLAG

CR ." OUTPUT TO DISPLAY (0) OR PRINTER (1) > " #INPUT DUP
      PRINTFLAG :=
      CASE
        0 OF CONSOLE ENDOF
        1 OF OUT>PRINTER ENDOF
      ENDCASE

;

\ Set HPLC plot data type.
: SET.FDPLOTFLAG

CR ." PLOT RAW (0) OR FILTERED (1) DATA > " #INPUT FDPLOTFLAG :=

;

\ Set HPLC plot window.
: SET.PS

CR ." ENTER PLOT OFFSET IN MINUTES > " #INPUT
      N1 10. * * 1 + PS :=
      CR ." ENTER PLOT RANGE IN MINUTES > " #INPUT
      N1 10. * * PR :=

;

\ Set HPLC data start point offset.
: SET.DATA.OFFSET

CR ." ENTER DATA OFFSET IN POINTS (" DATA.OFFSET . ." ) > " #INPUT
      DATA.OFFSET :=

;

\ Set HPLC data file name offset.
: SET.CYCLE.OFFSET

CR ." ENTER CYCLE.OFFSET > " #INPUT
      CYCLE.OFFSET :=

;

\ Set HPLC parameters.
: SET.HPLC.PARAMETERS

CR ." DATA ACQUISITION RATE (" N1 6 / . ." ) > " #INPUT DUP 6. * N1 :=
      15 * PEAK.WINDOW :=
      CR ." DATA OFFSET POINTS (" DATA.OFFSET . ." ) > " #INPUT DATA.OFFSET :=
      CR ." CHROMATOGRAM MINUTES (" PN N1 10. * / FIX . ." ) > " #INPUT
      N1 10. * * DUP PN := PR :=
```

```
\ Change default full name AA labels.
: SET.AANAMES

NORMAL.DISPLAY
    CR ."   AA1 -- "  AA1 "TYPE ."          AA14 -- "  AA14 "TYPE
    CR ."   AA2 -- "  AA2 "TYPE ."          AA15 -- "  AA15 "TYPE
    CR ."   AA3 -- "  AA3 "TYPE ."          AA16 -- "  AA16 "TYPE
    CR ."   AA4 -- "  AA4 "TYPE ."          AA17 -- "  AA17 "TYPE
    CR ."   AA5 -- "  AA5 "TYPE ."          AA18 -- "  AA18 "TYPE
    CR ."   AA6 -- "  AA6 "TYPE ."          AA19 -- "  AA19 "TYPE
    CR ."   AA7 -- "  AA7 "TYPE ."          AA20 -- "  AA20 "TYPE
    CR ."   AA8 -- "  AA8 "TYPE ."          AA21 -- "  AA21 "TYPE
    CR ."   AA9 -- "  AA9 "TYPE ."          AA22 -- "  AA22 "TYPE
    CR ."  AA10 -- " AA10 "TYPE ."          AA23 -- "  AA23 "TYPE
    CR ."  AA11 -- " AA11 "TYPE ."          AA24 -- "  AA24 "TYPE
    CR ."  AA12 -- " AA12 "TYPE ."          AA25 -- "  AA25 "TYPE
    CR ."  AA13 -- " AA13 "TYPE ."          EXIT ROUTINE > 0"
    CR CR ." AMINO ACID NUMBER > " #INPUT DUP AA# :=
    0 =
    IF
    ELSE
       CR CR ." AMINO ACID NAME > " "INPUT
       " AA" AA# "." 32 "COMPRESS "CAT EXEC.NAME ":=
       EXEC.NAME "EXEC
       ":=
       MYSELF
    THEN

;

\ Select full name AA label.
: GET.AANAME

" AA" AA# "." 32 "COMPRESS "CAT EXEC.NAME ":=
  EXEC.NAME "EXEC
  AANAME ":=

;

\ Change 3 letter code AA labels.
: SET.AACODES

NORMAL.DISPLAY
    CR ."   1AA -- "  1AA "TYPE ."          14AA -- "  14AA "TYPE
    CR ."   2AA -- "  2AA "TYPE ."          15AA -- "  15AA "TYPE
    CR ."   3AA -- "  3AA "TYPE ."          16AA -- "  16AA "TYPE
    CR ."   4AA -- "  4AA "TYPE ."          17AA -- "  17AA "TYPE
    CR ."   5AA -- "  5AA "TYPE ."          18AA -- "  18AA "TYPE
    CR ."   6AA -- "  6AA "TYPE ."          19AA -- "  19AA "TYPE
    CR ."   7AA -- "  7AA "TYPE ."          20AA -- "  20AA "TYPE
    CR ."   8AA -- "  8AA "TYPE ."          21AA -- "  21AA "TYPE
    CR ."   9AA -- "  9AA "TYPE ."          22AA -- "  22AA "TYPE
    CR ."  10AA -- " 10AA "TYPE ."          23AA -- "  23AA "TYPE
    CR ."  11AA -- " 11AA "TYPE ."          24AA -- "  24AA "TYPE
    CR ."  12AA -- " 12AA "TYPE ."          25AA -- "  25AA "TYPE
    CR ."  13AA -- " 13AA "TYPE ."          EXIT ROUTINE > 0 "
    CR CR ." AMINO ACID NUMBER > " #INPUT DUP AA# :=
    0 =
```

```
    IF
    ELSE
      CR CR ." AMINO ACID NAME > " "INPUT
      AA# "." 32 "COMPRESS " AA" "CAT EXEC.NAME ":=
      EXEC.NAME "EXEC
      ":=
      . MYSELF
    THEN

;

\ Select 3 letter code AA label.
: GET.AACODE

AA# "." 32 "COMPRESS " AA" "CAT EXEC.NAME ":=
   EXEC.NAME "EXEC

;

\ Set raw data array parameters for fits.
: SET.SEQUENCE.PARAMETERS

CR ." TOTAL NUMBER OF CYCLES > " #INPUT #CYCLES :=
   CR ." FIT IN ONE (1) OR TWO (2) SEGMENTS > " #INPUT DUP FITFLAG :=
   1 =
   IF
      #CYCLES INDEX4 :=
   ELSE
      #CYCLES 2 / 5 + INDEX4 :=
   THEN
   0 INDEX3 :=
   INDEX4 12 / FIX DUP AA.POLY.TIMES := 1 + AA.FIT.TIMES :=
   AA.POLY.TIMES 2 <
   IF 2 AA.POLY.TIMES := THEN
   AA.POLY.TIMES 6 >=
   IF 6 AA.POLY.TIMES := 6 AA.FIT.TIMES := THEN
   #CYCLES 15 / FIX DUP LAG.POLY.TIMES :=
   0 =
   IF 1 LAG.POLY.TIMES := THEN
   CR ." NUMBER OF AMINO ACIDS > " #INPUT #AAS :=
   CR ." PROTEIN NAME - AMOUNT > " "INPUT PROTEIN.NAME ":=

;

\ Change default fit parameters.
: SET.FIT.PARAMETERS

CR ." NUMBER OF FIT ITERATIONS (" AA.FIT.TIMES .." ) > "
   #INPUT AA.FIT.TIMES :=
   CR ." DEGREE OF AA POLYNOMIAL FIT (" AA.POLY.TIMES .." ) > "
   #INPUT AA.POLY.TIMES :=
   CR ." DEGREE OF LAG POLYNOMIAL FIT (" LAG.POLY.TIMES .." ) > "
   #INPUT LAG.POLY.TIMES :=
   CR ." HIGH DISCARD LEVEL (" AA.MAX.DISCARD .." ) > "
   #INPUT AA.MAX.DISCARD :=
   CR ." LOW DISCARD LEVEL (" AA.MIN.DISCARD .." ) > "
   #INPUT AA.MIN.DISCARD :=
\ Calculate background vs cycle for each AA in raw data set.
\ Generate AA.BACK.DATA values.
```

\ Generate AA.STD.DEV values from linear polynomial fit to AA.BACK.DATA values.
\ Normalize AA.BACK.DATA values using AA.STD.DEV array values.
\ Generate display plots of raw and fitted AA values vs cycle.
: AA.BACK.FIT

GRAPHICS.DISPLAY
  DISPLAY.COLORS
  FITFLAG 0 DO

AAS 1 + 1 DO \ Loop will repeat for each AA.

STACK.CLEAR
      INDEX4 DUP DUP
      POINTS1 := POINTS2 :=
      REAL RAMP
      AA.FIT.INDEX SUB[ 1 , INDEX4 ] := \ Initialize fit array index.
      INDEX4 0 DO \ Fill fit array with AA values.

AA.RAW.DATA [ J I INDEX3 + #AAS * + ] \ Get AA value from AA.RAW.DATA.
        AA.FIT.DATA [ I 1 + ] := \ Load into fit array.

LOOP
      AA.FIT.DATA SUB[ 1 , INDEX4 ]
      AA.WORK.DATA SUB[ 1 , INDEX4 ] := \ Make working copy of fit array.
      0. STD.DEV.WORK := \ Initialize working standard deviation array.
      AA.FIT.TIMES 0 DO \ Loop through iterations of polynomial fit.

STACK.CLEAR
        STD.DEV.WORK [ 10 ] 0. > \ Check for fit stop flag.
        IF LEAVE THEN \ Leave loop after this fit iteration if stop flag was set
           \ in previous iteration.
        AA.FIT.INDEX SUB[ 1 , POINTS1 ] \ X index values.
        AA.FIT.DATA SUB[ 1 , POINTS1 ] \ Y raw values.
        AA.POLY.TIMES LEASTSQ.POLY.FIT \ Least squares polynomial fit.
        INDEX4 REAL RAMP SWAP POLY[X] DUP \ Generate Y fit values
           \ over entire range of cycles.
        AA.POLY.DATA SUB[ 1 , INDEX4 ] := \ Make copy of fit values.
        AA.FIT.INDEX SUB[ 1 , POINTS1 ] \ Select fit values at cycles
        LOOKUP \ with acceptable data points.
        AA.FIT.DATA SUB[ 1 , POINTS1 ] \ Calculate residuals between
        SWAP - DUP \ fit and raw data.
        AA.RESIDS SUB[ 1 , POINTS1 ] := \ Make copy of residuals.
        VARIANCE SQRT DUP DUP \ Calculate standard deviation.
        AA.STD.DEV := \ Load value into AA.STD.DEV.
        CR . \ Display value on monitor.
        STD.DEV.WORK [ I 1 + ] := \ Load value into STD.DEV.WORK.
        I 0 > \ Is this other than first fit?
        IF \ If so, test for stop condition by calculating ratio
           \ between standard deviation for this and previous fit.
          STD.DEV.WORK [ I 1 + ] 2 * STD.DEV.WORK [ I ] >
          IF \ If ratio is < 2 set stop flag.
            1. STD.DEV.WORK [ 10 ] :=
          THEN
        THEN
        I 0 = \ Is this first iteration?
        IF \ If so, lower acceptable raw values will be within
           \ .2 x AA.MIN.DISCARD standard deviation units of fit.
          AA.RESIDS SUB[ 1 , POINTS1 ] AA.MIN.DISCARD 5. / NEG *
        ELSE \ If not, lower acceptable raw values will be within

```
              \ AA.MIN.DISCARD standard deviation units of fit.
    AA.RESIDS SUB[ 1 , POINTS1 ] AA.MIN.DISCARD NEG *
THEN
AA.STD.DEV [<] \ Find lower acceptable raw values.
AA.RESIDS SUB[ 1 , POINTS1 ] AA.MAX.DISCARD *
AA.STD.DEV [<] \ Find upper acceptable raw values.
MIN DUP \ Find lower AND upper acceptable raw values.
[ ]SUM POINTS2 := \ Count them and set subarray index.
TRUE.INDICES \ Use indices of acceptable raw values
AA.FIT.INDEX SUB[ 1 , POINTS1 ] \ to find corresponding
SWAP LOOKUP DUP \ fit array index values.
AA.FIT.INDEX SUB[ 1 , POINTS2 ] := \ Reset X values for next iteration.
AA.WORK.DATA SUB[ 1 , INDEX4 ] \ Use reset X values to
SWAP LOOKUP \ select new Y values.
AA.FIT.DATA SUB[ 1 , POINTS2 ] := \ Reset Y values for next iteration.
POINTS2
POINTS1 := \ Reset subarray index.

LOOP
COLOR2 COLOR
INDEX4 REAL RAMP INDEX3 +
AA.WORK.DATA SUB[ 1 , INDEX4 ]
XY.AUTO.PLOT \ Plot raw data.
COLOR3 COLOR
INDEX4 REAL RAMP INDEX3 +
AA.POLY.DATA SUB[ 1 , INDEX4 ]
XY.DATA.PLOT \ Plot fit data.
AA.WORK.DATA SUB[ 1 , INDEX4 ] \ Take work array data.
AA.POLY.DATA SUB[ 1 , INDEX4 ] - DUP \ Subtract fit array data.
AA.WORK.DATA SUB[ 1 , INDEX4 ] := \ Make background subtracted
AA.FIT.DATA SUB[ 1 , INDEX4 ] := \ work and fit array data sets.
STACK.CLEAR
INDEX4 DUP DUP \ Prepare to calculate standard deviation of linear
POINTS1 := POINTS2 := \ fit to background corrected data.
REAL RAMP
AA.FIT.INDEX SUB[ 1 , INDEX4 ] := \ Initialize fit array index.
AA.POLY.TIMES 2 =
IF
  2
ELSE
  3
THEN
0 DO \ Loop through 2 or 3 iterations of polynomial fit.

STACK.CLEAR
  AA.FIT.INDEX SUB[ 1 , POINTS1 ] \ X index values.
  AA.FIT.DATA SUB[ 1 , POINTS1 ] \ Y raw values.
  1 LEASTSQ.POLY.FIT \ Least squares polynomial fit.
  INDEX4 REAL RAMP SWAP POLY[X] DUP \ Generate Y fit values over
     \ entire range of cycles.
  AA.POLY.DATA SUB[ 1 , INDEX4 ] := \ Make copy of fit values.
  AA.FIT.INDEX SUB[ 1 , POINTS1 ] \ Select fit values at cycles
  LOOKUP \ with acceptable data points.
  AA.FIT.DATA SUB[ 1 , POINTS1 ] \ Calculate residuals between
  SWAP - DUP                     \ fit and raw data.
  AA.RESIDS SUB[ 1 , POINTS1 ] := \ Make copy of residuals.
  VARIANCE SQRT DUP \ Calculate standard deviation.
  AA.STD.DEV := \ Load value into AA.STD.DEV.
  CR . \ Display value on monitor.
```

```
    I 0 = \ Is this first iteration?
    IF \ If so, lower acceptable raw values will be within
        \ .4 x AA.MIN.DISCARD standard deviation units of fit.
      AA.RESIDS SUB[ 1 , POINTS1 ] AA.MIN.DISCARD 2.5 / NEG *
    ELSE \ If not, lower acceptable raw values will be within
        \ AA.MIN.DISCARD standard deviation units of fit.
      AA.RESIDS SUB[ 1 , POINTS1 ] AA.MIN.DISCARD NEG *
    THEN
    AA.STD.DEV [<] \ Find lower acceptable raw values.
    AA.RESIDS SUB[ 1 , POINTS1 ] AA.MAX.DISCARD *
    AA.STD.DEV [<] \ Find upper acceptable raw values.
    MIN DUP \ Find lower AND upper acceptable raw values.
    [ ]SUM POINTS2 := \ Count them and set subarray index.
    TRUE.INDICES \ Use indices of acceptable raw
    AA.FIT.INDEX SUB[ 1 , POINTS1 ] \ values to find corresponding
    SWAP LOOKUP DUP \ fit array index values.
    AA.FIT.INDEX SUB[ 1 , POINTS2 ] := \ Reset X values for next iteration.
    AA.WORK.DATA SUB[ 1 , INDEX4 ] \ Use reset X values to
    SWAP LOOKUP \ select new Y values.
    AA.FIT.DATA SUB[ 1 , POINTS2 ] := \ Reset Y values for next iteration.
    POINTS2
    POINTS1 := \ Reset subarray index.

LOOP
  AA.FIT.DATA SUB[ 1 , POINTS2 ] \ Calculate standard deviation
  VARIANCE SQRT \ of acceptable data points.
  DUP AA.STD.DEV :=
  INDEX3 0 =
  IF
    0 M :=
    AA.STD.DEV1 [ I ] := \ Load value into AA.STD.DEV1.
  ELSE
    5 M :=
    AA.STD.DEV2 [ I ] := \ Load value into AA.STD.DEV2.
  THEN
  INDEX4 M DO \ Load background corrected-normalized data into AA.BACK.DATA.

AA.WORK.DATA [ I 1 + ] \ Get background corrected data value.
    AA.STD.DEV / \ Divide by standard deviation.
    AA.BACK.DATA [ J I INDEX3 + #AAS * + ] := \ Load into AA.BACK.DATA.
  LOOP

LOOP
  INDEX4 10 - INDEX3 :=
  #CYCLES INDEX4 - 10 + INDEX4 :=

LOOP

;

\ Generates best guess sequence call from AA.BACK.DATA.
\ Uses sequence call to fill BETA.VAL with raw lag values.
\ Fits BETA.VAL to polynomial to generate fit lag values.
: CALCULATE.LAG STACK.CLEAR
  LAGCYCLES CYCLE# + #CYCLES > \ Set start/stop limits for sequence
  IF #CYCLES CYCLE# - LAGCYCLES := THEN \ call/lag calculation loop.
  LAGCYCLES CYCLE# + CYCLE# DO \ Generate raw lag data array.
```

```
    #AAS 1 + 1 DO \ Get values for every AA in an individual cycle.

AA.LAG.DATA [ I #AAS J 1 - * + ] \ Get AA value from data array.
        CYCLE.VAL [ I ] := \ Load into CYCLE.VAL.

LOOP
    CYCLE.VAL SUB[ 1 , #AAS ]
    SORT&INDEX \ Sort CYCLE.VAL values.
    [ #AAS ] AA# := \ Get number of AA with highest value.
    [ #AAS ] \ Get value of this AA.
    AA.BACK.DATA [ AA# #AAS I * + ] \ Get value of this AA in next cycle.
    SWAP / \ Take ratio (Yn+1/Yn).
    BETA.VAL [ I ] := \ Load into raw lag data array.

LOOP
    #CYCLES 1 - REAL RAMP \ X index values.
    BETA.VAL SUB[ 1 , #CYCLES 1 - ] \ Y raw lag values.
    LAG.POLY.TIMES LEASTSQ.POLY.FIT \ Least squares polynomial fit.
    #CYCLES 1 - REAL RAMP
    SWAP
    POLY[X] DUP \ Generate fitted lag values.
    BETA.FIT SUB[ 1 , #CYCLES 1 - ] := \ Make copy of fitted lag values.
    BETA.VAL SUB[ 1 , #CYCLES 1 - ] \ Calculate standard deviation
    - VARIANCE SQRT \ between raw and fitted lag values.
    STD.DEV := \ Make copy of standard deviation.
    BETA.VAL SUB[ 1 , #CYCLES 1 - ] \ Make working copy of fitted lag values.
    BETA.WORK SUB[ 1 , #CYCLES 1 - ] :=
    #CYCLES 1 DO \ Find and mark unacceptable raw lag values.

BETA.FIT [ I ] \ Get fitted lag value.
        BETA.VAL [ I ] \ Get raw lag value.
        - DUP * SQRT \ Calculate absolute value of difference.
        STD.DEV > \ Is difference larger than fit standard deviation?
        IF \ If so,
            0. BETA.WORK [ I ] := \ set raw lag value to 0.
        THEN LOOP
    BETA.WORK SUB[ 1 , #CYCLES 1 - ] 0. [<>] \ Find indices of non-zero values
    TRUE.INDICES \ to serve as new X axis index.
    DUP
    BETA.WORK SUB[ 1 , #CYCLES 1 - ] \ Find non-zero values to serve
    SWAP LOOKUP \ as new Y lag values.
    LAG.POLY.TIMES LEASTSQ.POLY.FIT \ Repeat least squares fit.
    #CYCLES 1 - REAL RAMP
    SWAP
    POLY[X] \ Generate revised fitted lag values.
    BETA.FIT SUB[ 1 , #CYCLES 1 - ] := \ Make copy of these values.

;

\ For current cycle (n), use fitted lag value from BETA.FIT (cycle n+1) to
\ calculate lag values for subsequent cycles (n+i).
\ For current cycle, call sequence; use lag to assist call.
\ Use actual value of sequence AA and theoretical lag values to correct
\ data array (cycles n through n+i).
: CORRECT.LAG

STACK.CLEAR
```

```
1 LAGCYCLES := \ Initialize counter.
0. BETA.DATA := \ Initialize theoretical lag ratios.
BETA.FIT [ CYCLE# ] DUP DUP
BETA.POINT :=
BETA.DATA [ 1 ] := \ Store (Yn+1/Yn).
CYCLE# /
BETA := \ Calculate (Yn+1/Yn/n).
CYCLE# #CYCLES 1 - < \ Check to see if there are more cycles in data array.
IF \ If so, calculate (Yn+i/Yn).
   11 2 DO I LAGCYCLES :=
      CYCLE# I + 1 - I / BETA * BETA.POINT * DUP \ Calculate next (Yn+i/Yn).
      BETA.POINT :=
      .01 < \ Is this value less than .01?
      IF LEAVE THEN \ If so, exit loop after this value.
      BETA.POINT
      BETA.DATA [ I ] := \ Store (Yn+i/Yn).
      I CYCLE# 1 + + #CYCLES > \ Check to see if there are more cycles.
      IF LEAVE THEN \ If not, exit loop.

LOOP
THEN
#AAS 1 + 1 DO \ Fill CYCLE.VAL array with AA values for current cycle.

AA.LAG.DATA [ I #AAS CYCLE# 1 - * + ] \ Get AA value.
   CYCLE.VAL [ I ] := \ Load into CYCLE.VAL array.

LOOP
CYCLE.VAL SUB[ 1 , #AAS ]
SORT&INDEX \ Sort CYCLE.VAL values.
SUB[ #AAS 2 - , 3 ] CYCLE.VAL SUB[ 7 , 3 ] := \ Select 3 largest
SUB[ #AAS 2 - , 3 ] CYCLE.VAL SUB[ 4 , 3 ] := \ CYCLE.VAL values.
CYCLE.VAL [ 6 ] CYCLE.VAL [ 5 ] / 3 < \ Is largest value < 3 times
   \ size of next largest value?
IF \ If so, check to see if addition of lag will affect sequence call.
   CYCLE.VAL SUB[ 4 , 3 ] CYCLE.VAL SUB[ 1 , 3 ] := \ Make working
      \ copy of 3 largest values.
   3 1 DO \ Test effect of lag correction on 3 largest values.

11 1 DO

CYCLE.VAL [ J 3 + ] BETA.DATA [ I ] * \ Calculate theoretical (Yn+i).
         BETA.POINT := \ Make copy of this value.
         CYCLE.VAL [ J 6 + ] #AAS CYCLE# 1 - I + * + \ Calculate array index
            \ of (Yn).
         INDEX2 := \ Make copy of this value.
         AA.LAG.DATA [ INDEX2 ] 0. >= \ Is actual (Yn+i)  0?
         IF \ If so, make correction.
         AA.LAG.DATA [ INDEX2 ] BETA.POINT > \ Is actual (Yn+i) >
            \ theoretical (Yn+i)?
         IF \ If so,
            CYCLE.VAL [ J ] BETA.POINT + \ add theoretical
            CYCLE.VAL [ J ] := \ (Yn+i) to (Yn).
            ELSE \ If not,
               CYCLE.VAL [ J ] AA.LAG.DATA [ INDEX2 ] + \ add
               CYCLE.VAL [ J ] := \ actual (Yn+i).
            THEN
         THEN
```

```
        BETA.DATA [ I 1 + ] .01 < \ Is next fitted lag value< .01?
        IF LEAVE THEN \ If so, exit loop.

LOOP

LOOP
    CYCLE.VAL SUB[ 1 , 3 ]
    SORT&INDEX \ Sort lag corrected AA values.
    [ 3 ] INDEX1 := \ Pick largest of these.
    CYCLE.VAL [ INDEX1 6 + ] AA# := \ Set AA number.
    CYCLE.VAL [ INDEX1 3 + ] AA.VAL := \ Set AA acid value.
  ELSE \ If largest is clearly largest, call it the sequence residue.
    CYCLE.VAL [ 9 ] AA# := \ Set AA number.
    CYCLE.VAL [ 6 ] AA.VAL := \ Set AA value.
  THEN
  11 1 DO \ Correct AA.LAG.DATA array values.

AA.VAL BETA.DATA [ I ] * \ Calculate theoretical (Yn+i).
    BETA.POINT := \ Make copy of this value.
    AA# #AAS CYCLE# 1 - * + DUP \ Calculate array index of (Yn).
    INDEX1 := \ Make copy of this value.
    #AAS I * + \ Calculate array index of (Yn+i).
    INDEX2 := \ Make copy of this value.
    AA.LAG.DATA [ INDEX2 ] 0.0001 >= \ Is actual (Yn+i) non-negative?

IF \ If so, make correction.
      AA.LAG.DATA [ INDEX2 ] BETA.POINT > \ Is actual (Yn+i) >
        \ theoretical (Yn+i)?
      IF \ If so,
        AA.LAG.DATA [ INDEX2 ] BETA.POINT - \ subtract theoretical (Yn+i)
        AA.LAG.DATA [ INDEX2 ] := \ from actual (Yn+i) and
        AA.LAG.DATA [ INDEX1 ] BETA.POINT + \ add theoretical (Yn+i) to
        AA.LAG.DATA [ INDEX1 ] := \ actual (Yn).
      ELSE AA.LAG.DATA [ INDEX1 ] AA.LAG.DATA [ INDEX2 ] + \ If not, add
        AA.LAG.DATA [ INDEX1 ] := \ actual (Yn+i) to (Yn) and
        0.0001 AA.LAG.DATA [ INDEX2 ] := \ set actual (Yn+i) to 0.
      THEN
    THEN
    BETA.DATA [ I 1 + ] .01 < \ Is next fitted lag value less than .01?
    IF LEAVE THEN \ If so, exit loop.

LOOP

;

\ Generates lag/background corrected data array.
: REMOVE.LAG

NORMAL.DISPLAY
  STACK.CLEAR
  AA.BACK.DATA SUB[ 1 , #CYCLES #AAS * ] \ Get AA.BACK.DATA.
  AA.LAG.DATA SUB[ 1 , #CYCLES #AAS * ] := \ Set working copy of AA.LAG.DATA
    \ that will be corrected one cycle at a time.
  #CYCLES 1 -
  LAGCYCLES := \ Initialize upper limit for CALCULATE.LAG loop.
  #CYCLES 1 DO I . \ Display cycle number on monitor.
    I CYCLE# := \ Set current cycle for lag correction.
    CALCULATE.LAG \ Calculate fitted lag values for this iteration.
```

```
          CORRECT.LAG \ Correct AA.LAG.DATA for current cycle.

LOOP

;

\ Correct AA.RAW.DATA array for HPLC sampling errors.
  : INJECT.CORRECT

NORMAL.DISPLAY
     #CYCLES 0 DO

STACK.CLEAR
        #AAS 1 + 1 DO \ Fill CYCLE.VAL with AA values for individual cycle.

AA.LAG.DATA [ I J 19 * + ] \ Get AA value from AA.LAG.DATA.
           CYCLE.VAL [ I ] := \ Load into CYCLE.VAL.

LOOP
        CYCLE.VAL SUB[ 1 , #AAS ]
        SORT \ Sort CYCLE.VAL.
        SUB[ 1 , #AAS 2 - ] \ Calculate average of all but
        [ ]SUM #AAS 2 - / DUP \ 2 highest AA values in CYCLE.VAL.
        INJECT.DEV := CR . \ Make copy of this value and display on monitor.
        #AAS 1 + 1 DO \ Correct each AA value in current cycle in AA.RAW.DATA
           \ based on this calculated CYCLE.VAL average.  New AA.RAW.DATA
           \ value is (old value - [average x AA standard deviation]).
           AA.RAW.DATA [ I J #AAS * + ] INJECT.DEV
           FITFLAG 2 = J #CYCLES 2 / FIX > AND
           IF
              AA.STD.DEV2 [ I ]
           ELSE
              AA.STD.DEV1 [ I ]
           THEN
           * - AA.RAW.DATA [ I J #AAS * + ] :=

LOOP

LOOP

;

\ Select AA data array for calculations.
  : SET.AA.DATA.TYPE

NORMAL.DISPLAY
     CR ." 1 -- RAW DATA"
     CR ." 2 -- BACKGROUND CORRECTED DATA"
     CR ." 3 -- LAG/BACKGROUND CORRECTED DATA"
     CR ." 4 -- RAW PEAK POSITION DATA"
     CR CR ." CHOICE > " #INPUT TYPE# :=

;

\ Set AA data for calculations.
  : USE.DATA.TYPE

TYPE#
  .  CASE
```

```
    1 OF AA.RAW.DATA ENDOF
    2 OF AA.BACK.DATA ENDOF
    3 OF AA.LAG.DATA ENDOF
    4 OF AA.POS.DATA ENDOF
  ENDCASE

;

\ Calls sequence use choice of AA data arrays.
\ Generates arrays of AA numbers and values from sequence calls.
\ Outputs sequence to choice of monitor and/or line printer.
: CALL.SEQUENCE STACK.CLEAR
  SET.AA.DATA.TYPE \ Select AA data array.
  SET.PRINTFLAG CR \ Select output mode.
  PROTEIN.NAME "TYPE CR CR
  1 INDEX1 := \ Initializes monitor full? counter.
  #CYCLES 1 + 1 DO

#AAS 1 + 1 DO \ Fill CYCLE.VAL with AA values from individual cycle.

USE.DATA.TYPE \ Get AA value from specified data array.
      [ I #AAS J 1 - * + ]
      CYCLE.VAL [ I ] := \ Load into CYCLE.VAL.

LOOP
    CYCLE.VAL SUB[ 1 , #AAS ]
    SORT&INDEX \ Sort CYCLE.VAL values.
    [ #AAS ] SEQUENCE# [ I ] := \ Load number of highest AA in SEQUENCE#.
    [ #AAS ] SEQUENCE.VAL [ I ] := \ Load value of highest AA in SEQUENCE.VAL.
    SEQUENCE# [ I ] AA# :=
    GET.AANAME \ Get name of AA.
    3 0 FIX.FORMAT I "." "TYPE \ Print cycle number,
    9 1 FIX.FORMAT SEQUENCE.VAL [ I ] "." "TYPE \ AA value,
    ."     " AANAME "TYPE CR \ and AA name.
    INDEX1 1 + INDEX1 := \ Increment monitor full? counter.
    INDEX1 24 > \ Is monitor full?
    IF \ If so,
      1 INDEX1 := \ reset counter,
      PRINTFLAG 0 = \ and if output is to monitor only
      IF \ pause to allow viewing.
        ." HIT ANY KEY TO CONTINUE"
        PCKEY ?DROP DROP
        NORMAL.DISPLAY
      THEN
    THEN LOOP
  PRINTFLAG 0 =
  -1 2 FIX.FORMAT
  IF \ If output is to monitor only,
    CR ." HIT ANY KEY TO CONTINUE" \ pause to allow viewing sequence,
    PCKEY ?DROP DROP
  ELSE
    12 EMIT \ else advance paper and return to monitor only output.
    CONSOLE
  THEN

;
```

```
\ Set plot labels.
: SET.LABELS

TYPE#
  CASE
    1 OF " (PEAK" LINE2.LABEL ":=
         "  AMOUNT" LINE3.LABEL ":=
         "   pmol)" LINE4.LABEL ":=
         " RAW DATA " TYPE.NAME ":= ENDOF
    2 OF " (STD." LINE2.LABEL ":=
         "  DEV." LINE3.LABEL ":=
         "  UNITS)" LINE4.LABEL ":=
         " BACKGROUND CORRECTED DATA" TYPE.NAME ":= ENDOF
    3 OF " (STD." LINE2.LABEL ":=
         "  DEV." LINE3.LABEL ":=
         "  UNITS)" LINE4.LABEL ":=
         " LAG/BACKGROUND CORRECTED DATA" TYPE.NAME ":= ENDOF
  ENDCASE

;

\ Plot labels.
: PLOT.LABELS

SET.LABELS
  .01 .55 POSITION " AMOUNT" LABEL
  .01 .5 POSITION LINE2.LABEL LABEL
  .01 .475 POSITION LINE3.LABEL LABEL
  .01 .45 POSITION LINE4.LABEL LABEL
  .5 .96 POSITION PROTEIN.NAME LABEL

;

\ Plot AA values vs. cycle - core routine.
: PLOT.AA.DATA.CORE

STACK.CLEAR
  VUPORT.CLEAR
  TYPE# 1 =
  IF
     SV [ AA# ] AA.VAL :=
  ELSE
     1 AA.VAL :=
  THEN
  #CYCLES 0 DO

USE.DATA.TYPE
     [ AA# I #AAS * + ]
     DUP
     AA.VAL / AA.WORK.DATA [ I 1 + ] :=
     AA.BACK.DATA [ AA# I #AAS * + ]
     FITFLAG 2 = I #CYCLES 2 / FIX > AND
     IF
        AA.STD.DEV2 [ AA# ]
     ELSE
        AA.STD.DEV1 [ AA# ]
     THEN
     * -
     AA.VAL / AA.POLY.DATA [ I 1 + ] :=
```

```
     LOOP
  GET.AANAME
  #CYCLES REAL RAMP
  AA.WORK.DATA SUB[ 1 , #CYCLES ]
  [ ]MIN DUP
  0. <
  IF
     NEG AA.WORK.DATA SUB[ 1 , #CYCLES ] +
  ELSE
     DROP AA.WORK.DATA SUB[ 1 , #CYCLES ]
  THEN
  XY.DATA.FIT
  XY.AXIS.PLOT
  COLOR3 COLOR
  " o" SOLID&SYMBOL
  AA.WORK.DATA SUB[ 1 , #CYCLES ]
  Y.DATA.PLOT
  SOLID
  TYPE# 1 =
  IF
     COLOR2 COLOR
     AA.POLY.DATA SUB[ 1 , #CYCLES ]
     Y.DATA.PLOT
  THEN
  HPFLAG 1 =
  IF
     COLOR1 COLOR
     NORMAL.COORDS
     .02 .06 POSITION AYMAX "." " FULL SCALE" "CAT LABEL
     .5 .06 POSITION " CYCLE" LABEL
     PLOT.LABELS
     .5 .9 POSITION AANAME LABEL
     TYPE# 1 =
     IF
        TYPE.NAME " WITH CALCULATED BACKGROUND " "CAT TYPE.NAME ":=
     THEN
     .5 .84 POSITION TYPE.NAME LABEL
  ELSE
     SCREEN.CLEAR
     ." AMINO ACID"
     CR ." NUMBER >" AA# .
     CR CR AYMAX .
     CR ." FULL"
     CR ." SCALE"
  THEN

;

\ Plot AA values vs. cycle.
: PLOT.AA.DATA

CR ." NUMBER OF CYCLES > " #INPUT #CYCLES := CR
  SET.AA.DATA.TYPE
  SET.HPFLAG
  CR CR ." AMINO ACID"
  CR ." NUMBER > " #INPUT AA# :=
  100 0 DO

PLOT.AA.DATA.CORE
```

```
    CR CR CR ." AMINO ACID"
    CR ." NUMBER > " #INPUT DUP AA# :=
    0 =
    IF
      LEAVE
    ELSE
      GET.HPFLAG
    THEN

LOOP

;

\ Bar plot AA values for 1 or 2 cycles - core routine.
: BAR.PLOT.CYCLE.VAL.CORE STACK.CLEAR
  VUPORT.CLEAR
  CR ." AUTO (0) OR"
  CR ." FIXED (1)"
  CR ." SCALE > " #INPUT DUP SCALEFLAG :=
  1 =
  IF
    CR CR ." CYCLE SCALE > " #INPUT CYCLE.SCALE :=
  THEN
  HPFLAG 1 =
  IF
    HORIZONTAL NO.LABELS
    INDEX1 2 =
    IF
      " CYCLES " CYCLE# 1 - "." "CAT " -" "CAT CYCLE# "." "CAT
      CYCLE.NAME ":=
    ELSE
      " CYCLE " CYCLE# "." "CAT
      CYCLE.NAME ":=
    THEN
  THEN
  SCALEFLAG 1 =
  IF
    60 REAL RAMP DUP
    1 - 60 / CYCLE.SCALE *
    XY.DATA.FIT
    XY.AXIS.PLOT
  THEN
  COLOR2 COLOR
  2 0 DO

#AAS 1 + 1 DO

USE.DATA.TYPE
    [ I CYCLE# INDEX1 - #AAS * + ]
    TYPE# 1 =
    IF
      SV [ I ] /
    THEN
    CYCLE.VAL [ I ] :=

LOOP
  #AAS REAL RAMP 3 * 2 I - -
```

```
        CYCLE.VAL SUB[ I , #AAS ]
        SCALEFLAG 1 =
        IF
           XY.DATA.BAR
        ELSE
           I 0 =
           IF
              XY.AUTO.BAR
           ELSE
              XY.DATA.BAR
           THEN
        THEN
        INDEX1 2 =
        IF
           CYCLE# 1 + CYCLE# :=
           COLOR3 COLOR
        ELSE
           LEAVE
        THEN

LOOP
HPFLAG 1 =
IF
   COLOR1 COLOR
   NORMAL.COORDS
   .162 .1 POSITION 1AA LABEL
   .202 .1 POSITION 2AA LABEL
   .242 .1 POSITION 3AA LABEL
   .282 .1 POSITION 4AA LABEL
   .322 .1 POSITION 5AA LABEL
   .362 .1 POSITION 6AA LABEL
   .402 .1 POSITION 7AA LABEL
   .442 .1 POSITION 8AA LABEL
   .482 .1 POSITION 9AA LABEL
   .522 .1 POSITION 10AA LABEL
   .562 .1 POSITION 11AA LABEL
   .602 .1 POSITION 12AA LABEL
   .642 .1 POSITION 13AA LABEL
   .682 .1 POSITION 14AA LABEL
   .722 .1 POSITION 15AA LABEL
   .762 .1 POSITION 16AA LABEL
   .802 .1 POSITION 17AA LABEL
   .842 .1 POSITION 18AA LABEL
   .882 .1 POSITION 19AA LABEL
   #AAS 20 =
   IF
      .922 .1 POSITION 20AA LABEL
   THEN
   PLOT.LABELS
   .5 .9 POSITION CYCLE.NAME LABEL
   .5 .84 POSITION TYPE.NAME LABEL
   .02 .06 POSITION AYMAX "." " FULL SCALE" "CAT LABEL
ELSE
   SCREEN.CLEAR
   ." CYCLE"
   CR ." NUMBER >" CYCLE# .
   CR CR AYMAX .
   CR ." FULL"
   CR ." SCALE"
```

THEN

;

\ Bar plot AA values for 1 or 2 cycles.
: BAR.PLOT.CYCLE.VAL

SET.AA.DATA.TYPE
  CR ." SINGLE (1) OR DOUBLE (2) CYCLE > " #INPUT INDEX1 :=
  SET.HPFLAG
  CR CR ." CYCLE"
  CR ." NUMBER > " #INPUT CYCLE# :=
  100 0 DO

BAR.PLOT.CYCLE.VAL.CORE
    CR CR CR ." CYCLE"
    CR ." NUMBER > " #INPUT DUP CYCLE# :=
    0 =
    IF
      LEAVE
    ELSE
      GET.HPFLAG
    THEN

LOOP
  ONERR:
    BELL
    NORMAL.DISPLAY
    CR ." ERROR #:" ?ERROR# . ." DETECTED"
    CR ." FIXED PLOT SCALE MAY BE TOO LOW"
    CR ." HIT ANY KEY TO CONTINUE"
    PCKEY ?DROP DROP
    MYSELF

;

\ Plot cumulative lag vs. cycle.
: PLOT.LAG.DATA

STACK.CLEAR
  SET.HPFLAG
  #CYCLES 1 - REAL RAMP
  BETA.WORK SUB[ 1 , #CYCLES 1 - ] 100 *
  XY.DATA.FIT
  XY.AXIS.PLOT
  COLOR3 COLOR
  " *" SYMBOL
  BETA.WORK SUB[ 1 , #CYCLES 1 - ] 100 *
  Y.DATA.PLOT
  COLOR2 COLOR
  SOLID
  BETA.FIT SUB[ 1 , #CYCLES 1 - ] 100 *
  Y.DATA.PLOT
  HPFLAG 1 =
  IF
    COLOR1 COLOR
    NORMAL.COORDS
    .5 .06 POSITION " CYCLE" LABEL
    .02 .6 POSITION " LAG" LABEL

```
       .025 .55 POSITION " (%)" LABEL
       .5 .96 POSITION PROTEIN.NAME LABEL
       .5 .9 POSITION " CUMULATIVE CYCLE LAG DATA" LABEL
   THEN
   CR ." HIT ANY KEY"
   CR ." TO CONTINUE"
   PCKEY ?DROP DROP

;

\ Calculate repetitive yield for each AA with multiple cycles.
\ Display on monitor or print to line printer.
: PRINT.REP.YIELD SET.PRINTFLAG \ Set output device.
   PRINTFLAG 0 =
   IF NORMAL.DISPLAY THEN
   CR PROTEIN.NAME "TYPE CR CR
   #AAS 1 + 1 DO \ Test each amino acid for repeats calls.

STACK.CLEAR
      1 INDEX1 := \ Reset counter for number of calls.
      #CYCLES 1 + 1 DO SEQUENCE# [ I ] J = \ Does call for this cycle match loop index?
         IF \ If so,
            I AA.FIT.INDEX [ INDEX1 ] := \ record this cycle number in AA.FIT.INDEX
            SEQUENCE.VAL [ I ] AA.FIT.DATA [ INDEX1 ] := \ and record its value
               \ in AA.FIT.DATA.
            INDEX1 1 + INDEX1 := \ Increment number of calls counter.
         THEN LOOP
      INDEX1 2 > \ Were any repeats found for this amino acid?
      IF \ If so, calculate and print repetitive yield.

INDEX1 3 = \ Were only 2 calls made for this amino acid?
      IF \ If so, calculate repetitive yield by nth root.
         AA.FIT.DATA [ 2 ] AA.FIT.DATA [ 1 ] / LN \ Calculate natural log
            \ of (Yj)/(Yi).
         AA.FIT.INDEX [ 2 ] AA.FIT.INDEX [ 1 ] - / EXP 100. * \ Divide this
            \ by (j-i), take exponential, and multiply by 100 to get percent.
         REP.YIELD := \ Set repetitive yield value.
      ELSE \ If not, calculate repetitive yield by least squares.
         AA.FIT.INDEX SUB[ 1 , INDEX1 1 - ] \ Get X values.
         AA.FIT.DATA SUB[ 1 , INDEX1 1 - ] \ Get Y values.
         LEASTSQ.EXP.FIT \ Perform least squares exponential fit.
         [ 1 ] EXP 100. * \ Take exponential of slope term and multiply
            \ by 100 to get percent.
         REP.YIELD := \ Set repetitive yield value.
      THEN
      I AA# := \ Get AA number for this round.
      GET.AANAME \ Look up full AA name.
      AANAME " (" "CAT AA.RY.NAME ":= \ Add left parenthesis to name.
      INDEX1 1 DO AA.RY.NAME AA.FIT.INDEX [ I ] FIX "." "CAT AA.RY.NAME ":=
            \ Add number of called cycle to name.
         I INDEX1 1 - < \ Are there more called cycles?
         IF \ If so,
```

```
            AA.RY.NAME " ," "CAT AA.RY.NAME ":= \ add comma.
        ELSE \ If not,
            AA.RY.NAME " ) " "CAT AA.RY.NAME ":= \ add right parenthesis
        THEN LOOP
      5 1 FIX.FORMAT REP.YIELD "." "TYPE .." % " AA.RY.NAME "TYPE CR \ Print
          \ repetitive yield, AA name, and cycle numbers.
      -1 2 FIX.FORMAT
    THEN LOOP
PRINTFLAG 1 =
IF 12 EMIT THEN
CONSOLE \ Return output to monitor.
CR ." HIT ANY KEY TO CONTINUE"
PCKEY ?DROP DROP \ Pause for keyboard input.

;

\ Retrieve HPLC data from disk
: GET.CHROMATOGRAM

FILENAME DEFER> FILE.OPEN
  STDFLAG 1 =
  IF
     SET.HPLC.PARAMETERS
  THEN
  1 SUBFILE FILE>UNNAMED.ARRAY SUB[ DATA.OFFSET , PN ] RD SUB[ 1 , PN ] :=
  FILE.CLOSE
  STACK.CLEAR

;

\ House convolution routine.
: HOUSE

[ ]SIZE M := \ Get size of HPLC data array.
  N 1 + REAL RAMP \ Generate triangle array.
  N REAL RAMP REV[ 1 ]
  CATENATE
  2 ALPHA * N / N 1 + / \ Scale triangle array.
  *
  2 N * 1 + REAL RAMP DUP \ Generate square array.
  [ = ]
  2 ALPHA * N 1 + * N - N / 2 N * 1 + / \ Scale square array.
  *
  - \ Combine triangle and square arrays to make house array.
  CONV.APER \ Convolve with HPLC data array.
  SUB[ N 1 + , M ] \ Get convolved data.

;

\ House convolve raw data and store as filtered data.
: HFILTER

STACK.CLEAR
  ALPHA1 ALPHA := \ Set alpha for frequency matched filter.
  N1 N := \ Set N to match peak width.
```

```
RD SUB[ 1 , PN ] HOUSE \ House convolve RD to generate smoothed data.
DUP \ Make copy of smoothed data.
ALPHA2 ALPHA := \ Set alpha for resolution enhancement.
HOUSE \ House convolve smoothed data to generate resolution enhanced,
   \ smoothed data.
SWAP - FD SUB[ 1 , PN ] := \ Subtract smoothed data from this and load in FD.
PN 1 + 1 DO \ Chop points below LOW.THRESH (usually 0) to 0.

FD [ I ] LOW.THRESH <
  IF
    0 FD [ I ] :=
  THEN

LOOP
.5 ALPHA := \ Set alpha for simple smooth.
N1 2 / N := \ Set N to match filtered data peak widths.
FD SUB[ 1 , PN ] HOUSE \ House convolve chopped filtered data.
3. / FD SUB[ 1 , PN ] := \ Scale and load in FD.
0. FD SUB[ 1 , N1 2 * ] := \ Set beginning points to 0.
0. FD SUB[ PN N1 2 * 1 - - , N1 2 * ] := \ Set end points to 0.

;

\ House convolve raw data to remove high frequency noise.
: HSMOOTH
   STACK.CLEAR
   ALPHA1 ALPHA := \ Set alpha for frequency matched filter.
   N1 N := \ Set N to match peak width.
   RD SUB[ 1 , PN ] HOUSE \ House convolve RD to generate smoothed data.
   FD SUB[ 1 , PN ] := \ Load in FD.

;

\ Set data maxima for HPLC plots.
: SET.PLOT.SCALE

-1 5 FIX.FORMAT
   CR CR ." CURRENT SCALE MAXIMUM FOR RAW DATA PLOT IS" RDPLOT.MAX .
   CR ." CURRENT SCALE MAXIMUM FOR FILTERED DATA PLOT IS" FDPLOT.MAX .
   CR CR ." DO YOU WANT TO CHANGE PLOT SCALES (Y) > " "INPUT
   " Y" "=
   IF
     CR ." ENTER RAW DATA SCALE MAXIMUM > " #INPUT RDPLOT.MAX :=
     CR ." ENTER FILTERED DATA SCALE MAXIMUM > " #INPUT FDPLOT.MAX :=
   THEN
   -1 2 FIX.FORMAT

;

\ Locate peaks in filtered data by looking for local maxima.
: FIND.PEAKS

0 PP := \ Initialize peak position array.
   0. PV := \ Initialize peak value array.
   0 M := \ Initialize number of peaks counter.
   INDEX3 1 DO \ Search from first to last data point in search window.

FD [ INDEX1 1 + ] FD [ INDEX1 ] > \ Is n+1 point > n point?
     IF \ If so, this signals start of peak.
```

```
        INDEX1 1 + INDEX2 := \ Set start of peak.
        40 1 DO \ Initiate search for top of peak.

1 INDEX1 + INDEX1 := \ Increment n counter
           INDEX1 INDEX3 >= \ Is n last point in search window?
           IF \ If so,
            LEAVE \ leave routine.
           ELSE
             FD [ INDEX1 1 + ] FD [ INDEX1 ] < \ Is n+1 point < n point?
             IF \ If so, n point is top of peak so:
               M 1 + M := \ Increment number of peaks counter.
               INDEX1 PP [ M ] := \ Load n in PP.
               40 1 DO \ Search for end of peak.

INDEX1 1 + INDEX1 := \ Increment n counter.
                  INDEX1 INDEX3 >= \ Is n last point in search window?
                  IF \ If so, integrate peak and store in PV.
                     FD SUB[ INDEX2 , INDEX1 INDEX2 - 1 + ] []SUM PV [ M ] :=
                     LEAVE
                  ELSE \ Check for peak end.
                     FD [ INDEX1 1 + ] FD [ INDEX1 ] > \ Is n+1 point > n point
                     FD [ INDEX1 1 + ] 0. = OR \ or equal to 0?
                     IF \ If so, then n was end of peak so integrate and store in PV.
                        FD SUB[ INDEX2 , INDEX1 INDEX2 - 1 + ] []SUM PV [ M ] :=
                        1. PV [ M 1 + ] := \ Store dummy value in PV as peak found fla
                        INDEX1 1 - INDEX1 :=
                        LEAVE \ Start looking for next peak.
                     THEN
                  THEN LOOP
               PV [ M 1 + ] 1. = \ Was peak found?
               IF LEAVE THEN \ If so, look for next peak.
             THEN
             INDEX1 INDEX3 >= \ If n was not top of peak, is n past last point
                \ in search window?
             IF LEAVE THEN \ If so, exit peak top search loop.
           THEN LOOP
      ELSE \ If n+1 is not start of peak,
        INDEX1 1 + INDEX1 := \ increment n counter.
      THEN
      INDEX1 INDEX3 >= \ Is n past last point in search window?
      IF LEAVE THEN \ If so, exit peak search loop.

LOOP \ If not go to next point in search window.

;

\ Locate reference peak position and determine shift from its standard position.
: GET.SHIFT STACK.CLEAR
  N1 7 * 1 + INDEX1 + INDEX3 := \ Set last point in peak search window equal
     \ to first point + 43 seconds of points.
  FIND.PEAKS \ Locate peaks in reference peak window.
  M 1 > \ Were multiple peaks found?
  IF \ If so,
```

```
    PV SUB[ 1 , M ] SORT&INDEX \ sort peak values,
    [ M ] M := \ choose largest peak,
    PP [ M ] \ and get its position.
  ELSE \ If not,
    PP [ 1 ] \ get position of the single peak.
  THEN

;

\ Get HPLC AA peak values and positions from CYCLE.VAL and CYCLE.POS and load
\ them into AA.RAW.DATA and AA.POS.DATA.
: SET.PEAKS CYCLE.VAL SUB[ 1 , #AAS ] \ Get CYCLE.VAL data for this cycle.
  AA.RAW.DATA SUB[ 1 CYCLE# 1 - #AAS * + , #AAS ] := \ Load into AA.RAW.DATA.
  S'FLAG 1 = \ Is S' data being used?
  IF \ If so, add its value to Serine value in AA.RAW.DATA.
    CYCLE.VAL [ #AAS 1 + ] AA.RAW.DATA [ 3 CYCLE# 1 - #AAS * + ] +
    AA.RAW.DATA [ 3 CYCLE# 1 - #AAS * + ] :=
  THEN
  CYCLE.POS SUB[ 1 , #AAS ] \ Get CYCLE.POS data for this cycle.
  AA.POS.DATA SUB[ 1 CYCLE# 1 - #AAS * + , #AAS ] := \ Load into AA.POS.DATA.

;

\ Locate AA and other peaks in HPLC.
\ Store AA peak values and positions.
: GET.PEAKS STACK.CLEAR
  REFPEAK1 N1 3.5 * - INDEX1 := \ Set start point for reference peak 1 search
    \ to REFPEAK1 - 21 seconds.
  GET.SHIFT \ Locate position of reference peak 1 in HPLC.
  REFPEAK1 - DUP REFSHIFT1 := R1P [ CYCLE# ] := \ Subtract REFPEAK1 to get
    \ reference peak 1 shift.
  REFPEAK2 N1 3.5 * - INDEX1 := \ Set start point for reference peak 2 search
    \ to REFPEAK2 - 21 seconds.
  GET.SHIFT \ Locate position of reference peak 2 in HPLC.
  REFPEAK2 - DUP REFSHIFT2 := R2P [ CYCLE# ] := \ Subtract REFPEAK2 to get
    \ reference peak 2 shift.
  #AAS S'FLAG + 1 + 1 DO \ Locate peak positions and values for each AA.

SP [ I ] DUP \ Get standard HPLC AA position.
    REFPOINT < \ Is it before REFPOINT?
    IF \ If so,
      REFSHIFT1 + \ add REFSHIFT1.
    ELSE \ If not,
      REFSHIFT2 + \ add REFSHIFT2.
    THEN
    PEAK.WINDOW - DUP INDEX1 := INDEX4 := \ Subtract peak window to set
      \ start of search window for AA peak.
    PEAK.WINDOW 2 * INDEX1 + INDEX3 := \ Set end of search window.
    FIND.PEAKS \ Locate peaks in AA window.
    M 0 > \ Was any peak found?
    IF \ If so:
      M 1 > \ Was more than one found?
      IF \ If so:
        PP SUB[ 1 , M ] PEAK.WINDOW INDEX4 + - ABS \ Calculate absolute
          \ distance from peak positions to midpoint of window.
```

```
                 SORT&INDEX \ Sort these values.
                 [ 1 ] M := \ Select the one closest to midpoint.
                 PP [ M ] CYCLE.POS [ I ] := \ Load its position in CYCLE.POS.
                 PV [ M ] CYCLE.VAL [ I ] := \ Load its value in CYCLE.VAL.
              ELSE \ If only 1 peak was found:
                 PV [ 1 ] CYCLE.VAL [ I ] := \ Load its value in CYCLE.VAL.
                 PP [ 1 ] CYCLE.POS [ I ] := \ Load its position in CYCLE.POS.
              THEN
           ELSE \ If no peaks were found:
              SP [ I ] \ Get standard AA position and
              CYCLE.POS [ I ] := \ load into CYCLE.POS.
              0. CYCLE.VAL [ I ] := \ Load 0 in CYCLE.VAL.
           THEN LOOP.
        SET.PEAKS \ Store cycle data in AA.RAW.DATA and AA.POS.DATA.
        1 INDEX1 := \ Set search window start point to 1.
        PN INDEX3 := \ Set search window end point to number of HPLC points.
        FULLFLAG 1 = \ Are all peaks in HPLC needed?
        IF \ If so,
           FIND.PEAKS \ locate them.
        THEN

;

\ Scale HPLC data for plots by removing Y offset and chopping at scale maxima.
: GET.SCALEDATA FDPLOTFLAG 1 =
   IF
      FD SUB[ PS , PR ] DUP []MIN - 1000000.D /
      SD SUB[ PS , PR ] :=
   ELSE
      RD SUB[ PS , PR ] DUP []MIN - 1000000.D /
      SD SUB[ PS , PR ] :=
   THEN
   PR PS + PS DO FDPLOTFLAG 1 =
      IF
         SD [ I ] FDPLOT.MAX >
         IF
            FDPLOT.MAX SD [ I ] :=
         THEN
      ELSE
         SD [ I ] RDPLOT.MAX >
         IF
            RDPLOT.MAX SD [ I ] :=
         THEN
      THEN

LOOP

;

\ List HPLC peaks on line printer.
: LIST.PEAKS

NORMAL.DISPLAY
```

```
  OUT>PRINTER
  STDFLAG 1 =
  IF
    ." PTH STANDARD" CR CR
  ELSE
    ." CYCLE" CYCLE# . CR CR
  THEN
  ." MIN         AREA         PMOL      AMINO ACID" CR CR
  #AAS S'FLAG + 1 + 1 DO

I AA# := GET.AANAME
    5 2 FIX.FORMAT CYCLE.POS [ I ] N1 10. * / .
    12 0 FIX.FORMAT CYCLE.VAL [ I ] DUP FIX .
    I 20 <
    IF
      11 2 FIX.FORMAT SV [ I ] / .
    ELSE
      ."              "
    THEN
    ."      " AANAME "TYPE CR

LOOP
  CR CR
  FULLFLAG 1 =
  IF
    M 1 + 1 DO 5 2 FIX.FORMAT PP [ I ] N1 10. * / "."
      12 0 FIX.FORMAT PV [ I ] 1.0 * FIX "."
      "CAT "TYPE CR

LOOP
  THEN
  12 EMIT
  CONSOLE
  -1 2 FIX.FORMAT

;

\ Plot HPLC data and report AA values.
: PLOT.PEAKS

STACK.CLEAR
  GET.SCALEDATA
  GET.HPFLAG
  ?PLOT.ROTATED
  IF
  ELSE
    PLOT.ROTATE
  THEN
  0. .5 VUPORT.ORIG 1. .5 VUPORT.SIZE
  PR REAL RAMP PS 1 - + N1 10. * /
  PR REAL RAMP 1 - PR /
  FDPLOTFLAG 1 =
  IF
    FDPLOT.MAX *
  ELSE
    RDPLOT.MAX *
```

```
THEN
XY.DATA.FIT
XY.AXIS.PLOT
PR REAL RAMP PS 1 - + N1 10. * /
SD SUB[ PS , PR ]
XY.DATA.PLOT
0. 0. VUPORT.ORIG 1. 1. VUPORT.SIZE
NORMAL.COORDS
STDFLAG 1 =
IF
   .47 .98 POSITION
   " PTH STANDARD" LABEL
ELSE
   .51 .98 POSITION
   " CYCLE" CYCLE# "." "CAT LABEL
THEN
.53 .52 POSITION " MIN" LABEL
.02 .46 POSITION
-1 4 FIX.FORMAT
FDPLOTFLAG 1 =
IF
   FDPLOT.MAX "." " AUFS" "CAT LABEL
ELSE
   RDPLOT.MAX "." " AUFS" "CAT LABEL
THEN
.087 .36 POSITION
" AA" LABEL
.174 .36 POSITION
" MIN" LABEL
.3 .36 POSITION
" AREA" LABEL
.42 .36 POSITION
" PMOL" LABEL
11 1 DO

.08 .33 I .03 * - POSITION
   I AA# := GET.AACODE LABEL
   5 2 FIX.FORMAT
   .157 .33 I .03 * - POSITION
   CYCLE.POS [ I ] N1 10. * / "." LABEL
   8 0 FIX.FORMAT
   .25 .33 I .03 * - POSITION
   CYCLE.VAL [ I ] FIX "." LABEL
   7 2 FIX.FORMAT
   .393 .33 I .03 * - POSITION
   CYCLE.VAL [ I ] SV [ I ] / "." LABEL

LOOP
.567 .36 POSITION
" AA" LABEL
.654 .36 POSITION
" MIN" LABEL
.78 .36 POSITION
" AREA" LABEL
.90 .36 POSITION
" PMOL" LABEL
#AAS S'FLAG 1 + + 11 DO

.56 .33 I 10 - .03 * - POSITION
```

```
  I AA# := GET.AACODE LABEL
  5 2 FIX.FORMAT
  .637 .33 I 10 - .03 * - POSITION
  CYCLE.POS [ I ] N1 10. * / "." LABEL
  8 0 FIX.FORMAT
  .73 .33 I 10 - .03 * - POSITION
  CYCLE.VAL [ I ] FIX "." LABEL
  I 20 <
  IF
    7 2 FIX.FORMAT
    .873 .33 I 10 - .03 * - POSITION
     CYCLE.VAL [ I ] SV [ I ] / "." LABEL
  THEN

LOOP
PLOT.ROTATE
GRAPHICS.DISPLAY
FULLFLAG 1 =
IF
  LIST.PEAKS
THEN
-1 2 FIX.FORMAT

;

\ Plot raw and filtered HPLC data.
: RDFDPLOT

STACK.CLEAR
SET.PLOT.SCALE
SET.HPFLAG
HPFLAG 1 =
IF
  ?PLOT.ROTATED
   IF
   ELSE
     PLOT.ROTATE
   THEN
THEN
0 FDPLOTFLAG :=
GET.SCALEDATA
.15 HPFLAG 1.5 * 10 / - .5 VUPORT.ORIG .8 HPFLAG 5. / + .5 VUPORT.SIZE
PR REAL RAMP PS 1 - + N1 10. * /
PR REAL RAMP 1 - PR / RDPLOT.MAX *
XY.DATA.FIT
XY.AXIS.PLOT
PR REAL RAMP PS 1 - + N1 10. * /
SD SUB[ PS , PR ]
XY.DATA.PLOT
STACK.CLEAR
1 FDPLOTFLAG :=
GET.SCALEDATA
.15 HPFLAG 1.5 * 10 / - 0 VUPORT.ORIG .8 HPFLAG 5. / + .5 VUPORT.SIZE
PR REAL RAMP PS 1 - + N1 10. * /
PR REAL RAMP 1 - PR / FDPLOT.MAX *
XY.DATA.FIT
XY.AXIS.PLOT
PR REAL RAMP PS 1 - + N1 10. * /
SD SUB[ PS , PR ]
```

```
XY.DATA.PLOT
0. 0. VUPORT.ORIG 1. 1. VUPORT.SIZE
NORMAL.COORDS
STDFLAG 1 =
IF
  .45 .98 POSITION
  " PTH STANDARD" LABEL
ELSE
  .497 .98 POSITION
  " CYCLE" CYCLE# "." "CAT LABEL
THEN
-1 4 FIX.FORMAT
.02 .54 POSITION RDPLOT.MAX "." " AUFS" "CAT LABEL
.53 .54 POSITION " MIN" LABEL
.02 .04 POSITION FDPLOT.MAX "." " AUFS" "CAT LABEL
.53 .04 POSITION " MIN" LABEL
-1 2 FIX.FORMAT
HPFLAG 1 =
IF
  PLOT.ROTATE
ELSE
  .3 .1 VUPORT.ORIG .7 .9 VUPORT.SIZE
  CR ." HIT ANY KEY"
  CR ." TO CONTINUE"
  PCKEY ?DROP DROP
THEN

;

: DISPLAY.STANDARDS

NORMAL.DISPLAY \ List 3 letter AA codes and current standard peak positions.
STACK.CLEAR
." 1 - " 1AA "TYPE ."  - " SP [ 1 ] .
."          14 - " 14AA "TYPE ."  - " SP [ 14 ] . CR
." 2 - " 2AA "TYPE ."  - " SP [ 2 ] .
."          15 - " 15AA "TYPE ."  - " SP [ 15 ] . CR
." 3 - " 3AA "TYPE ."  - " SP [ 3 ] .
."          16 - " 16AA "TYPE ."  - " SP [ 16 ] . CR
." 4 - " 4AA "TYPE ."  - " SP [ 4 ] .
."          17 - " 17AA "TYPE ."  - " SP [ 17 ] . CR
." 5 - " 5AA "TYPE ."  - " SP [ 5 ] .
."          18 - " 18AA "TYPE ."  - " SP [ 18 ] . CR
." 6 - " 6AA "TYPE ."  - " SP [ 6 ] .
."          19 - " 19AA "TYPE ."  - " SP [ 19 ] . CR
." 7 - " 7AA "TYPE ."  - " SP [ 7 ] .
."          20 - " 20AA "TYPE ."  - " SP [ 20 ] . CR
." 8 - " 8AA "TYPE ."  - " SP [ 8 ] .
."          21 - " 21AA "TYPE ."  - " SP [ 21 ] . CR
." 9 - " 9AA "TYPE ."  - " SP [ 9 ] .
."          22 - " 22AA "TYPE ."  - " SP [ 22 ] . CR
." 10 - " 10AA "TYPE ."  - " SP [ 10 ] .
."          23 - " 23AA "TYPE ."  - " SP [ 23 ] . CR
." 11 - " 11AA "TYPE ."  - " SP [ 11 ] .
."          24 - " 24AA "TYPE ."  - " SP [ 24 ] . CR
." 12 - " 12AA "TYPE ."  - " SP [ 12 ] .
."          25 - " 25AA "TYPE ."  - " SP [ 25 ] . CR
." 13 - " 13AA "TYPE ."  - " SP [ 13 ] .
."          0 - EXIT ROUTINE" CR CR
```

```
;

: AA.POSITION.PROMPT

GET.AANAME
  AANAME "TYPE ."  POSITION > " #INPUT INDEX1 * FIX DUP DUP
  INDEX2 := SP [ AA# ] := CYCLE.POS [ AA# ] := CR
  PP SUB[ 1 , M ] INDEX2 - ABS \ Locate peak closest to standard position.
  SORT&INDEX
  [ 1 ] INDEX2 :=
  PV [ INDEX2 ] DUP CYCLE.VAL [ AA# ] := STD.PMOL / SV [ AA# ] := \ Load
    \ peak value in CYCLE.VAL and SV.

;

\ Set HPLC standard AA and reference peak parameters.
: SET.STANDARD 5 1 DO

NORMAL.DISPLAY
    CR ." PMOL IN STANDARD > " #INPUT STD.PMOL :=
    CR ." NUMBER OF AMINO ACIDS > " #INPUT #AAS :=
    CR ." INCLUDE S ( Y ) > " "INPUT
    " Y" "= IF 1 S'FLAG := ELSE 0 S'FLAG := THEN
    CR ." WILL NUMBERS BE ENTERED AS DATA POINTS ( 0 ) OR MINUTES ( 1 ) > "
    #INPUT 1 =
    IF
      N1 10. * INDEX1 := \ Convert minutes to data points.
    ELSE
      1 INDEX1 :=
    THEN
    CR ." REFPEAK1 POSITION > " #INPUT INDEX1 * FIX REFPEAK1 :=
    CR ." REFPEAK2 POSITION > " #INPUT INDEX1 * FIX REFPEAK2 :=
    CR ." REFPOINT POSITION > " #INPUT INDEX1 * FIX REFPOINT :=
    CR CR ." ARE THESE PARAMETERS CORRECT (Y) > " "INPUT
    " Y" "=
    IF LEAVE THEN
  LOOP
  CR CR ." DO YOU WANT TO SET ALL AA STANDARD POSITIONS (Y) > " "INPUT
  " Y" "=
  IF
    #AAS S'FLAG 1 + + 1 DO

I AA# :=
      DISPLAY.STANDARDS
      AA.POSITION.PROMPT

LOOP
  THEN
  50 1 DO

DISPLAY.STANDARDS
    CR ." AMINO ACID NUMBER > " #INPUT DUP AA# :=
    0 =
    IF
      LEAVE
    ELSE \ Enter new standard AA peak position.
      AA.POSITION.PROMPT
    THEN
```

LOOP

;

\ Ask for filename.
: FILENAME?

CR ." DATA DISK DRIVE ( A: B: C: ) > " "INPUT "DUP DRIVE.LETTER ":=
   CR ." FILE NAME > " "INPUT "CAT FILENAME ":=

;

\ Get HPLC standard from disk, set HPLC parameters, and set standard AA data.
: GET.STANDARD STACK.CLEAR
   0. SV := \ Initialize HPLC standard AA peak value array.
   0 SP := \ Initialize HPLC standard AA peak position array.
   1 STDFLAG :=
   FILENAME?
   GET.CHROMATOGRAM \ Get HPLC data from disk.
   HFILTER \ House convolve raw HPLC data and store as filtered data.
   1 INDEX1 := \ Set search window start point to 1.
   PN INDEX3 := \ Set search window end point to number of HPLC points.
   FIND.PEAKS \ Locate all peaks in HPLC.
   GRAPHICS.DISPLAY
   PR PS 1 - - REAL RAMP PS 1 - +
   FD SUB[ PS , PR PS 1 - - ] XY.AUTO.PLOT \ Plot filtered HPLC on monitor.
   OUT>PRINTER CONSOLE.OFF
   M 1 + 1 DO \ List all peak positions (as data points) and values on printer.
      PP [ I ] . PV [ I ] . CR LOOP
   12 EMIT 12 EMIT
   CONSOLE
   CR ." FIND AA"
   CR ." PEAKS AND"
   CR ." HIT ANY KEY"
   CR ." TO RESUME"
   PCKEY ?DROP DROP \ Pause to mark AA and reference peaks on printer output.
   SET.AANAMES \ Change full AA names as necessary.
   SET.AACODES \ Change 3 letter AA codes as necessary.
   SET.STANDARD \ Set HPLC standard and reference parameters and peaks.
   NORMAL.DISPLAY
   CR ." PRINT PEAK REPORT IN SHORT (0) OR FULL (1) > " #INPUT FULLFLAG :=
   CR ." OUTPUT TO PRINTER (0) OR PLOTTER (1) > " #INPUT DUP HPFLAG :=
   1 =
   IF
      SET.PLOT.SCALE \ Set plot scale.
      SET.PS \ Set plot offset.
      SET.FDPLOTFLAG \ Set plot data type.
      CR CR ." INSERT PLOTTER PAPER AND HIT ANY KEY TO CONTINUE"
      PCKEY ?DROP DROP
      PLOT.PEAKS \ Plot HPLC.
   ELSE
      LIST.PEAKS \ List peaks on line printer.
   THEN
   12 EMIT
   0 STDFLAG :=

```
0 HPFLAG :=

;

\ Store AA.RAW.DATA on disk.
: STORE.AA.RAW.DATA

FILENAME?
  FILE.TEMPLATE
    2 COMMENTS
    REAL DIM[ 2000 ] SUBFILE
    REAL DIM[ 2000 ] SUBFILE
    REAL DIM[ 2000 ] SUBFILE
    INTEGER DIM[ 2000 ] SUBFILE
    REAL DIM[ 25 ] SUBFILE
    REAL DIM[ 25 ] SUBFILE
    REAL DIM[ 25 ] SUBFILE
    INTEGER DIM[ 100 ] SUBFILE
    INTEGER DIM[ 100 ] SUBFILE
    INTEGER DIM[ 25 ] SUBFILE
  END
  FILENAME DEFER> FILE.CREATE
  FILENAME DEFER> FILE.OPEN
  1 SUBFILE AA.RAW.DATA ARRAY>FILE
  2 SUBFILE AA.BACK.DATA ARRAY>FILE
  3 SUBFILE AA.LAG.DATA ARRAY>FILE
  4 SUBFILE AA.POS.DATA ARRAY>FILE
  5 SUBFILE AA.STD.DEV1 ARRAY>FILE
  6 SUBFILE AA.STD.DEV2 ARRAY>FILE
  7 SUBFILE SV ARRAY>FILE
  8 SUBFILE R1P ARRAY>FILE
  9 SUBFILE R2P ARRAY>FILE
  10 SUBFILE SP ARRAY>FILE
  FILE.CLOSE

;

\ Should AA.RAW.DATA be stored on disk before proceeding?
: STORE.AA.RAW.DATA?

CR ." THIS ROUTINE WILL ALTER THE AA.RAW.DATA ARRAY"
  CR ." DO YOU WISH TO STORE THE ORIGINAL AA.RAW.DATA ARRAY (Y) > " "INPUT
  " Y" "=
  IF
    STORE.AA.RAW.DATA
  THEN

;

\ Recall AA.RAW.DATA from disk.
: GET.AA.RAW.DATA

FILENAME?
  FILENAME DEFER> FILE.OPEN
  1 SUBFILE FILE>UNNAMED.ARRAY AA.RAW.DATA :=
  2 SUBFILE FILE>UNNAMED.ARRAY AA.BACK.DATA :=
  3 SUBFILE FILE>UNNAMED.ARRAY AA.LAG.DATA :=
  4 SUBFILE FILE>UNNAMED.ARRAY AA.POS.DATA :=
  5 SUBFILE FILE>UNNAMED.ARRAY AA.STD.DEV1 :=
```

```
  6 SUBFILE FILE>UNNAMED.ARRAY AA.STD.DEV2 :=
  7 SUBFILE FILE>UNNAMED.ARRAY SV :=
  8 SUBFILE FILE>UNNAMED.ARRAY R1P :=
  9 SUBFILE FILE>UNNAMED.ARRAY R2P :=
  10 SUBFILE FILE>UNNAMED.ARRAY SP :=
  FILE.CLOSE

;

\ Set analyze HPLC parameters.
: SET.ANALYZE.PARAMETERS

SET.DATA.OFFSET
  SET.CYCLE.OFFSET
  CR ." PRINT PEAK REPORT IN SHORT (0) OR FULL (1) > " #INPUT FULLFLAG :=
  CR ." OUTPUT TO PRINTER (0) OR PLOTTER (1) > " #INPUT DUP HPFLAG :=
  1 =
  IF
     SET.PLOT.SCALE
     SET.PS
     SET.FDPLOTFLAG .
  THEN

;

\ Perform HPLC analysis.
: HPLC.ANALYZE

GET.CHROMATOGRAM
  HFILTER GET.PEAKS
  HPFLAG 1 =
  IF
     CR CR ." INSERT PLOTTER PAPER AND HIT ANY KEY TO CONTINUE"
     PCKEY ?DROP DROP
     PLOT.PEAKS
  ELSE
     LIST.PEAKS
  THEN

;

\ Process single chromatogram, report data, and store in AA data files.
: ANALYZE.CHROMATOGRAM SET.ANALYZE.PARAMETERS
  FILENAME?
  FILENAME 46 "NUMBER CYCLE.OFFSET - CYCLE# :=
  HPLC.ANALYZE

;

\ Process multiple chromatograms, report data, and store in AA data files.
: ANALYZE.CHROMATOGRAMS SET.ANALYZE.PARAMETERS
  CR ." DATA DISK DRIVE ( A: B: C: ) > " "INPUT DRIVE.LETTER ":=
  CR ." FIRST DATA FILE NUMBER > " #INPUT INDEX1 :=
  CR ." LAST DATA FILE NUMBER > " #INPUT 1 + INDEX2 :=
  INDEX2 INDEX1 DO
```

```
    I CYCLE.OFFSET - CYCLE# :=
    DRIVE.LETTER I "." 32 "COMPRESS "CAT " .DAT" "CAT FILENAME ":=
    HPLC.ANALYZE

LOOP

;

: COMPRESSED 15 ASCII" "TYPE ;

: PICA 18 ASCII" "TYPE ;

: ULON 27 ASCII" "TYPE 45 ASCII" "TYPE 49 ASCII" "TYPE ;

: ULOFF 27 ASCII" "TYPE 45 ASCII" "TYPE 48 ASCII" "TYPE ;

: PRINT.ARRAY

SET.AA.DATA.TYPE
  CR ." ENTER HEADER INFORMATION >" CR "INPUT
  OUT>PRINTER CONSOLE.OFF
  COMPRESSED ULON "TYPE CR CR
  ULOFF ."           " ULON ." PTH AMINO ACID" CR
  ." CYCLE" ULOFF ."    " ULON ." Asp"
  #AAS 1 + 2 DO

ULOFF ."      "
    I AA# := GET.AACODE
    ULON "TYPE

LOOP
  ULOFF CR
  #CYCLES 0 DO 4 0 FIX.FORMAT
    I 1 + "." "TYPE
    7 1 FIX.FORMAT
    #AAS 1 + 1 DO

USE.DATA.TYPE [ I J #AAS * + ] "." "TYPE

LOOP
    CR

LOOP
  12 EMIT PICA CONSOLE -1 2 FIX.FORMAT

;

\ System menu.
: MAIN.MENU

NORMAL.DISPLAY
  STACK.CLEAR
  -1 2 FIX.FORMAT
  CR ."  0 - EXIT.MENU" ."           16 - SET.HPLC.PARAMETERS"
  CR ."  1 - AA.BACK.FIT" ."         17 - SMOOTH.CHROMATOGRAM"
  CR ."  2 - REMOVE.LAG" ."          18 - GET/LIST.PEAKS"
  CR ."  3 - INJECT.CORRECT" ."      19 - GET/SET.STANDARD"
```

```
CR ." 4 - CALL.SEQUENCE" ."              20 - ANALYZE.CHROMATOGRAM"
CR ." 5 - PLOT.AA.DATA" ."               21 - PLOT.RAW/FILTER.CHROMATOGRAM"
CR ." 6 - BAR.PLOT.CYCLE.VAL" ."         22 - SET.PLOT.WINDOW"
CR ." 7 - PLOT.LAG.DATA" ."              23 - SET.DATA.OFFSET"
CR ." 8 - PRINT.REP.YIELD" ."            24 - SET.CYCLE.OFFSET"
CR ." 9 - SET.DISPLAY.TYPE" ."           25 - SET.PLOT.SCALE"
CR ." 10 - SET.FIT.PARAMETERS" ."        26 - PLOT.PEAKS"
CR ." 11 - SET.AANAMES" ."               27 - ANALYZE.CHROMATOGRAMS"
CR ." 12 - SET.AACODES" ."               28 - GET.AA.RAW.DATA"
CR ." 13 - SET.SEQUENCE.PARAMETERS" ."   29 - STORE.AA.RAW.DATA"
CR ." 14 - AA.BACK.FIT/REMOVE.LAG" ."    30 - PRINT.DATA.ARRAY"
CR ." 15 - AA.BACK.FIT/REMOVE.LAG/INJECT.CORRECT'
CR CR ." CHOICE > " #INPUT
NORMAL.DISPLAY
CASE
  0 OF ABORT ENDOF
  1 OF SET.SEQUENCE.PARAMETERS AA.BACK.FIT ENDOF
  2 OF REMOVE.LAG ENDOF
  3 OF STORE.AA.RAW.DATA? INJECT.CORRECT ENDOF
  4 OF CALL.SEQUENCE ENDOF
  5 OF PLOT.AA.DATA ENDOF
  6 OF BAR.PLOT.CYCLE.VAL ENDOF
  7 OF PLOT.LAG.DATA ENDOF
  8 OF PRINT.REP.YIELD ENDOF
  9 OF SET.EGAFLAG ENDOF
  10 OF SET.FIT.PARAMETERS ENDOF
  11 OF SET.AANAMES ENDOF
  12 OF SET.AACODES ENDOF
  13 OF SET.SEQUENCE.PARAMETERS ENDOF
  14 OF SET.SEQUENCE.PARAMETERS AA.BACK.FIT REMOVE.LAG ENDOF
  15 OF SET.SEQUENCE.PARAMETERS AA.BACK.FIT REMOVE.LAG STORE.AA.RAW.DATA?
     INJECT.CORRECT ENDOF
  16 OF SET.HPLC.PARAMETERS ENDOF
  17 OF HSMOOTH ENDOF
  18 OF GET.PEAKS LIST.PEAKS ENDOF
  19 OF GET.STANDARD ENDOF
  20 OF ANALYZE.CHROMATOGRAM ENDOF
  21 OF RDFDPLOT ENDOF
  22 OF SET.PS ENDOF
  23 OF SET.DATA.OFFSET ENDOF
  24 OF SET.CYCLE.OFFSET ENDOF
  25 OF SET.PLOT.SCALE ENDOF
  26 OF PLOT.PEAKS ENDOF
  27 OF ANALYZE.CHROMATOGRAMS ENDOF
  28 OF GET.AA.RAW.DATA ENDOF
  29 OF STORE.AA.RAW.DATA ENDOF
  30 OF PRINT.ARRAY ENDOF
ENDCASE
MYSELF
ONERR:
  BELL
  NORMAL.DISPLAY
  CR ." ERROR #:" ?ERROR# ." DETECTED"
  CR ." HIT ANY KEY TO CONTINUE"
  PCKEY ?DROP DROP
  MYSELF
```

APPENDIX II

18K PROTEIN - Raw Data

TABLE 1

PTH AMINO ACID

| CYCLE | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 1 | 25.3 | 3.5 | 1.3 | 1.1 | 1.6 | 35.0 | 410.5 | .7 | 7.3 | 1.5 | .2 | 2.2 | .7 | 3.9 | 7.0 | 2.0 | 2.6 | 2.4 | 2.5 |
| 2 | 11.0 | .8 | 220.0 | 3.2 | 1.7 | 30.1 | 14.0 | .4 | 7.4 | 2.3 | .1 | 4.9 | .3 | 2.7 | 4.9 | 3.1 | 6.1 | 5.4 | 9.2 |
| 3 | 4.4 | .8 | 23.0 | 5.0 | 67.4 | 25.8 | 7.1 | .2 | 7.1 | 5.9 | .2 | 4.0 | .1 | 5.5 | 5.0 | 8.1 | 5.6 | 24.0 | 9.3 |
| 4 | 3.8 | 1.4 | 11.0 | 9.1 | 6.0 | 26.5 | 8.8 | .2 | 6.8 | 4.7 | .4 | 6.0 | 1.0 | 4.1 | 5.6 | 17.4 | 7.1 | 37.9 | 372.0 |
| 5 | 3.4 | 1.4 | 11.8 | 9.8 | 65.0 | 27.9 | 11.5 | .3 | 6.5 | 7.9 | .4 | 10.6 | .9 | 6.3 | 5.8 | 18.0 | 7.0 | 46.2 | 31.0 |
| 6 | 3.3 | 1.6 | 14.8 | 13.5 | 9.0 | 258.0 | 17.9 | .4 | 7.0 | 9.2 | .7 | 13.0 | .3 | 13.5 | 5.6 | 18.0 | 7.2 | 51.8 | 24.1 |
| 7 | 2.4 | 1.4 | 13.3 | 13.0 | 5.5 | 39.0 | 13.3 | .5 | 8.2 | 8.9 | .4 | 15.2 | 2.0 | 18.3 | 12.0 | 24.0 | 10.1 | 491.5 | 27.4 |
| 8 | 4.0 | 2.7 | 15.6 | 16.7 | 62.0 | 34.4 | 15.7 | .6 | 9.1 | 10.5 | .4 | 13.0 | 3.1 | 22.0 | 5.3 | 30.4 | 10.1 | 110.4 | 22.2 |
| 9 | 3.0 | 7.2 | 24.3 | 19.7 | 10.4 | 38.5 | 20.8 | .8 | 10.9 | 11.0 | .6 | 229.0 | 3.4 | 19.5 | 5.5 | 35.3 | 12.1 | 82.9 | 24.8 |
| 10 | 2.9 | 3.0 | 23.3 | 19.4 | 7.3 | 39.0 | 21.3 | .7 | 15.0 | 14.3 | .7 | 80.0 | 3.0 | 265.5 | 4.9 | 31.0 | 13.4 | 74.0 | 26.0 |
| 11 | 3.3 | 2.1 | 24.0 | 17.0 | 8.2 | 40.7 | 21.8 | .7 | 13.3 | 14.8 | .8 | 40.5 | 3.9 | 82.9 | 6.0 | 269.5 | 16.1 | 79.6 | 30.5 |
| 12 | 4.1 | 3.5 | 27.2 | 18.0 | 9.9 | 181.0 | 23.6 | .8 | 13.9 | 17.1 | 1.1 | 28.0 | 3.7 | 33.9 | 5.0 | 94.1 | 17.9 | 79.0 | 31.5 |
| 13 | 4.3 | 5.0 | 31.8 | 18.4 | 11.0 | 216.0 | 26.9 | .9 | 12.3 | 17.7 | 1.1 | 27.3 | 3.1 | 22.9 | 5.4 | 46.0 | 18.2 | 86.0 | 31.3 |
| 14 | 4.2 | 4.9 | 31.4 | 16.6 | 9.2 | 92.9 | 26.4 | .9 | 78.1 | 20.0 | .9 | 24.5 | 3.2 | 19.2 | 3.8 | 31.8 | 17.4 | 85.3 | 35.3 |
| 15 | 4.0 | 5.8 | 32.5 | 18.2 | 36.1 | 60.9 | 31.0 | .8 | 33.3 | 27.9 | 1.0 | 24.1 | 3.2 | 20.8 | 4.1 | 28.3 | 18.0 | 89.0 | 35.0 |
| 16 | 4.1 | 5.9 | 33.8 | 18.6 | 17.8 | 135.0 | 35.1 | .7 | 18.4 | 29.0 | .9 | 24.2 | 3.5 | 22.5 | 5.9 | 29.6 | 19.8 | 93.1 | 36.3 |
| 17 | 4.3 | 6.2 | 32.4 | 19.0 | 11.0 | 151.0 | 37.4 | 1.1 | 15.0 | 27.3 | 1.4 | 24.6 | 4.4 | 26.1 | 5.8 | 32.4 | 22.5 | 93.8 | 36.1 |
| 18 | 4.9 | 6.0 | 35.8 | 19.0 | 9.1 | 74.0 | 37.9 | 1.3 | 14.0 | 29.5 | 1.6 | 26.0 | 7.0 | 26.0 | 5.7 | 32.3 | 22.1 | 94.0 | 155.0 |
| 19 | 4.0 | 5.6 | 35.1 | 18.1 | 9.4 | 48.6 | 36.1 | 1.4 | 13.6 | 28.1 | 1.3 | 26.1 | 7.1 | 26.0 | 5.4 | 32.7 | 23.0 | 92.3 | 158.5 |
| 20 | 5.1 | 5.8 | 40.8 | 18.1 | 9.6 | 42.5 | 36.0 | 1.8 | 12.6 | 29.3 | 1.1 | 28.0 | 7.0 | 26.8 | 7.5 | 32.3 | 21.4 | 255.5 | 78.2 |
| 21 | 5.1 | 5.3 | 36.4 | 17.4 | 9.0 | 38.0 | 31.5 | 1.9 | 54.0 | 28.3 | 1.4 | 21.4 | 6.8 | 27.0 | 6.0 | 33.1 | 20.9 | 132.3 | 40.0 |
| 22 | 6.5 | 6.3 | 37.4 | 18.0 | 8.8 | 39.6 | 122.5 | 2.0 | 24.1 | 28.0 | 1.2 | 26.5 | 6.9 | 27.0 | 5.1 | 34.0 | 21.5 | 97.1 | 30.6 |
| 23 | 7.4 | 8.0 | 97.3 | 18.1 | 9.0 | 43.3 | 60.8 | 2.1 | 15.3 | 28.5 | 1.2 | 28.2 | 7.0 | 28.0 | 5.1 | 33.3 | 21.9 | 92.2 | 31.4 |
| 24 | 7.1 | 8.2 | 57.6 | 17.4 | 23.2 | 41.0 | 39.1 | 1.6 | 11.9 | 29.9 | 1.0 | 27.1 | 6.1 | 26.6 | 4.8 | 32.0 | 19.7 | 84.6 | 31.3 |
| 25 | 8.1 | 8.3 | 90.0 | 18.0 | 12.3 | 40.0 | 34.0 | 1.9 | 11.0 | 28.8 | 1.1 | 28.0 | 5.7 | 27.0 | 5.9 | 31.9 | 19.5 | 82.0 | 33.2 |
| 26 | 9.3 | 8.5 | 101.1 | 19.0 | 10.6 | 41.2 | 33.8 | 1.7 | 10.3 | 31.0 | 1.0 | 28.0 | 5.5 | 29.1 | 5.2 | 31.1 | 20.0 | 78.7 | 33.0 |
| 27 | 6.3 | 7.2 | 48.2 | 16.1 | 6.9 | 35.4 | 30.5 | 2.0 | 10.0 | 25.4 | 1.1 | 25.1 | 5.8 | 27.3 | 5.5 | 31.1 | 19.0 | 146.0 | 32.1 |
| 28 | 8.0 | 8.1 | 39.6 | 18.0 | 8.4 | 37.3 | 33.0 | 2.0 | 10.0 | 88.0 | 1.1 | 26.1 | 6.1 | 29.9 | 5.3 | 33.0 | 19.0 | 104.0 | 33.2 |
| 29 | 8.2 | 8.2 | 36.2 | 18.1 | 8.3 | 36.3 | 85.9 | 2.1 | 9.9 | 48.0 | 1.1 | 25.0 | 6.0 | 28.2 | 5.0 | 31.9 | 17.3 | 83.6 | 34.0 |
| 30 | 7.0 | 8.1 | 33.7 | 18.0 | 8.5 | 37.5 | 48.0 | 2.1 | 9.0 | 33.3 | 1.2 | 27.5 | 6.1 | 29.1 | 4.2 | 32.0 | 59.5 | 76.5 | 34.2 |
| 31 | 8.1 | 8.5 | 35.4 | 18.3 | 17.2 | 36.3 | 35.2 | 2.4 | 9.4 | 29.7 | .9 | 26.8 | 6.5 | 29.0 | 4.4 | 31.1 | 30.6 | 76.3 | 33.0 |
| 32 | 7.6 | 8.7 | 33.5 | 19.5 | 11.0 | 35.6 | 29.6 | 2.0 | 9.6 | 27.5 | 1.0 | 27.2 | 6.5 | 27.5 | 18.6 | 31.3 | 21.1 | 72.9 | 31.1 |
| 33 | 9.0 | 9.5 | 36.4 | 20.0 | 17.0 | 37.8 | 30.6 | 2.7 | 9.0 | 27.3 | .9 | 27.7 | 6.5 | 29.8 | 9.5 | 32.4 | 16.7 | 75.0 | 32.5 |
| 34 | 9.5 | 9.1 | 36.0 | 19.6 | 9.8 | 38.4 | 32.0 | 3.0 | 20.2 | 27.2 | .8 | 29.2 | 6.7 | 29.5 | 5.0 | 33.0 | 16.4 | 75.2 | 34.6 |
| 35 | 9.3 | 9.4 | 35.5 | 19.3 | 12.9 | 36.0 | 31.4 | 2.4 | 12.2 | 26.6 | 1.0 | 28.7 | 5.2 | 28.7 | 3.6 | 32.2 | 15.1 | 71.3 | 33.7 |
| 36 | 8.4 | 8.8 | 31.6 | 16.1 | 8.3 | 33.9 | 29.4 | 2.6 | 9.1 | 24.2 | .9 | 28.0 | 5.5 | 29.0 | 3.5 | 31.5 | 14.0 | 99.5 | 33.5 |
| 37 | 8.0 | 9.5 | 46.8 | 17.6 | 7.6 | 37.0 | 30.6 | 2.7 | 8.7 | 24.9 | .7 | 28.8 | 7.0 | 30.5 | 3.5 | 31.9 | 15.4 | 82.5 | 34.1 |
| 38 | 7.8 | 9.0 | 37.5 | 36.0 | 6.9 | 35.5 | 29.0 | 2.4 | 8.0 | 24.0 | .7 | 26.2 | 6.0 | 28.0 | 3.6 | 30.6 | 14.0 | 71.5 | 32.5 |
| 39 | 8.5 | 9.3 | 34.2 | 25.1 | 6.6 | 34.7 | 28.3 | 2.1 | 7.6 | 22.7 | .8 | 26.8 | 5.4 | 46.2 | 3.2 | 30.4 | 14.1 | 68.0 | 32.0 |
| 40 | 7.5 | 9.0 | 31.0 | 20.0 | 5.8 | 33.7 | 28.2 | 2.4 | 7.9 | 22.7 | .8 | 26.7 | 5.3 | 35.3 | 3.1 | 47.3 | 13.5 | 65.4 | 32.1 |
| 41 | 7.9 | 9.1 | 41.2 | 16.9 | 5.1 | 31.0 | 26.2 | 2.7 | 7.9 | 21.4 | .6 | 21.4 | 5.1 | 28.4 | 3.1 | 35.5 | 13.0 | 62.4 | 29.5 |
| 42 | 6.4 | 8.2 | 27.5 | 14.6 | 4.6 | 28.0 | 23.1 | 1.7 | 6.1 | 17.9 | .6 | 21.6 | 4.5 | 23.6 | 2.5 | 27.6 | 11.7 | 53.2 | 38.8 |
| 43 | 7.6 | 9.8 | 30.4 | 15.7 | 4.8 | 30.0 | 24.5 | 2.5 | 6.5 | 20.0 | .5 | 31.2 | 4.8 | 21.8 | 2.6 | 27.5 | 12.3 | 59.9 | 31.1 |
| 44 | 6.2 | 9.6 | 26.6 | 15.5 | 6.9 | 30.1 | 24.4 | 2.1 | 6.5 | 19.0 | .6 | 29.4 | 5.0 | 23.7 | 2.8 | 27.1 | 12.6 | 58.1 | 30.0 |
| 45 | 7.0 | 9.8 | 27.5 | 15.5 | 6.0 | 35.2 | 25.2 | 2.1 | 6.8 | 20.7 | .6 | 26.2 | 4.9 | 25.2 | 3.0 | 27.5 | 12.2 | 59.7 | 28.9 |
| 46 | 7.4 | 9.7 | 25.6 | 15.1 | 4.7 | 37.8 | 21.2 | 2.0 | 7.0 | 19.8 | .6 | 23.6 | 4.5 | 21.0 | 2.5 | 27.4 | 12.0 | 58.0 | 27.2 |
| 47 | 6.9 | 9.6 | 25.4 | 14.0 | 4.4 | 33.0 | 30.4 | 2.0 | 6.2 | 19.0 | .5 | 22.7 | 4.7 | 23.0 | 2.4 | 26.5 | 11.6 | 54.7 | 25.8 |
| 48 | 6.8 | 9.7 | 23.8 | 14.4 | 4.5 | 30.2 | 34.8 | 1.8 | 6.7 | 18.3 | .6 | 22.1 | 4.2 | 22.7 | 2.7 | 25.8 | 11.2 | 54.6 | 26.1 |
| 49 | 6.0 | 9.3 | 23.3 | 13.8 | 4.0 | 27.7 | 29.4 | 1.7 | 7.0 | 17.9 | .6 | 22.3 | 4.0 | 28.6 | 2.5 | 25.5 | 11.6 | 53.8 | 25.5 |
| 50 | 5.8 | 9.2 | 22.0 | 13.4 | 3.8 | 27.5 | 24.7 | 2.0 | 6.5 | 17.7 | .6 | 21.3 | 11.0 | 27.8 | 2.1 | 25.0 | 11.7 | 53.4 | 25.2 |
| 51 | 6.5 | 9.0 | 22.6 | 13.5 | 3.8 | 25.8 | 21.3 | 3.1 | 5.7 | 16.5 | .6 | 20.4 | 8.1 | 23.2 | 2.4 | 24.5 | 11.8 | 50.5 | 23.5 |
| 52 | 6.1 | 9.1 | 26.4 | 13.7 | 3.5 | 25.8 | 21.2 | 2.5 | 6.0 | 16.9 | .6 | 19.4 | 5.5 | 21.5 | 2.7 | 23.9 | 11.1 | 52.0 | 24.1 |
| 53 | 6.5 | 9.1 | 25.4 | 13.3 | 3.3 | 28.6 | 20.5 | 2.1 | 6.0 | 16.1 | .6 | 19.3 | 4.2 | 20.5 | 2.3 | 23.6 | 11.3 | 48.8 | 23.0 |

18K PROTEIN - Raw Data (Asp Background *Corrected*)

TABLE 2

| CYCLE | PTH AMINO ACID |||||||||||||||||| 
|---|---|---|---|---|---|---|---|---|---|---|---|---|---|---|---|---|---|---|
| | Asp | Asn | Glu | Gln | Thr | Gly | Ala | His | Ser | Tyr | Arg | Pro | Met | Val | Trp | Phe | Ile | Lys | Leu |
| 1 | 68.5 | 3.5 | 1.3 | 1.1 | 1.6 | 35.0 | 410.5 | .7 | 7.3 | 1.5 | .2 | 2.2 | .7 | 3.9 | 7.0 | 2.0 | 2.6 | 2.4 | 2.5 |
| 2 | 22.3 | .8 | 220.0 | 3.2 | 1.7 | 30.1 | 14.0 | .4 | 7.4 | 2.3 | .1 | 4.9 | .3 | 2.7 | 4.9 | 3.1 | 6.1 | 5.4 | 9.2 |
| 3 | 1.5 | .8 | 23.0 | 5.0 | 67.4 | 25.8 | 7.1 | .2 | 7.1 | 5.9 | .2 | 4.0 | .4 | 5.5 | 5.0 | 8.1 | 5.6 | 24.0 | 9.3 |
| 4 | .4 | 1.4 | 11.0 | 9.1 | 6.0 | 26.5 | 8.8 | .2 | 6.8 | 4.7 | .4 | 6.0 | 1.0 | 4.1 | 5.6 | 17.4 | 7.1 | 37.9 | 372.0 |
| 5 | -.3 | 1.4 | 11.8 | 9.8 | 65.0 | 27.9 | 11.5 | .3 | 6.5 | 7.9 | .4 | 10.6 | .9 | 6.3 | 5.9 | 18.0 | 7.0 | 46.2 | 31.0 |
| 6 | -.1 | 1.6 | 14.8 | 13.5 | 9.0 | 258.0 | 17.9 | .4 | 7.0 | 9.2 | .7 | 13.0 | .3 | 13.5 | 5.6 | 18.0 | 7.2 | 51.8 | 24.1 |
| 7 | -2.8 | 1.4 | 13.3 | 13.0 | 5.5 | 39.0 | 13.3 | .5 | 8.2 | 8.9 | .4 | 15.2 | 2.0 | 18.3 | 12.0 | 24.0 | 10.1 | 491.5 | 27.4 |
| 8 | 2.6 | 2.7 | 15.6 | 16.7 | 62.0 | 34.4 | 15.7 | .6 | 9.1 | 10.5 | .4 | 13.0 | 3.1 | 22.0 | 5.3 | 30.4 | 10.1 | 110.4 | 22.2 |
| 9 | -.7 | 7.2 | 24.3 | 19.7 | 10.4 | 38.5 | 20.8 | .8 | 10.9 | 11.0 | .6 | 229.0 | 3.4 | 19.5 | 5.5 | 35.3 | 12.1 | 82.9 | 24.8 |
| 10 | -1.2 | 3.0 | 23.3 | 19.4 | 7.3 | 39.0 | 21.3 | .7 | 15.0 | 14.3 | .7 | 80.0 | 3.0 | 265.5 | 4.9 | 31.0 | 13.4 | 74.0 | 26.0 |
| 11 | -.2 | 2.1 | 24.0 | 17.0 | 8.2 | 40.7 | 21.8 | .7 | 13.3 | 14.8 | .8 | 40.5 | 3.9 | 82.9 | 6.0 | 269.5 | 16.1 | 79.6 | 30.5 |
| 12 | 2.1 | 3.5 | 27.2 | 18.0 | 9.9 | 181.0 | 23.6 | .8 | 13.9 | 17.1 | 1.1 | 28.0 | 3.7 | 33.9 | 5.0 | 94.1 | 17.9 | 79.0 | 31.5 |
| 13 | 2.2 | 5.0 | 31.8 | 18.4 | 11.0 | 216.0 | 26.9 | .9 | 12.3 | 17.7 | 1.1 | 27.3 | 3.1 | 22.9 | 5.4 | 46.0 | 18.2 | 86.0 | 31.3 |
| 14 | 1.2 | 4.9 | 31.4 | 16.6 | 9.2 | 92.9 | 26.4 | .9 | 78.1 | 20.0 | .9 | 24.5 | 3.2 | 19.2 | 3.8 | 31.8 | 17.4 | 85.3 | 35.3 |
| 15 | -.1 | 5.8 | 32.5 | 18.2 | 36.1 | 60.9 | 31.0 | .8 | 33.3 | 27.9 | 1.0 | 21.1 | 3.2 | 20.8 | 4.1 | 28.3 | 18.0 | 89.0 | 35.0 |
| 16 | -.6 | 5.9 | 33.8 | 18.6 | 17.8 | 135.0 | 35.1 | .7 | 18.4 | 29.0 | .9 | 24.2 | 3.5 | 22.5 | 5.9 | 29.6 | 19.8 | 93.1 | 36.3 |
| 17 | -.8 | 6.2 | 32.4 | 19.0 | 11.0 | 151.0 | 37.4 | 1.1 | 15.0 | 27.3 | 1.4 | 21.6 | 4.4 | 26.1 | 5.8 | 32.4 | 22.5 | 93.8 | 36.1 |
| 18 | .3 | 6.0 | 35.8 | 19.0 | 9.1 | 74.0 | 37.9 | 1.3 | 14.0 | 29.5 | 1.6 | 26.0 | 7.0 | 26.0 | 5.7 | 32.3 | 22.1 | 91.0 | 155.0 |
| 19 | -3.7 | 5.6 | 35.1 | 18.1 | 9.4 | 48.6 | 36.1 | 1.4 | 13.6 | 28.1 | 1.3 | 26.1 | 7.1 | 26.0 | 5.4 | 32.7 | 23.0 | 92.3 | 158.5 |
| 20 | -1.0 | 5.8 | 40.8 | 18.1 | 9.6 | 42.5 | 36.0 | 1.8 | 12.6 | 29.3 | 1.1 | 28.0 | 7.0 | 26.8 | 7.5 | 32.3 | 21.4 | 255.5 | 78.2 |
| 21 | -2.1 | 5.3 | 36.4 | 17.4 | 9.0 | 38.0 | 31.5 | 1.9 | 54.0 | 28.3 | 1.4 | 24.4 | 6.8 | 27.0 | 6.0 | 33.1 | 20.9 | 132.3 | 40.0 |
| 22 | 1.5 | 6.3 | 37.4 | 18.0 | 8.8 | 39.6 | 122.5 | 2.0 | 24.1 | 28.0 | 1.2 | 26.5 | 6.9 | 27.0 | 5.1 | 31.0 | 21.5 | 97.1 | 30.6 |
| 23 | 3.5 | 8.0 | 97.3 | 18.1 | 9.0 | 43.3 | 60.8 | 2.1 | 15.3 | 28.5 | 1.2 | 28.2 | 7.0 | 28.0 | 5.1 | 33.3 | 21.9 | 92.2 | 31.4 |
| 24 | 1.5 | 8.2 | 57.6 | 17.4 | 23.2 | 41.0 | 39.1 | 1.6 | 11.9 | 29.9 | 1.0 | 27.1 | 6.1 | 26.6 | 4.8 | 32.0 | 19.7 | 84.6 | 31.3 |
| 25 | 3.8 | 8.3 | 90.0 | 18.0 | 12.3 | 40.0 | 34.0 | 1.9 | 11.0 | 28.8 | 1.1 | 28.0 | 5.7 | 27.0 | 5.9 | 31.9 | 19.5 | 82.0 | 33.2 |
| 26 | 6.8 | 8.5 | 101.1 | 19.0 | 10.6 | 41.2 | 33.8 | 1.7 | 10.3 | 31.0 | 1.0 | 28.0 | 5.5 | 29.1 | 5.2 | 31.1 | 20.0 | 78.7 | 33.0 |
| 27 | -4.1 | 7.2 | 48.2 | 16.1 | 6.9 | 35.4 | 30.5 | 2.0 | 10.0 | 25.4 | 1.1 | 25.1 | 5.8 | 27.3 | 5.5 | 31.1 | 19.0 | 146.0 | 32.1 |
| 28 | .7 | 8.1 | 39.6 | 18.0 | 8.4 | 37.3 | 33.0 | 2.0 | 10.0 | 88.0 | 1.1 | 26.1 | 6.1 | 29.9 | 5.3 | 33.0 | 19.0 | 104.0 | 33.2 |
| 29 | .6 | 8.2 | 36.2 | 18.1 | 8.3 | 36.3 | 85.9 | 2.1 | 9.9 | 48.0 | 1.1 | 25.0 | 6.0 | 28.2 | 5.0 | 31.9 | 17.3 | 83.6 | 34.0 |
| 30 | -4.1 | 8.1 | 33.7 | 18.0 | 8.5 | 37.5 | 48.0 | 2.1 | 9.0 | 33.3 | 1.2 | 27.5 | 6.1 | 29.1 | 4.2 | 32.0 | 59.5 | 76.5 | 34.2 |
| 31 | 2.2 | 8.5 | 35.4 | 18.3 | 17.2 | 36.3 | 35.2 | 2.4 | 9.4 | 29.7 | .9 | 26.8 | 6.5 | 29.0 | 4.4 | 31.1 | 30.6 | 76.3 | 33.0 |
| 32 | -.7 | 8.7 | 33.5 | 19.5 | 11.0 | 35.6 | 29.6 | 2.0 | 9.6 | 27.5 | 1.0 | 27.2 | 6.5 | 27.5 | 18.6 | 31.3 | 21.1 | 72.9 | 31.1 |
| 33 | 4.6 | 9.5 | 36.4 | 20.0 | 17.0 | 37.8 | 30.6 | 2.7 | 9.0 | 27.3 | .9 | 27.7 | 6.5 | 29.8 | 9.5 | 32.4 | 16.7 | 75.0 | 32.5 |
| 34 | 6.3 | 9.1 | 36.0 | 19.6 | 9.8 | 38.4 | 32.0 | 3.0 | 20.2 | 27.2 | .8 | 29.2 | 6.7 | 29.5 | 5.0 | 33.0 | 16.4 | 75.2 | 34.6 |
| 35 | 5.2 | 9.4 | 35.5 | 19.3 | 12.9 | 36.0 | 31.4 | 2.4 | 12.2 | 26.6 | 1.0 | 28.7 | 5.2 | 28.7 | 3.6 | 32.2 | 15.1 | 71.3 | 33.7 |
| 36 | 1.3 | 8.8 | 31.6 | 16.1 | 8.3 | 33.9 | 29.4 | 2.6 | 9.1 | 24.2 | .9 | 28.0 | 5.5 | 29.0 | 3.5 | 31.5 | 14.0 | 99.5 | 33.5 |
| 37 | -.4 | 9.5 | 46.8 | 17.6 | 7.6 | 37.0 | 30.6 | 2.7 | 8.7 | 24.9 | .7 | 28.8 | 7.0 | 30.5 | 3.5 | 31.9 | 15.4 | 82.5 | 34.1 |
| 38 | -1.0 | 9.0 | 37.5 | 36.0 | 6.9 | 35.5 | 29.0 | 2.4 | 8.0 | 24.0 | .7 | 26.2 | 6.0 | 28.0 | 3.6 | 30.6 | 14.0 | 71.5 | 32.5 |
| 39 | 2.2 | 9.3 | 34.2 | 25.1 | 6.6 | 34.7 | 28.3 | 2.1 | 7.6 | 22.7 | .8 | 26.8 | 5.4 | 46.2 | 3.2 | 30.4 | 14.1 | 68.0 | 32.0 |
| 40 | -1.6 | 9.0 | 31.0 | 20.0 | 5.8 | 33.7 | 28.2 | 2.4 | 7.9 | 22.7 | .8 | 26.7 | 5.3 | 35.3 | 3.1 | 47.3 | 13.5 | 65.4 | 32.1 |
| 41 | .6 | 9.1 | 41.2 | 16.9 | 5.1 | 31.9 | 26.2 | 2.7 | 7.9 | 21.4 | .6 | 24.4 | 5.1 | 28.4 | 3.1 | 35.5 | 13.0 | 62.4 | 29.5 |
| 42 | -5.2 | 8.2 | 27.5 | 14.6 | 4.6 | 28.0 | 23.1 | 1.7 | 6.1 | 17.9 | .6 | 21.6 | 4.5 | 23.6 | 2.5 | 27.6 | 11.7 | 53.2 | 38.8 |
| 43 | .5 | 9.8 | 30.4 | 15.7 | 4.8 | 30.0 | 24.5 | 2.5 | 6.5 | 20.0 | .5 | 31.2 | 4.8 | 24.8 | 2.6 | 27.5 | 12.3 | 59.9 | 34.1 |
| 44 | -4.7 | 9.6 | 26.6 | 15.5 | 6.9 | 30.1 | 24.4 | 2.1 | 6.5 | 19.0 | .6 | 29.4 | 5.0 | 23.7 | 2.8 | 27.1 | 12.6 | 58.1 | 30.0 |
| 45 | -.6 | 9.8 | 27.5 | 15.5 | 6.0 | 35.2 | 25.2 | 2.1 | 6.8 | 20.7 | .6 | 26.2 | 4.9 | 25.2 | 3.0 | 27.5 | 12.2 | 59.7 | 28.9 |
| 46 | 1.8 | 9.7 | 25.6 | 15.1 | 4.7 | 37.8 | 24.2 | 2.0 | 7.0 | 19.8 | .6 | 23.6 | 4.5 | 24.0 | 2.5 | 27.4 | 12.0 | 58.0 | 27.2 |
| 47 | .5 | 9.6 | 25.4 | 14.0 | 4.4 | 33.0 | 30.4 | 2.0 | 6.2 | 19.0 | .5 | 22.7 | 4.7 | 23.0 | 2.4 | 26.5 | 11.6 | 54.7 | 25.8 |
| 54 | 9.5 | 9.2 | 24.4 | 13.6 | 3.6 | 28.0 | 20.7 | 2.0 | 5.6 | 17.2 | .6 | 20.9 | 3.8 | 20.6 | 2.7 | 23.3 | 10.8 | 51.2 | 23.5 |
| 55 | 7.5 | 13.7 | 20.6 | 12.6 | 3.1 | 24.7 | 18.6 | 1.8 | 6.0 | 15.7 | .6 | 18.9 | 4.0 | 19.5 | 2.2 | 22.2 | 10.2 | 46.8 | 21.8 |
| 56 | 6.3 | 12.0 | 19.4 | 12.3 | 3.4 | 23.0 | 17.8 | 1.5 | 4.6 | 14.6 | .6 | 18.3 | 2.8 | 17.0 | 2.1 | 21.4 | 10.3 | 45.3 | 26.7 |
| 57 | 4.9 | 9.5 | 17.1 | 11.4 | 2.9 | 21.0 | 16.4 | 1.4 | 4.8 | 13.5 | .6 | 17.2 | 2.6 | 17.7 | 2.4 | 20.1 | 9.8 | 42.8 | 27.8 |
| 58 | 5.7 | 9.5 | 19.1 | 12.6 | 2.8 | 22.0 | 17.0 | 1.4 | 4.8 | 14.3 | .6 | 18.0 | 2.6 | 17.1 | 2.4 | 20.4 | 9.2 | 44.0 | 24.6 |
| 59 | 6.1 | 8.8 | 18.9 | 12.1 | 3.0 | 21.8 | 16.7 | 1.6 | 5.1 | 17.5 | .5 | 18.1 | 3.0 | 17.0 | 2.2 | 21.8 | 9.9 | 42.8 | 21.2 |
| 60 | 5.4 | 8.5 | 18.1 | 11.6 | 3.0 | 21.2 | 20.3 | 1.4 | 5.0 | 14.9 | .5 | 17.9 | 2.8 | 16.0 | 1.9 | 22.8 | 9.2 | 42.5 | 20.1 |

| Cycle | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 48 | .8 | 9.7 | 23.8 | 14.4 | 4.5 | 30.2 | 34.8 | 1.8 | 6.7 | 18.3 | .6 | 22.1 | 4.2 | 22.7 | 2.7 | 25.8 | 11.2 | 54.6 | 26.1 |
| 49 | -1.8 | 9.3 | 23.3 | 13.8 | 4.0 | 27.7 | 29.4 | 1.7 | 7.0 | 17.9 | .6 | 22.3 | 4.0 | 28.6 | 2.5 | 25.5 | 11.6 | 53.8 | 25.5 |
| 50 | -1.9 | 9.2 | 22.0 | 13.4 | 3.8 | 27.5 | 24.7 | 2.0 | 6.5 | 17.7 | .6 | 21.3 | 11.0 | 27.8 | 2.1 | 25.0 | 11.7 | 53.4 | 25.2 |
| 51 | 1.7 | 9.0 | 22.6 | 13.5 | 3.8 | 25.8 | 21.3 | 3.1 | 5.7 | 16.5 | .6 | 20.4 | 8.1 | 23.2 | 2.4 | 24.5 | 11.8 | 50.5 | 23.5 |
| 52 | .6 | 9.1 | 26.4 | 13.7 | 3.5 | 25.8 | 21.2 | 2.5 | 6.0 | 16.9 | .6 | 19.4 | 5.5 | 21.5 | 2.7 | 23.9 | 11.1 | 52.0 | 24.1 |
| 53 | 2.9 | 9.1 | 25.4 | 13.3 | 3.3 | 28.6 | 20.5 | 2.1 | 6.0 | 16.1 | .6 | 19.3 | 4.2 | 20.5 | 2.3 | 23.6 | 11.3 | 48.8 | 23.0 |
| 54 | 16.0 | 9.2 | 24.4 | 13.6 | 3.6 | 28.0 | 20.7 | 2.0 | 5.6 | 17.2 | .6 | 20.9 | 3.8 | 20.6 | 2.7 | 23.3 | 10.8 | 51.2 | 23.5 |
| 55 | 7.9 | 13.7 | 20.6 | 12.6 | 3.1 | 24.7 | 18.6 | 1.8 | 6.0 | 15.7 | .6 | 18.9 | 4.0 | 19.5 | 2.2 | 22.2 | 10.2 | 46.8 | 21.8 |
| 56 | 3.1 | 12.0 | 19.4 | 12.3 | 3.4 | 23.0 | 17.8 | 1.5 | 4.6 | 14.6 | .6 | 18.3 | 2.8 | 17.9 | 2.1 | 21.4 | 10.3 | 45.3 | 26.7 |
| 57 | -2.6 | 9.5 | 17.1 | 11.4 | 2.9 | 21.0 | 16.4 | 1.4 | 4.8 | 13.5 | .6 | 17.2 | 2.6 | 17.7 | 2.4 | 20.1 | 9.8 | 42.9 | 27.8 |
| 58 | .7 | 9.5 | 19.1 | 12.6 | 2.8 | 22.0 | 17.0 | 1.4 | 4.8 | 18.3 | .6 | 19.0 | 2.6 | 17.1 | 2.4 | 20.4 | 9.2 | 44.0 | 24.6 |
| 59 | 2.3 | 8.8 | 18.9 | 12.1 | 3.0 | 21.8 | 16.7 | 1.6 | 5.1 | 17.5 | .5 | 19.1 | 3.0 | 17.0 | 2.2 | 21.8 | 9.9 | 42.9 | 21.2 |
| 60 | -1.0 | 8.5 | 18.1 | 11.6 | 3.0 | 21.2 | 20.3 | 1.4 | 5.0 | 14.9 | .5 | 17.9 | 2.8 | 16.9 | 1.9 | 22.8 | 9.2 | 42.5 | 20.1 |

18K PROTEIN - Raw Data (Asp, Asn Background Corrected)  TABLE 3

PTH AMINO ACID

| Cycle | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 1 | 68.5 | 18.0 | 1.3 | 1.1 | 1.6 | 35.0 | 410.5 | .7 | 7.3 | 1.5 | .2 | 2.2 | .7 | 3.9 | 7.0 | 2.0 | 2.6 | 2.4 | 2.5 |
| 2 | 22.3 | 1.6 | 220.0 | 3.2 | 1.7 | 30.1 | 14.0 | .4 | 7.4 | 2.3 | .1 | 4.9 | .3 | 2.7 | 4.9 | 3.1 | 6.1 | 5.4 | 9.2 |
| 3 | 1.5 | -.2 | 23.0 | 5.0 | 67.4 | 25.8 | 7.1 | .2 | 7.1 | 5.9 | .2 | 4.0 | .4 | 5.5 | 5.0 | 8.1 | 5.6 | 24.0 | 9.3 |
| 4 | .4 | 1.2 | 11.0 | 9.1 | 6.0 | 26.5 | 8.8 | .2 | 6.8 | 4.7 | .1 | 6.0 | 1.0 | 4.1 | 5.6 | 17.4 | 7.1 | 37.9 | 372.0 |
| 5 | -.3 | -.5 | 11.8 | 9.8 | 65.0 | 27.9 | 11.5 | .3 | 6.5 | 7.9 | .4 | 10.6 | .9 | 6.3 | 5.8 | 18.0 | 7.0 | 46.2 | 31.0 |
| 6 | -.1 | -1.2 | 14.8 | 13.5 | 9.0 | 258.0 | 17.9 | .4 | 7.0 | 9.2 | .7 | 13.0 | .3 | 13.5 | 5.6 | 18.0 | 7.2 | 51.8 | 24.1 |
| 7 | -2.8 | -4.0 | 13.3 | 13.0 | 5.5 | 39.0 | 13.3 | .5 | 8.2 | 8.9 | .1 | 15.2 | 2.0 | 18.3 | 12.0 | 24.0 | 10.1 | 491.5 | 27.4 |
| 8 | 2.6 | 1.2 | 15.6 | 16.7 | 62.0 | 34.4 | 15.7 | .6 | 9.1 | 10.5 | .4 | 13.0 | 3.1 | 22.0 | 5.3 | 30.4 | 10.1 | 110.4 | 22.2 |
| 9 | -.7 | 23.7 | 24.3 | 19.7 | 10.4 | 38.5 | 20.8 | .8 | 10.9 | 11.0 | .6 | 229.0 | 3.4 | 19.5 | 5.5 | 35.3 | 12.1 | 92.9 | 24.8 |
| 10 | -1.2 | -.5 | 23.3 | 19.4 | 7.3 | 39.0 | 21.3 | .7 | 15.0 | 14.3 | .7 | 80.0 | 3.0 | 265.5 | 4.9 | 31.0 | 13.4 | 74.0 | 26.0 |
| 11 | -.2 | -7.0 | 24.0 | 17.0 | 8.2 | 40.7 | 21.8 | .7 | 13.3 | 14.8 | .8 | 49.5 | 3.9 | 82.9 | 6.0 | 269.5 | 16.1 | 79.6 | 30.5 |
| 12 | 2.1 | -1.0 | 27.2 | 18.0 | 9.9 | 181.0 | 23.6 | .8 | 13.9 | 17.1 | 1.1 | 28.0 | 3.7 | 33.9 | 5.0 | 94.1 | 17.9 | 79.0 | 31.5 |
| 13 | 2.2 | 5.4 | 31.8 | 18.4 | 11.0 | 216.0 | 26.9 | .9 | 12.3 | 17.7 | 1.1 | 27.3 | 3.1 | 22.9 | 5.1 | 46.0 | 18.2 | 86.0 | 31.3 |
| 14 | 1.2 | 3.3 | 31.4 | 16.6 | 9.2 | 92.9 | 26.4 | .9 | 78.1 | 20.0 | .9 | 24.5 | 3.2 | 19.2 | 3.9 | 31.8 | 17.4 | 85.3 | 35.3 |
| 15 | -.1 | 6.6 | 32.5 | 18.2 | 36.1 | 60.9 | 31.0 | .8 | 33.3 | 27.9 | 1.0 | 24.1 | 3.2 | 20.8 | 4.1 | 28.3 | 18.0 | 89.0 | 35.0 |
| 16 | -.6 | 5.6 | 33.8 | 18.6 | 17.8 | 135.0 | 35.1 | .7 | 18.4 | 29.0 | .9 | 24.2 | 3.5 | 22.5 | 5.9 | 29.6 | 19.8 | 93.1 | 36.3 |
| 17 | -.8 | 5.8 | 32.4 | 19.0 | 11.0 | 151.0 | 37.4 | 1.1 | 15.0 | 27.3 | 1.1 | 24.6 | 4.4 | 26.1 | 5.8 | 32.4 | 22.5 | 93.8 | 36.1 |
| 18 | .3 | 3.2 | 35.8 | 19.0 | 9.1 | 74.0 | 37.9 | 1.3 | 14.0 | 29.5 | 1.6 | 26.0 | 7.0 | 26.0 | 5.7 | 32.3 | 22.1 | 94.0 | 155.0 |
| 19 | -3.7 | -.4 | 35.1 | 18.1 | 9.4 | 48.6 | 36.1 | 1.4 | 13.6 | 28.1 | 1.3 | 26.1 | 7.1 | 26.0 | 5.4 | 32.7 | 23.0 | 92.3 | 158.5 |
| 20 | -1.0 | -.7 | 40.8 | 18.1 | 9.6 | 42.5 | 36.0 | 1.8 | 12.6 | 29.3 | 1.1 | 28.0 | 7.0 | 26.8 | 7.5 | 32.3 | 21.4 | 255.5 | 78.2 |
| 21 | -2.1 | -4.8 | 36.4 | 17.4 | 9.0 | 38.0 | 31.5 | 1.9 | 54.0 | 28.3 | 1.4 | 24.4 | 6.8 | 27.0 | 6.0 | 33.1 | 20.9 | 132.3 | 40.0 |
| 22 | 1.5 | -.8 | 37.4 | 18.0 | 8.8 | 39.6 | 122.5 | 2.0 | 24.1 | 28.0 | 1.2 | 26.5 | 6.9 | 27.0 | 5.1 | 34.0 | 21.5 | 97.1 | 30.6 |
| 23 | 3.5 | 7.0 | 97.3 | 18.1 | 9.0 | 43.3 | 60.8 | 2.1 | 15.3 | 28.5 | 1.2 | 28.2 | 7.0 | 28.0 | 5.1 | 33.3 | 21.9 | 92.2 | 31.4 |
| 24 | 1.5 | 6.7 | 57.6 | 17.4 | 23.2 | 41.0 | 39.1 | 1.6 | 11.9 | 29.9 | 1.0 | 27.1 | 6.1 | 26.6 | 4.8 | 32.0 | 19.7 | 84.6 | 31.3 |
| 25 | 3.8 | 5.9 | 90.0 | 18.0 | 12.3 | 40.0 | 34.0 | 1.9 | 11.0 | 28.8 | 1.1 | 28.0 | 5.7 | 27.0 | 5.9 | 31.9 | 19.5 | 82.0 | 33.2 |
| 26 | 6.8 | 5.7 | 101.1 | 19.0 | 10.6 | 41.2 | 33.8 | 1.7 | 10.3 | 31.0 | 1.0 | 28.0 | 5.5 | 29.1 | 5.2 | 31.1 | 20.0 | 78.7 | 33.0 |
| 27 | -4.1 | -2.5 | 48.2 | 16.1 | 6.9 | 35.4 | 30.5 | 2.0 | 10.0 | 25.4 | 1.1 | 25.1 | 5.8 | 27.3 | 5.5 | 31.1 | 19.0 | 146.0 | 32.1 |
| 28 | .7 | 1.1 | 39.6 | 18.0 | 8.4 | 37.3 | 33.0 | 2.0 | 10.0 | 88.0 | 1.1 | 26.1 | 6.1 | 29.9 | 5.3 | 33.0 | 19.0 | 104.0 | 33.2 |
| 29 | .6 | .4 | 36.2 | 18.1 | 8.3 | 36.3 | 85.9 | 2.1 | 3.9 | 48.0 | 1.1 | 25.0 | 6.0 | 28.2 | 5.0 | 31.9 | 17.3 | 83.6 | 34.0 |
| 30 | -4.1 | -1.4 | 33.7 | 18.0 | 8.5 | 37.5 | 48.0 | 2.1 | 9.0 | 33.3 | 1.2 | 27.5 | 6.1 | 29.1 | 4.2 | 32.0 | 59.5 | 76.5 | 34.2 |
| 31 | 2.2 | .5 | 35.4 | 18.3 | 17.2 | 36.3 | 35.2 | 2.4 | 9.4 | 29.7 | .9 | 26.8 | 6.5 | 29.0 | 4.4 | 31.1 | 30.6 | 76.3 | 33.0 |
| 32 | -.7 | 1.0 | 33.5 | 19.5 | 11.0 | 35.6 | 29.6 | 2.0 | 9.6 | 27.5 | 1.0 | 27.2 | 6.5 | 27.5 | 18.6 | 31.3 | 21.1 | 72.9 | 31.1 |
| 33 | 4.6 | 5.7 | 36.4 | 20.0 | 17.0 | 37.8 | 30.6 | 2.7 | 9.0 | 27.3 | .9 | 27.7 | 6.5 | 29.8 | 9.5 | 32.4 | 16.7 | 75.0 | 32.5 |
| 34 | 6.3 | 2.4 | 36.0 | 19.6 | 9.8 | 38.4 | 32.0 | 3.0 | 20.2 | 27.2 | .8 | 29.2 | 6.7 | 29.5 | 5.0 | 33.0 | 16.4 | 75.2 | 34.6 |
| 35 | 5.2 | 3.8 | 35.5 | 19.3 | 12.9 | 36.0 | 31.4 | 2.4 | 12.2 | 26.6 | 1.0 | 28.7 | 5.2 | 28.7 | 3.6 | 32.2 | 15.1 | 71.3 | 33.7 |
| 36 | 1.3 | -.9 | 31.6 | 16.1 | 8.3 | 33.9 | 29.4 | 2.6 | 9.1 | 24.2 | .9 | 20.0 | 5.5 | 29.0 | 3.5 | 31.5 | 14.0 | 99.5 | 33.5 |
| 37 | -.4 | 3.4 | 46.8 | 17.6 | 7.6 | 37.0 | 30.6 | 2.7 | 8.7 | 24.9 | .7 | 28.8 | 7.0 | 30.5 | 3.5 | 31.9 | 15.4 | 82.5 | 34.1 |
| 38 | -1.0 | -.5 | 37.5 | 36.0 | 6.9 | 35.5 | 29.0 | 2.4 | 8.0 | 24.0 | .7 | 26.2 | 6.0 | 28.0 | 3.6 | 30.6 | 14.0 | 71.5 | 32.5 |
| 39 | 2.2 | 1.1 | 34.2 | 25.1 | 6.6 | 34.7 | 28.3 | 2.1 | 7.6 | 22.7 | .8 | 26.8 | 5.4 | 46.2 | 3.2 | 30.4 | 14.1 | 68.0 | 32.0 |
| 40 | -1.6 | -1.2 | 31.0 | 20.0 | 5.8 | 33.7 | 28.2 | 2.4 | 7.9 | 22.7 | .8 | 26.7 | 5.3 | 35.3 | 3.1 | 47.3 | 13.5 | 65.4 | 32.1 |
| 41 | .6 | -.9 | 41.2 | 16.9 | 5.1 | 31.0 | 26.2 | 2.7 | 7.9 | 21.4 | .6 | 24.4 | 5.1 | 28.4 | 3.1 | 35.5 | 13.0 | 62.4 | 29.5 |

| CYCLE | | | | | | | | | | | | | | | | | | |
|---|---|---|---|---|---|---|---|---|---|---|---|---|---|---|---|---|---|---|
| 42 | -5.2 | -7.2 | 27.5 | 14.6 | 4.6 | 28.0 | 23.1 | 1.7 | 6.1 | 17.9 | .6 | 21.6 | 4.5 | 23.6 | 2.5 | 27.6 | 11.7 | 53.2 | 38.8 |
| 43 | .5 | 3.4 | 30.4 | 15.7 | 4.8 | 30.0 | 24.5 | 2.5 | 6.5 | 20.0 | .5 | 31.2 | 4.8 | 24.8 | 2.6 | 27.5 | 12.3 | 59.9 | 34.1 |
| 44 | -4.7 | 1.9 | 26.6 | 15.5 | 6.9 | 30.1 | 24.4 | 2.1 | 6.5 | 19.0 | .6 | 29.4 | 5.0 | 23.7 | 2.8 | 27.1 | 12.6 | 58.1 | 30.0 |
| 45 | -.6 | 3.2 | 27.5 | 15.5 | 6.0 | 35.2 | 25.2 | 2.1 | 6.8 | 20.7 | .6 | 26.2 | 4.9 | 25.2 | 3.0 | 27.5 | 12.2 | 59.7 | 28.9 |
| 46 | 1.8 | 2.5 | 25.6 | 15.1 | 4.7 | 37.8 | 24.2 | 2.0 | 7.0 | 19.8 | .6 | 23.6 | 4.5 | 21.0 | 2.5 | 27.4 | 12.0 | 58.0 | 27.2 |
| 47 | .5 | 1.8 | 25.4 | 14.0 | 4.4 | 33.0 | 30.4 | 2.0 | 6.2 | 19.0 | .5 | 22.7 | 4.7 | 23.0 | 2.4 | 26.5 | 11.6 | 51.7 | 25.8 |
| 48 | .8 | 2.6 | 23.8 | 14.4 | 4.5 | 30.2 | 31.8 | 1.8 | 6.7 | 18.3 | .6 | 22.1 | 4.2 | 22.7 | 2.7 | 25.8 | 11.2 | 54.6 | 26.1 |
| 49 | -1.8 | -.0 | 23.3 | 13.8 | 4.0 | 27.7 | 29.4 | 1.7 | 7.0 | 17.9 | .6 | 22.3 | 4.0 | 28.6 | 2.5 | 25.5 | 11.6 | 53.8 | 25.5 |
| 50 | -1.9 | -.5 | 22.0 | 13.4 | 3.8 | 27.5 | 24.7 | 2.0 | 6.5 | 17.7 | .6 | 21.3 | 11.0 | 27.8 | 2.1 | 25.0 | 11.7 | 53.4 | 25.2 |
| 51 | 1.7 | -1.6 | 22.6 | 13.5 | 3.8 | 25.8 | 21.3 | 3.1 | 5.7 | 16.5 | .6 | 20.1 | 8.1 | 23.2 | 2.1 | 24.5 | 11.8 | 50.5 | 23.5 |
| 52 | .6 | -.7 | 26.4 | 13.7 | 3.5 | 25.8 | 21.2 | 2.5 | 6.0 | 16.9 | .6 | 19.4 | 5.5 | 21.5 | 2.7 | 23.9 | 11.1 | 52.0 | 24.1 |
| 53 | 2.9 | -.3 | 25.4 | 13.3 | 3.3 | 28.6 | 20.5 | 2.1 | 6.0 | 16.1 | .6 | 19.3 | 1.2 | 20.5 | 2.3 | 23.6 | 11.3 | 48.8 | 23.0 |
| 54 | 16.0 | .7 | 24.4 | 13.6 | 3.6 | 28.0 | 20.7 | 2.0 | 5.6 | 17.2 | .6 | 20.9 | 3.8 | 20.6 | 2.7 | 23.3 | 10.8 | 51.2 | 23.5 |
| 55 | 7.9 | 31.6 | 20.6 | 12.6 | 3.1 | 24.7 | 18.6 | 1.8 | 6.0 | 15.7 | .6 | 18.9 | 4.0 | 19.5 | 2.2 | 22.2 | 10.2 | 46.8 | 21.8 |
| 56 | 3.1 | 20.6 | 19.4 | 12.3 | 3.4 | 23.0 | 17.8 | 1.5 | 4.6 | 14.6 | .6 | 18.3 | 2.8 | 17.9 | 2.1 | 21.4 | 10.3 | 45.3 | 26.7 |
| 57 | -2.6 | 4.3 | 17.1 | 11.4 | 2.9 | 21.0 | 16.4 | 1.4 | 4.8 | 13.5 | .6 | 17.2 | 2.6 | 17.7 | 2.4 | 20.1 | 9.8 | 42.8 | 27.8 |
| 58 | .7 | 4.9 | 19.1 | 12.6 | 2.8 | 22.0 | 17.0 | 1.4 | 4.8 | 19.3 | .6 | 19.0 | 2.6 | 17.1 | 2.4 | 20.4 | 9.2 | 44.0 | 24.6 |
| 59 | 2.3 | .8 | 18.9 | 12.1 | 3.0 | 21.8 | 16.7 | 1.6 | 5.1 | 17.5 | .5 | 19.1 | 3.0 | 17.0 | 2.2 | 21.9 | 9.9 | 42.8 | 21.2 |
| 60 | -1.0 | -.5 | 18.1 | 11.6 | 3.0 | 21.2 | 20.3 | 1.4 | 5.0 | 11.9 | .5 | 17.9 | 2.8 | 16.3 | 1.9 | 22.8 | 9.2 | 42.5 | 20.1 |

18K PROTEIN - Background Corrected Data          TABLE 4

| CYCLE | PTH AMINO ACID | | | | | | | | | | | | | | | | | |
|---|---|---|---|---|---|---|---|---|---|---|---|---|---|---|---|---|---|---|
| | Asp | Asn | Glu | Gln | Thr | Gly | Ala | His | Ser | Tyr | Arg | Pro | Met | Val | Trp | Phe | Ile | Lys | Leu |
| 1 | 68.5 | 18.0 | .7 | 1.9 | .8 | 10.3 | 173.6 | 9.2 | 6.7 | .4 | 4.1 | 1.9 | 1.7 | 5.0 | 6.2 | .4 | .6 | .9 | .0 |
| 2 | 22.3 | 1.6 | 174.8 | -.4 | -.7 | 5.4 | 4.2 | 2.9 | 4.8 | -.3 | -.1 | 4.0 | -1.3 | -.0 | -.9 | -2.9 | 4.6 | -2.9 | 1.6 |
| 3 | 1.5 | -.2 | 13.4 | -2.8 | 69.3 | 1.0 | .2 | -1.6 | 2.6 | 3.2 | .3 | -.2 | -1.8 | .1 | -.6 | -1.9 | .6 | .2 | -.8 |
| 4 | .4 | 1.2 | 1.5 | 4.8 | 1.4 | -.4 | -.1 | -2.3 | .6 | -.6 | 2.9 | -1.2 | .2 | -1.7 | 1.4 | 3.8 | .9 | 1.7 | 225.8 |
| 5 | -.3 | -.5 | .0 | -.0 | 64.4 | -1.2 | .0 | -1.2 | -1.2 | 2.2 | 1.2 | .7 | -1.5 | -1.9 | 2.0 | 1.2 | -2.9 | 1.3 | 8.7 |
| 6 | -.1 | -1.2 | .4 | 7.9 | 2.6 | 122.8 | 1.8 | -.3 | -1.9 | 2.0 | 6.1 | .7 | -5.8 | 1.1 | 1.3 | -1.7 | -4.1 | .3 | 2.6 |
| 7 | -2.8 | -4.0 | -2.7 | .2 | -2.0 | 2.2 | -1.1 | .7 | -1.6 | -.6 | -2.1 | .7 | 1.7 | 4.9 | 22.9 | 1.7 | -.7 | 175.5 | 3.1 |
| 8 | 2.6 | 1.2 | -2.7 | 9.7 | 58.7 | -1.4 | -.9 | 1.5 | -1.5 | -.4 | -3.6 | -3.5 | 6.0 | 7.2 | .1 | 6.0 | -2.9 | 18.4 | -1.6 |
| 9 | -.7 | 23.7 | 2.7 | 17.3 | 2.2 | -.1 | .4 | 4.2 | -.3 | -1.9 | -.6 | 213.1 | 6.3 | 2.3 | .7 | 9.0 | -1.0 | 5.0 | -1.2 |
| 10 | -1.2 | -.5 | .3 | 12.6 | -1.6 | -.6 | -.2 | 1.1 | 3.9 | .9 | .2 | 60.9 | 2.9 | 300.5 | -1.4 | 3.0 | -.4 | -.6 | -1.5 |
| 11 | -.2 | -7.0 | -.7 | .3 | -1.0 | -.3 | -.7 | -.1 | 1.3 | -.6 | 1.1 | 19.7 | 6.2 | 76.3 | 2.2 | 241.9 | 3.2 | -.0 | .5 |
| 12 | 2.1 | -1.0 | .5 | 1.9 | .6 | 75.8 | -.6 | .5 | 1.5 | .7 | 6.6 | 5.9 | 3.8 | 15.1 | -1.3 | 64.1 | 5.1 | -1.7 | .3 |
| 13 | 2.2 | 5.4 | 2.9 | 1.7 | 1.7 | 94.5 | .2 | 1.1 | -.8 | -.5 | 5.5 | 4.2 | -.6 | .5 | .0 | 14.7 | 4.1 | -.0 | -.4 |
| 14 | 1.2 | 3.3 | 1.4 | -6.6 | -.3 | 27.1 | -.6 | -.3 | 76.8 | .9 | .0 | .5 | -1.5 | -5.1 | -5.5 | -.3 | 1.1 | -1.2 | 1.6 |
| 15 | -.1 | 6.6 | 1.2 | -1.2 | 28.9 | 9.5 | .8 | -3.6 | 23.7 | 10.6 | 1.3 | -.6 | -2.8 | -4.1 | -4.5 | -4.4 | 1.0 | -.4 | 1.0 |
| 16 | -.6 | 5.6 | 1.2 | -.1 | 9.0 | 19.9 | 2.1 | -6.9 | 6.0 | 10.3 | -1.8 | -1.0 | -2.5 | -2.8 | 1.5 | -3.4 | 3.5 | .7 | 1.5 |
| 17 | -.8 | 5.8 | -.8 | 1.3 | 1.7 | 58.6 | 2.6 | -.7 | 2.0 | 6.0 | 8.6 | -1.1 | .8 | .9 | 1.2 | -.8 | 7.9 | .7 | 1.2 |
| 18 | .3 | 3.2 | 1.1 | 1.4 | -.2 | 16.8 | 2.4 | 1.6 | .9 | 7.5 | 12.4 | .0 | 13.0 | .2 | .8 | -1.0 | 6.2 | .7 | 76.1 |
| 19 | -3.7 | -.4 | -.2 | -1.8 | .2 | 3.1 | 1.3 | 2.0 | .5 | 3.8 | 5.2 | -.1 | 12.3 | -.3 | -.1 | -.6 | 7.3 | .0 | 78.2 |
| 20 | -1.0 | -.7 | 3.8 | -1.3 | .6 | -.0 | 1.0 | 8.2 | -.4 | 4.1 | .3 | 1.6 | 10.7 | .2 | 7.0 | -.8 | 3.6 | 66.3 | 27.6 |
| 21 | -2.1 | -4.8 | -.3 | -3.5 | .1 | -2.2 | -1.2 | 8.6 | 19.8 | 1.3 | 6.6 | -2.1 | 8.6 | .1 | 2.0 | .2 | 2.1 | 16.7 | 3.6 |
| 22 | 1.5 | -.8 | .1 | -.4 | .0 | -1.0 | 37.3 | 9.0 | 13.8 | -.4 | 1.9 | -.1 | 8.2 | -.2 | -.9 | 1.3 | 3.0 | 2.9 | -2.2 |
| 23 | 3.5 | 7.0 | 48.1 | .6 | .4 | 1.3 | 10.9 | 9.4 | 3.7 | -.7 | 1.8 | 1.6 | 7.8 | .8 | -.8 | .9 | 3.7 | 1.4 | -1.6 |
| 24 | 1.5 | 6.7 | 15.8 | -1.5 | 15.9 | .4 | 1.6 | -1.6 | .1 | .6 | -2.7 | .5 | 2.4 | -1.1 | -1.6 | -.1 | -.7 | -1.2 | -1.5 |
| 25 | 3.8 | 5.9 | 41.8 | 1.3 | 4.1 | .2 | -.6 | 2.7 | -.5 | -1.7 | -.3 | 1.5 | -.4 | -.8 | 2.4 | .1 | -.9 | -1.6 | -.2 |
| 26 | 6.8 | 5.7 | 50.7 | 5.6 | 2.3 | 1.2 | -.7 | -2.5 | -.9 | 1.2 | -2.3 | 1.5 | -2.1 | 1.6 | .3 | -.5 | .4 | -2.3 | -.1 |
| 27 | -4.1 | -2.5 | 8.0 | -5.7 | -1.8 | -1.7 | -2.0 | 1.8 | -.8 | -7.4 | .2 | -1.5 | -1.0 | -.7 | 1.6 | -.3 | -1.2 | 25.7 | -.6 |
| 28 | .7 | 1.1 | 1.2 | 1.6 | -.2 | -.3 | -.8 | .4 | -.4 | 86.1 | .7 | -.5 | .1 | 2.3 | 1.3 | 1.8 | -.6 | 9.3 | .2 |
| 29 | .6 | .4 | -1.3 | 1.6 | -.5 | -.6 | 21.3 | 1.0 | -.1 | 26.6 | 1.2 | -1.7 | -.6 | .0 | .8 | .7 | -3.3 | 1.7 | .8 |
| 30 | -4.1 | -1.4 | -3.0 | .4 | -.6 | .2 | 5.9 | -.3 | -.7 | 5.2 | 4.2 | .7 | -.3 | .9 | -1.5 | .8 | 82.1 | -.5 | 1.0 |
| 31 | 2.2 | .5 | -.3 | .3 | 42.0 | -.2 | 5.5 | 2.2 | .5 | 2.2 | -.6 | -1.0 | 2.9 | .6 | .3 | -2.5 | 44.1 | .1 | -2.0 |
| 32 | -.7 | 1.0 | -1.5 | 5.9 | 14.3 | -1.0 | -1.9 | -2.8 | 2.5 | -.6 | 6.6 | -.6 | 2.9 | -4.0 | 127.1 | -1.9 | 15.5 | -2.1 | -6.1 |
| 33 | 4.6 | 5.7 | 1.4 | 8.4 | 42.9 | 2.8 | .1 | 4.7 | .5 | .2 | 3.7 | .3 | 3.1 | 2.7 | 48.3 | 1.4 | 3.0 | 1.0 | -3.0 |
| 34 | 6.3 | 2.4 | 1.5 | 7.0 | 10.7 | 4.3 | 2.6 | 7.9 | 59.0 | 1.3 | .6 | 4.3 | 4.4 | 2.0 | 10.0 | 3.4 | 3.4 | 2.4 | 1.9 |
| 35 | 5.2 | 3.8 | 1.6 | 6.2 | 25.9 | .9 | 2.4 | .9 | 18.9 | 1.4 | 12.0 | 3.0 | -3.7 | .1 | -1.0 | 1.9 | .6 | -.3 | .5 |

TABLE 5

18K PROTEIN - Background Corrected Data (Cycles 1-37 Lag Corrected)

| CYCLE | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 1 | 68.5 | 18.0 | .7 | 1.9 | .8 | 10.3 | 157.2 | 9.2 | 6.7 | .4 | 4.1 | 4.9 | 1.7 | 5.0 | 6.2 | .4 | .6 | .9 | .0 |
| 2 | 22.3 | 1.6 | 170.7 | -.4 | -.7 | 5.4 | 20.7 | 2.9 | 4.8 | -.3 | -.1 | 4.0 | -1.3 | -.0 | -.9 | -2.9 | 4.6 | -2.9 | 1.6 |
| 3 | 1.5 | -.2 | 17.5 | -2.8 | 70.6 | 1.0 | .2 | -1.6 | 2.6 | 3.2 | .3 | -.2 | -1.8 | .1 | -.6 | -1.9 | .6 | .2 | -.8 |
| 4 | .4 | 1.2 | 1.5 | 4.8 | .0 | -.4 | -.1 | -2.3 | .6 | -.6 | 2.9 | -1.2 | .2 | -4.7 | 1.4 | 3.8 | .9 | 1.7 | 234.5 |
| 5 | -.3 | -.5 | .0 | -.0 | 67.0 | -1.2 | .0 | -1.2 | -1.2 | 2.2 | 1.2 | .7 | -1.5 | -4.8 | 2.0 | 1.2 | -2.0 | 1.3 | .0 |
| 6 | -.1 | -1.2 | .4 | 7.9 | .0 | 125.0 | 1.8 | -.3 | -1.9 | 2.0 | 6.1 | .7 | -5.8 | 1.4 | 1.3 | -1.7 | -4.1 | .3 | 2.6 |
| 7 | -2.8 | -4.0 | -2.7 | .2 | -2.0 | .0 | -1.1 | .7 | -1.6 | -.6 | -2.1 | .7 | 1.7 | 4.9 | 22.9 | 1.7 | -.7 | 197.9 | 3.1 |
| 8 | 2.6 | 1.2 | -2.7 | 9.7 | 60.9 | -1.4 | -.9 | 1.5 | -1.5 | -.4 | -3.6 | -3.5 | 6.0 | 7.2 | .1 | 6.0 | -2.9 | .0 | -1.6 |
| 9 | -.7 | 23.7 | 2.7 | 17.3 | .0 | -.1 | .4 | 4.2 | -.3 | -1.9 | -.6 | 271.7 | 6.3 | 2.3 | .7 | 9.0 | -1.0 | 1.0 | -1.2 |
| 10 | -1.2 | -.5 | .3 | 12.6 | -1.6 | -.6 | -.2 | 1.1 | 3.9 | .9 | .2 | 9.3 | 2.9 | 380.6 | -1.4 | 3.0 | -.4 | -.6 | -1.5 |
| 11 | -.2 | -7.0 | -.7 | .3 | -1.0 | -.3 | -.7 | -.1 | 1.3 | -.6 | 1.1 | 12.7 | 6.2 | .0 | 2.2 | 315.3 | 3.2 | -.0 | .5 |
| 12 | 2.1 | -1.0 | .5 | 1.9 | .6 | 99.2 | -.6 | .5 | 1.5 | .7 | 6.6 | 5.9 | 3.8 | 3.3 | -1.3 | .0 | 5.1 | -1.7 | .3 |
| 13 | 2.2 | 5.4 | 2.9 | 1.7 | 1.7 | 98.0 | .2 | 1.1 | -.8 | -.5 | 5.5 | 1.2 | -.6 | .5 | .0 | 5.3 | 4.1 | -.0 | -.4 |
| 14 | 1.2 | 3.3 | 1.4 | -6.6 | -.3 | 3.3 | -.6 | -.3 | 102.3 | .8 | .0 | .5 | -1.5 | -5.1 | -5.5 | -.3 | 1.1 | -1.2 | 1.6 |
| 15 | -.1 | 6.6 | 1.2 | -1.2 | 38.3 | 6.3 | .8 | -3.6 | 1.7 | 10.6 | 1.3 | -.6 | -2.9 | -4.1 | -4.5 | -4.4 | 1.0 | -.4 | 1.0 |
| 16 | -.6 | 5.6 | 1.2 | -.1 | .8 | 66.0 | 2.1 | -6.9 | 2.4 | 10.3 | -1.8 | -1.0 | -2.5 | -2.8 | 1.5 | -3.4 | 3.5 | .7 | 1.5 |
| 17 | -.8 | 5.8 | -.8 | 1.3 | .5 | 59.3 | 2.6 | -.7 | 2.0 | 6.0 | 8.6 | -1.1 | .8 | .9 | 1.2 | -.8 | 7.9 | .7 | 1.2 |
| 18 | .3 | 3.2 | 1.1 | 1.4 | -.2 | 2.0 | 2.4 | 1.6 | .9 | 7.5 | 12.4 | .0 | 13.0 | .2 | .8 | -1.0 | 6.2 | .7 | 101.1 |
| 19 | -3.7 | -.4 | -.2 | -1.8 | .2 | 1.1 | 1.3 | 2.0 | .5 | 3.8 | 5.2 | -.1 | 12.3 | -.3 | -.1 | -.6 | 7.3 | .0 | 75.5 |
| 20 | -1.0 | -.7 | 3.8 | -1.3 | .6 | -.0 | 1.0 | 8.2 | -.4 | 4.1 | .3 | 1.6 | 10.7 | .2 | .7 | -.8 | 3.6 | 85.8 | 7.8 |
| 21 | -2.1 | -4.8 | -.3 | -3.5 | .1 | -2.2 | -1.2 | 8.6 | 61.7 | 1.3 | 6.6 | -2.1 | 8.6 | .1 | 2.0 | .2 | 2.1 | .0 | 1.1 |
| 22 | 1.5 | -.8 | .1 | -.4 | .0 | -1.0 | 49.2 | 9.0 | .0 | -.4 | 1.9 | -.1 | 8.2 | -.2 | -.9 | 1.3 | 3.0 | .2 | -2.2 |
| 23 | 3.5 | 7.0 | 63.4 | .6 | .4 | 1.3 | .5 | 9.4 | 1.7 | -.7 | 1.8 | 1.6 | 7.8 | .8 | -.8 | .9 | 3.7 | 1.4 | -1.6 |
| 24 | 1.5 | 6.7 | 2.5 | -1.5 | 20.7 | .4 | .0 | -1.6 | .1 | .6 | -2.7 | .5 | 2.4 | -1.1 | -1.6 | -.1 | -.7 | -1.2 | -1.5 |
| 25 | 3.8 | 5.9 | 52.6 | 1.3 | .0 | .2 | -.6 | 2.7 | -.5 | -1.7 | -.3 | 1.5 | -.4 | -.8 | 2.4 | .1 | -.9 | -1.6 | -.2 |
| 26 | 6.8 | 5.7 | 47.3 | 5.6 | 1.7 | 1.2 | -.7 | -2.5 | -.9 | 1.2 | -2.3 | 1.5 | -2.1 | 1.6 | .3 | -.5 | .4 | -2.3 | -.1 |
| 27 | -4.1 | -2.5 | .0 | -5.7 | -1.8 | -1.7 | -2.0 | 1.8 | -.8 | -7.4 | .2 | -1.5 | -1.0 | -.7 | 1.6 | -.3 | -1.2 | 34.2 | -.6 |
| 28 | .7 | 1.1 | .0 | 1.6 | -.2 | -.3 | -.8 | .4 | -.4 | 115.2 | .7 | -.5 | .1 | 2.3 | 1.3 | 1.8 | -.6 | 1.9 | .2 |
| 29 | .6 | .4 | -1.3 | 1.6 | -.5 | -.6 | 28.8 | 1.0 | -.1 | 1.3 | 1.2 | -1.7 | -.6 | .0 | .8 | .7 | -3.3 | .6 | .8 |
| 36 | 1.3 | -.9 | -1.2 | -8.0 | 5.8 | -1.8 | .2 | 3.1 | 4.0 | -1.8 | 8.5 | 1.4 | -1.6 | 1.5 | -.7 | .7 | -1.7 | 28.5 | .7 |
| 37 | -.4 | 3.4 | 12.1 | -.1 | 3.6 | 3.8 | 2.5 | 4.3 | 2.9 | .7 | -.1 | 4.1 | 7.4 | 6.6 | .5 | 2.7 | 3.8 | 13.1 | 2.8 |
| 38 | -1.0 | -.5 | 4.9 | 87.1 | 1.5 | 2.2 | .9 | 1.0 | .3 | .2 | 1.0 | -2.3 | 2.3 | .3 | 2.5 | .1 | .4 | 3.6 | .4 |
| 39 | 2.2 | 1.1 | 2.7 | 37.3 | 1.2 | 1.7 | .6 | -2.2 | -.8 | -1.0 | 6.8 | .3 | -.5 | 53.8 | .0 | .7 | 1.6 | 1.5 | .4 |
| 40 | -1.6 | -1.2 | .7 | 14.7 | -1.4 | 1.0 | 1.1 | 1.5 | 1.7 | .2 | 7.6 | 1.0 | -.4 | 23.6 | .1 | 48.1 | .6 | .2 | 1.7 |
| 41 | .6 | -.9 | 9.8 | 1.6 | -3.5 | -2.5 | -1.0 | 5.2 | 2.7 | -1.1 | -1.6 | -4.1 | -.8 | 5.0 | 1.0 | 17.1 | -.2 | -1.4 | -2.6 |
| 42 | -5.2 | -7.2 | -1.0 | -7.7 | -4.6 | -6.3 | -4.7 | -5.7 | -5.7 | -6.4 | -1.1 | -10.5 | -3.4 | -7.5 | -3.4 | -3.1 | -3.6 | -9.1 | 18.6 |
| 43 | .5 | 3.4 | 2.1 | -1.1 | -2.6 | -2.1 | -2.0 | 3.8 | -2.7 | -1.5 | -5.6 | 17.4 | -.9 | -2.5 | -1.7 | -2.0 | -1.0 | -1.2 | 9.9 |
| 44 | -4.7 | 1.9 | -.4 | -.5 | 8.2 | -.9 | -1.4 | -.2 | -1.8 | -2.3 | -.3 | 13.9 | 1.1 | -4.2 | .8 | -1.7 | .6 | -1.6 | 2.6 |
| 45 | -.6 | 3.2 | 1.0 | 1.1 | 5.1 | 8.2 | .5 | .3 | .6 | 1.9 | -.1 | 6.6 | 1.4 | 1.8 | 3.3 | .8 | -.0 | 1.2 | 1.7 |
| 46 | 1.8 | 2.5 | .0 | .9 | .1 | 13.5 | -.1 | -.3 | 2.5 | 1.2 | .1 | 1.0 | -.0 | -.0 | -.5 | 1.9 | -.1 | .9 | -.4 |
| 47 | .5 | 1.8 | .5 | -2.7 | -.3 | 6.8 | 9.5 | .3 | -.8 | .7 | -4.7 | .1 | 2.0 | -1.2 | -.8 | .9 | -.8 | -1.1 | -2.0 |
| 48 | .8 | 2.6 | -.3 | .8 | 1.2 | 3.4 | 16.5 | -1.4 | 2.5 | .2 | .3 | .0 | .1 | -.3 | 2.4 | .3 | -1.5 | .1 | .1 |
| 49 | -1.8 | -.0 | -.1 | -.5 | -.2 | .5 | 9.7 | -1.9 | 4.8 | .3 | .4 | 2.2 | -.1 | 18.1 | 1.1 | .8 | .3 | .5 | .3 |
| 50 | -1.9 | -.5 | -.6 | -.9 | -.3 | 1.3 | 3.9 | 2.1 | 3.0 | .8 | .4 | .9 | 10.2 | 17.8 | -2.0 | .7 | 1.2 | 1.4 | 1.0 |
| 51 | 1.7 | -1.6 | .5 | 1.0 | .5 | -.4 | -.1 | 15.1 | -.4 | -.7 | .5 | -.1 | 21.7 | 6.3 | 1.1 | .5 | 2.1 | -.3 | -1.2 |
| 52 | .6 | -.7 | 4.1 | 3.3 | -.2 | .6 | .7 | 8.9 | 1.8 | .7 | .5 | -1.4 | 10.9 | 3.1 | 4.1 | -.0 | .4 | 2.3 | 1.3 |
| 53 | 2.9 | -.3 | 3.8 | 2.6 | -.5 | 6.1 | .6 | 4.9 | 2.4 | -.2 | .6 | -.4 | 4.4 | 1.8 | .9 | .1 | 1.6 | .3 | .2 |
| 54 | 16.0 | .7 | 3.4 | 5.2 | 1.5 | 6.1 | 1.8 | 4.3 | 1.0 | 2.3 | .8 | 5.2 | 3.0 | 3.7 | 4.7 | .2 | .6 | 3.7 | 2.3 |
| 55 | 7.9 | 31.6 | .7 | 1.5 | -.4 | 1.8 | -.3 | 2.5 | 3.6 | .0 | .9 | .7 | 4.8 | 2.0 | .5 | -2.1 | -.6 | .4 | -.3 |
| 56 | 3.1 | 20.6 | .0 | .9 | 1.4 | -.1 | -.5 | -.5 | -3.1 | -1.6 | 1.2 | -.1 | -1.2 | -1.2 | -.2 | -3.7 | .4 | -.1 | 11.0 |
| 57 | -2.6 | 4.3 | -1.5 | -2.6 | -.6 | -2.4 | -1.5 | -1.3 | -1.6 | -3.3 | 1.5 | -2.4 | -1.7 | -.5 | 2.6 | -6.9 | -.5 | -1.6 | 11.1 |
| 58 | .7 | 4.9 | .4 | 3.5 | -.9 | -.0 | .3 | -1.0 | -1.2 | 5.7 | 1.9 | .3 | -1.1 | -1.9 | 2.8 | -5.9 | -1.6 | .4 | 7.9 |
| 59 | 2.3 | .8 | .4 | 1.5 | .0 | .4 | .9 | 1.5 | .8 | 1.1 | -2.5 | .9 | 1.7 | -.2 | 1.1 | 6.7 | 1.4 | -.0 | 1.1 |
| 60 | -1.0 | -.5 | -.1 | -.8 | -.0 | .1 | 7.0 | -.6 | .6 | -.4 | -1.9 | .4 | 1.0 | .4 | -1.4 | .5 | .1 | .4 | -1.0 |

| CYCLE | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 30 | -4.1 | -1.4 | -3.0 | .4 | -.6 | .2 | .0 | -.3 | -.7 | 1.5 | 4.2 | .7 | -.3 | .9 | -1.5 | .8 | 112.5 | -.5 | 1.0 |
| 31 | 2.2 | .5 | -.3 | .3 | 58.1 | -.2 | 4.4 | 2.2 | .5 | 2.2 | -.6 | -1.0 | 2.9 | .6 | .3 | -2.5 | 18.1 | .1 | -2.0 |
| 32 | -.7 | 1.0 | -1.5 | 5.9 | .6 | -1.0 | -1.9 | -2.8 | 2.5 | -.6 | 6.6 | -.6 | 2.9 | -4.0 | 177.7 | -1.9 | 11.1 | -2.1 | -6.1 |
| 33 | 4.6 | 5.7 | 1.4 | 8.4 | 53.9 | 2.8 | .1 | 4.7 | .5 | .2 | 3.7 | .3 | 3.1 | 2.7 | 5.0 | 1.4 | 3.0 | 1.0 | -3.0 |
| 34 | 6.3 | 2.4 | 1.5 | 7.0 | .0 | 4.3 | 2.6 | 7.9 | 82.0 | 1.3 | .6 | 4.3 | 4.4 | 2.0 | 2.6 | 3.4 | 3.4 | 2.4 | 1.9 |
| 35 | 5.2 | 3.8 | 1.6 | 6.2 | 31.1 | .9 | 2.4 | .9 | .0 | 1.4 | 12.0 | 3.0 | -3.7 | .1 | -1.0 | 1.9 | .6 | -.3 | .5 |
| 36 | 1.3 | -.9 | -1.2 | -8.0 | .0 | -1.8 | .2 | 3.1 | .0 | -1.8 | 8.5 | 1.4 | -1.6 | 1.5 | -.7 | .7 | -1.7 | 43.0 | .7 |
| 37 | -.4 | 3.4 | 18.3 | -.1 | 1.8 | 3.8 | 2.5 | 4.3 | 2.9 | .7 | -.1 | 4.1 | 7.4 | 6.6 | .5 | 2.7 | 3.8 | 1.4 | 2.8 |
| 38 | -1.0 | -.5 | .0 | 87.1 | 1.2 | 2.2 | .9 | 1.0 | .3 | .2 | -1.0 | -2.3 | 2.3 | .3 | 2.5 | .1 | .4 | 1.2 | .4 |
| 39 | 2.2 | 1.1 | 1.5 | 37.3 | 1.2 | 1.7 | .6 | -2.2 | -.8 | -1.0 | 6.8 | .3 | -.5 | 53.8 | .0 | .7 | 1.6 | 1.1 | .4 |
| 40 | -1.6 | -1.2 | .5 | 14.7 | -1.4 | 1.0 | 1.1 | 1.5 | 1.7 | .2 | 7.6 | 1.0 | -.4 | 23.6 | .1 | 48.1 | .6 | .2 | 1.7 |
| 41 | .6 | -.9 | 9.8 | 1.6 | -3.5 | -2.5 | -1.0 | 5.2 | 2.7 | -1.1 | -1.6 | -4.1 | -.8 | 5.0 | 1.0 | 17.1 | -.2 | -1.4 | -2.6 |
| 42 | -5.2 | -7.2 | -1.0 | -7.7 | -4.6 | -6.3 | -4.7 | -5.7 | -5.7 | -6.4 | -1.1 | -10.5 | -3.4 | -7.5 | -3.4 | -3.1 | -3.6 | -9.1 | 18.6 |
| 43 | .5 | 3.4 | 2.1 | -1.1 | -2.6 | -2.1 | -2.0 | 3.8 | -2.7 | -1.5 | -5.6 | 17.4 | -.9 | -2.5 | -1.7 | -2.0 | -1.0 | -1.2 | 9.9 |
| 44 | -4.7 | 1.9 | -.4 | -.5 | 8.2 | -.9 | -1.4 | -.2 | -1.8 | -2.3 | -.3 | 13.9 | 1.1 | -4.2 | .8 | -1.7 | .6 | -1.6 | 2.6 |
| 45 | -.6 | 3.2 | 1.0 | 1.1 | 5.1 | 8.2 | .5 | .3 | .6 | 1.9 | -.1 | 6.6 | 1.4 | 1.8 | 3.3 | .8 | -.0 | 1.2 | 1.7 |
| 46 | 1.8 | 2.5 | .0 | .9 | .1 | 13.5 | -.1 | -.3 | 2.5 | 1.2 | .1 | 1.0 | -.0 | -.0 | -.5 | 1.9 | -.1 | .9 | -.4 |
| 47 | .5 | 1.8 | .5 | -2.7 | -.3 | 6.8 | 9.5 | .3 | -.8 | .7 | -4.7 | .1 | 2.0 | -1.2 | -.8 | .9 | -.8 | -1.1 | -2.0 |
| 48 | .8 | 2.6 | -.3 | .8 | 1.2 | 3.4 | 16.5 | -1.4 | 2.5 | .2 | .3 | .0 | .1 | -.3 | 2.4 | .3 | -1.5 | .1 | .1 |
| 49 | -1.8 | -.0 | -.1 | -.5 | -.2 | .5 | 9.7 | -1.9 | 4.8 | .3 | .4 | 2.2 | -.1 | 18.4 | 1.1 | .8 | .3 | .5 | .3 |
| 50 | -1.9 | -.5 | -.6 | -.9 | -.3 | 1.3 | 3.9 | 2.1 | 3.0 | .8 | .4 | .9 | 40.2 | 17.8 | -2.0 | .7 | 1.2 | 1.4 | 1.0 |
| 51 | 1.7 | -1.6 | .5 | 1.0 | .5 | -.4 | -.1 | 15.1 | -.4 | -.7 | .5 | -.1 | 24.7 | 6.3 | 1.1 | .5 | 2.1 | -.3 | -1.2 |
| 52 | .6 | -.7 | 4.1 | 3.3 | -.2 | .6 | .7 | 8.9 | 1.8 | .7 | .5 | -1.4 | 10.9 | 3.1 | 4.1 | -.0 | .4 | 2.3 | 1.3 |
| 53 | 2.9 | -.3 | 3.8 | 2.6 | -.5 | 6.1 | .6 | 4.9 | 2.4 | -.2 | .6 | -.4 | 4.4 | 1.8 | .9 | .1 | 1.6 | .3 | .2 |
| 54 | 16.0 | .7 | 3.4 | 5.2 | 1.5 | 6.1 | 1.8 | 4.3 | 1.0 | 2.3 | .8 | 5.2 | 3.0 | 3.7 | 4.7 | .2 | .6 | 3.7 | 2.3 |
| 55 | 7.9 | 31.6 | .7 | 1.5 | -.4 | 1.8 | -.3 | 2.5 | 3.6 | .0 | .9 | .7 | 4.8 | 2.0 | .5 | -2.1 | -.6 | .4 | -.3 |
| 56 | 3.1 | 20.6 | .0 | .9 | 1.4 | -.1 | -.5 | -.5 | -3.1 | -1.6 | 1.2 | -.1 | -1.2 | -1.2 | -.2 | -3.7 | .4 | -.1 | 11.0 |
| 57 | -2.6 | 4.3 | -1.5 | -2.6 | -.6 | -2.4 | -1.5 | -1.3 | -1.6 | -3.3 | 1.5 | -2.4 | -1.7 | -.5 | 2.6 | -6.9 | -.5 | -1.6 | 14.1 |
| 58 | .7 | 4.9 | .4 | 3.5 | -.9 | -.0 | .3 | -1.0 | -1.2 | 5.7 | 1.9 | .3 | -1.1 | -1.0 | 2.8 | -5.9 | -1.6 | .4 | 7.9 |
| 59 | 2.3 | .8 | .4 | 1.5 | .0 | .4 | .9 | 1.5 | .2 | 1.1 | -2.5 | .9 | 1.7 | -.2 | 1.1 | 6.2 | 1.4 | -.0 | 1.1 |
| 60 | -1.0 | -.5 | -.1 | -.8 | -.0 | .1 | 7.0 | -.6 | .6 | -.1 | -1.3 | .4 | 1.8 | .4 | -1.4 | .5 | .1 | .4 | -1.0 |

18K PROTEIN – Background Corrected Data (Cycles 1-38 Lag Corrected)

TABLE 6

PTH AMINO ACID

| CYCLE | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 1 | 68.5 | 18.0 | .7 | 1.9 | .8 | 10.3 | 157.2 | 9.2 | 6.7 | .1 | 1.1 | 4.9 | 1.7 | 5.0 | 6.2 | .4 | .6 | .9 | .0 |
| 2 | 22.3 | 1.6 | 170.7 | -.4 | -.2 | 5.4 | 20.7 | 2.9 | 4.8 | -.3 | -.1 | 4.0 | -1.3 | -.0 | -.9 | -2.9 | 4.6 | -2.9 | 1.6 |
| 3 | 1.5 | -.2 | 17.5 | -2.8 | 70.6 | 1.0 | .2 | -1.6 | 2.6 | 3.2 | .3 | -.2 | -1.8 | .1 | -.6 | -1.9 | .6 | .2 | -.8 |
| 4 | .4 | 1.2 | 1.5 | 4.8 | .0 | -.4 | -.1 | -2.3 | .6 | -.6 | 2.9 | -1.2 | .2 | -4.7 | 1.4 | 3.8 | .9 | 1.7 | 234.5 |
| 5 | -.3 | -.5 | .0 | -.0 | 67.0 | -1.2 | .0 | -1.2 | -1.2 | 2.2 | 1.2 | .7 | -1.5 | -4.8 | 2.0 | 1.2 | -2.0 | 1.3 | .0 |
| 6 | -.1 | -1.2 | .4 | 7.9 | .0 | 125.0 | 1.8 | -.3 | -1.9 | 2.0 | 6.1 | .7 | -5.8 | 1.4 | 1.3 | -1.7 | -4.1 | .3 | 2.6 |
| 7 | -2.8 | -4.0 | -2.7 | .2 | -2.0 | .0 | -1.1 | .7 | -1.6 | -.6 | -2.1 | .7 | 1.7 | 4.9 | 22.9 | 1.7 | -.7 | 197.9 | 3.1 |
| 8 | 2.6 | 1.2 | -2.7 | 9.7 | 60.9 | -1.4 | -.9 | 1.5 | -1.5 | -.4 | -3.6 | -3.5 | 6.0 | 7.2 | .1 | 6.0 | -2.9 | .0 | -1.6 |
| 9 | -.7 | 23.7 | 2.7 | 17.3 | .0 | -.1 | .4 | 4.2 | -.3 | -1.9 | -.6 | 271.7 | 6.3 | 2.3 | .7 | 9.0 | -1.0 | 1.0 | -1.2 |
| 10 | -1.2 | -.5 | .3 | 12.6 | -1.6 | -.6 | -.2 | 1.1 | 3.9 | .9 | .2 | 9.3 | 2.9 | 398.6 | -1.1 | 3.0 | -.4 | -.6 | -1.5 |
| 11 | -.2 | -7.0 | -.7 | .3 | -1.0 | -.3 | -.7 | -.1 | 1.3 | -.6 | 1.1 | 12.7 | 6.2 | .0 | 2.2 | 315.3 | 3.2 | -.0 | .5 |
| 12 | 2.1 | -1.0 | .5 | 1.9 | .6 | 99.2 | -.6 | .5 | 1.5 | .7 | 6.6 | 5.9 | 3.8 | 3.3 | -1.3 | .0 | 5.1 | -1.7 | .3 |
| 13 | 2.2 | 5.4 | 2.9 | 1.7 | 1.7 | 98.0 | .2 | 1.1 | -.8 | -.5 | 5.5 | 4.2 | -.6 | .5 | .9 | 5.3 | 4.1 | -.0 | -.4 |
| 14 | 1.2 | 3.3 | 1.4 | -6.6 | -.3 | 3.3 | -.6 | -.3 | 102.3 | .8 | .0 | .5 | -1.5 | -5.1 | -5.5 | -.3 | 1.1 | -1.2 | 1.6 |
| 15 | -.1 | 6.6 | 1.2 | -1.2 | 39.3 | 6.3 | .8 | -3.6 | 1.7 | 10.6 | 1.3 | -.6 | -2.8 | -4.1 | -1.5 | -4.4 | 1.0 | -.4 | 1.0 |
| 16 | -.6 | 5.6 | 1.2 | -.1 | .8 | 66.0 | 2.1 | -6.9 | 2.4 | 10.3 | -1.8 | -1.0 | -2.5 | -2.8 | 1.5 | -3.4 | 3.5 | .7 | 1.5 |
| 17 | -.8 | 5.8 | -.8 | 1.3 | .5 | 59.3 | 2.6 | -.7 | 2.0 | 6.0 | 8.6 | -1.1 | .8 | .9 | 1.2 | -.8 | 7.9 | .7 | 1.2 |
| 18 | .3 | 3.2 | 1.1 | 1.4 | -.2 | 2.0 | 2.4 | 1.6 | .9 | 7.5 | 12.1 | .0 | 13.0 | .2 | .8 | -1.0 | 6.2 | .7 | 101.1 |
| 19 | -3.7 | -.4 | -.2 | -1.8 | .2 | 1.1 | 1.3 | 2.0 | .5 | 3.8 | 5.2 | -.1 | 12.3 | -.3 | -.1 | -.6 | 7.3 | .0 | 75.5 |
| 20 | -1.0 | -.7 | 3.8 | -1.3 | .6 | -.0 | 1.0 | 8.2 | -.4 | 4.1 | .3 | 1.6 | 10.7 | .2 | 7.0 | -.8 | 3.6 | 85.8 | 7.8 |
| 21 | -2.1 | -4.8 | -.3 | -3.5 | .1 | -2.2 | -1.2 | 8.6 | 61.7 | 1.3 | 6.6 | -2.1 | 8.6 | .1 | 2.0 | .2 | 2.1 | .0 | 1.1 |
| 22 | 1.5 | -.8 | .1 | -.4 | .0 | -1.0 | 49.2 | 9.0 | .0 | -.4 | 1.9 | -.1 | 8.2 | -.2 | -.9 | 1.3 | 3.0 | .2 | -2.2 |
| 23 | 3.5 | 7.0 | 63.4 | .6 | .4 | 1.3 | .5 | 9.4 | 1.7 | -.7 | 1.8 | 1.6 | 7.8 | .8 | -.8 | .9 | 3.7 | 1.4 | -1.6 |

| CYCLE | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 24 | 1.5 | 6.7 | 2.5 | -1.5 | 20.7 | .4 | .0 | -1.6 | .1 | .6 | -2.7 | .5 | 2.4 | -1.1 | -1.6 | -.1 | -.7 | -1.2 | -1.5 |
| 25 | 3.8 | 5.9 | 52.6 | 1.3 | .0 | .2 | -.6 | 2.7 | -.5 | -1.7 | -.3 | 1.5 | -.4 | -.8 | 2.4 | .1 | -.9 | -1.6 | -.2 |
| 26 | 6.8 | 5.7 | 47.3 | 5.6 | 1.7 | 1.2 | -.7 | -2.5 | -.9 | 1.2 | -2.3 | 1.5 | -2.1 | 1.6 | .3 | -.5 | .4 | -2.3 | -.1 |
| 27 | -4.1 | -2.5 | .0 | -5.7 | -1.8 | -1.7 | -2.0 | 1.8 | -.8 | -7.4 | .2 | -1.5 | -1.0 | -.7 | 1.6 | -.3 | -1.2 | 34.2 | -.6 |
| 28 | .7 | 1.1 | .0 | 1.6 | -.2 | -.3 | -.8 | .4 | -.4 | 115.2 | .7 | -.5 | .1 | 2.3 | 1.3 | 1.8 | -.6 | 1.9 | .2 |
| 29 | .6 | .4 | -1.3 | 1.6 | -.5 | -.6 | 28.8 | 1.0 | -.1 | 1.3 | 1.2 | -1.7 | -.6 | .0 | .8 | .7 | -3.3 | .6 | .8 |
| 30 | -4.1 | -1.4 | -3.0 | .4 | -.6 | .2 | .0 | -.3 | -.7 | 1.5 | 4.2 | .7 | -.3 | .9 | -1.5 | .8 | 112.5 | -.5 | 1.0 |
| 31 | 2.2 | .5 | -.3 | .3 | 58.1 | -.2 | 4.4 | -2.2 | .5 | 2.2 | -.6 | -1.0 | 2.9 | .6 | .3 | -2.5 | 18.1 | .1 | -2.0 |
| 32 | -.7 | 1.0 | -1.5 | 5.9 | .6 | -1.0 | -1.9 | -2.8 | 2.5 | -.6 | 6.6 | -.6 | 2.9 | -4.0 | 177.7 | -1.9 | 11.1 | -2.1 | -6.1 |
| 33 | 4.6 | 5.7 | 1.4 | 8.4 | 53.9 | 2.8 | .1 | 4.7 | .5 | .2 | 3.7 | .3 | 3.1 | 2.7 | 5.0 | 1.4 | 3.0 | 1.0 | -3.0 |
| 34 | 6.3 | 2.4 | 1.5 | 7.0 | .0 | 4.3 | 2.6 | 7.9 | 82.0 | 1.3 | .6 | 4.3 | 4.4 | 2.0 | 2.6 | 3.4 | 3.4 | 2.4 | 1.9 |
| 35 | 5.2 | 3.8 | 1.6 | 6.2 | 31.1 | .9 | 2.4 | .9 | .0 | 1.4 | 12.0 | 3.0 | -3.7 | .1 | -1.0 | 1.9 | .6 | -.3 | .5 |
| 36 | 1.3 | -.9 | -1.2 | -8.0 | .0 | -1.8 | .2 | 3.1 | .0 | -1.8 | 0.5 | 1.4 | -1.6 | 1.5 | -.7 | .7 | -1.7 | 43.0 | .7 |
| 37 | -.4 | 3.4 | 18.3 | -.1 | 1.8 | 3.8 | 2.5 | 4.3 | 2.9 | .7 | -.1 | 4.1 | 7.4 | 6.6 | .5 | 2.7 | 3.8 | 1.4 | 2.8 |
| 38 | -1.0 | -.5 | .0 | 135.5 | 1.2 | 2.2 | .9 | 1.0 | .3 | .2 | 1.0 | -2.3 | 2.3 | .3 | 2.5 | .1 | .4 | 1.2 | .4 |
| 39 | 2.2 | 1.1 | 1.5 | .0 | 1.2 | 1.7 | .6 | -2.2 | -.8 | -1.0 | 6.8 | .3 | -.5 | 53.8 | .0 | .7 | 1.6 | 1.1 | .4 |
| 40 | -1.6 | -1.2 | .5 | 5.1 | -1.4 | 1.0 | 1.1 | 1.5 | 1.7 | .2 | 7.6 | 1.0 | -.4 | 23.6 | .1 | 48.1 | .6 | .2 | 1.7 |
| 41 | .6 | -.9 | 9.8 | .1 | -3.5 | -2.5 | -1.0 | 5.2 | 2.7 | -1.1 | -1.6 | -4.1 | -.8 | 5.0 | 1.0 | 17.1 | -.2 | -1.4 | -2.6 |
| 42 | -5.2 | -7.2 | -1.0 | -7.7 | -4.6 | -6.3 | -4.7 | -5.7 | -5.7 | -6.4 | -1.1 | -10.5 | -3.4 | -7.5 | -3.4 | -3.1 | -3.6 | -9.1 | 18.6 |
| 43 | .5 | 3.4 | 2.1 | -1.1 | -2.6 | -2.1 | -2.0 | 3.8 | -2.7 | -1.5 | -5.6 | 17.4 | -.9 | -2.5 | -1.7 | -2.0 | -1.0 | -1.2 | 9.9 |
| 44 | -4.7 | 1.9 | -.4 | -.5 | 8.2 | -.9 | -1.4 | -.2 | -1.8 | -2.3 | -.3 | 13.9 | 1.1 | -4.2 | .8 | -1.7 | .6 | -1.6 | 2.6 |
| 45 | -.6 | 3.2 | 1.0 | 1.1 | 5.1 | 8.2 | .5 | .3 | .6 | 1.9 | -.1 | 6.6 | 1.4 | 1.8 | 3.3 | .8 | -.0 | 1.2 | 1.7 |
| 46 | 1.8 | 2.5 | .0 | .9 | .1 | 13.5 | -.1 | -.3 | 2.5 | 1.2 | .1 | 1.0 | -.0 | -.0 | -.5 | 1.9 | -.1 | .9 | -.4 |
| 47 | .5 | 1.8 | .5 | -2.7 | -.3 | 6.8 | 9.5 | .3 | -.8 | .7 | -4.7 | .1 | 2.0 | -1.2 | -.8 | .9 | -.8 | -1.1 | -2.0 |
| 48 | .8 | 2.6 | -.3 | .8 | 1.2 | 3.4 | 16.5 | -1.4 | 2.5 | .2 | .3 | .0 | .1 | -.3 | 2.4 | .3 | -1.5 | .1 | .1 |
| 49 | -1.8 | -.0 | -.1 | -.5 | -.2 | .5 | 9.7 | -1.9 | 4.8 | .3 | .4 | 2.2 | -.1 | 18.4 | 1.1 | .8 | .3 | .5 | .3 |
| 50 | -1.9 | -.5 | -.6 | -.9 | -.3 | 1.3 | 3.9 | 2.1 | 3.0 | .8 | .4 | .9 | 40.2 | 17.8 | -2.0 | .7 | 1.2 | 1.4 | 1.0 |
| 51 | 1.7 | -1.6 | .5 | 1.0 | .5 | -.4 | -.1 | 15.1 | -.4 | -.7 | .5 | -.1 | 24.7 | 6.3 | 1.1 | .5 | 2.1 | -.3 | -1.2 |
| 52 | .6 | -.7 | 4.1 | 3.3 | -.2 | .6 | .7 | 8.9 | 1.8 | .7 | .5 | -1.1 | 10.9 | 3.1 | 4.1 | -.0 | .4 | 2.3 | 1.3 |
| 53 | 2.9 | -.3 | 3.8 | 2.6 | -.5 | 6.1 | .6 | 4.9 | 2.4 | -.2 | .6 | -.4 | 4.1 | 1.8 | .9 | .1 | 1.6 | .3 | .2 |
| 54 | 16.0 | .7 | 3.4 | 5.2 | 1.5 | 6.1 | 1.8 | 4.3 | 1.0 | 2.3 | .8 | 5.2 | 3.0 | 3.7 | 4.7 | .2 | .6 | 3.7 | 2.3 |
| 55 | 7.9 | 31.6 | .7 | 1.5 | -.4 | 1.8 | -.3 | 2.5 | 3.6 | .0 | .9 | .7 | 4.8 | 2.0 | .5 | -2.1 | -.6 | .4 | -.3 |
| 56 | 3.1 | 20.6 | .0 | .9 | 1.4 | -.1 | -.5 | -.5 | -3.1 | -1.6 | 1.2 | -.1 | -1.2 | -1.2 | -.2 | -3.7 | .4 | -.1 | 11.0 |
| 57 | -2.6 | 4.3 | -1.5 | -2.6 | -.6 | -2.4 | -1.5 | -1.3 | -1.6 | -3.3 | 1.5 | -2.4 | -1.7 | -.5 | 2.6 | -6.9 | -.5 | -1.6 | 14.1 |
| 58 | .7 | 4.9 | .4 | 3.5 | -.9 | -.0 | .3 | -1.0 | -1.2 | 5.7 | 1.9 | .3 | -1.1 | -1.0 | 2.9 | -5.9 | -1.6 | .4 | 7.9 |
| 59 | 2.3 | .8 | .4 | 1.5 | .0 | .1 | .9 | 1.5 | .8 | 4.1 | -2.5 | .9 | 1.7 | -.2 | 1.1 | 6.2 | 1.4 | -.0 | 1.1 |
| 60 | -1.0 | -.5 | -.1 | -.8 | -.0 | .1 | 7.0 | -.6 | .6 | -.4 | -1.3 | .1 | 1.0 | .1 | -1.4 | .5 | .1 | .4 | -1.0 |

18K PROTEIN – Background, Lag Corrected Data

TABLE 7

PTH AMINO ACID

| CYCLE | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 1 | 68.5 | 18.0 | .7 | 1.9 | .8 | 10.3 | 157.2 | 9.2 | 6.7 | .4 | 4.1 | 4.9 | 1.7 | 5.0 | 6.2 | .4 | .6 | .9 | .0 |
| 2 | 22.3 | 1.6 | 170.7 | -.4 | -.7 | 5.4 | 20.7 | 2.9 | 4.8 | -.3 | -.1 | 4.0 | -1.3 | -.0 | -.9 | -2.9 | 4.6 | -2.9 | 1.6 |
| 3 | 1.5 | -.2 | 17.5 | -2.8 | 70.6 | 1.0 | .2 | -1.6 | 2.6 | 3.2 | .3 | -.2 | -1.8 | .1 | -.6 | -1.9 | .6 | .2 | -.8 |
| 4 | .4 | 1.2 | 1.5 | 4.8 | .0 | -.4 | -.1 | -2.3 | .6 | -.6 | 2.9 | -1.2 | .2 | -4.7 | 1.4 | 3.8 | .9 | 1.7 | 234.5 |
| 5 | -.3 | -.5 | .0 | -.0 | 67.0 | -1.2 | .0 | -1.2 | -1.2 | 2.2 | 1.2 | .7 | -1.5 | -4.8 | 2.0 | 1.2 | -2.0 | 1.3 | .0 |
| 6 | -.1 | -1.2 | .4 | 7.9 | .0 | 125.0 | 1.8 | -.3 | -1.9 | 2.0 | 6.1 | .7 | -5.8 | 1.4 | 1.3 | -1.7 | -4.1 | .3 | 2.6 |
| 7 | -2.8 | -4.0 | -2.7 | .2 | -2.0 | .0 | -1.1 | .7 | -1.6 | -.6 | -2.1 | .7 | 1.7 | 4.9 | 22.9 | 1.7 | -.7 | 197.9 | 3.1 |
| 8 | 2.6 | 1.2 | -2.7 | 9.7 | 60.9 | -1.4 | -.9 | 1.5 | -1.5 | -.4 | -3.6 | -3.5 | 6.0 | 7.2 | .1 | 6.0 | -2.9 | .0 | -1.6 |
| 9 | -.7 | 23.7 | 2.7 | 17.3 | .0 | -.1 | .4 | 4.2 | -.3 | -1.9 | -.6 | 271.7 | 6.3 | 2.3 | .7 | 9.0 | -1.0 | 1.0 | -1.2 |
| 10 | -1.2 | -.5 | .3 | 12.6 | -1.6 | -.6 | -.2 | 1.1 | 3.9 | .9 | .2 | 9.3 | 2.9 | 388.6 | -1.4 | 3.0 | -.4 | -.6 | -1.5 |
| 11 | -.2 | -7.0 | -.7 | .3 | -1.0 | -.3 | -.7 | -.1 | 1.3 | -.6 | 1.1 | 12.7 | 6.2 | .0 | 2.2 | 315.3 | 3.2 | -.0 | .5 |
| 12 | 2.1 | -1.0 | .5 | 1.9 | .6 | 99.2 | -.6 | .5 | 1.5 | .7 | 6.6 | 5.9 | 3.8 | 3.3 | -1.3 | .0 | 5.1 | -1.7 | .3 |
| 13 | 2.2 | 5.4 | 2.9 | 1.7 | 1.7 | 98.0 | .2 | 1.1 | -.8 | -.5 | 5.5 | 4.2 | -.6 | .5 | .0 | 5.3 | 4.1 | -.0 | -.4 |
| 14 | 1.2 | 3.3 | 1.4 | -6.6 | -.3 | 3.3 | -.6 | -.3 | 102.3 | .8 | .0 | .5 | -1.5 | -5.1 | -5.5 | -.3 | 1.1 | -1.2 | 1.6 |
| 15 | -.1 | 6.6 | 1.2 | -1.2 | 38.3 | 6.3 | .8 | -3.6 | 1.7 | 10.6 | 1.3 | -.6 | -2.8 | -4.1 | -4.5 | -4.4 | 1.0 | -.4 | 1.0 |
| 16 | -.6 | 5.6 | 1.2 | -.1 | .8 | 66.0 | 2.1 | -6.9 | 2.4 | 10.3 | -1.8 | -1.0 | -2.5 | -2.8 | 1.5 | -3.4 | 3.5 | .7 | 1.5 |
| 17 | -.8 | 5.8 | -.8 | 1.3 | .5 | 59.3 | 2.6 | -.7 | 2.0 | 6.0 | 8.6 | -1.1 | .8 | .9 | 1.2 | -.8 | 7.9 | .7 | 1.2 |
| 18 | .3 | 3.2 | 1.1 | 1.4 | -.2 | 2.0 | 2.4 | 1.6 | .9 | 7.5 | 12.4 | .0 | 13.0 | .2 | .8 | -1.0 | 6.2 | .7 | 101.1 |

| | | | | | | | | | | | | | | | | | | | |
|---|---|---|---|---|---|---|---|---|---|---|---|---|---|---|---|---|---|---|---|
| 19 | -3.7 | -.4 | -.2 | -1.8 | .2 | 1.1 | 1.3 | 2.0 | .5 | 3.8 | 5.2 | -.1 | 12.3 | -.3 | -.1 | -.6 | 7.3 | .0 | 75.5 |
| 20 | -1.0 | -.7 | 3.8 | -1.3 | .6 | -.0 | 1.0 | 8.2 | -.4 | 4.1 | .3 | 1.6 | 10.7 | .2 | 7.0 | -.8 | 3.6 | 85.8 | 7.8 |
| 21 | -2.1 | -4.8 | -.3 | -3.5 | .1 | -2.2 | -1.2 | 8.6 | 64.7 | 1.3 | 6.6 | -2.1 | 8.6 | .1 | 2.0 | .2 | 2.1 | .0 | 1.1 |
| 22 | 1.5 | -.8 | .1 | -.4 | .0 | -1.0 | 49.2 | 9.0 | .0 | -.4 | 1.9 | -.1 | 8.2 | -.2 | -.9 | 1.3 | 3.0 | .2 | -2.2 |
| 23 | 3.5 | 7.0 | 63.4 | .6 | .4 | 1.3 | .5 | 9.4 | 1.7 | -.7 | 1.8 | 1.6 | 7.8 | .8 | -.8 | .9 | 3.7 | 1.4 | -1.6 |
| 24 | 1.5 | 6.7 | 2.5 | -1.5 | 20.7 | .4 | .0 | -1.6 | .1 | .6 | -2.7 | .5 | 2.4 | -1.1 | -1.6 | -.1 | -.7 | -1.2 | -1.5 |
| 25 | 3.8 | 5.9 | 52.6 | 1.3 | .0 | .2 | -.6 | 2.7 | -.5 | -1.7 | -.3 | 1.5 | -.4 | -.8 | 2.4 | .1 | -.9 | -1.6 | -.2 |
| 26 | 6.8 | 5.7 | 47.3 | 5.6 | 1.7 | 1.2 | -.7 | -2.5 | -.9 | 1.2 | -2.3 | 1.5 | -2.1 | 1.6 | .3 | -.5 | .4 | -2.3 | -.1 |
| 27 | -4.1 | -2.5 | .0 | -5.7 | -1.8 | -1.7 | -2.0 | 1.8 | -.8 | -7.4 | .2 | -1.5 | -1.0 | -.7 | 1.6 | -.3 | -1.2 | 34.2 | -.6 |
| 28 | .7 | 1.1 | .0 | 1.6 | -.2 | -.3 | -.8 | .4 | -.4 | 115.2 | .7 | -.5 | .1 | 2.3 | 1.3 | 1.8 | -.6 | 1.9 | .2 |
| 29 | .6 | .4 | -1.3 | 1.6 | -.5 | -.6 | 28.8 | 1.0 | -.1 | 1.3 | 1.2 | -1.7 | -.6 | .0 | .8 | .7 | -3.3 | .6 | .8 |
| 30 | -4.1 | -1.4 | -3.0 | .4 | -.6 | .2 | .0 | -.3 | -.7 | 1.5 | 4.2 | .7 | -.3 | .9 | -1.5 | .8 | 112.5 | -.5 | 1.0 |
| 31 | 2.2 | .5 | -.3 | .3 | 58.1 | -.2 | 4.4 | 2.2 | .5 | 2.2 | -.6 | -1.0 | 2.9 | .6 | .3 | -2.5 | 18.1 | .1 | -2.0 |
| 32 | -.7 | 1.0 | -1.5 | 5.9 | .6 | -1.0 | -1.9 | -2.8 | 2.5 | -.6 | 6.6 | -.6 | 2.9 | -4.0 | 177.7 | -1.9 | 11.1 | -2.1 | -6.1 |
| 33 | 4.6 | 5.7 | 1.4 | 8.4 | 53.9 | 2.8 | .1 | 4.7 | .5 | .2 | 3.7 | .3 | 3.1 | 2.7 | 5.0 | 1.4 | 3.0 | 1.0 | -3.0 |
| 34 | 6.3 | 2.4 | 1.5 | 7.0 | .0 | 4.3 | 2.6 | 7.9 | 82.0 | 1.3 | .6 | 4.3 | 4.4 | 2.0 | 2.6 | 3.4 | 3.4 | 2.4 | 1.9 |
| 35 | 5.2 | 3.8 | 1.6 | 6.2 | 31.1 | .9 | 2.4 | .9 | .0 | 1.4 | 12.0 | 3.0 | -3.7 | .1 | -1.0 | 1.9 | .6 | -.3 | .5 |
| 36 | 1.3 | -.9 | -1.2 | -8.0 | .0 | -1.8 | .2 | 3.1 | .0 | -1.8 | 8.5 | 1.4 | -1.6 | 1.5 | -.7 | .7 | -1.7 | 43.0 | .7 |
| 37 | -.4 | 3.4 | 18.3 | -.1 | 1.8 | 3.8 | 2.5 | 4.3 | 2.9 | .7 | -.1 | 4.1 | 7.4 | 6.6 | .5 | 2.7 | 3.8 | 1.4 | 2.8 |
| 38 | -1.0 | -.5 | .0 | 135.5 | 1.2 | 2.2 | .9 | 1.0 | .3 | .2 | 1.0 | -2.3 | 2.3 | .3 | 2.5 | .1 | .4 | 1.2 | .4 |
| 39 | 2.2 | 1.1 | 1.5 | .0 | 1.2 | 1.7 | .6 | -2.2 | -.8 | -1.0 | 6.8 | .3 | -.5 | 82.4 | .0 | .7 | 1.6 | 1.1 | .4 |
| 40 | -1.6 | -1.2 | .5 | 5.1 | -1.4 | 1.0 | 1.1 | 1.5 | 1.7 | -.2 | 7.6 | 1.0 | -.4 | .0 | .1 | 65.2 | .6 | .2 | 1.7 |
| 41 | .6 | -.9 | 11.1 | .1 | -3.5 | -2.5 | -1.0 | 5.2 | 2.7 | -1.1 | -1.6 | -4.1 | -.8 | .0 | 1.0 | .0 | -.2 | -1.4 | -2.6 |
| 42 | -5.2 | -7.2 | -1.0 | -7.7 | -4.6 | -6.3 | -4.7 | -5.7 | -5.7 | -6.4 | -1.1 | -10.5 | -3.4 | -7.5 | -3.4 | -3.1 | -3.6 | -9.1 | 31.7 |
| 43 | .5 | 3.4 | .7 | -1.1 | -2.6 | -2.1 | -2.0 | 3.8 | -2.7 | -1.5 | -5.6 | 30.2 | -.9 | -2.5 | -1.7 | -2.0 | -1.0 | -1.2 | .0 |
| 44 | -4.7 | 1.9 | -.4 | -.5 | 13.0 | -.9 | -1.4 | -.2 | -1.8 | -2.3 | -.3 | 4.3 | 1.1 | -4.2 | .8 | -1.7 | .6 | -1.6 | .0 |
| 45 | -.6 | 3.2 | 1.0 | 1.1 | .4 | 14.9 | .5 | .3 | .6 | 1.9 | -.1 | 3.9 | 1.4 | 1.8 | 3.3 | .8 | -.0 | 1.2 | 1.2 |
| 46 | 1.8 | 2.5 | .0 | .9 | .0 | 16.1 | -.1 | -.3 | 2.5 | 1.2 | .1 | .5 | -.0 | -.0 | -.5 | 1.9 | -.1 | .9 | -.4 |
| 47 | .5 | 1.8 | .5 | -2.7 | -.3 | .0 | 17.9 | .3 | -.8 | .7 | -4.7 | .1 | 2.0 | -1.2 | -.8 | .9 | -.8 | -1.1 | -2.0 |
| 48 | .8 | 2.6 | -.3 | .8 | 1.2 | 1.4 | 21.5 | -1.4 | 2.5 | .2 | .3 | .0 | .1 | -.3 | 2.4 | .3 | -1.5 | .1 | .1 |
| 49 | -1.8 | -.0 | -.1 | -.5 | -.2 | .1 | .0 | -1.9 | 4.8 | .3 | .4 | 2.2 | -.1 | 39.7 | 1.1 | .8 | .3 | .5 | .3 |
| 50 | -1.9 | -.5 | -.6 | -.9 | -.3 | 1.3 | .4 | 2.1 | 3.0 | .8 | .4 | .9 | 79.5 | 3.8 | -2.0 | .7 | 1.2 | 1.4 | 1.0 |
| 51 | 1.7 | -1.6 | .5 | 1.0 | .5 | -.4 | -.1 | 29.0 | -.4 | -.7 | .5 | -.1 | .0 | .8 | 1.1 | .5 | 2.1 | -.3 | -1.2 |
| 52 | .6 | -.7 | 4.1 | 6.7 | -.2 | .6 | .5 | .0 | 1.8 | .7 | .5 | -1.4 | .0 | 1.6 | 4.1 | -.0 | .4 | 2.3 | 1.3 |
| 53 | 2.9 | -.3 | 7.1 | .3 | -.5 | 6.1 | .6 | 1.0 | 2.4 | -.2 | .6 | -.4 | 1.3 | 1.5 | .9 | .1 | 1.6 | .3 | .2 |
| 54 | 27.0 | .7 | .8 | 4.3 | 1.5 | 6.1 | 1.8 | 3.3 | 1.0 | 2.3 | .8 | 5.2 | 2.4 | 3.7 | 4.7 | .2 | .6 | 3.7 | 2.3 |
| 55 | .0 | 54.7 | .0 | 1.3 | -.4 | 1.8 | -.3 | 2.3 | 3.6 | .0 | .9 | .7 | 4.8 | 2.0 | .5 | -2.1 | -.6 | .4 | -.3 |
| 56 | .0 | 2.8 | .0 | .9 | 1.4 | -.1 | -.5 | -.5 | -3.1 | -1.6 | 1.2 | -.1 | -1.2 | -1.2 | -.2 | -3.7 | .4 | -.1 | 18.5 |
| 57 | -2.6 | .0 | -1.5 | -2.6 | -.6 | -2.4 | -1.5 | -1.3 | -1.6 | -3.3 | 1.5 | -2.4 | -1.7 | -.5 | 2.6 | -6.9 | -.5 | -1.6 | 13.0 |
| 58 | .7 | 3.9 | .4 | 3.5 | -.9 | -.0 | .3 | -1.0 | -1.2 | 10.1 | 1.9 | .3 | -1.1 | -1.0 | 2.8 | -5.9 | -1.6 | .4 | 2.7 |
| 59 | 2.3 | .8 | .4 | 1.5 | .0 | .4 | .9 | 1.5 | .8 | .0 | -2.5 | .9 | 1.7 | -.2 | 1.1 | 6.7 | 1.4 | -.0 | .0 |
| 60 | -1.0 | -.5 | -.1 | -.8 | -.0 | .1 | 7.0 | -.6 | .6 | -.4 | -1.9 | .4 | 1.0 | .4 | -1.4 | .0 | .1 | .4 | -1.0 |

18K PROTEIN - Raw Data (Cycle 1 Injection Corrected)

TABLE 8

PTH AMINO ACID

| CYCLE | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 1 | 24.0 | 2.7 | -3.9 | .0 | -2.3 | 27.3 | 400.6 | .5 | 3.7 | -1.3 | .0 | -2.0 | -.1 | .4 | 5.8 | -2.2 | .5 | -8.0 | -4.2 |
| 2 | 11.0 | .8 | 220.0 | 3.2 | 1.7 | 30.1 | 14.0 | .4 | 7.4 | 2.3 | .1 | 4.9 | .3 | 2.7 | 4.9 | 3.1 | 6.1 | 5.4 | 9.2 |
| 3 | 4.4 | .8 | 23.0 | 5.0 | 67.4 | 25.8 | 7.1 | .2 | 7.1 | 5.9 | .2 | 4.0 | .4 | 5.5 | 5.0 | 8.1 | 5.6 | 24.0 | 9.3 |
| 4 | 3.8 | 1.4 | 11.0 | -9.1 | 6.0 | 26.5 | 8.8 | .2 | 6.8 | 4.7 | .4 | 6.0 | 1.0 | 4.1 | 5.6 | 17.4 | 7.1 | 37.9 | 372.0 |
| 5 | 3.4 | 1.4 | 11.8 | 9.8 | 65.0 | 27.9 | 11.5 | .3 | 6.5 | 7.9 | .1 | 10.6 | .9 | 6.3 | 5.8 | 18.0 | 7.0 | 46.2 | 31.0 |
| 6 | 3.3 | 1.6 | 14.8 | 13.5 | 9.0 | 258.0 | 17.9 | .4 | 7.0 | 9.2 | .7 | 13.0 | .3 | 13.5 | 5.6 | 18.0 | 7.2 | 51.8 | 24.1 |
| 7 | 2.4 | 1.4 | 13.3 | 13.0 | 5.5 | 39.0 | 13.3 | .5 | 8.2 | 8.9 | .4 | 15.2 | 2.0 | 18.3 | 12.0 | 24.0 | 10.1 | 491.5 | 27.1 |
| 8 | 4.0 | 2.7 | 15.6 | 16.7 | 62.0 | 34.4 | 15.7 | .6 | 9.1 | 10.5 | .4 | 13.0 | 3.1 | 22.0 | 5.3 | 30.4 | 10.1 | 110.4 | 22.2 |
| 9 | 3.0 | 7.2 | 24.3 | 19.7 | 10.4 | 38.5 | 20.8 | .8 | 10.9 | 11.0 | .6 | 229.0 | 3.4 | 19.5 | 5.5 | 35.3 | 12.1 | 82.9 | 24.8 |
| 10 | 2.9 | 3.0 | 23.3 | 19.4 | 7.3 | 39.0 | 21.3 | .7 | 15.0 | 14.3 | .7 | 90.0 | 3.0 | 265.5 | 4.9 | 31.0 | 13.4 | 74.0 | 26.0 |
| 11 | 3.3 | 2.1 | 24.0 | 17.0 | 8.2 | 40.7 | 21.8 | .7 | 13.3 | 11.8 | .8 | 40.5 | 3.9 | 82.9 | 6.0 | 269.5 | 16.1 | 79.6 | 30.5 |
| 12 | 4.1 | 3.5 | 27.2 | 18.0 | 9.9 | 181.0 | 23.6 | .8 | 13.9 | 17.1 | 1.1 | 28.0 | 3.7 | 33.9 | 5.0 | 91.1 | 17.9 | 79.0 | 31.5 |

| CYCLE | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 13 | 4.3 | 5.0 | 31.8 | 18.4 | 11.0 | 216.0 | 26.9 | .9 | 12.3 | 17.7 | 1.1 | 27.3 | 3.1 | 22.9 | 5.4 | 46.0 | 18.2 | 86.0 | 31.3 |
| 14 | 4.2 | 4.9 | 31.4 | 16.6 | 9.2 | 92.9 | 26.4 | .9 | 78.1 | 20.0 | .9 | 24.5 | 3.2 | 19.2 | 3.9 | 31.9 | 17.4 | 85.3 | 35.3 |
| 15 | 4.0 | 5.8 | 32.5 | 18.2 | 36.1 | 60.9 | 31.0 | .8 | 33.3 | 27.9 | 1.0 | 21.1 | 3.2 | 20.8 | 4.1 | 28.3 | 18.0 | 89.0 | 35.0 |
| 16 | 4.1 | 5.9 | 33.8 | 18.6 | 17.8 | 135.0 | 35.1 | .7 | 18.4 | 29.0 | .9 | 21.2 | 3.5 | 22.5 | 5.9 | 29.6 | 19.8 | 93.1 | 36.3 |
| 17 | 4.3 | 6.2 | 32.4 | 19.0 | 11.0 | 151.0 | 37.4 | 1.1 | 15.0 | 27.3 | 1.1 | 21.6 | 4.4 | 26.1 | 5.8 | 32.4 | 22.5 | 93.9 | 36.1 |
| 18 | 4.9 | 6.0 | 35.8 | 19.0 | 9.1 | 74.0 | 37.9 | 1.3 | 14.0 | 29.5 | 1.6 | 26.0 | 7.0 | 26.0 | 5.7 | 32.3 | 22.1 | 94.0 | 155.0 |
| 19 | 4.0 | 5.6 | 35.1 | 18.1 | 9.4 | 48.6 | 36.1 | 1.4 | 13.6 | 28.1 | 1.3 | 26.1 | 7.1 | 26.0 | 5.4 | 32.7 | 23.0 | 92.3 | 158.5 |
| 20 | 5.1 | 5.8 | 40.8 | 18.1 | 9.6 | 42.5 | 36.0 | 1.8 | 12.6 | 29.3 | 1.1 | 28.0 | 7.0 | 26.8 | 7.5 | 32.3 | 21.4 | 255.5 | 78.2 |
| 21 | 5.1 | 5.3 | 36.4 | 17.4 | 9.0 | 38.0 | 31.5 | 1.9 | 54.0 | 28.3 | 1.1 | 21.4 | 6.8 | 27.0 | 6.0 | 33.1 | 20.9 | 132.3 | 40.0 |
| 22 | 6.5 | 6.3 | 37.4 | 18.0 | 8.8 | 39.6 | 122.5 | 2.0 | 24.1 | 28.0 | 1.2 | 26.5 | 6.9 | 27.0 | 5.1 | 34.0 | 21.5 | 97.1 | 30.6 |
| 23 | 7.4 | 8.0 | 97.3 | 18.1 | 9.0 | 43.3 | 60.8 | 2.1 | 15.3 | 29.5 | 1.2 | 28.2 | 7.0 | 28.0 | 5.1 | 33.3 | 21.9 | 92.2 | 31.4 |
| 24 | 7.1 | 8.2 | 57.6 | 17.4 | 23.2 | 41.0 | 39.1 | 1.6 | 11.9 | 29.9 | 1.0 | 27.1 | 6.1 | 26.6 | 4.8 | 32.0 | 19.7 | 84.6 | 31.3 |
| 25 | 8.1 | 8.3 | 90.0 | 18.0 | 12.3 | 40.0 | 34.0 | 1.9 | 11.0 | 28.8 | 1.1 | 28.0 | 5.7 | 27.0 | 5.9 | 31.9 | 19.5 | 82.0 | 33.2 |
| 26 | 9.3 | 8.5 | 101.1 | 19.0 | 10.6 | 41.2 | 33.8 | 1.7 | 10.3 | 31.0 | 1.0 | 28.0 | 5.5 | 29.1 | 5.2 | 31.1 | 20.0 | 78.7 | 33.0 |
| 27 | 6.3 | 7.2 | 48.2 | 16.1 | 6.9 | 35.4 | 30.5 | 2.0 | 10.0 | 25.4 | 1.1 | 25.1 | 5.8 | 27.3 | 5.5 | 31.1 | 19.0 | 146.0 | 32.1 |
| 28 | 8.0 | 8.1 | 39.6 | 18.0 | 8.4 | 37.3 | 33.0 | 2.0 | 10.0 | 88.0 | 1.1 | 26.1 | 6.1 | 29.9 | 5.3 | 33.0 | 19.0 | 104.0 | 33.2 |
| 29 | 8.2 | 8.2 | 36.2 | 18.1 | 8.3 | 35.3 | 85.9 | 2.1 | 9.9 | 48.0 | 1.1 | 25.0 | 6.0 | 28.2 | 5.0 | 31.9 | 17.3 | 83.6 | 34.0 |
| 30 | 7.0 | 8.1 | 33.7 | 18.0 | 8.5 | 37.5 | 48.0 | 2.1 | 9.0 | 33.3 | 1.2 | 27.5 | 6.1 | 29.1 | 4.2 | 32.0 | 59.5 | 76.5 | 34.2 |
| 31 | 8.1 | 8.5 | 35.4 | 18.3 | 17.2 | 36.3 | 35.2 | 2.4 | 9.4 | 29.7 | .9 | 26.8 | 6.5 | 29.0 | 4.4 | 31.1 | 30.6 | 76.3 | 33.0 |
| 32 | 7.6 | 8.7 | 33.5 | 19.5 | 11.0 | 35.6 | 29.6 | 2.0 | 9.6 | 27.5 | 1.0 | 27.2 | 6.5 | 27.5 | 18.6 | 31.3 | 21.1 | 72.9 | 31.1 |
| 33 | 9.0 | 9.5 | 36.4 | 20.0 | 17.0 | 37.8 | 30.6 | 2.7 | 9.0 | 27.3 | .9 | 27.7 | 6.5 | 29.8 | 9.5 | 32.4 | 16.7 | 75.0 | 32.5 |
| 34 | 9.5 | 9.1 | 36.0 | 19.6 | 9.8 | 38.4 | 32.0 | 3.0 | 20.2 | 27.2 | .8 | 29.2 | 6.7 | 29.5 | 5.0 | 33.0 | 16.4 | 75.2 | 34.6 |
| 35 | 9.3 | 9.4 | 35.5 | 19.3 | 12.9 | 36.0 | 31.4 | 2.4 | 12.2 | 26.6 | 1.0 | 28.7 | 5.2 | 28.7 | 3.6 | 32.2 | 15.1 | 71.3 | 33.7 |
| 36 | 8.4 | 8.8 | 31.6 | 16.1 | 8.3 | 33.9 | 29.4 | 2.6 | 9.1 | 24.2 | .9 | 28.0 | 5.5 | 29.0 | 3.5 | 31.5 | 14.0 | 99.5 | 33.5 |
| 37 | 8.0 | 9.5 | 46.8 | 17.6 | 7.6 | 37.0 | 30.6 | 2.7 | 8.7 | 24.9 | .7 | 28.8 | 7.0 | 30.5 | 3.5 | 31.9 | 15.4 | 82.5 | 34.1 |
| 38 | 7.8 | 9.0 | 37.5 | 36.0 | 6.9 | 35.5 | 29.0 | 2.4 | 8.0 | 24.0 | .7 | 26.2 | 6.0 | 28.0 | 3.6 | 30.6 | 14.0 | 71.5 | 32.5 |
| 39 | 8.5 | 9.3 | 34.2 | 25.1 | 6.6 | 31.7 | 28.3 | 2.1 | 7.6 | 22.7 | .8 | 26.8 | 5.4 | 46.2 | 3.2 | 30.4 | 14.1 | 68.0 | 32.0 |
| 40 | 7.5 | 9.0 | 31.0 | 20.0 | 5.8 | 33.7 | 28.2 | 2.4 | 7.9 | 22.7 | .8 | 26.7 | 5.3 | 35.3 | 3.1 | 47.3 | 13.5 | 65.4 | 32.1 |
| 41 | 7.9 | 9.1 | 41.2 | 16.9 | 5.1 | 31.0 | 26.2 | 2.7 | 7.9 | 21.4 | .6 | 24.4 | 5.1 | 28.4 | 3.1 | 35.5 | 13.0 | 62.4 | 29.5 |
| 42 | 6.4 | 8.2 | 27.5 | 14.6 | 4.6 | 28.0 | 23.1 | 1.7 | 6.1 | 17.9 | .6 | 21.6 | 4.5 | 23.6 | 2.5 | 27.6 | 11.7 | 53.2 | 38.8 |
| 43 | 7.6 | 9.8 | 30.4 | 15.7 | 4.8 | 30.0 | 24.5 | 2.5 | 6.5 | 20.0 | .5 | 31.2 | 4.8 | 24.8 | 2.6 | 27.5 | 12.3 | 59.9 | 34.1 |
| 44 | 6.2 | 9.6 | 26.6 | 15.5 | 6.9 | 30.1 | 24.4 | 2.1 | 6.5 | 19.0 | .6 | 29.4 | 5.0 | 23.7 | 2.8 | 27.1 | 12.6 | 58.1 | 30.0 |
| 45 | 7.0 | 9.8 | 27.5 | 15.5 | 6.0 | 35.2 | 25.2 | 2.1 | 6.8 | 20.7 | .6 | 26.2 | 4.9 | 25.2 | 3.0 | 27.5 | 12.2 | 59.7 | 28.9 |
| 46 | 7.4 | 9.7 | 25.6 | 15.1 | 4.7 | 37.8 | 24.2 | 2.0 | 7.0 | 19.8 | .6 | 23.6 | 4.5 | 21.0 | 2.5 | 27.4 | 12.0 | 58.0 | 27.2 |
| 47 | 6.9 | 9.6 | 25.4 | 14.9 | 4.4 | 33.0 | 30.1 | 2.0 | 6.2 | 19.0 | .5 | 22.7 | 4.7 | 23.0 | 2.4 | 26.5 | 11.6 | 54.7 | 25.8 |
| 48 | 6.8 | 9.7 | 23.8 | 14.4 | 4.5 | 30.2 | 31.8 | 1.8 | 6.7 | 18.3 | .6 | 22.1 | 4.2 | 22.7 | 2.7 | 25.8 | 11.2 | 54.6 | 26.1 |
| 49 | 6.0 | 9.3 | 23.3 | 13.8 | 4.0 | 27.7 | 29.4 | 1.7 | 7.0 | 17.9 | .6 | 22.3 | 4.0 | 28.6 | 2.5 | 25.5 | 11.6 | 53.8 | 25.5 |
| 50 | 5.8 | 9.2 | 22.0 | 13.4 | 3.8 | 27.5 | 24.7 | 2.0 | 6.5 | 17.7 | .6 | 21.3 | 11.0 | 27.8 | 2.1 | 25.0 | 11.7 | 53.4 | 25.2 |
| 51 | 6.5 | 9.0 | 22.6 | 13.5 | 3.8 | 25.8 | 21.3 | 3.1 | 5.7 | 16.5 | .6 | 20.4 | 8.1 | 23.2 | 2.4 | 24.5 | 11.8 | 50.5 | 23.5 |
| 52 | 6.1 | 9.1 | 26.4 | 13.7 | 3.5 | 25.8 | 21.2 | 2.5 | 6.0 | 16.9 | .6 | 19.4 | 5.5 | 21.5 | 2.7 | 23.9 | 11.1 | 52.0 | 24.1 |
| 53 | 6.5 | 9.1 | 25.4 | 13.3 | 3.3 | 28.6 | 20.5 | 2.1 | 6.0 | 16.1 | .6 | 19.3 | 4.2 | 20.5 | 2.3 | 23.6 | 11.3 | 48.8 | 23.0 |
| 54 | 9.5 | 9.2 | 24.4 | 13.6 | 3.6 | 28.0 | 20.7 | 2.0 | 5.6 | 17.2 | .6 | 20.9 | 3.8 | 20.6 | 2.7 | 23.3 | 10.8 | 51.2 | 23.5 |
| 55 | 7.5 | 13.7 | 20.6 | 12.6 | 3.1 | 24.7 | 18.6 | 1.8 | 6.0 | 15.7 | .6 | 18.9 | 4.0 | 19.5 | 2.2 | 22.2 | 10.2 | 46.8 | 21.8 |
| 56 | 6.3 | 12.0 | 19.4 | 12.3 | 3.4 | 23.0 | 17.8 | 1.5 | 4.6 | 14.6 | .6 | 18.3 | 2.8 | 17.9 | 2.1 | 21.4 | 10.3 | 45.3 | 26.7 |
| 57 | 4.9 | 9.5 | 17.1 | 11.4 | 2.9 | 21.0 | 16.4 | 1.4 | 4.8 | 13.5 | .6 | 17.2 | 2.6 | 17.7 | 2.4 | 20.1 | 9.8 | 42.8 | 27.8 |
| 58 | 5.7 | 9.5 | 19.1 | 12.6 | 2.8 | 22.0 | 17.0 | 1.4 | 4.8 | 13.3 | .6 | 18.0 | 2.6 | 17.1 | 2.4 | 20.1 | 9.2 | 41.0 | 24.6 |
| 59 | 6.1 | 8.8 | 18.9 | 12.1 | 3.0 | 21.0 | 16.7 | 1.6 | 5.1 | 17.5 | .5 | 18.1 | 3.0 | 17.0 | 2.2 | 24.8 | 9.9 | 42.9 | 24.2 |
| 60 | 5.4 | 8.5 | 18.1 | 11.6 | 3.0 | 21.2 | 20.3 | 1.4 | 5.0 | 11.7 | .5 | 17.9 | 2.3 | 16.9 | 1.9 | 22.8 | 9.2 | 42.5 | 20.1 |

18K PROTEIN - Raw Data (Cycles 1-2 + *Injection* Corrected)

TABLE 9

PTH AMINO ACID

| CYCLE | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 1 | 24.0 | 2.7 | -3.9 | .0 | -2.3 | 27.3 | 400.6 | .5 | 3.7 | -1.3 | .0 | -2.0 | -.1 | .4 | 5.8 | -2.2 | .5 | -8.0 | -4.2 |
| 2 | 10.4 | .4 | 217.4 | 2.7 | -.3 | 26.2 | 9.0 | .3 | 5.6 | .9 | .0 | 2.8 | -.1 | 1.0 | 4.3 | 1.0 | 5.0 | .2 | 5.8 |
| 3 | 4.4 | .8 | 23.0 | 5.0 | 67.4 | 25.8 | 7.1 | .2 | 7.1 | 5.9 | .2 | 4.0 | .4 | 5.5 | 5.0 | 8.1 | 5.6 | 24.0 | 9.3 |
| 4 | 3.8 | 1.4 | 11.0 | 9.1 | 6.0 | 26.5 | 8.8 | .2 | 6.8 | 4.7 | .4 | 6.0 | 1.0 | 4.1 | 5.6 | 17.4 | 7.1 | 37.9 | 372.0 |
| 5 | 3.4 | 1.4 | 11.8 | 9.8 | 65.0 | 27.9 | 11.5 | .3 | 6.5 | 7.9 | .4 | 10.6 | .9 | 6.3 | 5.8 | 18.0 | 7.0 | 46.2 | 31.0 |
| 6 | 3.3 | 1.6 | 14.8 | 13.5 | 9.0 | 258.0 | 17.9 | .4 | 7.0 | 9.2 | .7 | 13.0 | .3 | 13.5 | 5.6 | 18.0 | 7.2 | 51.9 | 24.1 |

| Cycle | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 7 | 2.4 | 1.4 | 13.3 | 13.0 | 5.5 | 39.0 | 13.3 | .5 | 8.2 | 8.9 | .4 | 15.2 | 2.0 | 18.3 | 12.0 | 24.0 | 10.1 | 491.5 | 27.4 |
| 8 | 4.0 | 2.7 | 15.6 | 16.7 | 62.0 | 34.4 | 15.7 | .6 | 9.1 | 10.5 | .4 | 13.0 | 3.1 | 22.0 | 5.3 | 30.4 | 10.1 | 110.4 | 22.2 |
| 9 | 3.0 | 7.2 | 24.3 | 19.7 | 10.4 | 38.5 | 20.8 | .8 | 10.9 | 11.0 | .6 | 229.0 | 3.4 | 19.5 | 5.5 | 35.3 | 12.1 | 82.9 | 24.3 |
| 10 | 2.9 | 3.0 | 23.3 | 19.4 | 7.3 | 39.0 | 21.3 | .7 | 15.0 | 14.3 | .7 | 89.0 | 3.0 | 265.5 | 4.9 | 31.0 | 13.4 | 74.0 | 26.0 |
| 11 | 3.3 | 2.1 | 24.0 | 17.0 | 8.2 | 40.7 | 21.8 | .7 | 13.3 | 14.8 | .8 | 40.5 | 3.9 | 82.9 | 6.0 | 269.5 | 16.1 | 79.6 | 30.5 |
| 12 | 4.1 | 3.5 | 27.2 | 18.0 | 9.9 | 181.0 | 23.6 | .8 | 13.9 | 17.1 | 1.1 | 28.0 | 3.7 | 33.9 | 5.0 | 94.1 | 17.9 | 79.0 | 31.5 |
| 13 | 4.3 | 5.0 | 31.8 | 18.4 | 11.0 | 216.0 | 26.9 | .9 | 12.3 | 17.7 | 1.1 | 27.3 | 3.1 | 22.9 | 5.4 | 46.0 | 18.2 | 86.0 | 31.3 |
| 14 | 4.2 | 4.9 | 31.4 | 16.6 | 9.2 | 92.9 | 26.4 | .9 | 78.1 | 20.0 | .9 | 24.5 | 3.2 | 19.2 | 3.8 | 31.8 | 17.4 | 85.3 | 35.3 |
| 15 | 4.0 | 5.8 | 32.5 | 18.2 | 36.1 | 60.9 | 31.0 | .8 | 33.3 | 27.9 | 1.0 | 21.1 | 3.2 | 20.8 | 4.1 | 28.3 | 18.0 | 89.0 | 35.0 |
| 16 | 4.1 | 5.9 | 33.8 | 18.6 | 17.8 | 135.0 | 35.1 | .7 | 18.1 | 29.0 | .9 | 21.2 | 3.5 | 22.5 | 5.9 | 29.6 | 19.8 | 93.1 | 36.3 |
| 17 | 4.3 | 6.2 | 32.4 | 19.0 | 11.0 | 151.0 | 37.4 | 1.1 | 15.0 | 27.3 | 1.4 | 21.6 | 4.4 | 26.1 | 5.8 | 32.4 | 22.5 | 93.9 | 36.1 |
| 18 | 4.9 | 6.0 | 35.8 | 19.0 | 9.1 | 74.0 | 37.9 | 1.3 | 11.0 | 29.5 | 1.6 | 26.0 | 7.0 | 26.0 | 5.7 | 32.3 | 22.1 | 94.0 | 155.0 |
| 19 | 4.0 | 5.6 | 35.1 | 18.1 | 9.4 | 48.6 | 36.1 | 1.4 | 13.6 | 28.1 | 1.3 | 26.1 | 7.1 | 26.0 | 5.4 | 32.7 | 23.0 | 92.3 | 158.5 |
| 20 | 5.1 | 5.8 | 40.8 | 18.1 | 9.6 | 42.5 | 36.0 | 1.8 | 12.6 | 29.3 | 1.1 | 28.0 | 7.0 | 26.8 | 7.5 | 32.3 | 21.4 | 255.5 | 78.2 |
| 21 | 5.1 | 5.3 | 36.4 | 17.4 | 9.0 | 38.0 | 31.5 | 1.9 | 54.0 | 28.3 | 1.1 | 21.4 | 6.8 | 27.0 | 6.0 | 33.1 | 20.9 | 132.3 | 40.0 |
| 22 | 6.5 | 6.3 | 37.4 | 18.0 | 8.8 | 39.6 | 122.5 | 2.0 | 24.1 | 28.0 | 1.2 | 26.5 | 6.9 | 27.0 | 5.1 | 34.0 | 21.5 | 97.1 | 30.6 |
| 23 | 7.4 | 8.0 | 97.3 | 18.1 | 9.0 | 43.3 | 60.8 | 2.1 | 15.3 | 28.5 | 1.2 | 28.2 | 7.0 | 28.0 | 5.1 | 33.3 | 21.9 | 92.2 | 31.4 |
| 24 | 7.1 | 8.2 | 57.6 | 17.4 | 23.2 | 41.0 | 39.1 | 1.6 | 11.9 | 29.9 | 1.0 | 27.1 | 6.1 | 26.6 | 4.8 | 32.0 | 19.7 | 84.6 | 31.3 |
| 25 | 8.1 | 8.3 | 90.0 | 18.0 | 12.3 | 40.0 | 34.0 | 1.9 | 11.0 | 28.8 | 1.1 | 28.0 | 5.7 | 27.0 | 5.9 | 31.9 | 19.5 | 82.0 | 33.2 |
| 26 | 9.3 | 8.5 | 101.1 | 19.0 | 10.6 | 41.2 | 33.8 | 1.7 | 10.3 | 31.0 | 1.0 | 28.0 | 5.5 | 29.1 | 5.2 | 31.1 | 20.0 | 78.7 | 33.0 |
| 27 | 6.3 | 7.2 | 48.2 | 16.1 | 6.9 | 35.4 | 30.5 | 2.0 | 10.0 | 25.4 | 1.1 | 25.1 | 5.8 | 27.3 | 5.5 | 31.1 | 19.0 | 146.0 | 32.1 |
| 28 | 8.0 | 8.1 | 39.6 | 18.0 | 8.4 | 37.3 | 33.0 | 2.0 | 10.0 | 88.0 | 1.1 | 26.1 | 6.1 | 29.9 | 5.3 | 33.0 | 19.0 | 104.0 | 33.2 |
| 29 | 8.7 | 8.2 | 36.2 | 18.1 | 8.3 | 36.3 | 85.9 | 2.1 | 9.9 | 48.0 | 1.1 | 25.0 | 6.0 | 28.2 | 5.0 | 31.9 | 17.3 | 83.6 | 34.0 |
| 30 | 7.0 | 8.1 | 33.7 | 18.0 | 8.5 | 37.5 | 48.0 | 2.1 | 9.0 | 33.3 | 1.2 | 27.5 | 6.1 | 29.1 | 4.2 | 32.0 | 59.5 | 76.5 | 34.2 |
| 31 | 8.1 | 8.5 | 35.4 | 18.3 | 17.2 | 36.3 | 35.2 | 2.4 | 9.4 | 29.7 | .9 | 26.8 | 6.5 | 29.0 | 4.4 | 31.1 | 30.6 | 76.3 | 33.0 |
| 32 | 7.6 | 8.7 | 33.5 | 19.5 | 11.0 | 35.6 | 29.6 | 2.0 | 9.6 | 27.5 | 1.0 | 27.2 | 6.5 | 27.5 | 18.6 | 31.3 | 21.1 | 72.9 | 31.1 |
| 33 | 9.0 | 9.5 | 36.1 | 20.0 | 17.0 | 37.8 | 30.6 | 2.7 | 9.0 | 27.3 | .9 | 27.7 | 6.5 | 29.8 | 9.5 | 32.4 | 16.7 | 75.0 | 32.5 |
| 34 | 9.5 | 9.1 | 36.0 | 19.6 | 9.8 | 38.4 | 32.0 | 3.0 | 20.2 | 27.2 | .8 | 29.2 | 6.7 | 29.5 | 5.0 | 33.0 | 16.4 | 75.2 | 34.6 |
| 35 | 9.3 | 9.4 | 35.5 | 19.3 | 12.9 | 36.0 | 31.4 | 2.4 | 12.2 | 26.6 | 1.0 | 28.7 | 5.2 | 28.7 | 3.6 | 32.2 | 15.1 | 71.3 | 33.7 |
| 36 | 8.4 | 8.8 | 31.6 | 16.1 | 8.3 | 33.9 | 29.4 | 2.6 | 9.1 | 24.2 | .9 | 28.0 | 5.5 | 29.0 | 3.5 | 31.5 | 14.0 | 99.5 | 33.5 |
| 37 | 8.0 | 9.5 | 46.8 | 17.6 | 7.6 | 37.0 | 30.6 | 2.7 | 8.7 | 24.9 | .7 | 28.8 | 7.0 | 30.5 | 3.5 | 31.9 | 15.4 | 82.5 | 34.1 |
| 38 | 7.8 | 9.0 | 37.5 | 36.0 | 6.9 | 35.5 | 29.0 | 2.4 | 8.0 | 24.0 | .7 | 26.2 | 6.0 | 28.0 | 3.6 | 30.6 | 14.0 | 71.5 | 32.5 |
| 39 | 8.5 | 9.3 | 34.2 | 25.1 | 6.6 | 34.7 | 28.3 | 2.1 | 7.6 | 22.7 | .8 | 25.8 | 5.4 | 46.2 | 3.2 | 30.4 | 14.1 | 68.0 | 32.0 |
| 40 | 7.5 | 9.0 | 31.0 | 20.0 | 5.8 | 33.7 | 28.2 | 2.4 | 7.9 | 22.7 | .8 | 26.7 | 5.3 | 35.3 | 3.1 | 47.3 | 13.5 | 65.4 | 32.1 |
| 41 | 7.9 | 9.1 | 41.2 | 16.9 | 5.1 | 31.0 | 26.2 | 2.7 | 7.3 | 21.4 | .6 | 24.4 | 5.1 | 28.4 | 3.1 | 35.5 | 13.0 | 62.4 | 29.5 |
| 42 | 6.4 | 8.2 | 27.5 | 14.6 | 4.6 | 28.0 | 23.1 | 1.7 | 6.1 | 17.9 | .6 | 21.6 | 4.5 | 23.6 | 2.5 | 27.6 | 11.7 | 53.2 | 38.8 |
| 43 | 7.6 | 9.8 | 30.4 | 15.7 | 4.8 | 30.0 | 24.5 | 2.5 | 6.5 | 20.0 | .5 | 31.2 | 4.8 | 24.8 | 2.6 | 27.5 | 12.3 | 59.9 | 34.1 |
| 44 | 6.2 | 9.6 | 26.6 | 15.5 | 6.9 | 30.1 | 24.4 | 2.1 | 6.5 | 19.0 | .6 | 29.4 | 5.0 | 23.7 | 2.8 | 27.1 | 12.6 | 59.1 | 30.0 |
| 45 | 7.0 | 9.8 | 27.5 | 15.5 | 6.0 | 35.2 | 25.2 | 2.1 | 6.8 | 20.7 | .6 | 26.2 | 4.9 | 25.2 | 3.0 | 27.5 | 12.2 | 59.7 | 28.9 |
| 46 | 7.4 | 9.7 | 25.6 | 15.1 | 4.7 | 37.8 | 24.2 | 2.0 | 7.0 | 19.8 | .6 | 23.6 | 4.5 | 24.0 | 2.5 | 27.4 | 12.0 | 58.0 | 27.2 |
| 47 | 6.9 | 9.6 | 25.4 | 14.0 | 4.4 | 33.0 | 30.4 | 2.0 | 6.2 | 19.0 | .5 | 22.7 | 4.7 | 23.0 | 2.4 | 26.5 | 11.6 | 54.7 | 25.8 |
| 48 | 6.8 | 9.7 | 23.8 | 14.4 | 4.5 | 30.2 | 31.8 | 1.8 | 6.7 | 18.3 | .6 | 22.1 | 4.2 | 22.7 | 2.7 | 25.8 | 11.2 | 54.6 | 26.1 |
| 49 | 6.0 | 9.3 | 23.3 | 13.8 | 4.0 | 27.7 | 29.4 | 1.7 | 7.0 | 17.9 | .6 | 22.3 | 4.0 | 28.6 | 2.5 | 25.5 | 11.6 | 53.8 | 25.5 |
| 50 | 5.8 | 9.2 | 22.0 | 13.4 | 3.8 | 27.5 | 24.7 | 2.0 | 6.5 | 17.7 | .6 | 21.3 | 11.0 | 27.8 | 2.1 | 25.0 | 11.7 | 53.4 | 25.2 |
| 51 | 6.5 | 9.0 | 22.6 | 13.5 | 3.8 | 25.8 | 21.3 | 3.1 | 5.7 | 16.5 | .6 | 20.4 | 8.1 | 23.2 | 2.4 | 24.5 | 11.8 | 50.5 | 23.5 |
| 52 | 6.1 | 9.1 | 26.4 | 13.7 | 3.5 | 25.8 | 21.2 | 2.5 | 6.0 | 16.9 | .6 | 19.4 | 5.5 | 21.5 | 2.7 | 23.9 | 11.1 | 52.0 | 24.1 |
| 53 | 6.5 | 9.1 | 25.4 | 13.3 | 3.3 | 28.6 | 20.5 | 2.1 | 6.0 | 16.1 | .6 | 19.3 | 4.2 | 20.5 | 2.3 | 23.6 | 11.3 | 48.8 | 23.0 |
| 54 | 9.5 | 9.2 | 24.4 | 13.6 | 3.6 | 28.0 | 20.7 | 2.0 | 5.6 | 17.2 | .6 | 20.9 | 3.8 | 20.6 | 2.7 | 23.3 | 10.8 | 51.2 | 23.5 |
| 55 | 7.5 | 13.7 | 20.6 | 12.6 | 3.1 | 24.7 | 18.6 | 1.8 | 6.0 | 15.7 | .6 | 18.9 | 4.0 | 19.5 | 2.2 | 22.2 | 10.2 | 46.8 | 21.8 |
| 56 | 6.3 | 12.0 | 19.4 | 12.3 | 3.4 | 23.0 | 17.8 | 1.5 | 4.6 | 14.6 | .6 | 18.3 | 2.8 | 17.9 | 2.1 | 21.4 | 10.3 | 45.3 | 26.7 |
| 57 | 4.9 | 9.5 | 17.1 | 11.4 | 2.9 | 21.0 | 16.4 | 1.4 | 4.8 | 13.5 | .6 | 17.2 | 2.6 | 17.7 | 2.4 | 20.1 | 9.8 | 42.8 | 27.8 |
| 58 | 5.7 | 9.5 | 19.1 | 12.6 | 2.8 | 22.0 | 17.0 | 1.4 | 4.8 | 13.3 | .6 | 19.0 | 2.6 | 17.1 | 2.4 | 20.4 | 9.2 | 44.0 | 24.6 |
| 59 | 6.1 | 8.8 | 18.9 | 12.1 | 3.0 | 21.8 | 16.7 | 1.6 | 5.1 | 17.5 | .5 | 19.1 | 3.0 | 17.0 | 2.2 | 21.8 | 9.9 | 42.8 | 21.2 |
| 60 | 5.4 | 8.5 | 18.1 | 11.6 | 3.0 | 21.2 | 20.3 | 1.4 | 5.0 | 14.9 | .5 | 17.9 | 2.8 | 16.9 | 1.9 | 22.9 | 9.2 | 42.5 | 20.1 |

18K PROTEIN - Raw Data (Injection Corrected)    TABLE 10

PTH AMINO ACID

| CYCLE | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 1 | 24.0 | 2.7 | -3.9 | .0 | -2.3 | 27.3 | 400.6 | .5 | 3.7 | -1.3 | .0 | -2.0 | -.1 | .4 | 5.8 | -2.2 | .5 | -8.0 | -4.2 |

| | | | | | | | | | | | | | | | | | | |
|---|---|---|---|---|---|---|---|---|---|---|---|---|---|---|---|---|---|---|
| 2 | 10.4 | .4 | 217.4 | 2.7 | -.3 | 26.2 | 9.0 | .3 | 5.6 | .9 | .0 | 2.8 | -.1 | 1.0 | 4.3 | 1.0 | 5.0 | .2 | 5.8 |
| 3 | 4.4 | .8 | 23.0 | 5.0 | 67.4 | 25.8 | 7.1 | .2 | 7.1 | 5.9 | .2 | 4.0 | .4 | 5.5 | 5.0 | 8.1 | 5.6 | 24.0 | 9.3 |
| 4 | 3.7 | 1.3 | 10.6 | 9.0 | 5.7 | 25.9 | 8.1 | .2 | 6.5 | 4.5 | .4 | 5.7 | .9 | 3.8 | 5.5 | 17.1 | 6.9 | 37.1 | 371.5 |
| 5 | 3.5 | 1.5 | 12.3 | 9.9 | 65.3 | 28.6 | 12.4 | .3 | 6.8 | 8.2 | .4 | 11.0 | 1.0 | 6.6 | 5.9 | 18.4 | 7.2 | 47.1 | 31.6 |
| 6 | 3.3 | 1.6 | 14.7 | 13.5 | 8.9 | 257.9 | 17.7 | .4 | 6.9 | 9.1 | .7 | 12.9 | .3 | 13.4 | 5.6 | 17.9 | 7.2 | 51.6 | 24.0 |
| 7 | 2.5 | 1.5 | 13.6 | 13.1 | 5.8 | 39.5 | 14.0 | .5 | 8.4 | 9.1 | .4 | 15.5 | 2.1 | 18.5 | 12.1 | 24.3 | 10.2 | 492.2 | 27.8 |
| 8 | 3.9 | 2.6 | 15.2 | 16.6 | 61.7 | 33.7 | 14.9 | .6 | 8.8 | 10.3 | .4 | 12.6 | 3.0 | 21.7 | 5.2 | 30.0 | 9.9 | 109.5 | 21.6 |
| 9 | 2.3 | 6.8 | 21.5 | 19.1 | 8.3 | 34.4 | 15.5 | .7 | 9.0 | 9.5 | .5 | 226.8 | 3.0 | 17.7 | 4.8 | 33.1 | 11.0 | 77.4 | 21.3 |
| 10 | 2.7 | 2.9 | 22.3 | 19.2 | 6.6 | 37.5 | 19.4 | .7 | 14.3 | 13.8 | .7 | 79.2 | 2.8 | 264.8 | 4.7 | 30.2 | 13.0 | 72.0 | 24.7 |
| 11 | 3.2 | 2.1 | 23.7 | 16.9 | 8.0 | 40.2 | 21.2 | .7 | 13.1 | 14.6 | .8 | 40.3 | 3.9 | 82.7 | 5.9 | 269.3 | 16.0 | 79.0 | 30.1 |
| 12 | 3.7 | 3.3 | 25.6 | 17.7 | 8.7 | 178.7 | 20.6 | .7 | 12.8 | 16.2 | 1.0 | 26.7 | 3.5 | 32.9 | 4.6 | 92.8 | 17.3 | 75.9 | 29.5 |
| 13 | 3.8 | 4.7 | 29.8 | 18.0 | 9.5 | 213.1 | 23.2 | .8 | 11.0 | 16.6 | 1.0 | 25.7 | 2.8 | 21.6 | 4.9 | 44.4 | 17.4 | 82.1 | 28.8 |
| 14 | 4.4 | 5.0 | 32.2 | 16.8 | 9.8 | 94.1 | 28.0 | .9 | 78.7 | 20.5 | .9 | 25.2 | 3.3 | 19.8 | 4.0 | 32.5 | 17.7 | 87.0 | 36.4 |
| 15 | 4.0 | 5.8 | 32.6 | 18.2 | 36.2 | 61.1 | 31.2 | .8 | 33.4 | 28.0 | 1.0 | 24.2 | 3.2 | 20.9 | 4.1 | 28.4 | 18.0 | 89.2 | 35.2 |
| 16 | 4.1 | 5.9 | 33.8 | 18.6 | 17.8 | 135.0 | 35.1 | .7 | 18.4 | 29.0 | .9 | 24.2 | 3.5 | 22.5 | 5.9 | 29.6 | 19.8 | 93.1 | 36.3 |
| 17 | 3.8 | 5.9 | 30.5 | 18.6 | 9.6 | 148.1 | 33.7 | 1.0 | 13.7 | 26.3 | 1.3 | 23.1 | 4.1 | 24.8 | 5.3 | 30.9 | 21.7 | 89.9 | 33.6 |
| 18 | 4.2 | 5.6 | 32.9 | 18.4 | 7.0 | 69.7 | 32.4 | 1.2 | 12.0 | 27.9 | 1.5 | 23.7 | 6.5 | 24.1 | 5.0 | 30.0 | 20.9 | 88.3 | 151.3 |
| 19 | 3.7 | 5.4 | 34.1 | 17.9 | 8.6 | 47.0 | 34.1 | 1.4 | 12.9 | 27.5 | 1.3 | 25.3 | 6.9 | 25.3 | 5.1 | 31.9 | 22.6 | 90.2 | 157.2 |
| 20 | 4.5 | 5.4 | 38.3 | 17.6 | 7.8 | 38.8 | 31.3 | 1.7 | 10.9 | 28.0 | 1.0 | 26.0 | 6.6 | 25.2 | 6.9 | 30.3 | 20.4 | 250.6 | 75.0 |
| 21 | 5.0 | 5.2 | 36.0 | 17.3 | 8.7 | 37.4 | 30.7 | 1.9 | 53.7 | 28.1 | 1.4 | 24.1 | 6.7 | 26.7 | 5.9 | 32.8 | 20.7 | 131.4 | 39.4 |
| 22 | 6.3 | 6.2 | 36.7 | 17.8 | 8.2 | 38.5 | 121.1 | 2.0 | 23.6 | 27.6 | 1.2 | 25.9 | 6.8 | 26.5 | 4.9 | 33.4 | 21.2 | 95.6 | 29.6 |
| 23 | 6.9 | 7.7 | 95.1 | 17.7 | 7.4 | 40.1 | 56.6 | 2.0 | 13.8 | 27.3 | 1.1 | 26.5 | 6.7 | 26.6 | 4.6 | 31.6 | 21.0 | 87.9 | 28.6 |
| 24 | 7.2 | 8.2 | 57.9 | 17.5 | 23.4 | 41.4 | 39.6 | 1.6 | 12.1 | 30.1 | 1.0 | 27.3 | 6.1 | 26.8 | 4.9 | 32.2 | 19.8 | 85.2 | 31.7 |
| 25 | 8.0 | 8.2 | 89.6 | 17.9 | 12.0 | 39.5 | 33.3 | 1.9 | 10.8 | 28.6 | 1.1 | 27.7 | 5.6 | 26.8 | 5.8 | 31.6 | 19.4 | 81.3 | 32.7 |
| 26 | 9.2 | 8.4 | 100.5 | 18.9 | 10.2 | 40.4 | 32.7 | 1.7 | 9.9 | 30.7 | 1.0 | 27.6 | 5.4 | 28.7 | 5.1 | 30.7 | 19.8 | 77.6 | 32.3 |
| 27 | 6.8 | 7.5 | 50.3 | 16.5 | 8.5 | 38.6 | 34.6 | 2.1 | 11.5 | 26.6 | 1.2 | 26.8 | 6.1 | 28.7 | 6.0 | 32.8 | 19.9 | 150.3 | 34.8 |
| 28 | 7.9 | 8.0 | 39.1 | 17.9 | 8.0 | 36.5 | 32.0 | 2.0 | 9.6 | 87.7 | 1.1 | 25.7 | 6.0 | 29.6 | 5.2 | 32.6 | 18.8 | 103.0 | 32.5 |
| 29 | 8.2 | 8.2 | 36.2 | 18.1 | 8.3 | 36.4 | 86.0 | 2.1 | 9.9 | 48.0 | 1.1 | 25.0 | 6.0 | 28.2 | 5.0 | 31.9 | 17.3 | 83.7 | 34.1 |
| 30 | 7.1 | 8.2 | 34.2 | 18.1 | 8.9 | 38.2 | 48.9 | 2.1 | 9.3 | 33.6 | 1.2 | 27.9 | 6.2 | 29.4 | 4.3 | 32.4 | 59.7 | 77.5 | 34.0 |
| 31 | 7.9 | 8.4 | 34.7 | 18.2 | 16.7 | 35.3 | 33.9 | 2.4 | 8.9 | 29.3 | .9 | 26.2 | 6.4 | 28.5 | 4.2 | 30.5 | 30.3 | 74.9 | 32.1 |
| 32 | 7.7 | 8.7 | 33.8 | 19.5 | 11.0 | 35.7 | 29.8 | 2.0 | 9.6 | 27.6 | 1.0 | 27.3 | 6.5 | 27.6 | 18.6 | 31.4 | 21.2 | 73.1 | 31.2 |
| 33 | 8.5 | 9.2 | 33.8 | 19.5 | 16.5 | 36.4 | 29.1 | 2.5 | 8.6 | 26.1 | .9 | 26.9 | 6.1 | 29.0 | 9.3 | 31.6 | 16.0 | 72.8 | 31.5 |
| 34 | 8.8 | 8.7 | 32.4 | 19.0 | 9.2 | 36.5 | 29.9 | 2.7 | 19.6 | 25.6 | .7 | 28.1 | 6.2 | 28.5 | 4.7 | 31.9 | 15.5 | 72.2 | 33.2 |
| 35 | 9.0 | 9.2 | 33.9 | 19.0 | 12.6 | 35.1 | 30.4 | 2.3 | 11.9 | 25.8 | 1.0 | 28.2 | 5.0 | 28.2 | 3.4 | 31.7 | 14.7 | 69.9 | 33.1 |
| 36 | 8.5 | 8.9 | 32.2 | 16.2 | 8.4 | 34.2 | 29.8 | 2.6 | 9.2 | 24.5 | .9 | 28.2 | 5.6 | 29.2 | 3.6 | 31.7 | 14.2 | 100.0 | 33.7 |
| 37 | 7.4 | 9.1 | 43.9 | 17.1 | 7.1 | 35.5 | 28.9 | 2.5 | 8.2 | 23.6 | .7 | 27.9 | 6.6 | 29.7 | 3.2 | 31.0 | 14.6 | 80.0 | 33.0 |
| 38 | 7.7 | 8.9 | 37.0 | 35.9 | 6.8 | 35.2 | 28.7 | 2.4 | 7.9 | 23.8 | .7 | 26.0 | 5.9 | 27.8 | 3.5 | 30.4 | 13.9 | 71.0 | 32.3 |
| 39 | 8.4 | 9.2 | 33.6 | 25.0 | 6.5 | 34.4 | 28.0 | 2.1 | 7.5 | 22.4 | .8 | 26.6 | 5.3 | 46.0 | 3.1 | 30.2 | 14.0 | 67.5 | 31.8 |
| 40 | 7.4 | 8.9 | 30.3 | 19.9 | 5.7 | 33.3 | 27.8 | 2.3 | 7.8 | 22.4 | .8 | 26.5 | 5.2 | 35.1 | 3.0 | 47.1 | 13.3 | 64.8 | 31.8 |
| 41 | 8.1 | 9.2 | 42.3 | 17.1 | 5.3 | 31.6 | 26.8 | 2.8 | 8.1 | 21.9 | .6 | 24.7 | 5.3 | 28.7 | 3.2 | 35.8 | 13.3 | 63.3 | 29.9 |
| 42 | 7.7 | 9.0 | 34.2 | 15.8 | 5.8 | 31.5 | 27.1 | 2.2 | 7.2 | 21.0 | .7 | 23.6 | 5.5 | 25.5 | 3.1 | 29.6 | 13.5 | 58.9 | 41.4 |
| 43 | 7.9 | 10.0 | 32.0 | 16.0 | 5.1 | 30.8 | 25.4 | 2.6 | 6.8 | 20.7 | .5 | 31.7 | 5.0 | 25.3 | 2.7 | 28.0 | 12.7 | 61.2 | 34.7 |
| 44 | 6.4 | 9.7 | 27.7 | 15.7 | 7.1 | 30.7 | 25.0 | 2.2 | 6.7 | 19.5 | .6 | 29.7 | 5.2 | 24.0 | 2.9 | 27.4 | 12.9 | 59.0 | 30.4 |
| 45 | 6.8 | 9.6 | 26.2 | 15.3 | 5.8 | 34.5 | 24.5 | 2.0 | 6.6 | 20.1 | .6 | 25.8 | 4.7 | 24.8 | 2.9 | 27.1 | 11.9 | 58.6 | 28.4 |
| 46 | 7.3 | 9.6 | 25.0 | 15.0 | 4.6 | 37.5 | 27.9 | 2.0 | 6.9 | 19.5 | .6 | 23.4 | 4.4 | 23.8 | 2.4 | 27.2 | 11.8 | 57.5 | 27.0 |
| 47 | 7.0 | 9.7 | 26.1 | 14.1 | 4.5 | 33.4 | 30.8 | 2.0 | 6.3 | 19.3 | .5 | 22.9 | 4.8 | 23.2 | 2.5 | 26.7 | 11.8 | 55.3 | 26.1 |
| 48 | 6.7 | 9.6 | 23.3 | 14.3 | 4.4 | 29.9 | 34.5 | 1.8 | 6.6 | 18.1 | .6 | 22.0 | 4.1 | 22.6 | 2.7 | 25.7 | 11.1 | 54.2 | 25.9 |
| 49 | 6.0 | 9.3 | 23.2 | 13.8 | 4.0 | 27.6 | 29.3 | 1.7 | 7.0 | 17.9 | .6 | 22.3 | 4.0 | 28.6 | 2.5 | 25.5 | 11.6 | 53.7 | 25.5 |
| 50 | 5.7 | 9.1 | 21.5 | 13.3 | 3.7 | 27.2 | 24.4 | 2.0 | 6.4 | 17.5 | .6 | 21.2 | 10.9 | 27.7 | 2.1 | 24.8 | 11.6 | 53.0 | 25.0 |
| 51 | 6.5 | 9.0 | 22.5 | 13.5 | 3.8 | 25.7 | 21.2 | 3.1 | 5.7 | 16.4 | .6 | 20.4 | 8.1 | 23.2 | 2.4 | 24.5 | 11.8 | 50.4 | 23.5 |
| 52 | 5.9 | 9.0 | 25.5 | 13.5 | 3.3 | 25.4 | 20.7 | 2.4 | 5.9 | 16.5 | .6 | 19.1 | 5.4 | 21.3 | 2.6 | 23.6 | 10.9 | 51.3 | 23.8 |
| 53 | 6.3 | 9.0 | 24.5 | 13.1 | 3.1 | 28.1 | 20.0 | 2.0 | 5.9 | 15.7 | .6 | 19.0 | 4.1 | 20.2 | 2.2 | 23.3 | 11.1 | 48.1 | 22.7 |
| 54 | 9.0 | 8.9 | 21.6 | 13.1 | 3.1 | 26.6 | 19.1 | 1.8 | 5.2 | 15.9 | .6 | 20.1 | 3.4 | 19.8 | 2.4 | 22.5 | 10.1 | 48.8 | 22.4 |
| 55 | 7.4 | 13.6 | 19.9 | 12.5 | 3.0 | 24.3 | 18.2 | 1.7 | 5.9 | 15.4 | .6 | 18.7 | 3.9 | 19.3 | 2.1 | 22.0 | 10.0 | 46.2 | 21.5 |
| 56 | 6.4 | 12.1 | 20.0 | 12.4 | 3.5 | 23.3 | 18.2 | 1.5 | 4.7 | 14.9 | .6 | 18.5 | 2.9 | 18.1 | 2.2 | 21.6 | 10.5 | 45.8 | 26.9 |
| 57 | 5.3 | 9.8 | 19.2 | 11.8 | 3.3 | 22.1 | 17.6 | 1.6 | 5.1 | 14.5 | .6 | 17.8 | 2.9 | 18.3 | 2.6 | 20.7 | 10.3 | 44.6 | 28.6 |
| 58 | 5.7 | 9.5 | 19.1 | 12.6 | 2.8 | 22.0 | 17.0 | 1.4 | 4.8 | 18.3 | .6 | 18.0 | 2.6 | 17.1 | 2.4 | 20.4 | 9.2 | 44.0 | 24.6 |
| 59 | 6.0 | 8.7 | 18.3 | 12.0 | 2.9 | 21.5 | 16.3 | 1.6 | 5.0 | 17.2 | .5 | 17.9 | 2.9 | 16.8 | 2.1 | 24.6 | 9.7 | 42.3 | 21.0 |
| 60 | 5.5 | 8.5 | 18.5 | 11.7 | 3.1 | 21.4 | 20.5 | 1.4 | 5.1 | 15.1 | .5 | 18.0 | 2.9 | 17.0 | 1.9 | 22.9 | 9.3 | 42.8 | 20.3 |

18K PROTEIN - Background Corrected Data (Injection Corrected)

TABLE 11

PTH AMINO ACID

| CYCLE | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 1 | 53.0 | 16.9 | -.3 | .1 | -.2 | 4.1 | 191.2 | 5.3 | -.1 | -.5 | .3 | -.5 | -.7 | .9 | -.0 | -.8 | .6 | -.4 | -1.5 |
| 2 | 16.4 | -1.0 | 201.0 | -.5 | .1 | 1.6 | 1.5 | 1.1 | 1.1 | .2 | -1.4 | 1.0 | -1.6 | -1.3 | -5.4 | -2.0 | 5.1 | -2.4 | 1.2 |
| 3 | 1.0 | -.1 | 17.9 | -1.2 | 80.4 | -.3 | -.2 | -1.2 | 1.9 | 4.7 | .7 | -.8 | .0 | 1.4 | -1.7 | .1 | 2.8 | 2.5 | .9 |
| 4 | -.0 | 1.8 | 3.4 | 5.1 | 3.7 | -1.7 | -.7 | -2.2 | -.3 | .7 | 2.6 | -1.9 | 1.7 | -3.2 | .9 | 3.9 | 2.1 | 3.5 | 180.3 |
| 5 | .2 | .7 | 2.0 | 1.2 | 74.7 | -1.3 | .5 | -.3 | -1.1 | 3.3 | 1.8 | 1.0 | .6 | -2.3 | 3.0 | 2.3 | -.3 | 3.6 | 8.5 |
| 6 | .1 | -.4 | 1.6 | 7.7 | 4.7 | 146.7 | 2.2 | .3 | -2.1 | 2.5 | 5.5 | .7 | -4.2 | 3.7 | 1.9 | -.4 | -3.0 | 1.9 | 3.1 |
| 7 | -1.7 | -3.4 | -1.9 | .9 | -.2 | 3.5 | -.4 | 1.6 | -.9 | .3 | -1.0 | 1.2 | 3.6 | 7.7 | 29.1 | 2.3 | -.2 | 178.9 | 3.7 |
| 8 | 2.4 | 2.9 | -2.9 | 8.9 | 66.8 | -1.2 | -.9 | 1.9 | -1.2 | -.3 | -2.8 | -3.5 | 7.3 | 9.6 | .9 | 4.9 | -3.0 | 19.5 | -.6 |
| 9 | -1.8 | 29.8 | .9 | 14.0 | 1.2 | -1.6 | -1.3 | 2.7 | -1.7 | -3.4 | -1.9 | 212.6 | 5.5 | 2.9 | -.5 | 5.6 | -3.3 | 3.9 | -1.9 |
| 10 | -.9 | .3 | -.4 | 10.9 | -1.6 | -.2 | -.3 | 1.0 | 5.5 | .0 | -.1 | 61.1 | 3.5 | 299.3 | -1.1 | 2.2 | -1.8 | -.4 | -1.1 |
| 11 | .5 | -7.3 | -1.0 | .3 | -.4 | .9 | -.2 | .3 | 3.1 | -.9 | 1.1 | 20.2 | 7.2 | 78.0 | 4.2 | 180.9 | 1.6 | .6 | .8 |
| 12 | 1.6 | -1.0 | -.9 | .8 | .2 | 90.6 | -1.2 | -.2 | 2.2 | -.7 | 4.8 | 5.3 | 3.7 | 16.4 | -1.2 | 47.3 | 2.2 | -2.2 | -.2 |
| 13 | 1.5 | 7.0 | 1.4 | .4 | 1.0 | 112.6 | -.7 | .1 | -1.0 | -2.1 | 3.6 | 3.3 | -1.2 | 1.5 | .0 | 10.1 | 1.0 | -.9 | -1.1 |
| 14 | 2.6 | 7.2 | 2.2 | -5.0 | 1.2 | 34.8 | .9 | 1.0 | 99.5 | .9 | .9 | 1.9 | .2 | -1.9 | -3.9 | .6 | .3 | .1 | 2.3 |
| 15 | 1.0 | 10.6 | 1.3 | -.6 | 33.2 | 13.1 | 1.9 | -3.1 | 31.9 | 8.9 | 1.5 | .3 | -1.9 | -1.7 | -3.4 | -2.9 | -.3 | .3 | 1.3 |
| 16 | .6 | 9.1 | 1.3 | .4 | 10.8 | 61.1 | 3.1 | -6.7 | 9.3 | 8.5 | -1.2 | -.3 | -1.9 | -.8 | 3.8 | -2.3 | 1.7 | 1.3 | 1.6 |
| 17 | -.9 | 7.1 | -2.8 | .4 | .9 | 69.6 | 1.9 | -2.0 | 2.2 | 3.4 | 6.1 | -1.9 | -.1 | 1.1 | 1.4 | -1.5 | 4.2 | -.3 | .0 |
| 18 | -.6 | 2.7 | -1.4 | -.0 | -2.1 | 18.6 | .8 | -.4 | -.3 | 4.1 | 8.5 | -1.6 | 11.2 | -.6 | -.0 | -2.2 | 2.2 | -1.1 | 58.8 |
| 19 | -2.7 | -.2 | -1.0 | -1.5 | .0 | 3.8 | 1.1 | 1.5 | 1.0 | 2.3 | 3.8 | -.3 | 11.9 | .1 | .5 | -.7 | 4.5 | -.3 | 61.7 |
| 20 | -1.4 | -2.3 | 2.3 | -2.0 | -.8 | -1.4 | -.7 | 6.7 | -1.8 | 1.6 | -1.2 | .2 | 9.0 | -.7 | 7.7 | -1.8 | .4 | 65.5 | 20.6 |
| 21 | -.9 | -5.6 | -.3 | -2.3 | .5 | -2.2 | -1.3 | 8.8 | 62.0 | .7 | 5.4 | -1.9 | 8.5 | .5 | 3.5 | .2 | .7 | 17.0 | 2.8 |
| 22 | 1.9 | -.9 | -.1 | .3 | .1 | -1.3 | 42.0 | 8.9 | 17.4 | -.9 | 1.3 | -.2 | 7.7 | -.2 | -.5 | .9 | 1.4 | 2.8 | -2.1 |
| 23 | 2.5 | 7.6 | 53.8 | .4 | -.8 | -.0 | 10.7 | 8.2 | 3.1 | -2.0 | .3 | .3 | 6.1 | -.6 | -1.9 | -.3 | 1.2 | .1 | -2.5 |
| 24 | 2.5 | 9.7 | 19.2 | .3 | 18.8 | 1.1 | 2.3 | -1.2 | .9 | .9 | -1.8 | 1.2 | 2.6 | -.7 | -.6 | .5 | -.7 | -.4 | -.9 |
| 25 | 3.9 | 7.9 | 48.5 | 2.5 | 5.0 | .1 | -.8 | 2.7 | -.7 | -1.4 | -.2 | 1.5 | -.7 | -1.1 | 3.4 | .2 | -1.2 | -1.3 | -.2 |
| 26 | 6.3 | 7.4 | 58.7 | 6.3 | 2.8 | 1.0 | -1.1 | -2.8 | -1.6 | 1.0 | -2.0 | 1.3 | -2.6 | 1.0 | .6 | -.3 | -.8 | -2.2 | -.3 |
| 27 | -1.1 | -.6 | 12.4 | -1.8 | .6 | .2 | -.2 | 4.0 | 1.2 | -4.4 | 2.0 | .5 | .7 | .8 | 4.7 | 1.5 | .7 | 28.2 | 1.1 |
| 28 | 1.1 | 1.3 | 2.2 | 2.9 | -.1 | -.9 | -1.3 | .4 | -1.0 | 74.6 | .6 | -.7 | -.3 | 1.6 | 1.7 | 1.4 | -.5 | 9.6 | .0 |
| 29 | 1.3 | 1.0 | -.0 | 3.3 | .0 | -.7 | 24.9 | 1.6 | -.1 | 23.8 | 1.6 | -1.4 | -.6 | -.1 | 1.4 | 1.0 | -2.2 | 2.4 | .9 |
| 30 | -2.4 | -.7 | -1.5 | 2.5 | .3 | .8 | 7.4 | .7 | -.4 | 5.7 | 4.4 | 1.3 | .2 | 1.2 | -.9 | 1.3 | 72.3 | .5 | 1.3 |
| 31 | .3 | -.1 | .1 | .2 | 54.6 | -3.4 | 7.6 | 2.3 | -1.1 | 4.6 | -1.3 | -1.6 | 2.1 | -1.3 | -.4 | -5.4 | 46.0 | -.7 | -4.4 |
| 32 | -.8 | 1.6 | -.4 | 6.7 | 19.7 | -1.3 | -3.1 | -4.2 | 4.7 | 1.0 | 8.5 | .8 | 3.1 | -4.7 | 126.4 | -2.1 | 16.5 | -1.8 | -7.1 |
| 33 | 1.5 | 4.3 | .1 | 7.0 | 55.4 | 1.5 | -4.1 | 2.9 | -1.1 | -2.0 | 2.6 | -.9 | .3 | 1.6 | 46.6 | -.8 | .5 | -.3 | -6.1 |
| 34 | 2.3 | -.9 | -.7 | 5.0 | 9.8 | 2.8 | -.6 | 6.2 | 71.8 | -1.6 | -1.7 | 2.7 | 1.0 | .1 | 8.2 | .9 | .1 | .9 | -.6 |
| 35 | 2.8 | 2.8 | 1.3 | 5.8 | 32.9 | -.0 | 2.0 | -1.5 | 23.0 | 1.4 | 13.0 | 3.0 | -6.7 | .0 | -1.1 | 1.0 | -1.2 | -1.2 | -.3 |
| 36 | 1.5 | -.6 | .2 | -6.1 | 7.7 | -1.4 | 1.3 | 4.3 | 6.4 | -1.1 | 11.2 | 3.2 | -1.9 | 4.8 | 1.2 | 1.9 | -1.6 | 58.2 | 2.5 |
| 37 | -1.7 | 1.0 | 13.1 | -1.2 | .6 | 3.4 | .2 | 1.9 | 1.3 | -2.1 | -1.7 | 3.0 | 5.2 | 7.9 | -.6 | .6 | 1.2 | 22.6 | 1.4 |
| 38 | -.7 | -1.2 | 6.4 | 84.9 | .4 | 3.9 | .9 | .0 | .4 | .6 | 1.6 | -2.1 | 1.6 | 2.1 | 3.2 | -.3 | -.4 | 7.9 | .7 |
| 39 | 1.7 | .9 | 3.6 | 36.7 | .0 | 3.0 | .2 | -4.5 | -1.0 | -1.8 | 8.1 | .7 | -1.6 | 75.0 | .6 | .3 | 1.8 | 3.6 | .6 |
| 40 | -1.2 | -2.1 | .7 | 14.6 | -3.6 | 1.5 | 1.1 | .6 | 1.9 | .0 | 8.7 | 1.4 | -1.5 | 33.5 | .4 | 61.6 | -.2 | .7 | 2.3 |
| 41 | 1.5 | .3 | 14.0 | 3.3 | -4.3 | -1.9 | -.1 | 8.1 | 5.0 | .4 | .0 | -2.7 | -.1 | 10.1 | 2.6 | 23.2 | .6 | .3 | -1.6 |
| 42 | .7 | -1.5 | 6.2 | -1.3 | .6 | -.6 | 2.0 | -.7 | .4 | -.8 | 5.8 | -4.7 | 2.5 | -.6 | 2.7 | 2.9 | 2.1 | -5.7 | 33.5 |
| 43 | 1.7 | 6.5 | 4.5 | .9 | -2.3 | -.9 | -1.1 | 6.8 | -1.3 | .2 | -4.1 | 21.5 | .5 | .0 | -.1 | -1.4 | .3 | 1.0 | 15.9 |
| 44 | -2.4 | 4.3 | .7 | 1.0 | 12.1 | .4 | -.6 | .6 | -.7 | -2.0 | 1.2 | 17.1 | 2.5 | -2.9 | 1.7 | -1.6 | 1.7 | -.9 | 5.4 |
| 45 | -1.0 | 3.6 | -.1 | .5 | 5.3 | 12.7 | -.6 | -1.4 | -.2 | 1.9 | -.8 | 6.8 | .6 | 2.2 | 2.0 | -.9 | -1.1 | .7 | 1.4 |
| 46 | 1.1 | 3.6 | -.7 | .6 | -.5 | 22.5 | -.7 | -1.3 | 2.9 | 1.6 | -.0 | 1.1 | -.2 | .2 | -1.4 | 1.3 | -.5 | .8 | -.8 |
| 47 | .8 | 4.2 | 1.1 | -1.9 | .5 | 12.8 | 20.6 | 1.1 | .0 | 2.5 | -1.3 | 1.2 | 3.5 | -.2 | -.8 | 1.4 | -.1 | -1.1 | -1.5 |
| 48 | .3 | 4.0 | -1.1 | .4 | 1.3 | 5.1 | 32.7 | -2.6 | 3.1 | -.0 | .2 | -.0 | .2 | -.7 | 1.2 | -.5 | -1.8 | -1.0 | .1 |
| 49 | -1.4 | 1.3 | -.6 | -.7 | -.0 | .4 | 19.8 | -2.9 | 6.4 | .7 | .6 | 2.6 | .4 | 25.0 | .1 | .8 | .5 | .4 | .7 |
| 50 | -1.8 | .4 | -1.7 | -1.5 | -.4 | 1.0 | 7.6 | 2.4 | 3.7 | .9 | .2 | .9 | 47.4 | 23.5 | -3.4 | .5 | 1.1 | 1.2 | 1.2 |
| 51 | .9 | -.6 | -.0 | .5 | 1.2 | -1.4 | .3 | 21.3 | -.2 | -1.2 | .6 | .0 | 29.6 | 8.0 | -.2 | 1.0 | 2.4 | -1.6 | -1.5 |
| 52 | -.3 | -.2 | 3.8 | 2.1 | -.5 | -.8 | .5 | 11.6 | 1.8 | .3 | -.0 | -2.3 | 12.6 | 2.6 | 2.2 | -.0 | -.1 | 2.2 | 1.1 |
| 53 | 1.2 | .2 | 3.3 | 1.4 | -.8 | 8.6 | .2 | 5.9 | 2.6 | -1.3 | .1 | -1.2 | 4.9 | .7 | -1.0 | .7 | 1.2 | -1.8 | -.5 |
| 54 | 9.5 | -.5 | .9 | 2.2 | -.3 | 5.9 | -.6 | 2.7 | -1.3 | .6 | -1.5 | 3.2 | 1.2 | 1.0 | 1.3 | -.6 | -1.5 | 1.7 | .3 |

18K PROTEIN – Background, Lag Corrected Data (Injection Corrected)

TABLE 12

PTH AMINO ACID

| CYCLE | Asp | Asn | Glu | Gln | Thr | Gly | Ala | His | Ser | Tyr | Arg | Pro | Met | Val | Trp | Phe | Ile | Lys | Leu |
|---|---|---|---|---|---|---|---|---|---|---|---|---|---|---|---|---|---|---|---|
| 55 | 4.9 | 40.0 | -.4 | .3 | -.5 | 1.5 | -1.4 | 2.6 | 1.2 | -.3 | .7 | .1 | 5.3 | 1.1 | -1.0 | -.5 | -1.1 | -1.3 | -.9 |
| 56 | 2.2 | 27.4 | .2 | .8 | 3.3 | .2 | .2 | -.2 | -2.9 | -1.2 | 2.2 | .4 | -.7 | -1.7 | -.4 | -.2 | 1.1 | -.1 | 16.0 |
| 57 | -1.0 | 8.4 | -.2 | -1.3 | 2.1 | -1.6 | .4 | .3 | .6 | -1.9 | 1.1 | -.8 | -.0 | 1.1 | 3.9 | -1.6 | 1.5 | -.5 | 21.9 |
| 58 | .2 | 6.6 | .1 | 3.0 | -.9 | -.3 | .3 | -1.9 | -1.1 | 11.8 | 2.7 | .2 | -1.7 | -1.8 | 2.6 | -1.3 | -1.7 | .2 | 11.0 |
| 59 | 1.1 | .6 | -.3 | .7 | -.5 | -.2 | .2 | .7 | .7 | 9.7 | -2.6 | .3 | .7 | -1.0 | .9 | 15.1 | 1.0 | -1.3 | 1.1 |
| 60 | -.6 | -.5 | .2 | -.5 | .2 | 1.0 | 13.7 | -1.3 | 1.5 | 1.9 | -.7 | .6 | .5 | 1.4 | -.2 | 10.1 | .3 | 1.5 | -.6 |
| 1 | 53.0 | 16.9 | -.3 | .1 | -.2 | 4.1 | 183.7 | 5.3 | -.1 | -.5 | .3 | -.5 | -.7 | .9 | -.0 | -.8 | .6 | -.4 | -1.5 |
| 2 | 16.4 | -1.0 | 202.0 | -.5 | .1 | 1.6 | 8.9 | 1.1 | 1.1 | .2 | -1.4 | 1.0 | -1.6 | -1.3 | -5.4 | -2.0 | 5.1 | -2.4 | 1.2 |
| 3 | 1.0 | -.1 | 16.9 | -1.2 | 84.0 | -.3 | -.2 | -1.2 | 1.9 | 4.7 | .7 | -.8 | .0 | 1.4 | -1.7 | .1 | 2.8 | 2.5 | .9 |
| 4 | -.0 | 1.8 | 3.4 | 5.1 | .1 | -1.7 | -.7 | -2.2 | -.3 | .7 | 2.6 | -1.9 | 1.7 | -3.2 | .9 | 3.9 | 2.1 | 3.5 | 188.8 |
| 5 | .2 | .7 | 2.0 | 1.2 | 79.4 | -1.3 | .5 | -.3 | -1.1 | 3.3 | 1.8 | 1.0 | .6 | -2.3 | 3.0 | 2.3 | -.3 | 3.6 | .0 |
| 6 | .1 | -.4 | 1.6 | 7.7 | .0 | 150.2 | 2.2 | .3 | -2.1 | 2.5 | 5.5 | .7 | -4.2 | 3.7 | 1.9 | -.4 | -3.0 | 1.9 | 3.1 |
| 7 | -1.7 | -3.4 | -1.9 | .9 | -.2 | .0 | -.4 | 1.6 | -.9 | .3 | -1.0 | 1.2 | 3.6 | 7.7 | 29.1 | 2.3 | -.2 | 201.1 | 3.7 |
| 8 | 2.4 | 2.9 | -2.9 | 8.9 | 68.0 | -1.2 | -.9 | 1.9 | -1.2 | -.3 | -2.8 | -3.5 | 7.3 | 9.6 | .9 | 4.9 | -3.0 | .0 | -.6 |
| 9 | -1.8 | 29.8 | .9 | 14.0 | .0 | -1.6 | -1.3 | 2.7 | -1.7 | -3.4 | -1.9 | 259.8 | 5.5 | 2.9 | -.5 | 5.6 | -3.3 | 1.3 | -1.9 |
| 10 | -.9 | .3 | -.4 | 10.9 | -1.6 | -.2 | -.3 | 1.0 | 5.5 | .0 | -.1 | 18.6 | 3.5 | 372.1 | -1.1 | 2.2 | -1.8 | -.4 | -1.1 |
| 11 | .5 | -7.3 | -1.0 | .3 | -.4 | .9 | -.2 | .3 | 3.1 | -.9 | 1.1 | 15.4 | 7.2 | 13.5 | 4.2 | 227.4 | 1.6 | .6 | .8 |
| 12 | 1.6 | -1.0 | -.9 | .8 | .2 | 114.9 | -1.2 | -.2 | 2.2 | -.7 | 4.8 | 5.3 | 3.7 | 8.1 | -1.2 | 5.9 | 2.2 | -2.2 | -.2 |
| 13 | 1.5 | 7.0 | 1.4 | .4 | 1.0 | 117.4 | -.7 | .1 | -1.0 | -2.1 | 3.6 | 3.3 | -1.2 | 1.5 | .0 | 5.0 | 1.9 | -.9 | -1.1 |
| 14 | 2.6 | 7.2 | 2.2 | -5.0 | 1.2 | 8.9 | .9 | 1.0 | 129.9 | .9 | .9 | 1.9 | .2 | -1.9 | -3.9 | .6 | .3 | .1 | 2.3 |
| 15 | 1.0 | 10.6 | 1.3 | -.6 | 43.1 | 9.9 | 1.9 | -3.1 | 5.4 | 8.9 | 1.5 | .3 | -1.9 | -1.7 | -3.4 | -2.9 | -.3 | .3 | 1.3 |
| 16 | .6 | 9.1 | 1.3 | .4 | 1.8 | 80.4 | 3.1 | -6.7 | 5.3 | 8.5 | -1.2 | -.3 | -1.8 | -.8 | 3.8 | -2.3 | 1.7 | 1.3 | 1.6 |
| 17 | -.9 | 7.1 | -2.8 | .4 | .0 | 70.2 | 1.9 | -2.0 | 2.2 | 3.4 | 6.1 | -1.9 | -.1 | 1.1 | 1.4 | -1.5 | 4.2 | -.3 | .0 |
| 18 | -.6 | 2.7 | -1.4 | -.0 | -2.1 | 1.0 | .8 | -.4 | -.3 | 4.1 | 8.5 | -1.6 | 11.2 | -.6 | -.0 | -2.2 | 2.2 | -1.1 | 78.9 |
| 19 | -2.7 | -.2 | -1.0 | -1.5 | .0 | 1.5 | 1.1 | 1.5 | 1.0 | 2.3 | 3.8 | -.3 | 11.9 | .1 | .5 | -.7 | 4.5 | -.3 | 60.2 |
| 20 | -1.4 | -2.3 | 2.3 | -2.0 | -.8 | -1.4 | -.7 | 6.7 | -1.8 | 1.6 | -1.2 | .2 | 9.0 | -.7 | 7.7 | -1.8 | .4 | 95.3 | 4.2 |
| 21 | -.9 | -5.6 | -.3 | -2.3 | .5 | -2.2 | -1.3 | 8.8 | 82.6 | .7 | 5.4 | -1.9 | 8.5 | .5 | 3.5 | .2 | .7 | .0 | .6 |
| 22 | 1.9 | -.9 | -.1 | .3 | .1 | -1.3 | 54.9 | 8.9 | .0 | -.9 | 1.3 | -.2 | 7.7 | -.2 | -.5 | .9 | 1.4 | .0 | -2.1 |
| 23 | 2.5 | 7.6 | 73.6 | .4 | -.8 | -.0 | .0 | 8.2 | .0 | -2.0 | .3 | .3 | 6.1 | -.6 | -1.9 | -.3 | 1.2 | .1 | -2.5 |
| 24 | 2.5 | 9.7 | 2.2 | .3 | 24.8 | 1.1 | .1 | -1.2 | .9 | .9 | -1.8 | 1.2 | 2.6 | -.7 | -.6 | .5 | -.7 | -.4 | -.9 |
| 25 | 3.9 | 7.9 | 62.4 | 2.5 | .0 | .1 | -.8 | 2.7 | -.7 | -1.4 | -.2 | 1.5 | -.7 | -1.1 | 3.4 | .2 | -1.2 | -1.3 | -.2 |
| 26 | 6.3 | 7.4 | 56.6 | 6.3 | 1.9 | 1.0 | -1.1 | -2.8 | -1.6 | 1.0 | -2.0 | 1.3 | -2.6 | 1.0 | .6 | -.3 | -.0 | -2.2 | -.3 |
| 27 | -1.1 | -.6 | .0 | -1.8 | .6 | .2 | -.2 | 4.0 | 1.2 | -4.4 | 2.0 | .5 | .7 | .8 | 4.7 | 1.5 | .7 | 38.9 | 1.1 |
| 28 | 1.1 | 1.3 | .0 | 2.9 | -.1 | -.9 | -1.3 | .4 | -1.0 | 102.4 | .6 | -.7 | -.3 | 1.6 | 1.7 | 1.4 | -.5 | .5 | .0 |
| 29 | 1.3 | 1.0 | -.0 | 3.3 | .0 | -.7 | 33.7 | 1.6 | -.1 | .0 | 1.6 | -1.4 | -.6 | -.1 | 1.4 | 1.0 | -2.2 | .8 | .1 |
| 30 | -2.4 | -.7 | -1.5 | 2.5 | .3 | .8 | .0 | .7 | -.4 | 1.7 | 4.4 | 1.3 | .2 | 1.2 | -.9 | 1.3 | 101.2 | .5 | 1.3 |
| 31 | .3 | -.1 | .1 | .2 | 76.7 | -3.4 | 6.2 | 2.3 | -1.1 | 4.6 | -1.3 | -1.6 | 2.1 | -1.3 | -.4 | -5.4 | 21.6 | -.7 | -4.4 |
| 32 | -.8 | 1.6 | -.4 | 6.7 | .9 | -1.3 | -3.1 | -4.2 | 4.7 | 1.0 | 8.5 | .8 | 3.1 | -4.7 | 179.0 | -2.1 | 12.1 | -1.8 | -7.1 |
| 33 | 1.5 | 4.3 | .1 | 7.0 | 65.4 | 1.5 | -4.1 | 2.9 | -1.1 | -2.0 | 2.6 | -.9 | .3 | 1.6 | 1.9 | -.8 | .5 | -.3 | -6.1 |
| 34 | 2.3 | -.9 | -.7 | 5.0 | .0 | 2.8 | -.6 | 6.2 | 100.1 | -1.6 | -1.7 | 2.7 | 1.0 | .1 | .3 | .9 | .1 | .9 | -.6 |
| 35 | 2.8 | 2.8 | 1.3 | 5.8 | 38.0 | -.0 | 2.0 | -1.5 | .0 | 1.4 | 13.0 | 3.0 | -6.7 | .0 | -1.1 | 1.0 | -1.2 | -1.2 | -.3 |
| 36 | 1.5 | -.6 | .2 | -6.1 | .0 | -1.4 | 1.3 | 4.3 | 1.1 | -1.1 | 11.2 | 3.2 | -1.9 | 4.8 | 1.2 | 1.9 | -1.6 | 86.1 | 2.5 |
| 37 | -1.7 | 1.0 | 20.0 | -1.2 | .0 | 3.4 | .2 | 1.9 | 1.3 | -2.1 | -1.7 | 3.0 | 5.2 | 7.9 | -.6 | .6 | 1.2 | .0 | 1.4 |
| 38 | -.7 | -1.2 | .9 | 131.2 | .1 | 3.9 | .9 | .0 | .4 | .6 | 1.6 | -2.1 | 1.6 | 2.1 | 3.2 | -.3 | -.4 | 3.3 | .7 |
| 39 | 1.7 | .9 | 2.4 | .0 | .0 | 3.0 | .2 | -4.5 | -1.0 | -1.8 | 8.1 | .7 | -1.6 | 116.2 | .6 | .3 | 1.0 | 2.9 | .6 |
| 40 | -1.2 | -2.1 | .5 | 6.2 | -3.6 | 1.5 | 1.1 | .6 | 1.9 | .0 | 8.7 | 1.4 | -1.5 | .0 | .4 | 87.6 | -.2 | .7 | 2.3 |
| 41 | 1.5 | .3 | 22.1 | 2.0 | -4.3 | -1.9 | -.1 | 8.1 | 5.0 | .4 | .0 | -2.7 | -.1 | 2.3 | 2.6 | .0 | .6 | .3 | -1.6 |
| 42 | .7 | -1.5 | .0 | -1.3 | .6 | -.6 | 2.0 | -.7 | .4 | -.8 | 5.8 | -4.7 | 2.5 | -.6 | 2.7 | .0 | 2.1 | -5.7 | 54.5 |
| 43 | 1.7 | 6.5 | 2.9 | .9 | -2.3 | -.9 | -1.1 | 6.8 | -1.3 | .2 | -4.1 | 35.9 | .5 | -.1 | -1.4 | .3 | 1.0 | .0 |
| 44 | -2.4 | 4.3 | .5 | 1.0 | 17.7 | .4 | -.6 | .6 | -.7 | -2.0 | 1.2 | 6.1 | 2.5 | -2.9 | 1.7 | -1.6 | 1.7 | -.9 | 1.1 |
| 45 | -1.0 | 3.6 | -.1 | .5 | .0 | 22.0 | -.6 | -1.4 | -.2 | 1.9 | -.8 | 3.9 | .6 | 2.2 | 2.0 | -.9 | -1.1 | .7 | .7 |
| 46 | 1.1 | 3.6 | -.7 | .6 | -.5 | 28.5 | -.7 | -1.3 | 2.9 | 1.6 | -.0 | .6 | -.2 | .2 | -1.4 | 1.3 | -.5 | .8 | -.8 |
| 47 | .8 | 4.2 | 1.1 | -1.9 | .2 | 1.3 | 38.5 | 1.1 | .0 | 2.5 | -4.3 | 1.2 | 3.5 | -.2 | -.8 | 1.4 | -.1 | -1.1 | -1.5 |
| 48 | .3 | 4.0 | -1.1 | .4 | 1.3 | 1.7 | 38.7 | -2.6 | 3.1 | -.0 | .2 | -.0 | .2 | -.7 | 1.2 | -.5 | -1.8 | -1.0 | .1 |

```
49  -1.4   1.3   -.6   -.7   -.0    .0   2.1  -2.9   6.4    .7    .6   2.6    .4  50.7    .1    .8    .5    .4    .7
50  -1.8    .4  -1.7  -1.5   -.4   1.0   2.0   2.1   3.7    .9    .2    .9  93.1   6.0  -3.1    .5   1.1   1.2   1.2
51   .9   -.6   -.0    .5   1.2  -1.4    .0  39.6   -.2  -1.2    .6    .0    .0   1.7   -.2   1.0   2.4  -1.6  -1.5
52  -.3   -.2   7.5   2.1   -.5   -.8    .3    .0   1.8    .3   -.0  -2.3    .1   1.1   2.2   -.0   -.1   2.2   1.1
53   1.2    .2    .6   1.4   -.8  16.3    .2    .8   2.6  -1.3    .1  -1.2   1.9    .4  -1.0    .7   1.2  -1.8   -.5
54  16.8   -.5    .0   2.2   -.3    .0   -.6   1.5  -1.3    .6  -1.5   3.2    .7   1.0   1.3   -.6  -1.5   1.7    .3
55   .0  78.8   -.4    .3   -.5    .0  -1.4   2.3   4.2   -.3    .7    .1   5.3   1.1  -1.0   -.5  -1.1  -1.3   -.9
56   .0    .0    .1    .8   3.3    .0    .2   -.2  -2.9  -1.2   2.2    .4   -.7  -1.7   -.1   -.2   1.1   -.1  33.0
57  -1.0    .0   -.2  -1.3   2.1  -1.6    .4    .3    .6  -1.9   1.1   -.0   -.0   1.1   3.9  -1.6   1.5   -.5  16.8
58    .1   4.1    .1   3.0   -.9   -.3    .3  -1.9  -1.1  22.3   2.7    .2  -1.7  -1.8   2.6  -1.3  -1.7    .2    .0
59   1.1    .1   -.3    .7   -.5   -.2    .2    .7    .7    .0  -2.6    .3    .7  -1.0    .9  25.5   1.0  -1.3    .0
60   -.6   -.5    .2   -.5    .2   1.0  13.7  -1.3   1.5    .0   -.7    .6    .5   1.4   -.2    .0    .3   1.5   -.6
```

What is claimed is:

1. A method of obtaining a baseline corrected chromatogram, said method using a discrete, linear, translation invariant filter function $a_N{}^\alpha$, where N is a measure of the filter function width and $\alpha$ is a parameter whose value determines signal to noise characteristics of the filter function, comprising the steps of:

performing a chromatographic analysis of a sample to obtain a first chromatogram;

filtering said first chromatogram with the filter function, with N set to approximate the width of peaks obtained in said first chromatogram, and set to filter out high frequency noise from said first chromatogram to obtain a second chromatogram having a first filtered baseline:

filtering said second chromatogram with the filter function, with N set to approximate the width of peaks obtained in said first chromatogram and $\alpha$ set to resolution enhance peaks in said second chromatogram to obtain a third chromatogram having a baseline which is substantially the same as said first filtered baseline; and subtracting said second chromatogram from said third chromatogram to obtain a fourth chromatogram which is baseline corrected.

2. The method of claim 1 further comrprising:

truncating said fourth chromatogram for values below a preselected threshhold to obtain a fifth chromatogram;

filtering said fifth chromatogram with the filter function with $\alpha$ set to remove high frequency noise and N set equal to the width of peaks in said fifth chromatogram to obtain a sixth chromatogram;

detecting peaks in said sixth chromatogram; and measuring the height of said peaks in said sixth chromatogram.

3. The method of claim 2 wherein said filter function is a shifted triangular filter function proportional to $$(N + 1 - |n|)\frac{2\alpha}{N(N+1)} - \frac{2\alpha(N+1) - N}{N(2N+1)}.$$

4. The method of claim 2 wherein peaks detected in said sixth chromatogram are compared with peaks in a reference chromatogram to identify the sample.

5. The method of claim 3 wherein said sample comprises a mixture of amino acid derivatives.

6. The method of claim 4 wherein said filter function is a shifted triangular filter function proportional to $$(N + 1 - |n|)\frac{2\alpha}{N(N+1)} - \frac{2\alpha(N+1) - N}{N(2N+1)}.$$

7. An apparatus for obtaining a baseline corrected chromatogram of a sample, said sample having a plurality of components, comprising:

separation means for separating and eluting said components at different times;

detection means for detecting said components that are eluted and for providing a signal corresponding to retention times in said separation means for said components, said signal hereinafter called a raw chromatogram; and computer means coupled to said detection means for analyzing said raw chromatogram, said computer means programmed to:

define a filter function $a_N{}^\alpha$ that is a discrete, linear, translation invariant function, where N is a measure of the filter function width and $\alpha$ is a parameter whose value determines signal to noise characteristics of the filter function;

filter said raw chromatogram with said filter function, with N set to approximate the width of peaks obtained in said raw chromatogram, and $\alpha$ set to filter out high frequency noise from said raw chromatogram to obtain a second chromatogram having a first filtered baseline;

filter said second chromatogram with said filter function, with N set to approximate the width of peaks obtained in said first chromatogram and $\alpha$ set to resolution enhance peaks in said second chromatogram to obtain a third chromatogram having a baseline which is substantially the same as said first filtered baseline; and subtract said second chromatogram from said third chromatogram to obtain a fourth chromatogram which is baseline corrected.

* * * * *